United States Patent
Whikehart et al.

(10) Patent No.: US 11,899,416 B2
(45) Date of Patent: Feb. 13, 2024

(54) SYSTEMS AND METHODS FOR HOLISTIC LOW CARBON INTENSITY FUEL AND HYDROGEN PRODUCTION

(71) Applicant: MARATHON PETROLEUM COMPANY LP, Findlay, OH (US)

(72) Inventors: David Whikehart, Findlay, OH (US); Gregory Herold, Findlay, OH (US)

(73) Assignee: MARATHON PETROLEUM COMPANY LP, Findlay, OH (US)

( * ) Notice: Subject to any disclaimer, the term of this patent is extended or adjusted under 35 U.S.C. 154(b) by 316 days.

(21) Appl. No.: 17/392,600

(22) Filed: Aug. 3, 2021

(65) Prior Publication Data
US 2022/0042406 A1    Feb. 10, 2022

Related U.S. Application Data

(60) Provisional application No. 63/113,186, filed on Nov. 12, 2020, provisional application No. 63/198,626, (Continued)

(51) Int. Cl.
*C10G 9/00* (2006.01)
*C10G 47/36* (2006.01)
(Continued)

(52) U.S. Cl.
CPC .............. *G05B 13/042* (2013.01); *C10G 9/00* (2013.01); *C10G 47/36* (2013.01); *C10L 1/02* (2013.01);
(Continued)

(58) Field of Classification Search
CPC .... C10G 2300/1011; C10G 2300/4043; C10G 47/36; C10G 9/00; C10L 1/02;
(Continued)

(56) References Cited

U.S. PATENT DOCUMENTS

| 7,797,205 B2 | 9/2010 | Song et al. |
| 8,354,065 B1 | 1/2013 | Sexton et al. |

(Continued)

FOREIGN PATENT DOCUMENTS

| AU | 2020101782 | 9/2020 |
| CN | 110029645 | 7/2019 |

(Continued)

OTHER PUBLICATIONS

Riverol, C et al., A Non-linear Autoregressive Eternal Inputs (NARX) model for estimating the mixing volumes between batches in TRANSMIX, International Journal of Heat and Mass Transfer 127, 2018, 161-163.

(Continued)

*Primary Examiner* — Ellen M Mcavoy
*Assistant Examiner* — Chantel Graham
(74) *Attorney, Agent, or Firm* — Womble Bond Dickinson (US) LLP

(57) ABSTRACT

Systems and methods to provide low carbon intensity (CI) hydrogen through one or more targeted reductions of carbon emissions based upon an analysis of carbon emissions associated with a combination of various options for feedstock procurement, feedstock refining, processing, or transformation, and hydrogen distribution pathways to end users. Such options are selected to maintain the total CI (carbon emissions per unit energy) of the hydrogen below a preselected threshold that defines an upper limit of CI for the hydrogen.

20 Claims, 61 Drawing Sheets

Related U.S. Application Data filed on Oct. 30, 2020, provisional application No. 63/066,912, filed on Aug. 18, 2020, provisional application No. 63/061,162, filed on Aug. 4, 2020.

(51) Int. Cl.

| | |
|---|---|
| *C10L 1/02* | (2006.01) |
| *C10L 1/04* | (2006.01) |
| *C10L 3/06* | (2006.01) |
| *C12P 7/06* | (2006.01) |
| *E21B 43/12* | (2006.01) |
| *E21B 43/25* | (2006.01) |
| *G01N 33/28* | (2006.01) |
| *G06Q 50/06* | (2012.01) |
| *G06Q 50/30* | (2012.01) |
| *G08C 17/02* | (2006.01) |
| *C12P 7/10* | (2006.01) |
| *C12P 19/02* | (2006.01) |
| *G05B 13/04* | (2006.01) |
| *C12M 1/00* | (2006.01) |
| *C12M 1/36* | (2006.01) |
| *G05B 19/418* | (2006.01) |
| *G01N 33/22* | (2006.01) |
| *G06Q 30/018* | (2023.01) |
| *G06Q 10/083* | (2023.01) |

(52) U.S. Cl.
CPC .............. *C10L 1/04* (2013.01); *C10L 3/06* (2013.01); *C12M 21/12* (2013.01); *C12M 41/48* (2013.01); *C12P 7/06* (2013.01); *E21B 43/12* (2013.01); *E21B 43/25* (2013.01); *G01N 33/225* (2013.01); *G01N 33/28* (2013.01); *G05B 19/4189* (2013.01); *G06Q 30/018* (2013.01); *G06Q 50/06* (2013.01); *G06Q 50/30* (2013.01); *G08C 17/02* (2013.01); *C10G 2300/1011* (2013.01); *C10G 2300/4043* (2013.01); *C10L 2200/0469* (2013.01); *C10L 2200/0476* (2013.01); *C10L 2230/14* (2013.01); *C10L 2270/10* (2013.01); *C10L 2290/24* (2013.01); *C10L 2290/58* (2013.01); *G05B 2219/45076* (2013.01); *G06Q 10/083* (2013.01); *Y02P 20/151* (2015.11)

(58) Field of Classification Search
CPC ............. C10L 1/04; C10L 2200/0469; C10L 2200/0476; C10L 2230/14; C10L 2270/10; C10L 2290/24; C10L 2290/58; C10L 3/06; C10L 1/026; C12M 21/12; C12M 41/48; C12P 7/06; C12P 19/02; C12P 7/10; E21B 43/12; E21B 43/25; G01N 33/225; G01N 33/28; G01N 33/2852; G05B 13/042; G05B 19/042; G05B 19/4189; G05B 2219/2639; G05B 2219/45076; G06Q 10/083; G06Q 30/018; G06Q 50/06; G06Q 50/30; G08C 17/02; Y02P 20/151; Y02P 20/10; Y02P 20/133; Y02P 30/00; Y02E 50/10
See application file for complete search history.

(56) References Cited

U.S. PATENT DOCUMENTS

| | | | |
|---|---|---|---|
| 10,605,411 | B2 | 3/2020 | Robbins et al. |
| 11,164,406 | B2 | 11/2021 | Meroux et al. |
| 11,270,393 | B2 | 3/2022 | Whikehart et al. |
| 11,320,095 | B2 | 5/2022 | Rady et al. |
| 11,334,794 | B2 | 5/2022 | Celano et al. |
| 11,448,773 | B2 | 9/2022 | Bennett |
| 11,550,273 | B2 | 1/2023 | Whikehart et al. |
| 11,578,638 | B2 | 2/2023 | Thobe |
| 11,635,735 | B2 | 4/2023 | Whikehart et al. |
| 11,715,950 | B2 | 8/2023 | Miller et al. |
| 11,720,526 | B2 | 8/2023 | Miller et al. |
| 11,789,414 | B2 | 10/2023 | King et al. |
| 2009/0305360 | A1 | 12/2009 | Breneman et al. |
| 2010/0332273 | A1 | 12/2010 | Balasubramanian et al. |
| 2011/0093127 | A1 | 4/2011 | Kaplan |
| 2014/0218242 | A1 | 8/2014 | Platzer |
| 2017/0160118 | A1* | 6/2017 | Williams ............... H04L 67/12 |
| 2020/0291316 | A1 | 9/2020 | Robbins et al. |
| 2020/0372375 | A1 | 11/2020 | Pathak et al. |
| 2021/0156521 | A1 | 5/2021 | Laschinger et al. |
| 2022/0041974 | A1 | 2/2022 | Whikehart et al. |
| 2022/0083017 | A1 | 3/2022 | Whikehart |
| 2022/0267810 | A1* | 8/2022 | Lyubovsky ........... C25B 15/081 |
| 2022/0343229 | A1 | 10/2022 | Gruber et al. |
| 2022/0398448 | A1 | 12/2022 | Jayaraman et al. |
| 2023/0015077 | A1 | 1/2023 | Kim |
| 2023/0078852 | A1 | 3/2023 | Campbell et al. |
| 2023/0082127 | A1 | 3/2023 | Whikehart et al. |
| 2023/0205148 | A1 | 6/2023 | King et al. |
| 2023/0259080 | A1 | 8/2023 | Whikehart et al. |
| 2023/0259088 | A1 | 8/2023 | Borup et al. |

FOREIGN PATENT DOCUMENTS

| | | |
|---|---|---|
| CN | 111062568 | 4/2020 |
| EP | 3739295 | 11/2020 |
| IN | 12812008 | 8/2010 |
| WO | 2006083273 | 8/2006 |
| WO | 2021152205 | 8/2021 |
| WO | 2022149501 | 7/2022 |
| WO | 2022157589 | 7/2022 |
| WO | 2023038579 | 3/2023 |
| WO | 2023137304 | 7/2023 |
| WO | 2023164683 | 8/2023 |

OTHER PUBLICATIONS

Cheng, Lifei et al., Logistics for world-wide crude oil transportation using discrete event simulation and optimal control, Computers and Chemical Engineering 28, 2004, 897-911.

Bush, Amy et al., Iterative Optimization and Simulation of Barge Traffic on an Inland Waterway, Proceedings of the 2003 Winter Simulation Conference, Jan. 2004, 1751-1756.

Smith, Laurence Douglas et al., Simulation of alternative approaches to relieving congestion at locks in a river transport system, The Journal of the Operational Research Society, vol. 60, No. 4, Apr. 2009, 519-533.

Martins, Marcella Scoczynski Ribeiro et al., Discrete Event Simulation for Petroleum Transfers Involving Harbors, Refineries and Pipelines, Rio Pipeline 2009 Conference & Exposition, Sep. 2009.

Elgowainy, Amgad et al., Energy Efficiency and Greenhouse Gas Emission Intensity of Petroleum Products at U.S. Refineries, Environ. Sci. Technol. 2014, 48, 7612-7624.

Argonne National Laboratory, General Motors Corporation, Well-to-Wheel Energy Use and Greenhouse Gas Emissions of Advanced Fuel/Vehicle Systems, North American Analysis, vol. 1, Apr. 2001.

Gordon, Deborah, et al., Know Your Oil, Creating a Global Oil-Climate Index, 2015 Carnegie Endowment for International Peace.

BP, BP sets ambition for net zero by 2050, fundamentally changing organisation to deliver, Feb. 12, 2020.

BP, from IOC to IEC, Second quarter 2020 financial results and strategy presentation, Aug. 2020.

BP p.l.c. Group results, Second quarter and half year 2020, London, Aug. 4, 2020.

Brinkman et al., Well-to-Wheels Analysis of Advanced Fuel/Vehicle Systems—A North American Study of Energy Use, Greenhouse Gas Emissions, and Criteria Pollutant Emissions, May 2005.

El-Houjeiri, Hassan M. et al., Oil Production Greenhouse Gas Emissions Estimator, Jun. 5, 2017.

(56) References Cited

OTHER PUBLICATIONS

Argonne National Laboratory, Cradle-to-Grave Lifecycle Analysis of U.S. Light-Duty Vehicle-Fuel Pathways: A Greenhouse Gas Emissions and Economic Assessment of Current (2015) and Future (2025-2030) Technologies, ANL/ESD-16/7, Rev. 1, Sep. 2016.

Forman, Grant S. et al., U.S. Refinery Efficiency: Impacts Analysis and Implications for Fuel Carbon Policy Implementation, Environmental Science & Technology, 2014.

Malins, Chris et al., Crude Oil Greenhouse Gas Emissions Calculation Methodology for the Fuel Quality Directive, The International Council on Clean Transportation to the European Commission Directorate-General for Climate Action, 2014.

Nimana, Balwinder et al., Life cycle assessment of greenhouse gas emissions from Canada's oil sands-derived transportation fuels, Department of Mechanical Engineering, University of Alberta, 2015.

Ramachandran, Srikkanth et al., Well to wheel analysis of low carbon alternatives for road traffic, Energy Environ. Sci. 2015, 8, 3313.

Toyota Motor Corporation, Well-to-Wheel Analysis of Greenhouse Gas Emissions of Automotive Fuels in the Japanese Context, Nov. 2004.

Vineyard, Donald, et al., A Comparison of Major Petroleum Life Cycle Models, Clean Technol Environ Policy. Apr. 2017; 19(3): 735-747. doi:10.1007/s10098-016-1260-6.

Lloyd's Register, Using technology to trace the carbon intensity of sustainable marine fuels, Feb. 15, 2023.

\* cited by examiner

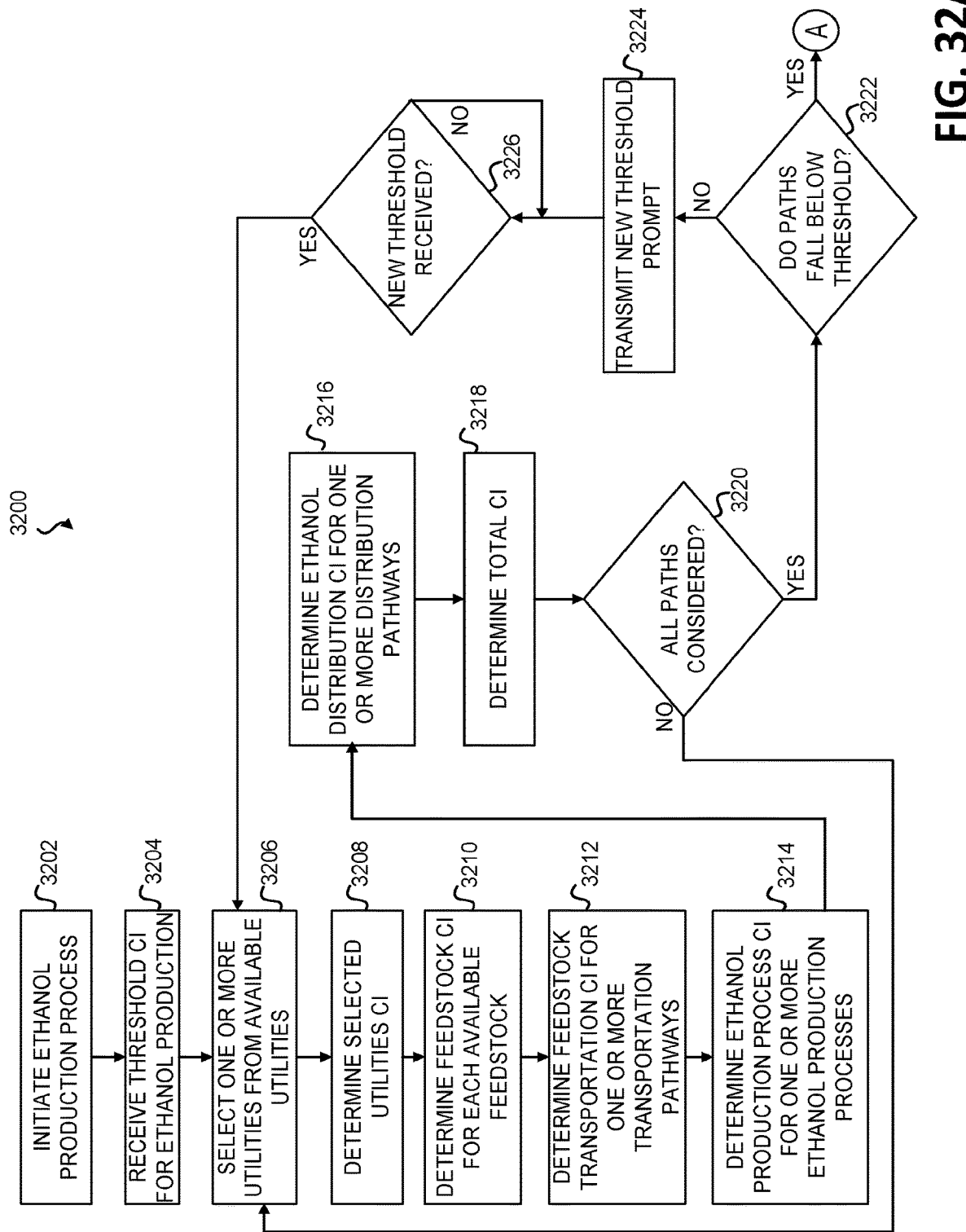

SYSTEMS AND METHODS FOR HOLISTIC LOW CARBON INTENSITY FUEL AND HYDROGEN PRODUCTION

CROSS REFERENCE TO RELATED APPLICATIONS

This application is related to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912 filed Aug. 18, 2020, titled "SYSTEMS AND METHODS FOR HOLISTIC LOW CARBON INTENSITY FUEL PRODUCTION," U.S. Provisional Application No. 63/198,626 filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186 filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety.

FIELD OF DISCLOSURE

Embodiments of this disclosure relate to low carbon intensity transportation fuel, low carbon intensity ethanol, and/or low carbon intensity hydrogen production, and more particularly, to systems and methods for procuring, refining/transforming, and making low carbon intensity transportation fuels, low carbon intensity ethanol, and low carbon intensity hydrogen available to end user consumers.

BACKGROUND

Certain gases, such as carbon dioxide, methane, nitrous oxide, hydrofluorocarbons, perfluorinated chemicals, sulfur hexafluoride, etc., when released to the atmosphere are purported to adversely contribute to climate change and have been labeled as greenhouse gases. To mitigate perceived climate change, much worldwide attention and focus has been placed on reducing the release of these greenhouse gases to atmosphere. Greenhouse gases, such as carbon dioxide, are directly released to atmosphere through the combustion of fossil fuels, biomass and other carbon-containing materials. However, providing services as well as the manufacturing and processing of goods contributes indirectly to the atmospheric release of carbon dioxide and other greenhouse gases. To quantify the direct and indirect release of greenhouse gases attributable to consumer and/or industrial activity, the carbon intensity or emission intensity was developed as a measure of the greenhouse gases emitted per unit of activity/production. With respect to transportation fuel and hydrogen production and use, the carbon intensity may be defined as the lifecycle greenhouse gases emitted per unit of energy. By assessing the lifecycle greenhouse gas emissions, all greenhouse gas emissions attributable to the fuel or hydrogen are accounted for during the entire lifecycle of the fuel or hydrogen from acquisition to processing to combustion. The carbon intensity for transportation fuels and hydrogen is often reported in units of grams of carbon dioxide equivalent per mega joule of energy. Because some greenhouse gases, such as methane, are considered to have a greater climatic effect than carbon dioxide, greenhouse gas emissions are reported in carbon dioxide equivalents.

Typical implementations of a low carbon intensity energy strategy may focus on the direct use by an end user or consumer of alternative, renewable sources of low carbon energy, such as power generated by wind, solar, or geothermal. For example, low carbon intensity renewable power may be generated at wind farms, solar farms, geothermal power plants/facilities, and/or hydroelectric facilities. Often, however, such farms and facilities are located at long distances from the end user or consumer. Thus, the alternative energy must be transferred from these remote locations to the end user over long distances, e.g., via high voltage transmission lines.

Inherent in such transmission is a loss of energy and an inefficient use of resources. Further, the transferred renewable power often is in a form that requires adaptation in order to be usable, which thereby increases its carbon intensity further. For example, to avoid conventional higher carbon intensity fuels in gasoline fueled vehicles, an end user or consumer may purchase an electric vehicle and install a home charging station to take advantage of renewable power. However, such choices may come at a considerable expense to the end user, who must purchase the electric vehicle and charging station. Moreover, the indirect use of higher carbon intensity fuels may also be overlooked. The construction of the electrical vehicles and their required accessories may contribute to significant carbon emissions if conducted using higher carbon intensity fuels. The production of electric vehicles may also create environmentally hazardous events and/or byproduct materials (e.g., mined nickel for use in batteries). Thus, this interplay may negate the overall environmental impact of the electric vehicle, even if energy is provided at a lower carbon intensity.

Similarly, renewable natural gas may often be produced at facilities located at long distances from the end user. Such long distances will necessitate transportation of the renewable natural gas via pipeline or truck to the end user or consumer. The use of conventional higher carbon intensity fuels or energy sources in such transportation will increase the carbon intensity of the renewable natural gas significantly.

Furthermore, a consumer that chooses the direct use of alternative, renewable energy source may continue to purchase higher carbon intensity liquid fuels from convenience stores or other retail outlets for occasions when electric vehicles are insufficient (e.g., long distance driving or lack of charging facilities). These higher carbon intensity liquid fuels originate in traditional refineries and similar facilities and are transported to such convenience stores with such transport further increasing the carbon intensity of the transportation fuel.

FIG. 1 illustrates a typical implementation 100 of a low carbon intensity energy strategy, which is largely focused on the use by the end user or consumer 102 of alternative, renewable sources of low carbon energy 108, 111, such as renewable natural gas produced from biomass wastes, electric power generated by wind, solar, geothermal, and/or hydroelectric sources, etc. As illustrated in FIG. 1, low carbon intensity renewable electric power 108 is generated at wind farms, solar arrays, geothermal power plants/facilities, and/or hydroelectric facilities. The electric power generated at these sources must often be transmitted long distances via high voltage transmission lines 109 to the renewable energy infrastructure 110 accessible by the consumer 102. This renewable energy infrastructure may include electric vehicles, charging stations, renewable natural gas pipelines and fueling stations, etc. However, when the renewable electric power reaches the consumer 102 via the renewable energy infrastructure 110, the consumer 102 may have to take further action, e.g., purchase an electric vehicle, in order to be able to properly make use of the renewable energy.

Renewable natural gas (RNG) is produced from biomass wastes at facilities 111, such as landfills, wastewater treatment plants, dairies, slaughterhouses and agricultural waste facilities, which are also oftentimes far from the consumer 102. The decomposition and/or biodegradation of biomass wastes produces methane and other gases. RNG is the methane that is separated via conventional separation techniques from other gases evolved during the decomposition of these biomass wastes. As a greenhouse gas, methane is considered to have a much greater impact than carbon dioxide, i.e., about 26 times the effect of carbon dioxide. Thus, reclaiming methane that would otherwise be released to atmosphere may significantly reduce greenhouse gas emissions. RNG is interchangeable with natural gas for pipeline and distribution purposes; therefore, the RNG may be marketed as a renewable energy and offered via typical distribution channels 107, e.g., truck or pipeline, to the end user or consumer 102. The renewable energy infrastructure 110, as shown in FIG. 1, encompasses the equipment and facilities necessary to permit such distribution channels for RNG, which allow the fuel to be accessible to the end user consumer 102. Again, however, the end user or consumer 102 may be forced to purchase vehicles powered by natural gas in order to be able to properly make use of the renewable energy.

As further illustrated in FIG. 1, the consumer 102, in many cases, will continue to purchase higher carbon intensity liquid fuels from convenience stores 104 or other retail outlets for occasions when electric vehicles are insufficient, e.g., long distance driving. Higher carbon intensity fuels 106 may also be transported 105 and employed indirectly by the consumer. Such indirect uses may include, but are not limited to, constructing and providing the renewable energy infrastructure 110 to permit the customer or consumer 102 to take advantage of the renewable energy. Further, higher CI liquid fuels may be necessary to produce the renewable energy and transport the renewable energy.

FIG. 17 illustrates a typical implementation 1700 of a hydrogen production strategy, which may largely focus on the use, by refinery processes, of high carbon intensity hydrogen 1711, such as hydrogen produced in a typical steam reforming process 1706 utilizing a typical natural gas feedstock 1704. As illustrated in FIG. 17, natural gas feedstock 1702 may be generated at wellheads or refineries. The natural gas feedstock 1702 generated at these sources may be transmitted long distances via pipeline, vehicle, marine vessel, or rail 1704 or may be transmitted via pipeline from a co-located refinery for use in a steam reforming process 1706. This steam reforming process 1706 may include a typical methane steam reformer located in a typical refinery. A typical steam reforming process 1706 may produce a high carbon intensity hydrogen 1711 and carbon dioxide 1708, the high carbon intensity due in part to carbon dioxide 1708 produced via the steam reforming process 1706. The carbon dioxide 1708 may be released into the atmosphere 1710. Further, the high carbon intensity hydrogen 1711 may be transported via pipeline/piping 1712 for refinery processing 1714 at a co-located or remote refinery. Such high carbon intensity hydrogen 1711 may further increase the carbon intensity of an output of the refinery processing 1714. The refinery processing 1714 (e.g., at a co-located refinery) may produce a high carbon intensity transportation fuel 1718 for use by an end user. The high carbon intensity transportation fuel 1718 may include a carbon intensity which is increased further, due to the use of the high carbon intensity hydrogen 1711.

Accordingly, Applicants have recognized a need for systems and methods to provide an energy consumer with low carbon intensity transportation fuels and low carbon intensity hydrogen through conventional pathways in which the low carbon intensity transportation fuels and low carbon intensity hydrogen are achieved through targeted reductions of carbon emissions associated with the various stages of fuel and hydrogen selection, production, and transport. The present disclosure is directed to embodiments of such systems and methods.

SUMMARY

The present disclosure is generally directed to systems and methods for providing a low carbon intensity (CI) transportation fuel and/or low CI hydrogen to an end user. The procuring of feedstocks, the refining or converting/transforming of those feedstocks into transportation fuels or hydrogen, respectively, and distribution of those transportation fuels or hydrogen to the end user (in other words, each stage of transportation fuel or hydrogen production) each may incrementally increase the carbon intensity of the transportation fuel or hydrogen. In some embodiments, the systems and methods may provide for the low CI transportation fuel to be obtained through one or more targeted reductions of carbon emissions associated with various options for feedstock procurement, feedstock transportation, feedstock refining and fuel product distribution pathways. In other embodiments, the systems and methods may provide for the low CI hydrogen to be obtained through one or more targeted reductions of carbon emissions associated with various options for feedstock procurement, feedstock transportation, feedstock conversion or transformation and hydrogen distribution pathways. Alternative, renewable energy sources, such as power generated from wind, solar, geothermal, and hydroelectric as well as renewable feedstocks obtained from plant and/or animal sources, may be used to reduce the carbon emissions of these various options. The resulting transportation fuels have a lower carbon intensity because the low carbon intensity alternative energy sources are integrated into the product fuels during feedstock selection, transportation, refining, and product distribution. Further, the resulting hydrogen may have a lower carbon intensity because the low carbon intensity alternative energy sources may be integrated into the hydrogen during feedstock selection, transportation, converting/transforming, and hydrogen distribution. The integration of alternative, renewable energy sources, which may be co-located geographically with conventional refineries, other transportation fuel processing facilities, and/or hydrogen production facilities or sources, reduces the added carbon intensity of transporting such energy directly to the consumer. Here, the consumer benefits at least three fold: First, conventional transportation fuels with a verified lower carbon intensity may be obtained; second, such low carbon conventional transportation fuels may be readily purchased from traditional retail outlets, such as convenience stores, without the consumer needing to purchase special vehicles and/or equipment, e.g., electric vehicles, to take advantage of the low carbon intensity energy afforded by alternative, renewable energy sources; and three, low CI hydrogen and/or low CI power produced via the low CI hydrogen may be integrated into various other processes or products, lowering the CI of those processes and offering a further variety of low CI products, e.g., vehicle fuel cells and/or low CI energy produced at a power plant or stationary fuel cell power system.

Accordingly, an embodiment of the disclosure is directed to a process to provide a low carbon intensity hydrogen obtained through one or more targeted reductions of carbon emissions associated with a combination of feedstock procurement, feedstock production and hydrogen distribution. The process may include identifying one or more sources of feedstock and one or more transportation pathways to transport feedstock from each of the one or more sources to a hydrogen production source. The process may include determining carbon emissions per unit energy of hydrogen associated with providing each identified feedstock from the one or more feedstock sources. The process may include determining carbon emissions per unit energy of hydrogen associated with each of the one or more transportation pathways. The process may include receiving at the hydrogen production source at least one feedstock selected from at least one of the one or more sources identified and transported by at least one of the one or more transportation pathways identified, the at least one feedstock defining a selected feedstock and the at least one transportation pathway defining a selected transportation pathway. The process may include converting the selected feedstock into hydrogen. The process may include determining a reduction in carbon emissions per unit energy of hydrogen that is attributable to two or more hydrogen production processes selected from a group including, powering at least a portion of hydrogen production source equipment with electricity generated by a renewable source, burning renewable natural gas in hydrogen production source fired heaters, generating steam through renewable natural gas-fed boilers, and sequestering carbon dioxide produced during the one or more hydrogen production processes, the determining the reduction in carbon emissions per unit energy being based in part upon pre-selected operating parameters for each of the two or more hydrogen production processes. The process may include operating the two or more hydrogen production processes to reduce carbon emissions per unit energy of hydrogen while converting the selected feedstock into the hydrogen. The process may include identifying distribution pathways to transport a quantity of the hydrogen to an end user location. The process may include determining carbon emissions per unit energy of hydrogen associated with each distribution pathway that transports the quantity of the hydrogen to the end user location. The process may include determining a total carbon emissions per unit energy of the hydrogen, the determining being a function of at least one or more of the determined carbon emissions per unit energy associated with providing the selected feedstock from its source, the determined carbon emissions per unit energy associated with the selected transportation pathway, the determined reduction in carbon emissions per unit energy associated with converting the selected feedstock together with operating the selected two or more hydrogen production processes, and the determined carbon emissions per unit energy associated with transporting the quantity of the hydrogen to the end user location through at least one distribution pathway.

The process may include determining the selected feedstock, the selected transportation pathway, the one or more hydrogen production processes and the at least one distribution pathway to maintain the total carbon emissions per unit energy of the hydrogen below a pre-selected total carbon emissions per unit energy threshold. The process may include maintaining a record of the total carbon emissions per unit energy associated with the quantity of the hydrogen. The process may include outputting the quantity of the hydrogen through the at least one distribution pathway as a low carbon intensity hydrogen.

In another embodiment, the process may further include determining a ratio of hydrogen that yields from converting each feedstock from the one or more sources. The at least one feedstock from at least one of the one or more sources may be selected from the group consisting of a low carbon intensity liquefied petroleum gas (LPG), a low carbon intensity naphtha, natural gas, and renewable natural gas and wherein the one or more sources of feedstock include one or more of a wellhead, a bio-feedstock plant, an offsite refinery, a co-located refinery, or a water source.

In another embodiment, the renewable source may include one or more of wind turbines, a solar array, a hydroelectric generator, a geothermal generator, or a stationary fuel cell power system.

Accordingly, an embodiment of the disclosure is directed to a system to operate a hydrogen production source for distribution of a low carbon intensity (CI) hydrogen therefrom and obtained through one or more targeted reductions of carbon emissions (CE) associated with combinations of various available feedstock to be supplied to various hydrogen production sources, various selected feedstock transportation and hydrogen distribution pathways, and various hydrogen production processes. The system may include a hydrogen production controller to control one or more various hydrogen production processes to be operated at one or more hydrogen production sources. The system may include a hydrogen integration controller in signal communication with the hydrogen production controller. The hydrogen integration controller may include one or more processors and memory storing instructions, the instructions, when executed by the one or more processors, to determine a feedstock CI for each of one or more available feedstock from one or more available feedstock sources to be supplied to the one or more hydrogen production sources from one or more available feedstock transportation pathways. The executed instructions may, for each one or more available feedstock, determine a feedstock transportation CI for each of one or more available feedstock transportation pathways based on (1) a volume of a feedstock transportation pathway, (2) fuel type utilized by the feedstock transportation pathway, and (3) distance to travel to the one or more hydrogen production sources. The executed instructions may determine a hydrogen production process CI for each of one or more hydrogen production processes based on: (1) one or more available hydrogen production processes available at the one or more hydrogen production sources, (2) a type of feedstock of the one or more available feedstock, and (3) a yield of each one or more available hydrogen production processes. The executed instructions may determine a utilities CI for each of one or more utilities based on: (1) a type of utility to be used during a hydrogen production process and (2) a utilities' source. The executed instructions may determine a hydrogen product distribution CI for each of one or more available hydrogen distribution pathway based on: (1) a volume of a hydrogen distribution pathway, (2) a type of the hydrogen distribution pathway, (3) fuel type utilized by the hydrogen distribution pathway, and (4) distance to travel for a delivery of hydrogen. The executed instructions may determine a set of combinations, each of the set of combinations including: (1) one or more available feedstock, (2) one or more available feedstock transportation pathways, (3) one or more hydrogen production processes of one or more hydrogen production sources, (4) one or more utilities, and (5) one or more available hydrogen distribution pathways. The executed instructions may determine a total CI for each of the set of combinations.

The executed instructions may determine a final selection from the set of combinations including a total CI less than or equal to a threshold CI, the threshold CI being defined as an upper limit of CI in providing hydrogen to an end user location that qualifies the hydrogen as a low CI hydrogen, the CI of the hydrogen being a function of the total carbon emissions per unit energy of the hydrogen. The final selection may include (1) a selected one or more available feedstock, (2) a selected one or more feedstock transportation pathways, (3) a selected one or more hydrogen production processes of one or more hydrogen production sources, (4) a selected one or more utilities, and (5) a selected one or more hydrogen distribution pathways. The executed instructions may, in response to the final selection, transmit a feedstock request based on the selected one or more available feedstock and the selected one or more feedstock transportation pathways. The executed instructions may, in response to a determined reception of the selected one or more available feedstock at the one or more hydrogen production sources, initiate, at the hydrogen production controller, the selected one or more hydrogen production processes of the one or more hydrogen production processes, and the selected one or more utilities to operate the selected one or more hydrogen production processes thereby to transform the selected one or more available feedstock to hydrogen. The executed instructions may, in response to determination of completion of the selected one or more hydrogen production processes, transmit a delivery request of the hydrogen via the selected one or more hydrogen distribution pathways.

Accordingly, an embodiment of the disclosure is directed to a hydrogen integration controller to operate one or more hydrogen production sources for distribution of a low carbon intensity (CI) hydrogen therefrom and obtained through one or more targeted reductions of carbon emissions (CE) associated with various available feedstock to be supplied to the one or more hydrogen production sources, various selected feedstock transportation and hydrogen distribution pathways, and various hydrogen production processes. The hydrogen integration controller may include a first input/output in signal communication with a procurement computing device. The hydrogen integration controller may be configured to determine a selection of one or more available feedstock, a selection of one or more feedstock transportation pathways, a selection of one or more hydrogen production processes at one or more hydrogen production sources, a selection of one or more utilities, and a selection of one or more hydrogen transportation pathways. Each selection may be based on (1) a determination of feedstock CI of one or more blends of the one or more available feedstock based on volume and type of feedstock, (2) a determination of feedstock transportation CI of one or more feedstock transportation pathways based on delivery distance and fuel type of the feedstock transportation pathway, (3) a determination of hydrogen production process CI of one or more hydrogen production processes at one or more hydrogen production sources based on the type of hydrogen production process, the volume and type of feedstock, and the length of time of the hydrogen production process, (4) a determination of utility CI of one or more utilities based on the type of utility utilized to operate the one or more hydrogen production processes and a distance the one or more utilities travel to the hydrogen production, (5) a determination of hydrogen distribution CI of one or more hydrogen distribution pathways based on delivery distance and fuel type of a hydrogen distribution pathway, and (6) a determination of one or more total CIs less than the threshold CI, the total CIs based on varying combinations of the determinations of CI.

The hydrogen integration controller may be configured to, in response to the selection of the one or more available feedstock, the selection of one or more feedstock transportation pathways, the selection of one or more hydrogen production processes at one or more hydrogen production sources, the selection of one or more utilities, and the selection of one or more hydrogen distribution pathways: transmit a feedstock request to the procurement computing device, the feedstock request including the selection of the one or more available feedstock and the selection of the one or more feedstock transportation pathways.

The hydrogen integration controller may be configured to a second input/output in signal communication with a hydrogen production controller, the hydrogen production controller to control one or more various hydrogen production processes to be operated at the one or more hydrogen production sources. The hydrogen integration controller may be configured to, in response to a determined reception of the selected one or more available feedstock at the one or more hydrogen production sources, determine actual feedstock CI and actual feedstock transportation CI. The hydrogen integration controller may be configured to, in response to a determination that the actual feedstock CI and actual feedstock transportation CI has increased in relation to the determined feedstock CI and determined feedstock transportation CI, determine one or more of a new selection of one or more hydrogen production processes, a new selection of one or more utilities, and a new selection of one or more hydrogen distribution pathways to maintain total CI. The hydrogen integration controller may be configured to initiate, at the hydrogen production controller, the selected one or more hydrogen production processes at the one or more hydrogen production sources and the selected one or more utilities to operate the selected one or more hydrogen production processes at the one or more hydrogen production sources thereby to transform the selected one or more available feedstock to hydrogen.

The hydrogen integration controller may include a third input/output in signal communication with a distribution computing device. The hydrogen integration controller may be configured to, in response to determination of completion of the selected one or more hydrogen production processes at the selected one or more hydrogen production sources. The hydrogen integration controller may be configured to determine an actual hydrogen production process CI and an actual utility CI. The hydrogen integration controller may be configured to, in response to a determination that the actual hydrogen production process CI and actual utility CI has increased in relation to the determined hydrogen production process CI and determined utility CI, determine one or more new selections of one or more hydrogen distribution pathways. The hydrogen integration controller may be configured to transmit a delivery request of the hydrogen via the selection of the one or more hydrogen distribution pathways to the distribution computing device.

Still other aspects and advantages of these embodiments and other embodiments, are discussed in detail herein. Moreover, it is to be understood that both the foregoing information and the following detailed description provide merely illustrative examples of various aspects and embodiments, and are intended to provide an overview or framework for understanding the nature and character of the claimed aspects and embodiments. Accordingly, these and other objects, along with advantages and features of the present disclosure herein disclosed, will become apparent through reference to the following description and the accompanying drawings. Furthermore, it is to be understood that the features of the various embodiments described herein are not mutually exclusive and may exist in various combinations and permutations.

BRIEF DESCRIPTION OF DRAWINGS

These and other features, aspects, and advantages of the disclosure will become better understood with regard to the following descriptions, claims, and accompanying drawings. It is to be noted, however, that the drawings illustrate only several embodiments of the disclosure and, therefore, are not to be considered limiting of the scope of the disclosure.

FIGS. 32A-B are flow diagrams, implemented in a controller, for managing the low carbon intensity ethanol production according to an embodiment.

DETAILED DESCRIPTION

Figure 1:
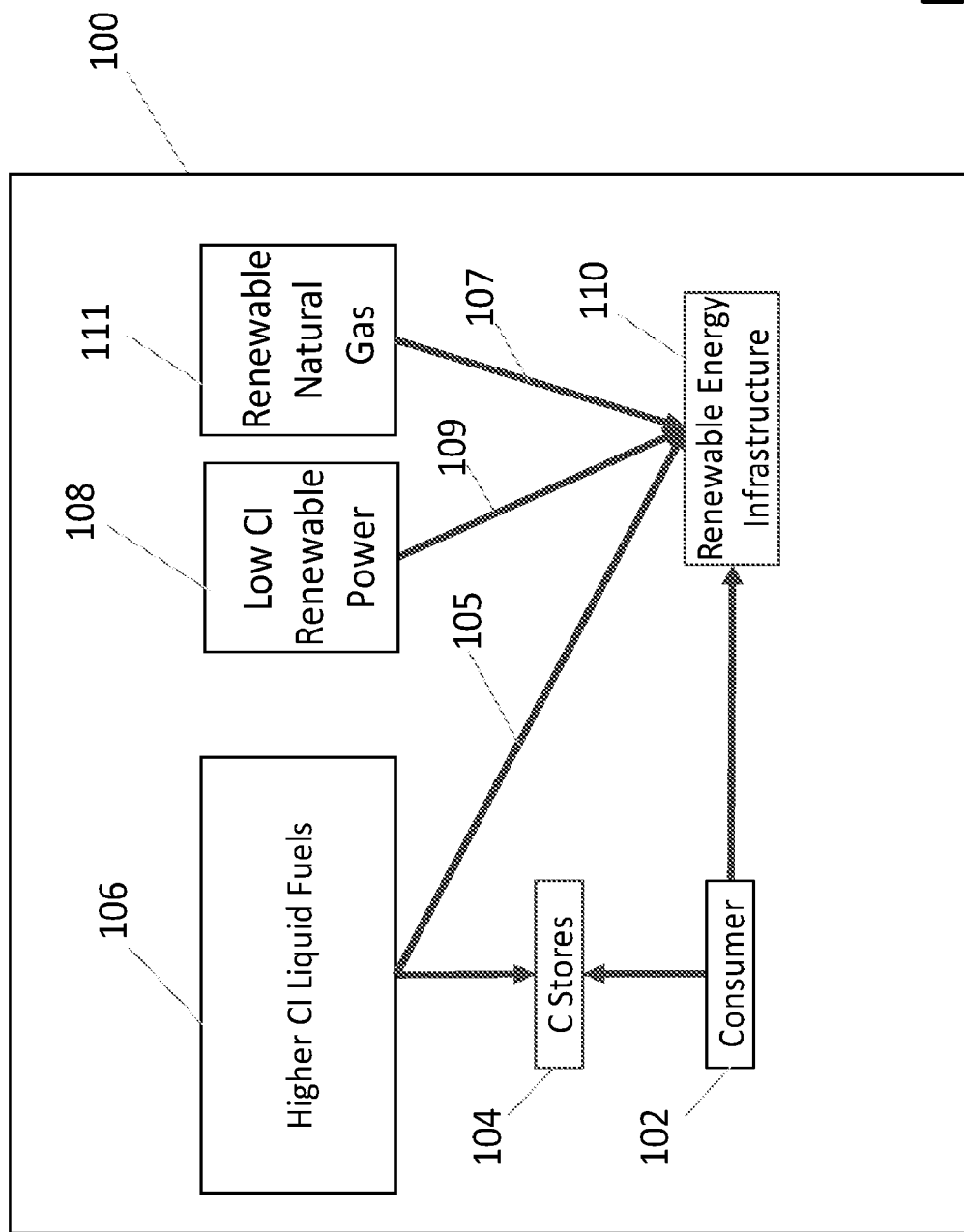
FIG. 1 is a simplified diagram that illustrates a typical implementation of a low carbon intensity energy strategy in which lower carbon fuel supplies and higher carbon fuel supplies are provided to the end user via separate distribution chains.

So that the manner in which the features and advantages of the embodiments of the systems and methods disclosed herein, as well as others that will become apparent, may be understood in more detail, a more particular description of embodiments of systems and methods briefly summarized above may be had by reference to the following detailed description of embodiments thereof, in which one or more are further illustrated in the appended drawings, which form a part of this specification. It is to be noted, however, that the drawings illustrate only various embodiments of the systems and methods disclosed herein and are therefore not to be considered limiting of the scope of the systems and methods disclosed herein as it may include other effective embodiments as well.

The present disclosure is directed to systems and methods for the production of low carbon intensity transportation fuels and other refined products. In one or more embodiments, systems and methods for providing a low carbon intensity (CI) transportation fuel to an end user are disclosed. In conventional refining, a suitable feedstock, e.g., a heavy, mid, and/or light crude, is selected, procured, and transported to the refinery. Certain refinery operations, including one or more of distilling, cracking, treating, separating and blending of refined products, are conducted to yield desired liquid transportation fuels. Such transportation fuels are then transported through various distribution pathways to retail outlets, e.g., convenience stores, for purchase by end user customers.

The present disclosure is further directed to systems and methods for the production of low carbon intensity hydrogen. In one or more embodiments, systems and methods for providing a low carbon intensity (CI) hydrogen to an end user are disclosed. Typically, hydrogen is produced via a steam reforming process co-located at a refinery. A suitable feedstock, e.g., methane or liquefied petroleum gas (LPG), is selected, procured, and transported to the co-located refinery and steam reformer. The steam reforming operations are conducted to yield desired liquid or gas hydrogen. The hydrogen is then transported through intra-refinery pipe or pipelines for use in various refinery operations, e.g., hydrotreating or hydrocracking. Further, the steam reforming operation typically produces carbon dioxide, which is normally released into the atmosphere.

The feedstocks selected for the production of transportation fuels have an initial or inherent carbon intensity, which is expressed as grams of carbon dioxide per unit energy. This initial or inherent carbon intensity represents the carbon emissions that would result if the feedstock—in its natural state without consideration of any pre- or post-processing—were to be combusted completely, e.g., complete combustion of the hydrocarbons to carbon dioxide and water based on stoichiometric combustion as would be understood by those skilled in the art. However, the procuring of such feedstocks, the refining of those feedstocks into transportation fuels, and distribution of those transportation fuels to the end user (in other words, each stage of fuel production) each may incrementally increase (or decrease) the carbon intensity of the final transportation fuel purchased by the end user. Nonetheless, it should be noted that this inherent or initial carbon intensity of the raw feedstock (i.e., of its fuel value) may often be the largest contributor to the overall carbon intensity of any transportation fuel that is produced therefrom. The carbon intensity of the final transportation fuel is increased if carbon emissions—expressed as grams of carbon dioxide equivalent per unit energy—result from such activities. For example, the determined grams of carbon dioxide equivalent per unit energy evolved as a result of the activity is added to the initial or inherent carbon intensity of the material that is the subject of the activity. Conversely, if activities that sequester carbon or mitigate the release of carbon emissions are employed, the carbon emissions may be negative or just slightly positive such that the carbon intensity of the transportation fuel is reduced or increases only slightly as a result of the activity.

Currently, renewable energy is produced and distributed directly to end users and oftentimes through dedicated channels. Frequently, the end users of such renewable energy must make special accommodations, e.g., renewable energy infrastructure purchases or significant travel to distribution points, in order to benefit from renewable energy. Moreover, energy sources having a higher carbon intensity, such as transportation fuels, are used in the construction and distribution of the renewable energy infrastructure or in the provision of renewable energy from its generation source to its procurement by end users. Such use of higher carbon intensity energy sources at least partially offset the low carbon intensity of renewable energy.

In some embodiments disclosed herein, the systems and methods may provide for low carbon intensity transportation fuels produced through one or more targeted reductions of carbon emissions associated with various options for feedstock procurement, feedstock transportation, feedstock refining, and fuel product/refined product/refined feedstock distribution pathways. Renewable energy sources, such as power generated from wind, solar, geothermal, and hydroelectric generators as well as renewable feedstocks obtained from biomass sources (e.g., plant crops/waste or animal waste), may be used to reduce the carbon emissions of these various options. The resulting transportation fuels have a lower carbon intensity because the low carbon intensity alternative energy sources are integrated into the product transportation fuels during feedstock selection, transportation, refining, and product distribution. The integration of alternative, renewable energy sources, which may be co-located geographically with conventional refineries and other transportation fuel processing facilities, reduces the added carbon intensity of transporting such energy directly to the consumer. The consumer purchaser of these lower carbon intensity transportation fuels and other refined products benefits in at least two ways: First, conventional transportation fuels are made available with carbon intensities that have been at least partially offset by processing steps that use the lower carbon intensities of alternative, renewable energies, such that lower carbon intensities of the alternative, renewable energies are integrated into the verifiably lower carbon intensity conventional transportation fuel. Second, such low carbon conventional transportation fuels may be readily purchased from traditional retail outlets, such as convenience stores, without the consumer needing to purchase special vehicles and/or equipment, e.g., electric vehicles, to take advantage of the low carbon intensity energy afforded by alternative, renewable energy sources.

Figure 2A:
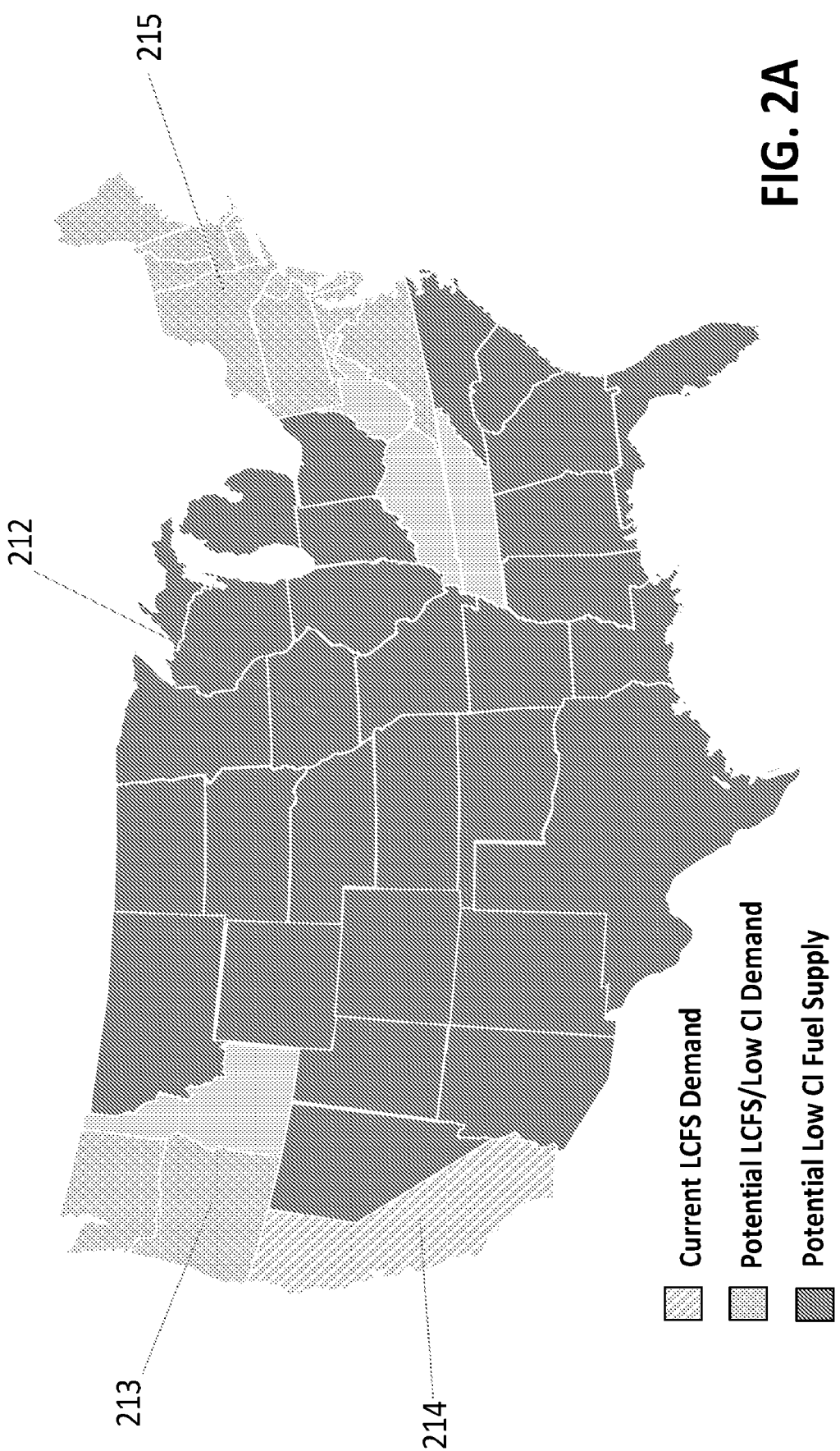
FIG. 2A is a map of the continental United States that illustrates the location of low carbon intensity energy supplies as compared to the locations of current and projected demands for low carbon intensity fuels.
Figure 2B:
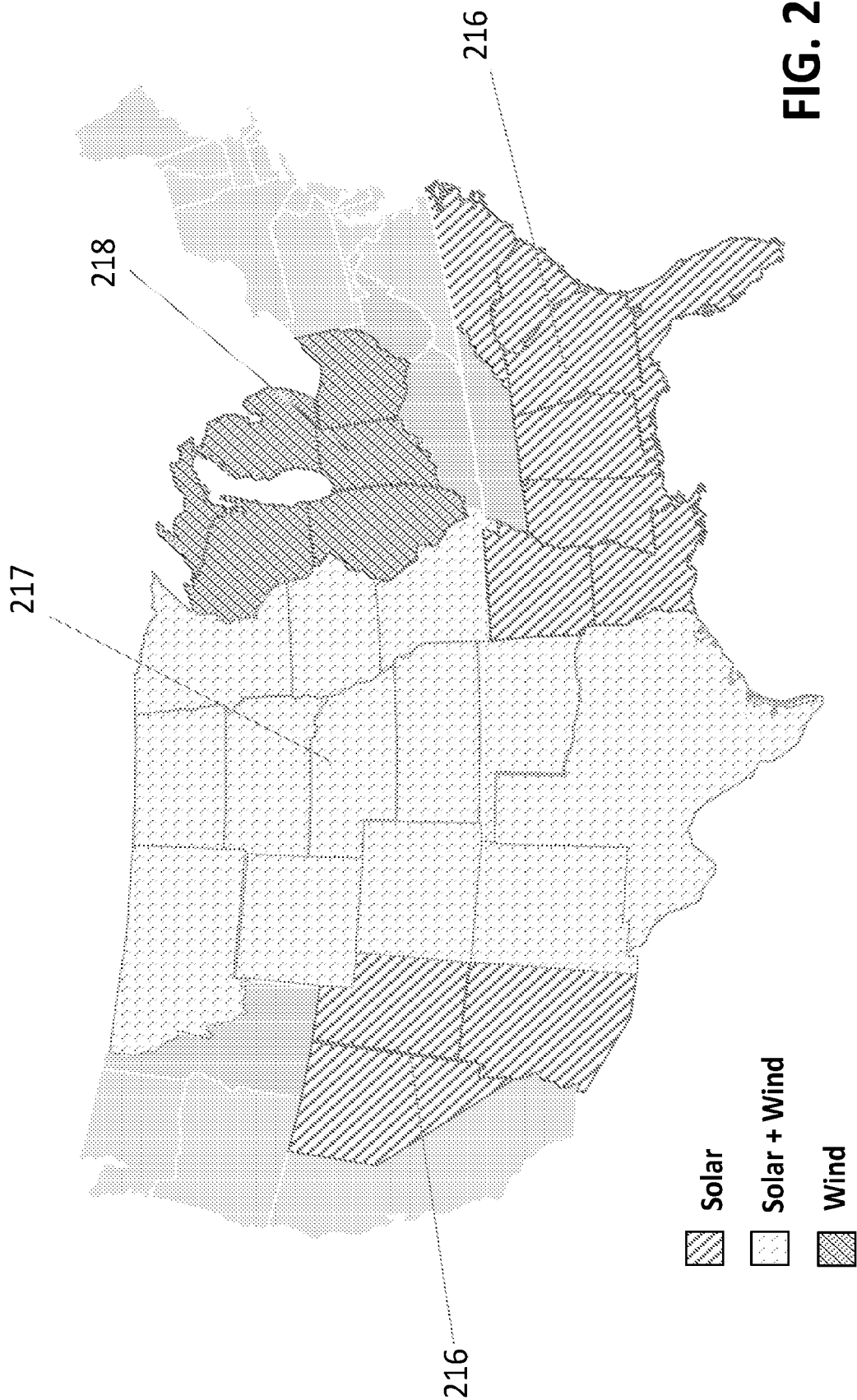
FIG. 2B is a map of the continental United States that illustrates those states that have the resource potential to supply wind energy, solar energy, and both wind and solar energy.
Figure 2C:
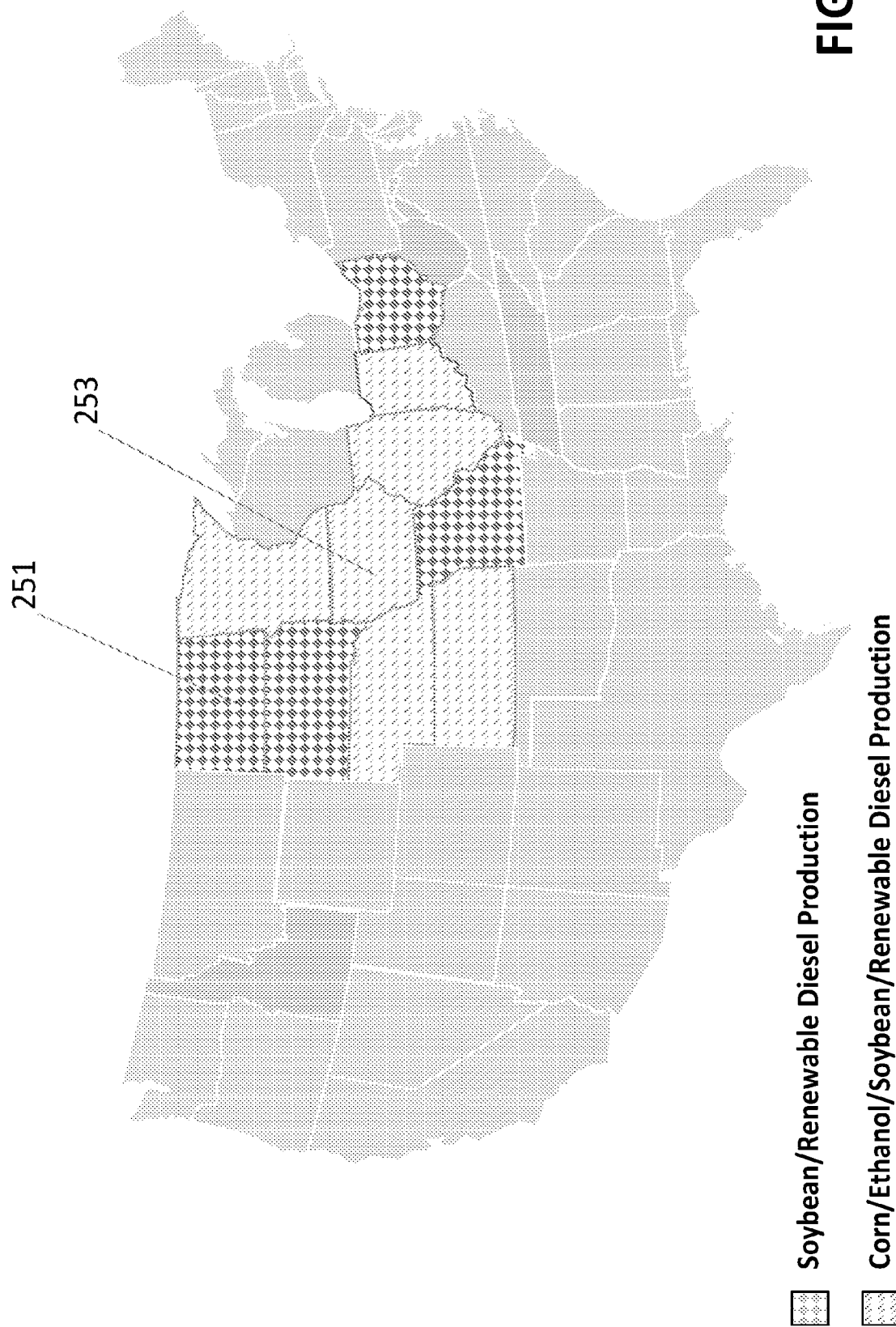
FIG. 2C is a map of the continental United States that illustrates those states that have major soybean and renewable diesel production as well those states that additionally have major corn and ethanol production.

As illustrated in FIG. 2A and FIG. 2B, Applicants recognized that considerable renewable wind power 218, solar power 216, or both 217 is available and currently generated in the central portion 212 of the United States, where there is high potential for supplying such low carbon intensity energy resources. As illustrated in FIG. 2C, Applicants also recognized that the central portion 212 of the United States houses a large number of biomass processing facilities, which produce corn ethanol 253, renewable diesel 251, 253, oil extraction from corn 253, beans 251, 253 and seeds, and renewable natural gas. As used herein, renewable natural gas is natural gas that is derived from the decomposition of organic wastes materials, such as food, animal, and agricultural wastes, garden and lawn clippings, organic materials in landfills, and waste paper, cardboard and wood products. Moreover, conventional hydrocarbon refineries are also present and co-located in the central portion 212 of the United States.

FIG. 2A also shows that the state of California 214 leads the current demand for low carbon fuels with its enacted low-carbon fuel standard (LCFS), which mandates a reduction in the carbon intensity of transportation fuels as compared to conventional petroleum fuels, i.e., gasoline and diesel, in order to reduce greenhouse gas (GHG) emissions. California has defined the carbon intensity (CI) of a fuel as the lifecycle GHG emissions per unit of transportation energy. This carbon intensity parameter is typically expressed in grams of carbon dioxide equivalent per mega Joule (gCO$_2$eq/MJ); however other units of measure may be used, e.g., gCO$_2$eq/bbl oil, with a standard conversion factor being used, e.g., to convert between barrels of oil and the energy value thereof. LCFS credits are assigned to transportation fuels based on their low carbon intensity. A sufficient number of such LCFS credits are then required to be in compliance with the LCFS program each year.

As further shown in FIG. 2A, several other states, predominately in the northwest portion 213 and northeast portion 215 of the United States, may soon enact such LCFS-type legislative mandates or have the potential to experience an increased consumer demand for low carbon fuels. Thus, as shown in FIGS. 2A-2C, and as recognized by Applicants, much of the supply of renewable energy sources must be transported or transmitted from where they are produced in the central portion 212 of United States to the locations where they are desired, i.e., the West Coast and East Coast. The transportation and/or transmission of these low carbon fuel supplies to consumers located remotely therefrom, especially with higher carbon intensity energy, often at least partially offsets the low carbon intensity fuels afforded by the renewable energy sources.

Figure 3A:
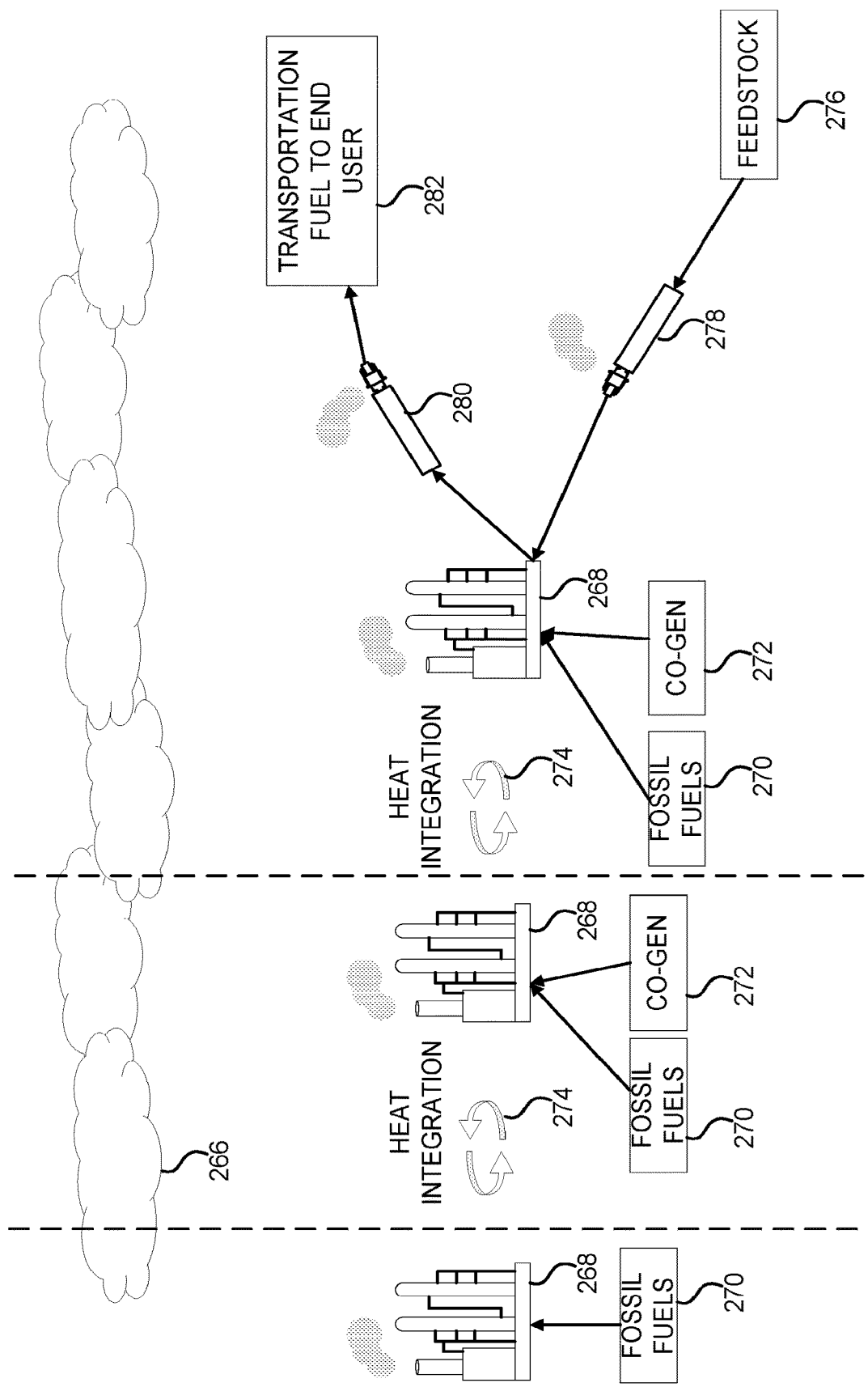
FIG. 3A is a diagram illustrating the progression of efforts to the carbon intensity of providing transportation fuels, which moved from conventional use of fossil fuels shown on the far left, to increased energy efficiency shown in the middle, to one or more embodiments of the present disclosure shown on the far right that reduce carbon intensity from feedstock procurement to transportation fuel delivery to an end user location.

FIG. 3A illustrates the progression of carbon intensity lowering efforts with respect to the production of transportation fuels. As shown on the far left, conventional refineries 268 used fossil fuels 270 with little regard to lowering carbon intensity. As shown in the middle, more recent efforts to increase energy efficiency, and reduce cost, through the use of co-generation 272 of power and steam, the use of heat exchange networks 274 to reduce heating and cooling utility requirements, have resulted in the overall reduction of fossil fuel usage in refining and thus the carbon intensity of the refining process, as well as emissions introduced to the atmosphere 266. As shown on the far right, and as disclosed in one or more embodiment of the present disclosure, a more holistic approach to reducing carbon intensity of transportation fuel production targets not only the refining portion of the process but also targets reductions in feedstock procurement 276, transportation 278 of selected feedstocks to the refinery 268, feedstock and refined product storage, and transportation 280 of refined product transportation fuel to an end user location 282, in essence, the entire lifecycle of providing a transportation fuel to an end user.

Figure 3B:
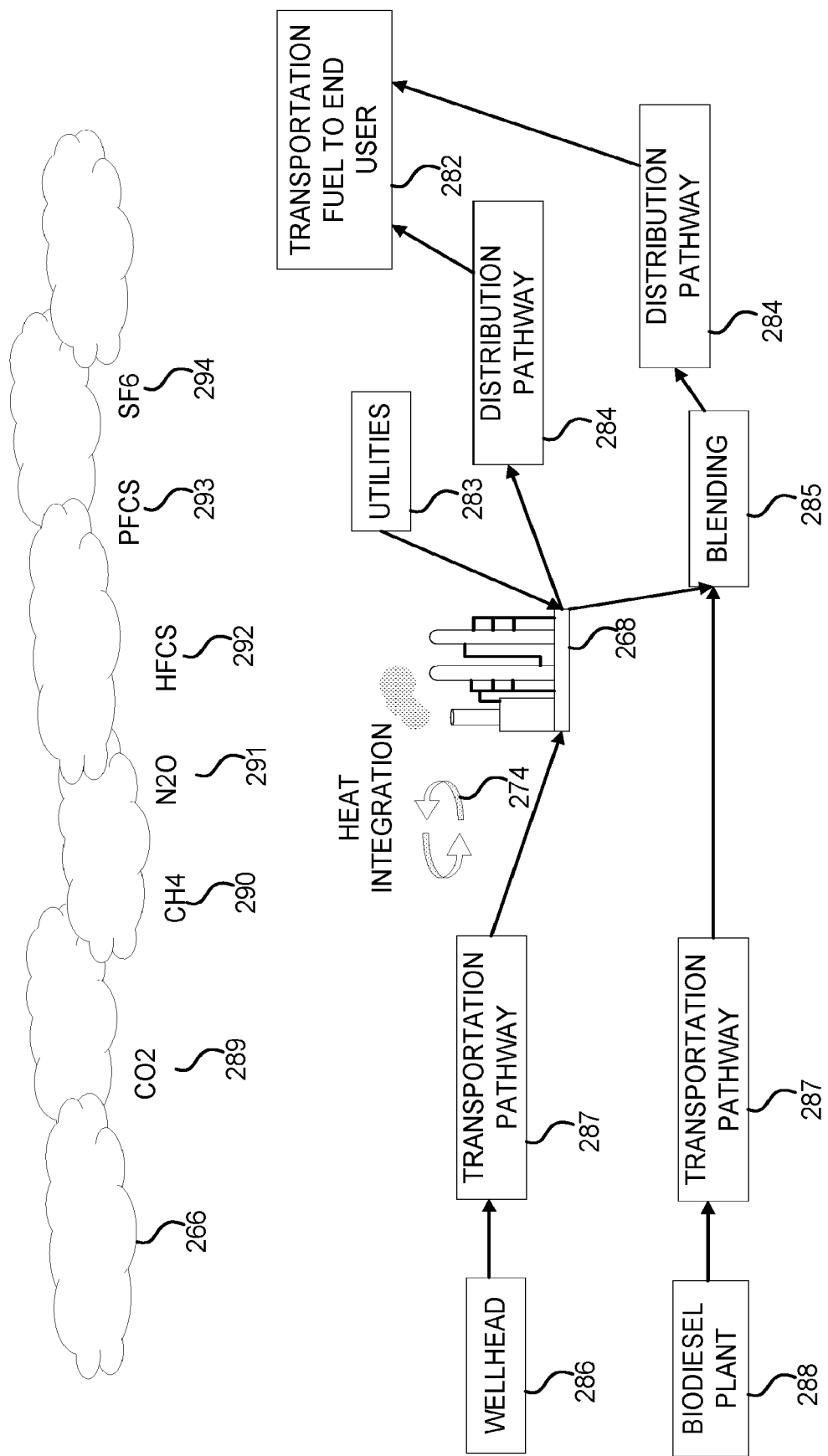
FIG. 3B is a diagram illustrating one or more embodiments that reduce carbon intensity from feedstock procurement to transportation fuel delivery to an end user location.

FIG. 3B illustrates, as noted above and as disclosed in one or more embodiments of the present disclosure, a more holistic approach to reducing carbon intensity, as well as limiting emission of certain chemicals into the atmosphere 266. Chemicals introduced into the atmosphere 266 as a result of a transportation fuel production may include carbon dioxide (CO$_2$) 289, methane (CH$_4$) 290, nitrous oxide (N$_2$O) 291, sulfur hexafluoride (SF$_6$) 294, hydrofluorocarbons (HFCs) 292, perfluorinated compounds (PFCs) 293, and/or other chemicals, as will be understood by those skilled in the art. As a more holistic approach to carbon intensity is sought, the carbon intensity of each process or stage in a transportation fuel production (e.g., indirect and direct processes or stages) may be considered to target carbon intensity reduction. As such, the carbon intensity associated with a wellhead 286 and/or biodiesel plant 288 may be considered for targeted carbon intensity reductions (in other words, an indirect process or stage in relation to the refinery). In other words, carbon intensity reductions may be sought via selections of different wellheads 286, biodiesel plants 288, and/or other feedstock sources. The carbon intensity of feedstock transportation pathways 287 (such as vehicular, rail, marine, or pipeline transportation) may be considered for targeted carbon intensity reductions (in other words, an indirect process or stage in relation to the refinery). Further, the carbon intensity at the refinery 268 may be considered for targeted carbon intensity reductions, such as by heat integration, refinery process unit reduction, and/or capacity increases. Such refinery processes may be considered direct processes or stages in relation to the refinery. The carbon intensity for other processes or stages may be considered for carbon intensity reduction, such as blending processes 285 (e.g., indirect), utilities 283 (e.g., indirect) to operate refinery processes at the refinery 268, and/or fuel product distribution pathways 284 for transportation of a refined product transportation fuel to an end user location 282 (e.g., indirect).

Figure 4:
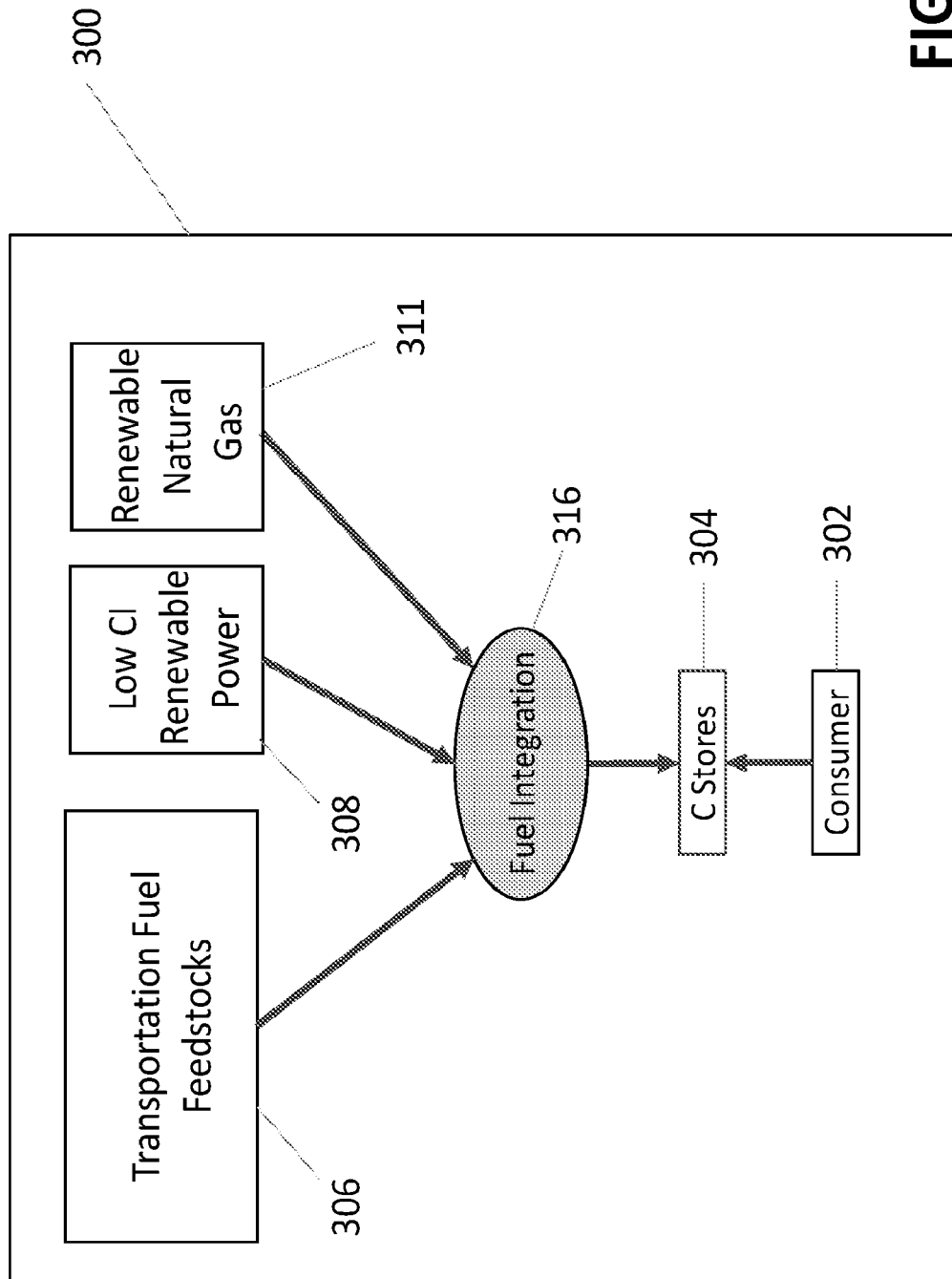
FIG. 4 is a simplified diagram that illustrates a novel implementation of a low carbon intensity energy strategy in which lower carbon energy is introduced and used during the acquisition and refining of higher carbon intensity feedstocks as well as the distribution of the resulting low carbon intensity fuels to the end user, according to one or more embodiment of the disclosure.

FIG. 4 illustrates a novel implementation 300 of a low carbon intensity energy strategy in which lower carbon intensity energy 308, 311 is integrated into the procurement and refining of transportation fuel feedstocks 306 as well as the distribution of resulting product fuels to locations 304 accessible to end users. Such integration of lower carbon intensity energy 308, 311 in the selection, acquisition, and refining of feedstocks and distribution of resulting products lowers the overall carbon intensity of conventional transportation and other refined products made available to the end user and/or consumer 302. Thus, Applicants recognized that a similar low carbon benefit to the direct use of alternative, renewable energy sources by the consumer (see FIG. 1) could be achieved by integrating the use of such low carbon energy in the processing of feedstocks to create conventional refined products that would ultimately by used by the consumer 302 through traditional liquid fuel pathways, e.g., fuels purchased at retail outlets (e.g., locations 304 accessible to end users). As illustrated in FIG. 4, low carbon intensity renewable power 308 is generated at wind farms, solar farms, geothermal power plants/facilities, and/or hydroelectric facilities. Rather than transmitting this electrical power over long distances directly to an end user and/or consumer 302, the renewable power is integrated near its generation into transportation fuel production processes, that may include the acquisition of transportation fuel feedstocks 306 and the processing of those feedstocks into fuel products at conventional refineries and other points of integration 316. Acquisition activities in which renewable electric power may be employed are far ranging and may include the production of crude oils from wells by pumps and other production equipment powered by the renewable electric power. Other acquisition activities may also include use of renewable electric power in electric power vehicles and/or pipeline pumps to transport the produced crude to the refinery 316. Further, renewable electric power may be used in electric power vehicles and/or pipeline pumps to transport the refined transportation fuel products to distribution points or locations 304 accessible by the end user and/or consumer 302.

Rather than being transported directly to consumers by truck and/or pipeline, renewable natural gas produced at waste facilities (e.g., lower carbon intensity energy 311) may also be integrated closer to its production. Similar to renewable electric power, renewable natural gas may be used to acquire transportation fuel feedstocks 306 and process those feedstocks into fuel products at conventional refineries and other points of integration 316. By way of example, and not limitation, such renewable natural gas may be burned in refinery fired heaters or used to generate refinery steam through renewable natural gas-fed boilers. Further, the renewable natural gas may be burned to power pumps for crude oil extraction and used in natural gas powered transportation modes, e.g., truck, rail, barge, etc., to transport feedstocks and/or finished transportation fuels.

Other alternative, low carbon intensity intermediates or intermediaries may be employed and integrated into the processing of transportation fuels and other refined products to lower the overall carbon intensity of the product fuels. For example, biodiesel may be generated from one or more renewable energy sources, e.g., soybeans, for blending into the refined transportation fuel. Such biodiesel generation may occur in close proximity to or co-located with a refinery. In one or more embodiments, such biodiesel may be transported to a blending location by truck, rail or barge that employs a low carbon intensity fuel, such as renewable natural gas, renewable diesel, or renewable electric power. Another alternative, low carbon intensity intermediate may include ethanol that is derived from corn and/or other plant-based materials. The blending location for these alternative, low carbon intensity intermediates may include the refined transportation fuel storage tanks at the refinery or at a downstream storage facility, the transportation mode for the refined transportation fuels, the terminal or rack for the distribution of the refined transportation fuels, or even at the retail outlet. Once at the blending location, the biodiesel, ethanol, or other low CI intermediate may be blended into the refined transportation fuel products to create the final transportation fuel.

As illustrated in FIG. 4, by employing low carbon energy sources to generate conventional liquid transportation fuels, the higher carbon intensity fuel feedstocks, e.g., fossil fuels, are lowered in carbon intensity. These conventional, lower carbon intensity liquid transportation fuels, which are verifiably lower in carbon emissions, are then transported and delivered to distribution points, such as a retail outlet or other locations 304 accessible to end users, for conventional purchase by the consumer 302. Thus, the consumer 302 is not required to purchase or use any special equipment, e.g., an electric or natural gas-powered vehicle, to realize the advantage of low carbon energy sources that may be far removed in distance from the consumer 302, because such low carbon energy sources have been integrated into purchased liquid transportation fuels.

Figure 5:
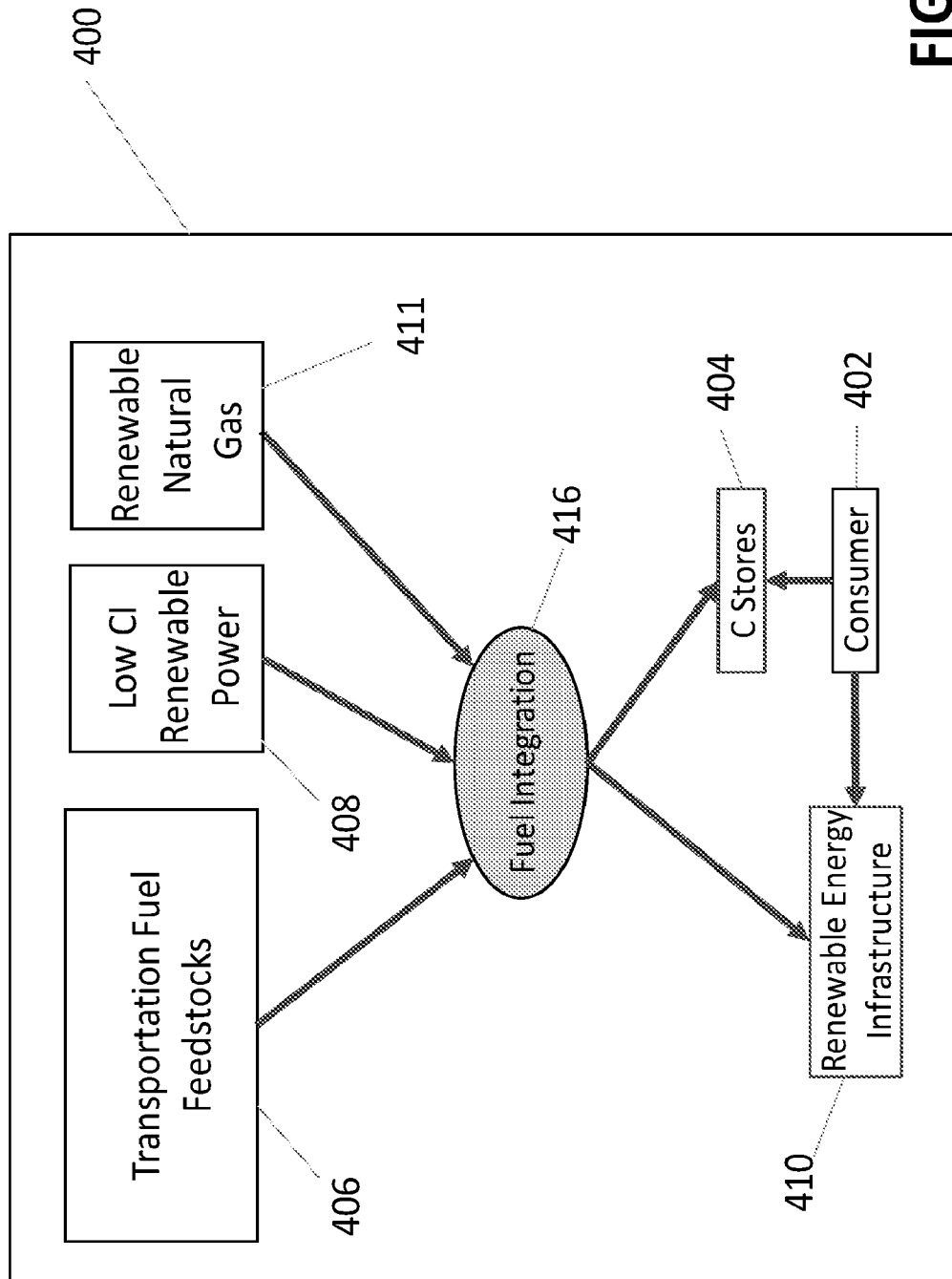
FIG. 5 is a simplified diagram that illustrates a novel implementation of a low carbon intensity energy strategy in which lower carbon energy is introduced and used during the acquisition and refining of higher carbon intensity feedstocks as well as the distribution of the resulting low carbon intensity fuels either directly through retail outlets to the end user or indirectly through the renewable energy infrastructure to the end user, according to one or more embodiments of the disclosure.

FIG. 5 illustrates another novel implementation 400 of a low carbon intensity energy strategy in which lower carbon intensity energy 408, 411 is integrated into the procurement and refining of transportation fuel feedstocks 406, e.g., at conventional refineries and other points of integration 416. Such integration is the same as that illustrated and described with respect to FIG. 4 and is not repeated herein. Similarly, other low carbon intensity intermediates, e.g. naphtha, biomass pyrolysis oil, may be integrated into the processing of conventional transportation fuels and other refined products to lower the overall carbon intensity of the product fuels. However, as shown in FIG. 5, the resulting low carbon intensity transportation fuel products support the existing renewable energy infrastructure 410 and are transported to locations 404 accessible to end users and/or consumers 402. In this way, the existing renewable energy infrastructure 410 also benefits from the use of renewable energy, e.g., wind power, solar power, geothermal power, etc. as well as low carbon intensity feedstock/intermediate selections, e.g., biomass feedstock, naphtha, biomass pyrolysis oil, etc. As example only, low carbon intensity transportation fuels and other refined products provided through this strategy may be used to at least partially construct and provide the renewable energy infrastructure 410, e.g., electric-powered vehicles, natural gas-powered vehicles, dedicated charging/refueling stations, to permit the customer and/or consumer 402 to take advantage of the renewable energy. Further, low carbon intensity fuels obtained from an integrated refinery 416 may be necessary to partially, if not fully, produce renewable energy, such as renewable diesel, low carbon intensity blending fuels (e.g., biodiesel and ethanol), and transport the renewable energy to distribution points accessible by the end user and/or consumer 402. Thus, low carbon intensity transportation fuels produced through the integration of renewable energy and/or low carbon intensity feedstocks may benefit the current range of transportation fuel options from pure renewables supplied directly to the consumer to more conventional—but low carbon intensity—liquid transportation fuels, such as gasoline, diesel and aviation fuels.

Figure 6:
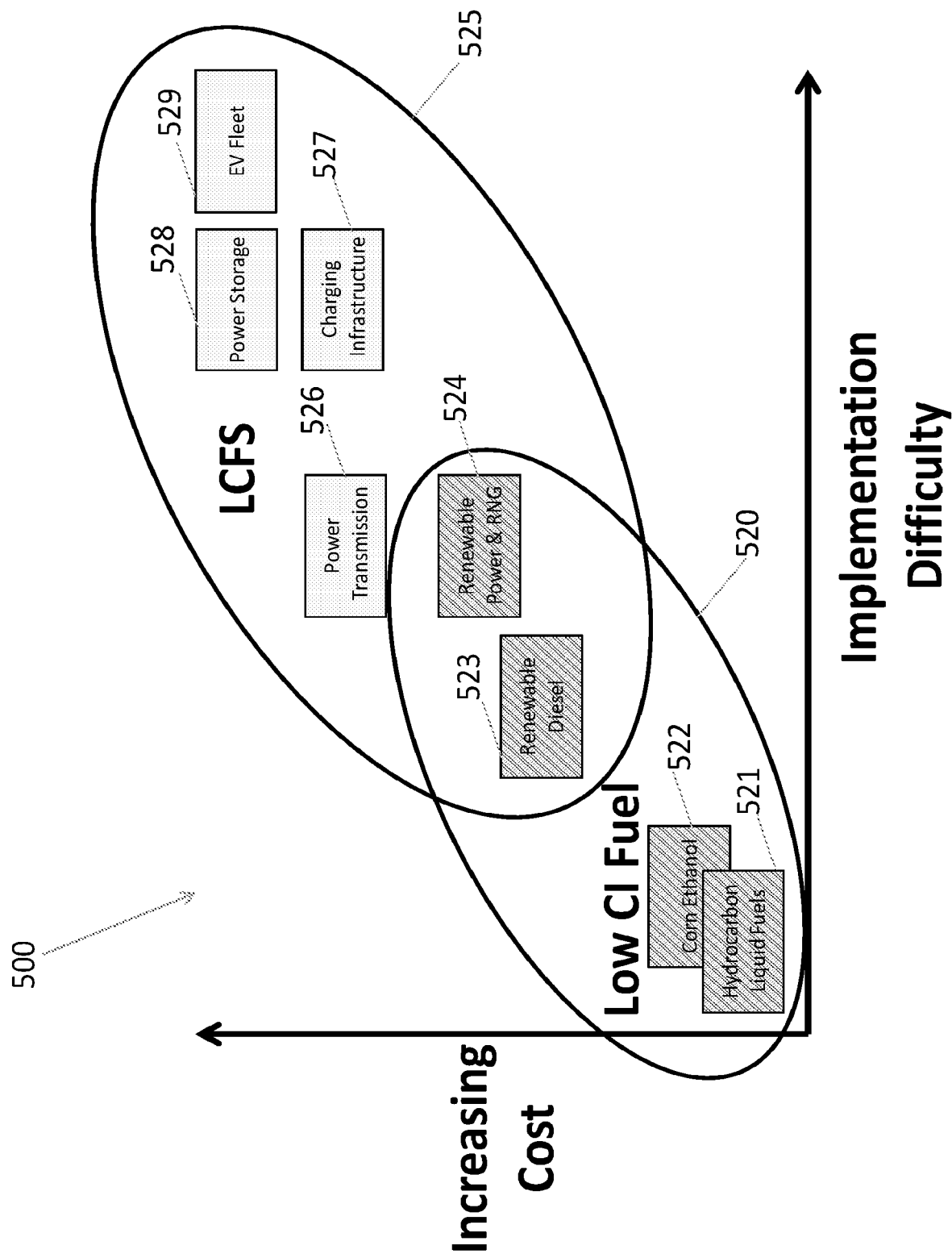
FIG. 6 is a simplified graph illustrating the cost versus difficulty of implementation of various low carbon intensity applications.

One aspect of the novel strategy disclosed herein is that it may be implemented with lower cost, greater ease, and with less risk. An expectation that a majority of consumers could be expected to purchase electric powered or natural gas powered vehicles to take advantage of renewable electric power and/or renewable natural gas has a high implementation risk in the face of cheaper conventional high carbon intensity fuels. Further, the implementation of an independent and dedicated renewable energy infrastructure to service all or even a majority of consumers is difficult at best, and uncertain, especially when distribution points for conventional fuels are ubiquitous. FIG. 6 presents a graph 500 of cost versus implementation risk for various low carbon intensity fuels and LCFS applications. The difficulty or risk of implementation increases from left to right along the x-axis while the cost increases from bottom to top along the y-axis. Overlaying the graph are two ellipses 520, 525, which roughly group the low carbon intensity fuel and the LCFS applications. The low carbon intensity fuels options include, but are not limited to, hydrocarbon liquid fuels 521, corn ethanol 522, renewable diesel 523, renewable power/RNG 524. Of these, low carbon intensity hydrocarbon liquid fuels 521 are the least costly, easiest to implement, and have the lowest risk, because conventional and widespread infrastructure already exists for the use of hydrocarbon liquid fuels. The cost, difficulty/risk of implementation, and risk incrementally increases for each of corn ethanol 522, renewable diesel 523, and renewable power/RNG 524.

In California, where a LCFS program has already been enacted, the LCFS applications provided on FIG. 5 are recognized as directly or indirectly meeting the requirements of the LCFS program. These LCFS applications include, but are not limited to, renewable diesel, renewable power/RNG 524, power transmission 526, charging infrastructure 527, power storage 528, and electric vehicle (EV) fleet 529. As shown, an electric vehicle (EV) fleet 529 represents the costliest, most difficult to implement, and riskiest of all of the low carbon fuel 520 and LCFS 525 options presented. The widespread and/or unconventional infrastructure needed to implement an effective EV fleet is at least partially responsible for its higher cost, difficulty of implementation, and greater risk. The cost, difficulty of implementation, and overall risk incrementally decreases for each of power storage 528, charging infrastructure 527, power transmission 526, renewable power/RNG 524, and renewable diesel 523. As shown on FIG. 5, the low CI fuel ellipse 520 and the LCFS ellipse 525 each overlap such that renewable diesel and renewable power/RNG are commonly grouped in both categories. Renewable diesel and renewable power/RNG both are low carbon intensity fuels and meet the requirements of LCFS as enacted.

FIG. 6 illustrates that applications that have been defined as meeting the requirements of LCFS generally have greater expense and have greater risk or difficulty in implementation than those applications grouped as low carbon intensity fuels. Applicants recognized that the LCFS applications that meet the LCFS program requirements largely depend on renewable electrical power, renewable natural gas, renewable diesel and that the benefits of low carbon intensity energy may be realized without great expense and without great risk or difficulty in implementation through the integration of low carbon energy and feedstocks into the production of low carbon intensity fuels as disclosed in one or more embodiments herein. Thus, conventional higher carbon intensity transportation fuels may be converted to conventional lower carbon intensity transportation fuels with carbon intensities that have been at least partially offset by the lower carbon intensities of these LCFS recognized alternative, renewable energies. Further, such low carbon conventional liquid transportation fuels may be readily purchased from traditional retail outlets, such as convenience stores, without the consumer needing to purchase special vehicles and/or equipment, e.g., an EV fleet 529, charging infrastructure 527, power storage 528, etc., to take advantage of low carbon intensity energy afforded by alternative, renewable energy sources.

Figure 7:
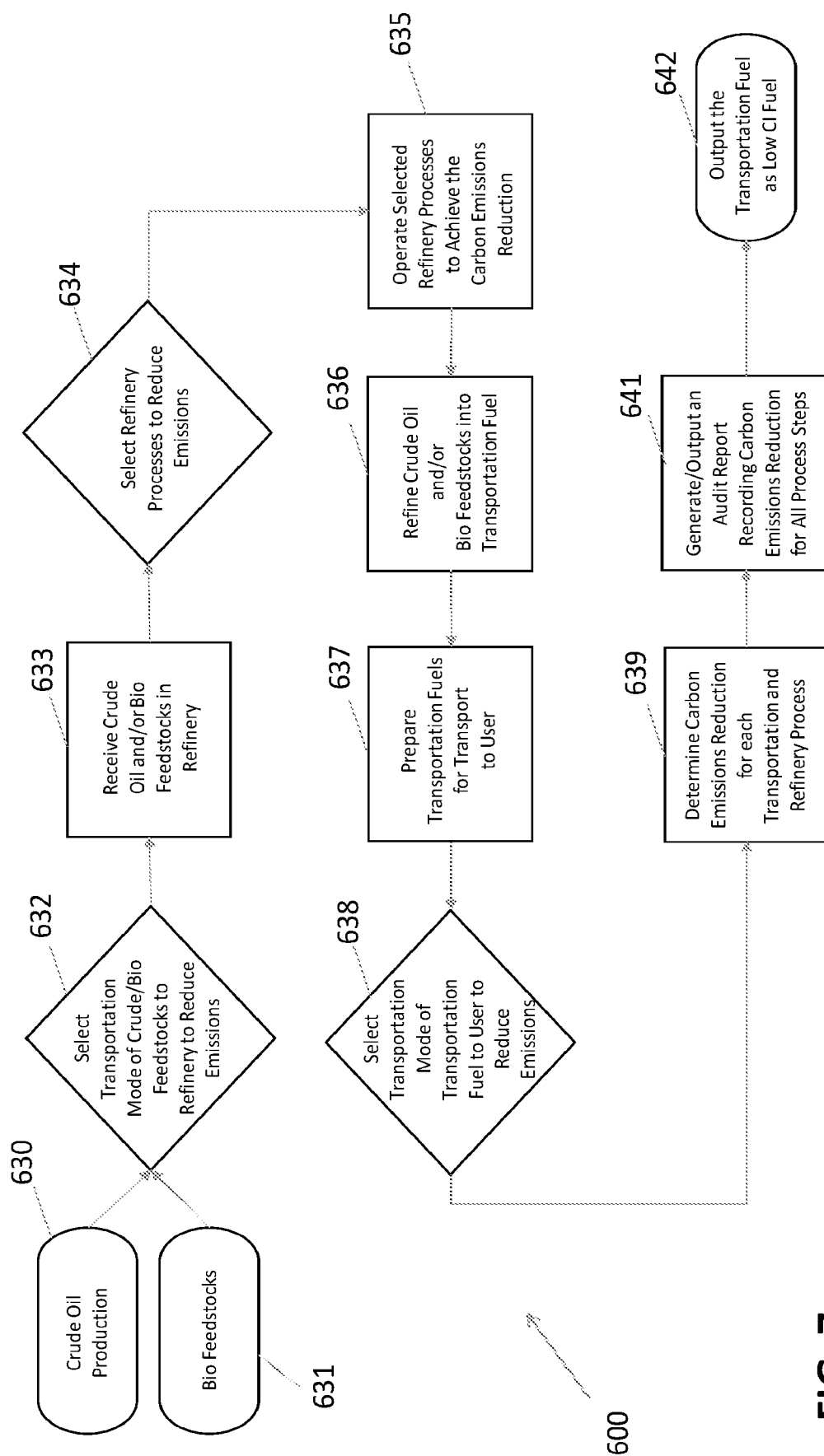
FIG. 7 is a flow diagram of low carbon intensity energy production in which lower carbon energy sources are integrated during the acquisition and refining of higher carbon intensity feedstocks into lower carbon intensity fuels as well as the distribution of the resulting lower carbon intensity fuels to the end user, according to one or more embodiment of the disclosure.

FIG. 7 illustrates one embodiment of a flow diagram 600 for low carbon intensity energy production in which lower carbon energy sources are integrated during the procurement and refining of higher carbon intensity feedstocks into lower carbon intensity fuels along with the transportation of the resulting lower carbon intensity fuels to a location accessible to the end user. As a first step, one or more feedstocks are selected for refining or other processing into conventional liquid transportation fuels. Such feedstocks may be selected from conventional sources, such as crude oils, or from alternative sources, such as soybeans, corn, rendered fats (tallow), etc. The crude oils may further be selected by geographical location, which may be indicative of their physical properties (e.g., light, medium, heavy crude) and thus refining difficulty, or by method of procurement, such as offshore, onshore, tar sand, etc. In one or more embodiments, feedstocks may be chosen in part based on their innate or inherent carbon intensity, which is expressed as grams of carbon dioxide equivalent per mega joule. Because the feedstock-converted-to-transportation fuel will ultimately be combusted to produce transportation energy, carbon dioxide and water, it is desired to start with feedstocks that yield high energy but have low carbon emissions. In other words, desirable feedstocks may include those that have an innate low carbon intensity or low grams of carbon dioxide equivalent evolved per mega joule of energy released as transportation energy. As noted earlier, this inherent carbon intensity of the raw feedstock may be the largest contributor to the overall carbon intensity of the final transportation fuel. For example, a heavy crude oil may have a high inherent carbon intensity such that even without any production or processing emissions, the carbon intensity of the final transportation fuel would be above a pre-selected threshold. In such case, carbon sequestration or some other carbon dioxide removal steps may be needed to offset the added carbon intensity incurred by processing the heavy crude oil. For this reason, the selection of the feedstock often sets the degrees of freedom or ability of the refiner to employ processing steps to permit the refined transportation fuel to satisfy a particular carbon intensity requirement. In one or more embodiments, the carbon intensity of the raw feedstock may be combined with the carbon intensity of procuring the raw feedstock, such that the carbon intensity of the feedstock is the cumulative carbon intensity to take possession of the feedstock at the source. In such case, the carbon intensity of the raw feedstock may be determined separately as known by those skilled in the art, e.g., from the literature, by calculation of stoichiometric combustion, by experiment, etc., such that the carbon intensity of the procurement (i.e., obtaining) itself may be understood apart from the carbon intensity of the feedstock. Alternative methods of procurement of the raw feedstock may then be assessed and selected to reduce the overall carbon intensity of the feedstock available at the source. In one or more embodiments, the inherent or innate carbon intensity of the transportation fuel itself, such as gasoline, diesel, aviation fuel, etc. (rather than the raw feedstock) is determined and the carbon intensities of processing steps to achieve such transportation fuel are either added to or subtracted from the carbon intensity of the fuel.

As shown in FIG. 7, the feedstock may be chosen from one or more of a crude oil 630 or a plant/animal-derived biomass 631. In addition to the innate carbon intensity of the feedstock, the carbon intensity of the processing to ready the feedstock for transport to the refinery or other processing facility should be considered. For example, with respect to crude oil, the production of the crude oil from one subterranean formation may be conducted at a much more energy intensive—and thus higher carbon intensity—manner than from another subterranean formation. In *Know Your Oil*, Gordan et. al. provide representative carbon intensities for various crude oil procurement methods. These carbon intensities range from approximately 450 kilograms of carbon dioxide equivalent per barrel for light crudes (e.g., minimal production effort) to greater than 800 kilograms of carbon dioxide equivalent per barrel for extra heavy crudes (e.g., which may be obtained from tar sands). Gordan et al. also gives carbon intensities for the procurement of crude oils from specific geographical locations. Those skilled in the art will also appreciate that carbon intensities may also be obtained from the literature, e.g., the California Air Resources Board at https://ww2.arb.ca.gov/resources/documents/lcfs-crude-oil-life-cycle-assessment, for the procurement of other crude oils. Thus, the carbon intensity of producing one crude versus another must be accounted for in the overall carbon intensity of using the selected crude oil. Similarly, the energy intensity of producing the biomass for ultimate biofuels must be considered. Whether the biomass is a pure waste product that would be landfilled and thus has no added carbon intensity or is specifically grown at higher carbon intensity (e.g., planting, fertilizing, harvesting, etc.) must be accounted for in the overall carbon intensity of the selected biomass. Those skilled in the art will also appreciate that carbon intensities for biomass and alternative feedstocks may be readily obtained from the literature, e.g., the California Air Resources Board at https://ww2.arb.ca.gov/resources/documents/lcfs-pathway-certified-carbon-intensities, etc.

Once a feedstock is selected, the mode of transportation may be selected at 632 to transport the crude oil 630 or biomass 631 to the refinery or other processing facility. Selection of a transportation mode 632 is dependent on several considerations. First, the distance between the source of the feedstock and the refinery or other processing facility will contribute to the overall carbon intensity of transporting the feedstock. For example, a Middle East crude will contribute a higher carbon intensity than a locally sourced crude on the basis of transportation distance alone. Second, the mode of transportation will also contribute to the overall carbon intensity of transporting the feedstock. For example, the amount of carbon intensity contributed to the overall carbon intensity of the fuel as a result of feedstock transportation will depend on whether the feedstock is transported by truck, rail, pipeline, ship/barge or other transportation model. An additional consideration and variable to be used in determining the carbon intensity of the particular mode of transportation to be used to transport the feedstock is the carbon intensity of the transportation fuel used in such transport. For example, a renewable diesel contributes a much lower carbon intensity to the overall carbon intensity of the transportation mode at 632 than would a conventional higher carbon intensity transportation fuel, such as diesel or gasoline. In one or more embodiments, the feedstock may be transported by truck, barge/ship, and/or rail (i.e., railroad) powered at least in part by one or more of renewable diesel, a renewable energy source (e.g., electric power generated by wind energy, solar energy, geothermal power plants/facilities, and/or a hydroelectric dam/generator), or a low carbon intensity transportation fuel. In one or more embodiments, the feedstock may alternatively, or in addition, be transported by pipeline using pumps that are powered at least in part by one or more of renewable diesel, a renewable power source (e.g., electric power generated by wind energy, solar energy, geothermal power plants/facilities, and/or a hydroelectric dam/generator), or a low carbon intensity transportation fuel. Thus, distance, mode, and mode fuel are variables that may be selected to minimize the carbon intensity attributed to the overall carbon intensity of the transportation fuel product as a result of transporting feedstock to the refinery or other processing facility.

As illustrated in FIG. 7, the feedstock is received at the refinery and/or processing facility at 633. The feedstock may need to be stored on-site for a period of time until it is refined or processed. Such storage is represented by block 633 and may include large tanks for the storage of crude oil, pyrolysis oil, naphtha, etc. and/or buildings for the storage of soybeans, tallow, corn, etc. The storage of crude oil and liquid hydrocarbons may cause volatile organic compound (VOC) emissions through working losses, breathing losses, and flashing losses. Working losses may occur as vapor is displaced from a tank or other storage vessel when the crude or other liquid hydrocarbon moves into a space, e.g., tank filling. Breathing losses are emissions resulting from changes in temperature and/or pressure over time. Flashing losses occur when a crude or other liquid hydrocarbon undergoes a pressure drop such that VOCs dissolved therein are flashed or released as gaseous emissions. These working losses, breathing losses, and flashing losses should be accounted for during hydrocarbon storage, because they contribute to the overall carbon intensity of converting feedstocks into transportation fuels as greenhouse gas emissions. Storage of crude oil and other volatile hydrocarbons should be controlled to minimize GHG emissions that contribute to the over carbon intensity of the feedstock to transportation fuel conversion.

After the feedstocks are received in the refinery or other processing facility at 633, the feedstocks are refined or otherwise processed into transportation fuels. However, certain refining processes may also be selected at 634 in conjunction with refining to minimize the carbon intensity of converting the feedstocks into transportation fuels and other refined products. As way of example and not limitation, the refining processes that may be selected to reduce carbon emissions during refinery operations include: powering at least a portion of refinery equipment (e.g., the refinery equipment including hydrotreaters, distillation towers, vacuum towers, crackers, reformers, and/or any other equipment utilized at a refinery) with electricity generated by a renewable source (e.g., wind, solar, hydroelectric, geothermal etc.), burning renewable natural gas in refinery fired heaters, generating refinery steam through renewable natural gas-fed boilers, generating electricity at or proximate the refinery through the letdown of high pressure steam across a power turbine, increasing heat integration across refinery processing units through a heat exchanger network, and/or reducing by one, two, three, or more the number of refinery processing units that refine the refinery feedstock (e.g., a refinery processing unit defined by groups or sections of refinery equipment utilized to refine the refinery feedstock). These refinery operations represent steps in the conversion process where low carbon intensity energy, such as renewable electric power, renewable natural gas, and/or renewable diesel, may be integrated to lower the overall carbon intensity of the resulting transportation fuel. Reducing the number of refining processing units that refine the refinery feedstock recognizes that a lower carbon intensity for the final transportation fuel may generally be obtained through reduced processing. One, two, three, four, or more of these refinery operation may be selected to achieve targeted reductions in carbon intensity through the refining and processing of feedstocks into transportations fuels, such as gasoline, diesel, and aviation fuel. While significant energy usage is required to convert feedstocks such as crude oil and/or biomass into transportation fuels, there are several refinery operations that may be employed to reduce this energy usage by at least a fraction. This then reduces the amount of high carbon intensity fossil fuels that must be combusted to supply such energy and thus lowers the carbon dioxide (and other greenhouse gas) emissions and carbon intensity of transforming feedstock to refined transportation fuel.

The selected refinery processes 635 are operated in conjunction with refining the crude oil and/or processing the biomass 636 (e.g., soybeans, corn, tallow, pyrolysis oil, etc.) to reduce the overall carbon intensity of the refining process. The refined and/or blended products may need to be stored on-site at the refinery for a period of time until transported. Such storage is represented by block 637 and may include a plurality of tanks for the storage of gasoline, diesel, aviation fuel and other transportation fuels. As with crude oil, such storage may cause volatile organic compound (VOC) emissions through working losses, breathing losses, and flashing losses. These working losses, breathing losses, and flashing losses should be accounted for and minimized during refined fuel storage 637, because they contribute to the overall carbon intensity of converting feedstocks into transportation fuels as greenhouse gas emissions.

After the transportation fuel is refined, the mode of transportation may be selected at 638 to transport the refined transportation fuel products to a location accessible to the end user, such as a retail outlet, convenience store, etc. Again, selection of a transportation mode 638 is dependent on several considerations. The distance between the refinery or other processing facility and the distribution location to the end user will contribute to the overall carbon intensity of transporting the finished transportation fuel. Second, the mode of transportation—by truck, rail, pipeline, ship/barge, or a combination thereof—will also contribute to the overall carbon intensity of transporting the finished transportation fuel. Further, the transportation fuel used in such transport is an additional variable that must be managed to minimize added carbon intensity from whatever mode of transportation is selected. For example, a renewable diesel contributes a much lower carbon intensity to the overall carbon intensity of the transportation mode at 638 than would a conventional higher carbon intensity transportation fuel, such as diesel or gasoline. In one or more embodiments, one or more of the plurality of refined products may be transported by truck, barge/ship, and/or rail (i.e., railroad) powered at least in part by one or more of renewable diesel, a renewable energy source (e.g., electric power generated by wind energy, solar energy, geothermal power plants/facilities, and/or a hydroelectric dam/generator), or a low carbon intensity transportation fuel. In one or more embodiments, one or more of the plurality of refined products may alternatively, or in addition, be transported by pipeline using pumps that are powered at least in part by one or more of renewable diesel, a renewable power source (e.g., electric power generated by wind energy, solar energy, geothermal power plants/facilities, and/or a hydroelectric dam/generator), or a low carbon intensity transportation fuel. Thus, distance, mode, and mode fuel are variables that may be selected to minimize the carbon intensity attributed to the overall carbon intensity of the transportation fuel product as a result of transporting finished transportation fuel products from the refinery or other processing facility to one or more distribution locations accessible to the end user/consumer.

In block 639, the carbon intensity of the transportation fuel is calculated as a function of one or more of: the carbon emissions per unit energy associated with procuring the selected refinery feedstock at the source (e.g., this may be the combined carbon intensity of the raw feedstock and the procurement thereof), the carbon emissions per unit energy associated with transporting the selected refinery feedstock from the source to the refinery, the carbon emissions per unit energy associated with storing the selected refinery feedstock, the carbon emissions per unit energy associated with refining the refinery feedstock into one or more of a plurality of refined products (e.g., gasoline, diesel, aviation fuel, etc.), the carbon emissions per unit energy reduction(s) associated with optionally operating two or more of the selected refinery processes (i.e., to reduce carbon emissions and thus carbon intensity), the carbon emissions per unit energy associated with storing one or more of the refined products as transportation fuel, the carbon emissions associated with transporting one or more of the refined products to a distribution location accessible to the user. In one or more embodiments, the carbon emissions per unit energy (or carbon intensity) of the feedstock is a variable of the function that is determined apart from the carbon emissions per unit energy (or carbon intensity) of the procurement (i.e., obtaining) of the feedstock, such that different procurement steps may be selected for a given feedstock. The carbon intensity of the transportation fuel may be further increased (or decreased) by additional processing and blending steps, as discussed infra, including, but not limited to, the carbon intensity associated with the production and blending of biodiesel and/or ethanol into the final transportation fuel. The total carbon emissions per unit energy or carbon intensity is the sum of the carbon emissions per unit energy for each step of the process from feedstock to final transportation fuel (including any blending) delivered to the distribution location. The carbon intensity associated with each of the above-described steps, e.g., from transportation of feedstock, to refining of the feedstock, to the distribution of the transportation fuel to the retail outlet, etc., may be individually determined as known by those skilled in the art, e.g., from the literature, by calculation of stoichiometric combustion and/or emissions release for each step, by experimentation, etc., such that the carbon intensity of the variations and/or options for each step may be compared and considered.

As will be understood by those skilled in the art, the carbon intensity of the transportation fuel is based on the yield of the transportation fuel from the feedstock. For example, if a feedstock yields 30% gasoline and 70% other refined products, then 30% of the carbon intensity associated with procuring, transporting, and refining the feedstock as a whole is attributed to the carbon intensity of the gasoline transportation fuel. If the CI of the feedstock and the associated CIs of the processing steps of the feedstock are known, then the CI attributable to the refined transportation fuel, such as gasoline, is the product of the summed CIs (of the feedstock and the processing steps) and the yield of the refined transportation fuel. In one or more embodiments, the carbon intensity of those processing steps involving only the refined fuel, e.g., distribution, storage emissions, etc., may be determined and considered in the total CI without respect to yield since only the refined fuel product is involved in those steps. Alternatively, the carbon intensity of those processing steps involving only the refined fuel may be determined as a function of the feedstock such that the CI attributable to the refined transportation fuel for these steps is the product of the feedstock carbon intensity and the yield of the refined transportation fuel. In one or more embodiments, the yield of the refined product (for a particular feedstock) and/or the CI of the feedstock may be adjusted to account for the emissions associated with or volume of emissions associated with one or more non-transportation fuel products that are refined from the common feedstock. Thus, knowing the yield of the refined product (i.e., the one or more transportation fuels) from the selected feedstock, those skilled in the art will appreciate that the carbon intensity of the transportation fuel may be reduced or minimized from the point of view of reducing carbon emissions per unit energy of the feedstock and/or the point of view of reducing carbon emissions per unit energy of the refined product as the transportation fuel. Regardless of how the threshold is pre-selected—by regulation, by end user/customer demand, or by marketing strategy—the total carbon emissions per unit energy or carbon intensity of the transportation fuel is determined and verified to be below the total carbon intensity threshold.

A record of at least the total carbon intensity is maintained at block 641 for each particular volume of finished transportation fuel provided to the end user, e.g., at an accessible distribution point. The record details the determined total carbon emissions per unit energy for providing the final transportation fuel to the distribution location accessible to the end user. The record may also contain the carbon emission per unit energy for each step in the entire process of converting feedstock into finished transportation fuel for verification and auditing purposes.

Finally, the quantity of finished transportation fuel, e.g., gasoline, diesel, aviation fuel, etc. is outputted at block 642 though the distribution mode or transport pathway as selected at 638 as a verifiable, low carbon intensity transportation fuel. This transportation fuel may be transported and delivered to a distribution location, e.g., a retail outlet, convenience store, etc., that is accessible to the end user.

Figure 8:
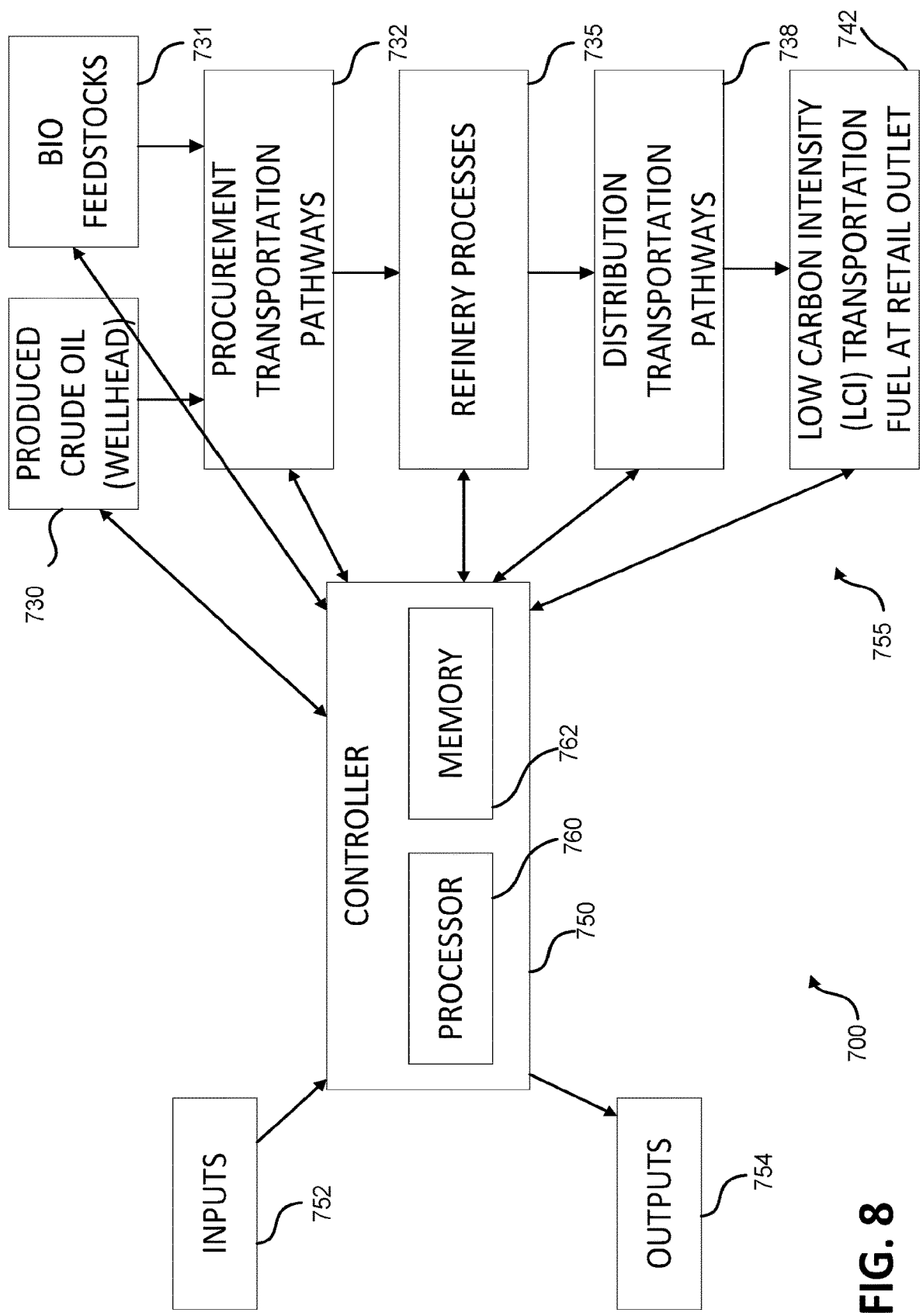
FIG. 8 is a simplified diagram illustrating a control system for managing the low carbon intensity energy production according to the shown flow chart.

FIG. 8 illustrates an embodiment of a control system 700 for managing low carbon intensity energy production, as represented by the flow diagram 755. The controller 750 of system 700, which includes a processor 760 and memory 762, uses certain inputs 752 and provides certain outputs 754 relative to the low carbon intensity energy production. These inputs 752 may include, but are not limited to, raw energy data regarding each production step, the carbon intensity of standard refinery processing steps, the definition of a low carbon intensity fuel in total grams of carbon dioxide equivalent per mega joule, algorithms for calculating carbon emissions for various process steps, yields of refined products based on the feedstock(s), and/or carbon emissions for process steps not determined by the controller 750.

Responsive to these inputs 752, controller 750 may perform several functions. In one or more embodiments, the controller 750 may receive raw process data from which the carbon emissions for each production step may be determined, and then determines the carbon emissions associated with that production step on a grams of carbon dioxide equivalent per mega joule basis. The controller 750 may also select one or more transportation and/or refinery processes to achieve a desired reduction in carbon emissions. For example, the controller 750 may select one or more transportation pathways to the exclusion of other viable transportation pathways in order to reduce the grams of carbon dioxide equivalent per mega joule for the material transported. The controller 750 may similarly select one or more refinery processes to achieve reductions in carbon emissions. These refinery processing reductions in carbon emissions may be as much as about 5%, about 10%, about 15%, about 20%, about 25%, or more as compared to standard refinery processing steps. In at least one embodiment, the controller 750 may verify the carbon emissions for each selected production step and generate an audit record with the total carbon intensity, e.g., grams of carbon dioxide equivalent per mega joule, for all production steps from feedstock being acquired from its source to the finished transportation fuels delivered to their distribution locations, i.e., from crude at the wellhead to gasoline/diesel/aviation fuel delivered to the end user.

Outputs 754 from the controller 750 may be displayed through a graphical user interface positioned at the refinery and/or at remote locations, such as at feedstock sources, transportation hubs, etc. These outputs 754 may include, but are not limited to, the selection and control of transportation and/or refinery processes, the determined carbon emissions (or emissions volume) for each possible production step, the verified carbon emissions for each selected production step, and/or an audit record detailing the total carbon intensity, e.g., grams of carbon dioxide equivalent per mega joule, for the complete production of distributed transportation fuel from selected feedstocks. In one or more embodiments, the audit record may list the carbon emissions for each production step so the total carbon intensity for the complete production of the transportation fuel may be verified. In one or more embodiments, controller 750 sends signals to process equipment, e.g. pumps, boiler, furnaces, etc. at the refinery or processing facility to implement the controller-determined strategy to achieve a low carbon transportation fuel production. In one or more embodiments, the controller 750 may send signals to acquire certain feedstocks, to transport one or more feedstocks, to store the one or more feedstocks, to store refined/processed products, and to transport one or more of those products to distribution locations.

FIG. 8 provides flow diagram 755 summarizing the flow diagram 600 of FIG. 7. As described herein, several production step variables account for low carbon intensity energy production. As shown, the feedstock may be selected from one or more crude oils at 730 and/or plant/animal-based feedstocks at 731, each at various locations relative to the refinery or processing facility. The feedstocks may be selected, at least in part, on the basis of their innate carbon intensity when combusted, as measured by grams of carbon dioxide equivalent per mega joule. Alternatively, and in addition, the feedstocks may be selected on the basis of the carbon intensity associated with their procurement or acquisition at the source. The selection of one or more procurement transportation modes 732 to transport such feedstock to the refinery or processing facilities increases the carbon emissions associated with the selected feedstock. These carbon emissions may be reduced by selecting lower carbon emission options from one or more of trucks, rail, pipeline or ship/barge, depending on the availability of such transportation modes and the distance to be transported. Other transportation mode variables include the type of transportation fuel used, e.g., a high carbon intensity fuel versus a renewable, low carbon intensity fuel. For example, renewable diesel may be used in trucks, trains, and ships/barges. However, renewable diesel and/or renewable electrical power may be used to operate pipeline pumps.

At the refinery or feedstock processing facility, refining and/or processing steps 735 are conducted to transform the feedstocks into liquid transportation fuels, such as gasoline, diesel, and/or aviation fuel. As will be appreciated by those skilled in the art, the feedstocks are refined into several other transportation fuels (liquefied natural gas, propane, butane, etc.) and non-transportation fuels (petrochemicals, asphalts, etc.). Each of these refined products may have its total carbon intensity reduced by the processes and systems disclosed herein. With respect to the refining of transportation fuels, the choice of refining and/or processing steps is largely dependent, however, on the properties and quantities of both the selected feedstocks and the desired transportation fuels. Thus, while the refining and/or processing steps are themselves variables, they also depend at least in part on other variables. Each of the refining and/or processing steps for a particular feedstock or intermediate has associated carbon emissions that increase the carbon intensity of its product, as measured in grams of carbon dioxide equivalent per mega joule. Responsive to input data, controller 750 determines the carbon intensity added for each refining and/or processing step, which is dependent on other variables, e.g., feedstock selection, desired product slate and properties.

The refining and/or processing steps 735 may have at least some of their carbon emissions offset such that their products have a lower carbon intensity than without the offset. For example, refinery and other processes that are driven by low carbon energy sources, such as renewables, may offset the higher carbon emissions of standard refining and/or processing steps. These offsetting processes may include one or more of: producing electrical power for the benefit of the refinery through renewable sources such as wind, solar, geothermal, and hydroelectric, employing renewable fuels such as renewable diesel and renewable natural gas in refinery boilers and fired heaters, increasing high pressure steam production at the refinery with strategic letdown, e.g., over a steam turbine, to provide steam at the desired pressure and added electrical power, applying heat integration techniques over a plurality of refinery processing units to minimize utility requirements, reducing by at least one or more the number of refinery processing units that refine the refinery feedstock, using low carbon intensity fuels for heat generation in the refinery, etc.

One or more distribution transportation modes 738 must also be selected to transport the final transportation fuel to a distribution location accessible to the end user. As with the transport of feedstocks, the transport of refined products increases the carbon emissions associated with the transportation fuel provided to the end user. These carbon emissions may be reduced by selecting lower carbon emission options from one or more of trucks, rail, pipeline or ship/barge, depending on the availability of such transportation modes and the distance to be transported. The type of transportation fuel used, e.g., a high carbon intensity fuel versus a renewable, low carbon intensity fuel, is another variable for each transportation mode that may be selected to reduce the carbon emissions associated with this production step. Finally, the liquid transportation fuel is made available to the end user at one or more distribution locations 742, such as retail outlets, convenience stores, etc. There, the liquid transportation fuel resides in a tank, e.g., an underground storage tank, until purchased by the consumer. The consumer then combusts the liquid transportation fuel, e.g., in an engine, which in many cases releases the majority of the carbon emissions associated with the transportation production lifecycle—from raw feedstock to finished low carbon emissions transportation fuel.

Figure 9:
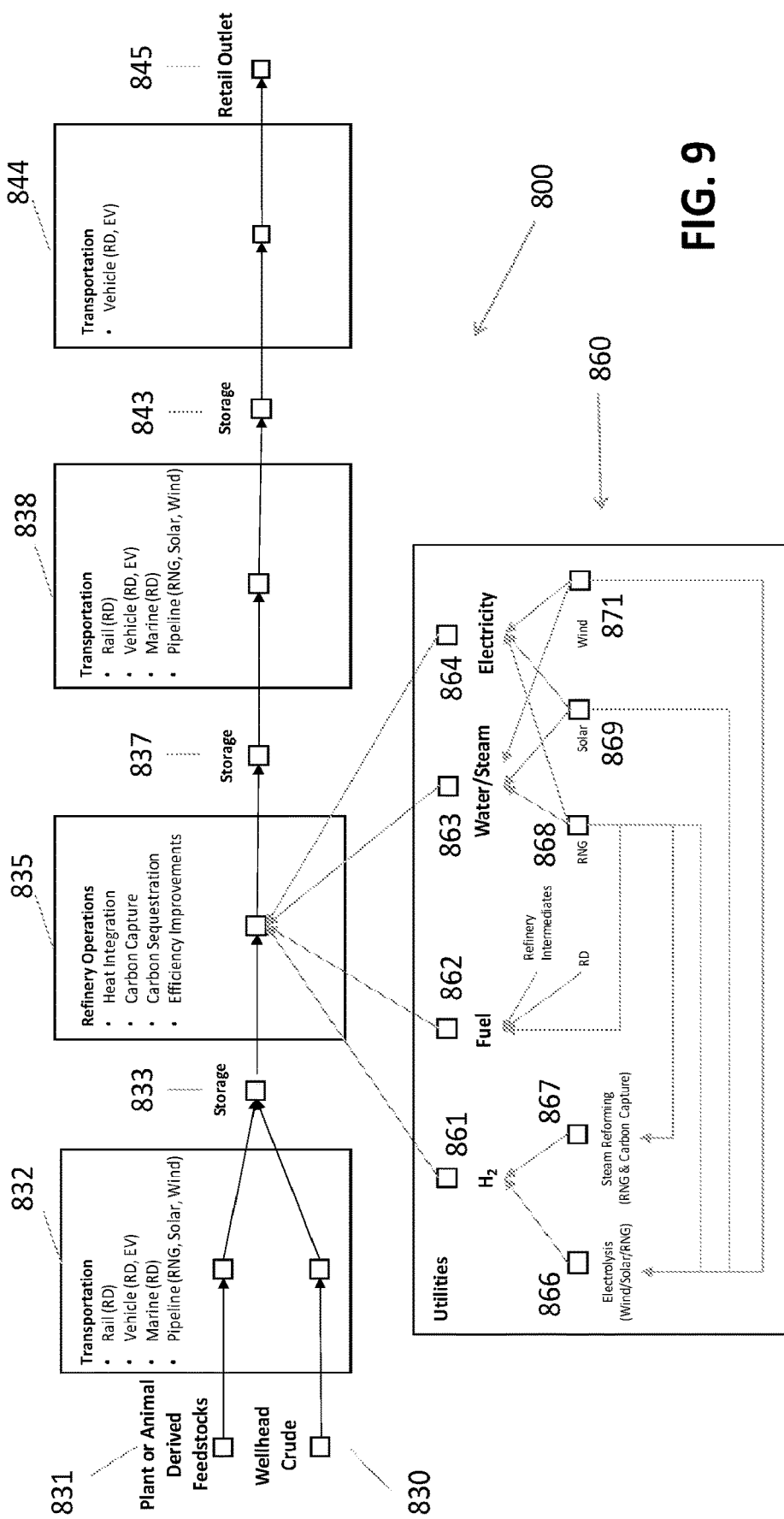
FIG. 9 is a nodal diagram illustrating the interconnectivity of lower carbon energy sources at various nodes during the acquisition and refining of higher carbon intensity feedstocks into lower carbon intensity fuels as well as the distribution of the resulting lower carbon intensity fuels to the end user, according to one or more embodiment of the disclosure.

FIG. 9 is a nodal diagram illustrating the interconnectivity of lower carbon energy sources at various nodes during the acquisition of higher carbon intensity feedstocks, the refining of those feedstocks into lower carbon intensity fuels, and the distribution of the lower carbon intensity fuels to a retail outlet for purchase by the end user. The flow diagram 800 is similar to the flow diagrams of FIG. 6 and FIG. 7. Selected crude 830 and/or plant/animal-based feedstocks 831 are transported via various transportation modes 832, which may include one or more of truck, rail, marine or pipeline transport. The transport mode may be selected to further limit carbon emissions by employing low carbon intensity fuels, such as renewable diesel, renewable natural gas, petroleum natural gas, etc. In one or more embodiments, the transported feed stocks are stored in tanks or facilities 833. The manner and length of time of such storage may be selected so as to decrease the carbon emissions resulting from storage.

The stored feedstocks are then refined and/or processed 835 (e.g., at a refinery, bioprocessing facility, etc.) through conventional processing steps, each of which increases (or in some situations decreases) the carbon emissions attributable to the refined/processed materials. However, as described previously, certain refinery processes may be employed to decrease the carbon emissions with respect to conventional processing steps. The most numerous of these carbon intensity reducing processing steps are associated with the utility infrastructure 860. In addition to the feedstock, refineries and/or biomass processing facilities largely depend on various utilities, including electrical power 864, fuel 862 (e.g., natural gas, diesel, refined intermediates), water/steam 863, and hydrogen 861, to operate. As shown in FIG. 8, there are several options for providing these required utilities with lower carbon intensity than they may otherwise normally be supplied. For example, electrical power 864 may be supplied by wind turbines 871, solar arrays 896, and/or renewable natural gas 868. Similarly, the pumping and treatment of water and the generation of steam may employ energy obtained from wind turbines 871, solar arrays 896, renewable natural gas 868, and/or geothermal power plants/facilities. Renewable natural gas may also be used along with one or more of renewable diesel and/or refinery intermediates as fuels for boilers and fired heaters. Hydrogen generation may be accomplished at lower carbon intensity through water electrolysis 866 and steam reforming 867. The electrolysis 866 may be powered by electricity generated from wind turbines, solar arrays, geothermal power plants/facilities, RNG-fired turbines, and/or RNG-produced steam letdown. The steam reforming may use renewable natural gas and may further include carbon capture/sequestration for further reductions in carbon emissions. Carbon capture/sequestration may also be used anywhere in the refinery and/or processing facility that hydrocarbon fuels are combusted to carbon dioxide and the carbon dioxide is released to atmosphere as a by-product. Sequestering carbon dioxide that otherwise would go to atmosphere may have a carbon emissions neutral effect or even subtract from the carbon intensity of the fuel product associated with the carbon sequestration. As further shown in FIG. 9, block 835 may include heat integration and efficiency improvements as additional techniques to reduce the carbon emissions attributable to converting feedstocks into transportation fuels.

In one or more embodiments, the refined products are stored in tanks or facilities 837 prior to transport. The manner and length of time of such storage may be selected so as to decrease the carbon emissions resulting from storage. After storage, the refined products are transported via various transportation modes 838 to distribution or storage depot 843 proximate the final distribution location 845, such as a retail outlet. The manner and length of time of such storage may be selected so as to decrease the carbon emissions resulting from storage. In one or more embodiments, the refined products are transported directly to the final distribution location without intermediate storage 843. As with the feedstock transportation 832, the transportation modes 838 for refined products may include one or more of truck, rail, marine or pipeline transport. The transport mode may be selected to further limit carbon emissions by employing low carbon intensity fuels, such as renewable diesel, renewable natural gas, regular natural gas, etc. Transportation fuels stored at distribution or storage depots 843 may then be transported the final mile to retail outlets, convenience stores, and other final distribution locations accessible to the end user consumer.

Downstream of the refining/processing step 835, biomass-derived intermediates or fuels, such as corn-derived ethanol, biodiesel, etc., may be blended at, e.g., storage 837, in the transportation mode 838 (e.g. in barge, truck, railcar or pipeline), in storage 843 (e.g. terminal/rack), in the transportation mode 844, or even at the retail outlet 845 to create a final transportation fuel formulation. For example, corn-derived ethanol may be processed from corn biomass feedstock at a facility for blending into gasoline. Such use of lower carbon intermediates, additives, and blending agents lowers the overall carbon intensity of the resulting transportation fuel when the total grams of carbon dioxide equivalent per mega joule is measured for the overall process of providing low carbon intensity transportation fuels to the end user. Such blending, and its possible carbon intensity lowering effect, should be considered in the determination of the overall carbon intensity for providing the final transportation fuel to the end user location 845.

Figure 10:
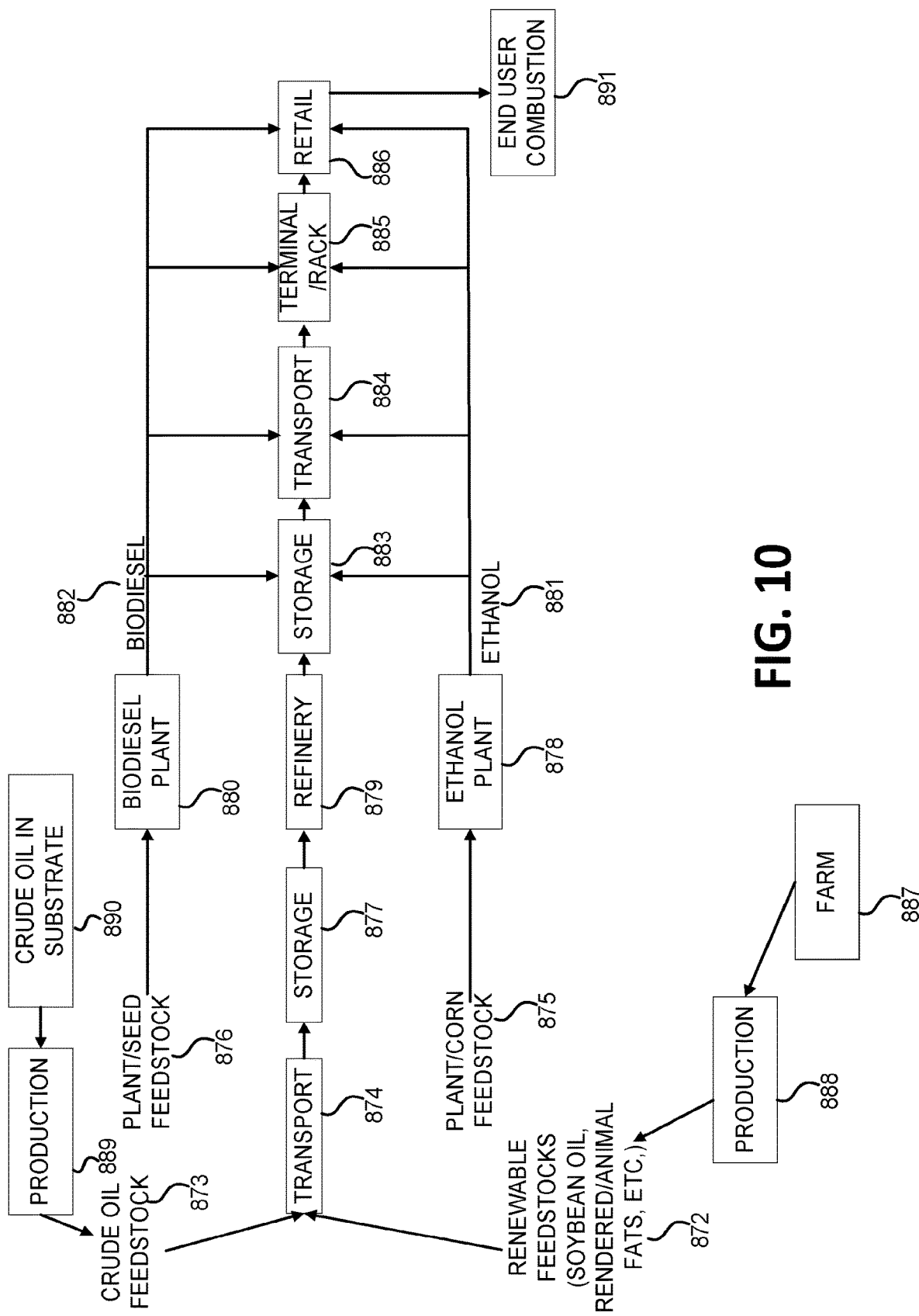
FIG. 10 is a diagram illustrating the various blending locations for biomass-derived biodiesel and/or ethanol with respect to the process described in FIG. 9.

FIG. 10 illustrates the general process, according to FIGS. 7 and 9 and as disclosed herein, to maintain the carbon intensity of a transportation fuel below a selected threshold subject to the selection of a crude feedstock 873 and/or a renewable feedstock 872, the transportation 874 of the selected feedstock, the storage 877 of the feedstock, the refining of the feedstock into one or more refined products at a refinery 879, the storage 883 of one or more refined products, and the transportation 884 of one or more refined products as transportation fuel to a terminal/rack 885 for final distribution to a retail outlet 886. It should be noted that selection of crude oil feedstock 873 may be based at least in part on the carbon intensity of its production 889 (e.g., fracking, offshore, tar sand steaming, etc.) as well as the innate or inherent carbon intensity of the crude oil as it exists in the subterranean formation 890. Similarly, renewable feedstock selection 872 may be based at least in part on the carbon intensity of its production 888 (e.g., fertilizing, feeding, harvesting, etc.) as well as the innate or inherent carbon intensity of the biomass feedstock as it exists, e.g., at the farm, pre-production. As further illustrated in FIG. 10, plant- and animal-derived fuels, additives, and blending agents may be produced apart from refinery 879. For example, a biodiesel plant 880 may use tallow and/or soybean feedstocks 876 to produce biodiesel 882. Moreover, an ethanol plant 878 may use corn and/or other plant-based feedstocks to produce ethanol 881. The biodiesel 882 and/or the ethanol 881 may then be blended into the refined products from refinery 879 in several blending locations, including at refined product storage tank 883, into barges, pipelines, rail cars, and trucks that transport 884 the refined products, at the terminal or rack 885, and even at tanks located at the retail outlet 886 (e.g., into underground tanks), prior to combustion thereof in end user engines. The use of renewables such as ethanol and/or biodiesel may facilitate the lowering of the overall carbon intensity of the resulting transportation fuel. Further, such fuels, additives, and blending agents may provide other benefits to the final transportation fuel, e.g., the improvement of oxygen content, etc. However, the carbon intensity of procuring feedstocks for, producing, and then transporting such fuels, additives, and blending agents must all be considered and added to the overall carbon intensity of the final transportation fuel to properly assess their carbon intensity impact.

Figure 11:
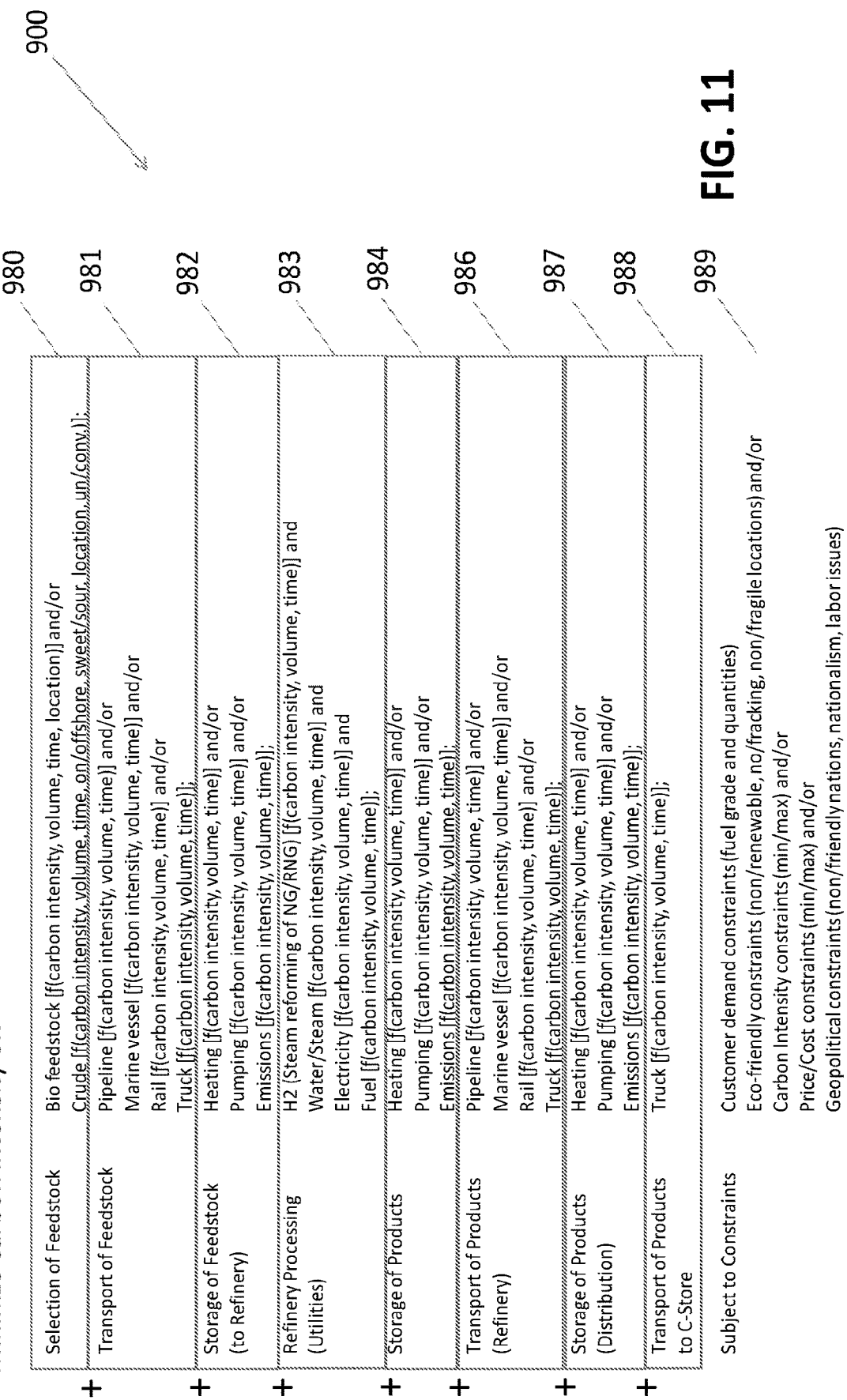
FIG. 11 is a chart illustrating an optimization routine that may be controller-operated to select various refining and/or processing options in order to minimize the carbon intensity of the resulting transportation fuels.

FIG. 11 provides a chart illustrating an optimization routine that may be controller-operated to select various feedstock, transportation, storage, and refining and/or processing options in order to minimize the carbon intensity of the resulting transportation fuels. The routine minimizes or reduces the carbon emissions (and thus the carbon intensity) of low carbon intensity transportation fuel production that includes the following steps: selecting a feedstock 980, transporting the feedstock 981, storing the feedstock 982, processing the feedstock into products at the refinery/bioprocessing facility 983, storing the products at the refinery/bioprocessing facility 984, transporting the products to a distribution hub or depot 986, storing the products at the distribution hub or depot 987, transporting the products to a retail outlet accessible to the consumer 988. The routine is subject to various constraints 989 including, but not limited to, customer demand for the transportation fuels of desired grades and quantities. Those skilled in the art will readily understand that one or more of the above steps may be omitted from any given run of the routine, especially if that step will not be performed in the production of transportation fuels.

Each of the steps illustrated in FIG. 11 include one or more variables that may be represented as functions of one or more sub-variables. With respect to selecting a feedstock 980, variables or options include, but are not limited to, plant/animal-based feedstock and crude oil. The selection of plant/animal-based feedstock may be dependent on sub-variables such as its carbon intensity, volume available, timing or availability, energy intensity (energy per mass), specific properties, and/or location. The selection of a crude oil may be dependent on sub-variables such as its carbon intensity, volume available, timing or availability, land or offshore sourcing, specific properties such as sulfur content, location, and/or production method (conventional or unconventional). With respect to transporting the feedstock 981 and transporting the products to a distribution hub or depot 986, variables or options include, but are not limited to pipeline, marine vessel, rail, and truck transport. The selection of any one or more of these options is dependent on sub-variables such as carbon intensity added by the option, transport volume capabilities, and timing or availability. With respect to transporting the products to a retail outlet 988, one option is truck transport but such truck transport is dependent on several sub-variables including carbon intensity added (i.e., by way of fuel used in transport), transport volume capabilities (i.e., different truck sizes), and timing or availability. With respect to storing the feedstock 982, storing the products at the refinery/bioprocessing facility 984, and storing the products at the distribution hub or depot 987, variables include, heating, pumping, and carbon emissions from the stored material. Each of these variables is dependent on several sub-variables including carbon intensity added, volume stored, and time stored. Finally, several variables or options for refining feedstocks 983 at the refinery or bioprocessing facility, i.e., the refinery processes, may be employed and some of which have been described hereinabove. Sub-variables commonly affecting these variables include, but are not limited to, the carbon intensity added (or subtracted) by the process, the volume capability, and the time to process.

It should be noted that the above variables and sub-variables have attributes that are inputs to the controller 750 (FIG. 8). Further, the mathematical functions of these variables may also be user inputs to the controller 750 (FIG. 8). When the routine is run, variables and sub-variables are selected from possible attributes to permit the required steps to be performed and drive the objective function to minimize carbon intensity of the transportation fuel. However, there are also constraints 989 added to the routine as shown in FIG. 11. In addition to the normal feasibility constraints for any given variable or sub-variable, the production of low carbon transportation fuels may also be guided and constrained by customer demand as to fuel grades and quantities, certain environmentally-friendly actions (e.g., use of renewable energy sources, avoidance of fracking in crude production (even though fracked crude may result in a relatively low CI), avoidance of feedstock selection from fragile environments, etc.), a carbon intensity minimum and/or maximum for a particular fuel, economic considerations to reign in cost of production, avoidance of geopolitical issues (e.g., embargoes on feedstock importation, nationalism concerns and potential unfair labor practices), among others.

Figure 12:
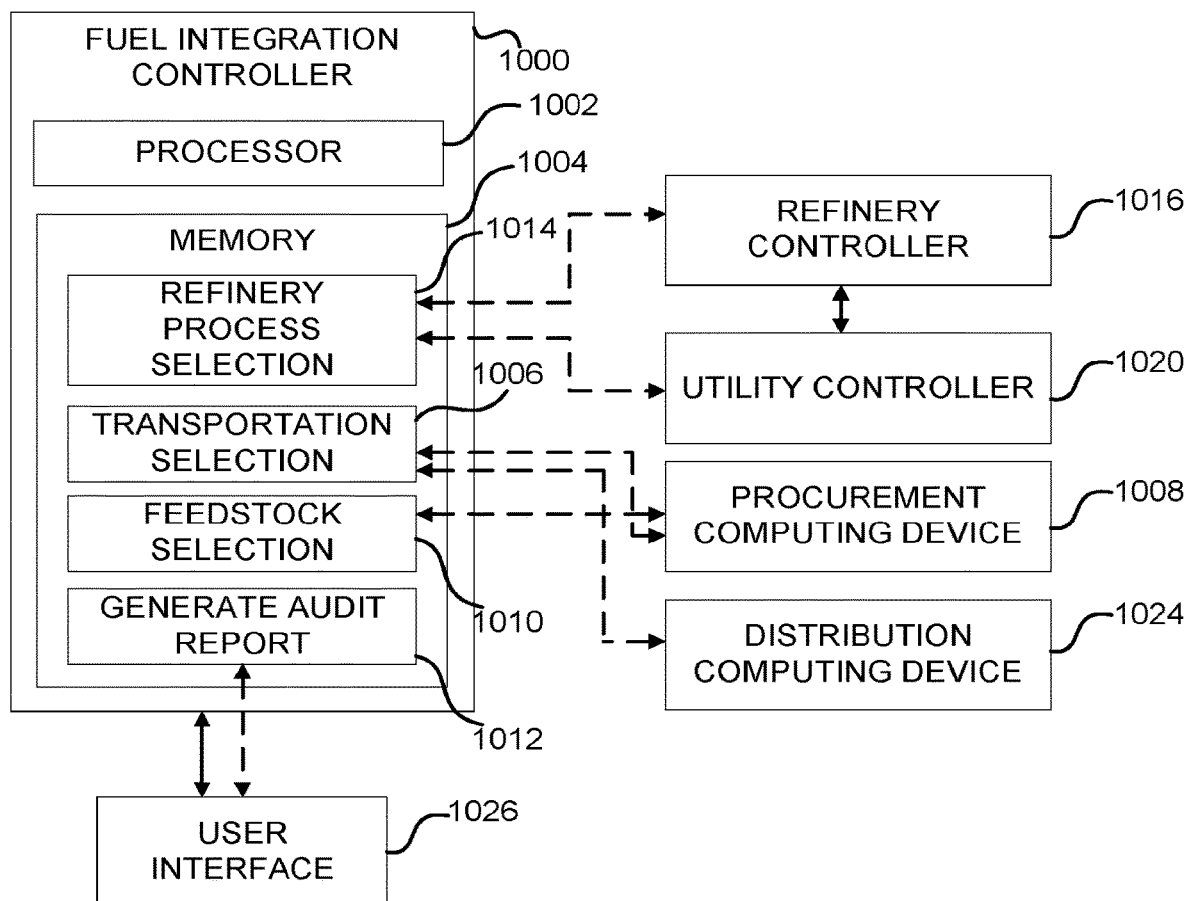
FIG. 12 is a simplified diagram illustrating a control system for managing the low carbon intensity energy production according to an embodiment.
Figure 13A:
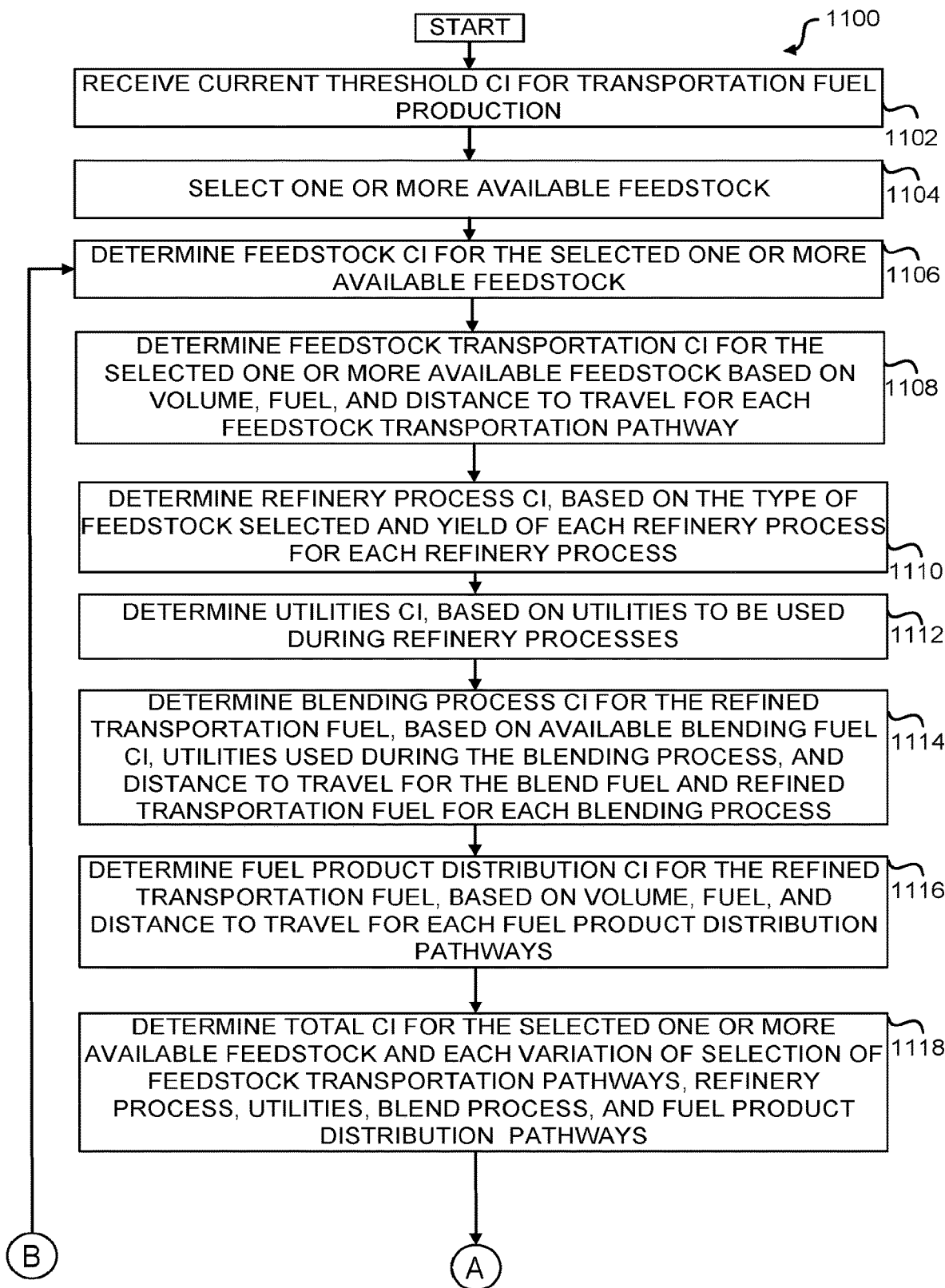
FIGS. 13A-E are flow diagrams, implemented in a controller, for managing the low carbon intensity energy production according to an embodiment.
Figure 13B:
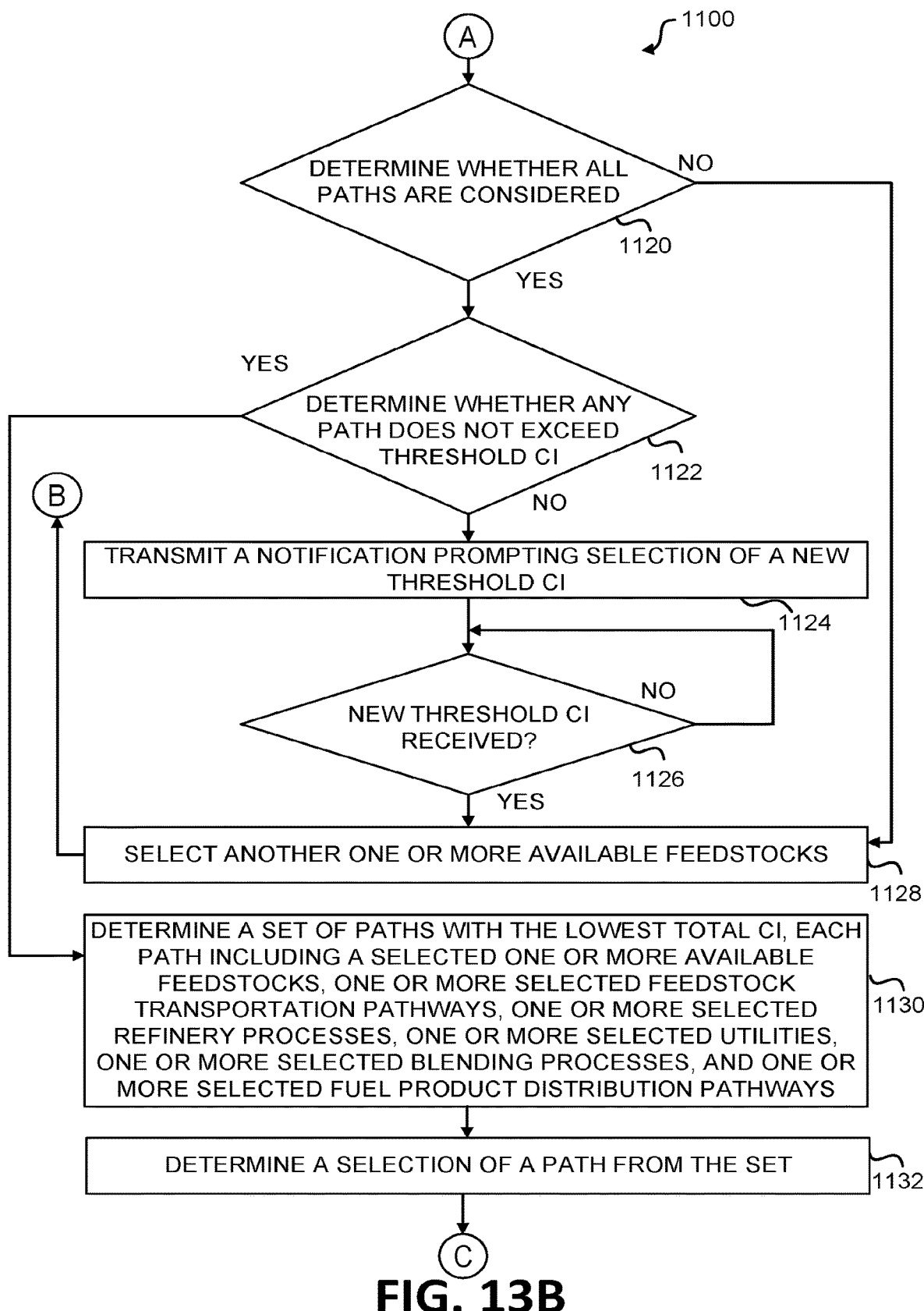
Figure 13C:
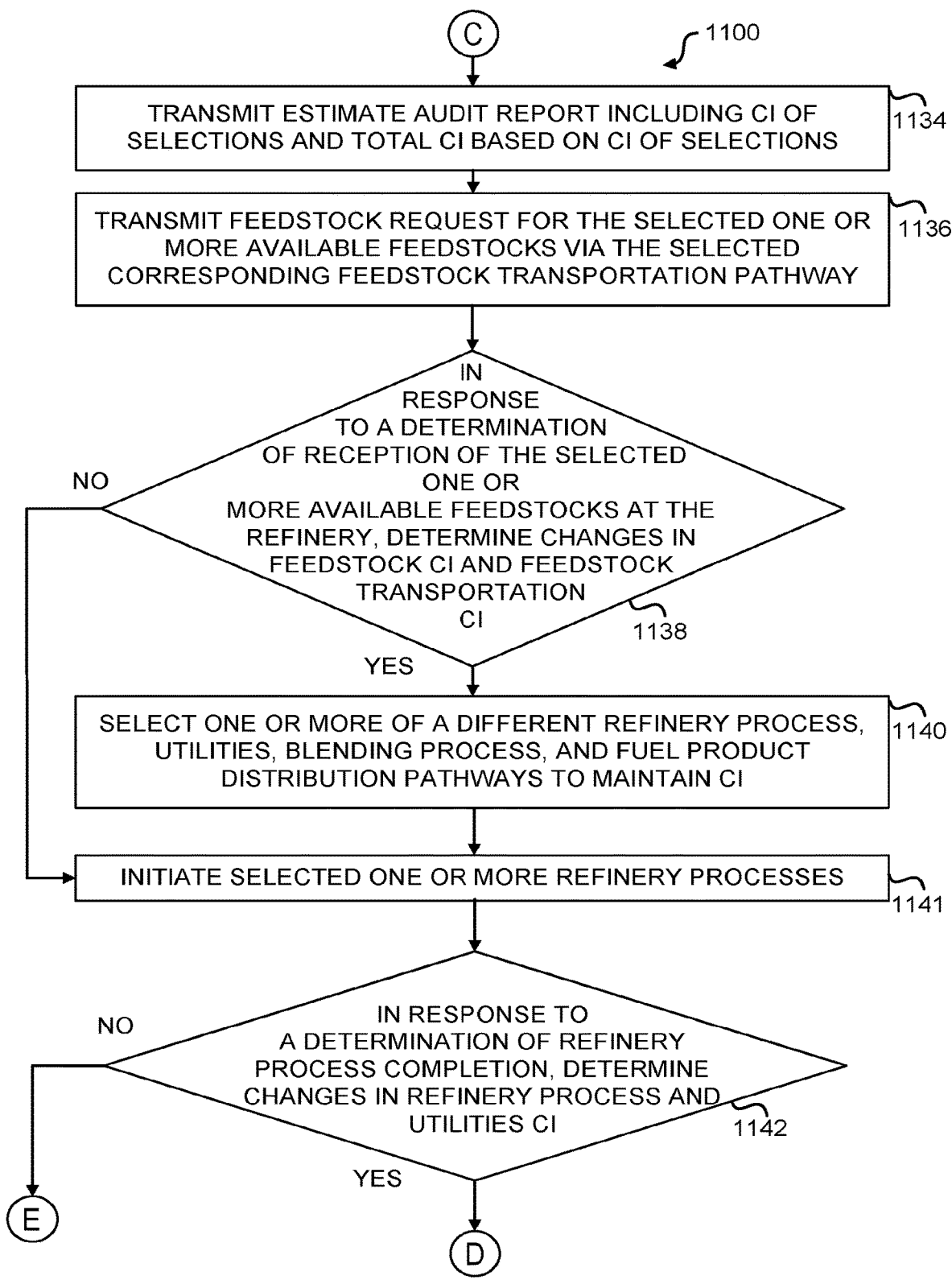
Figure 13D:
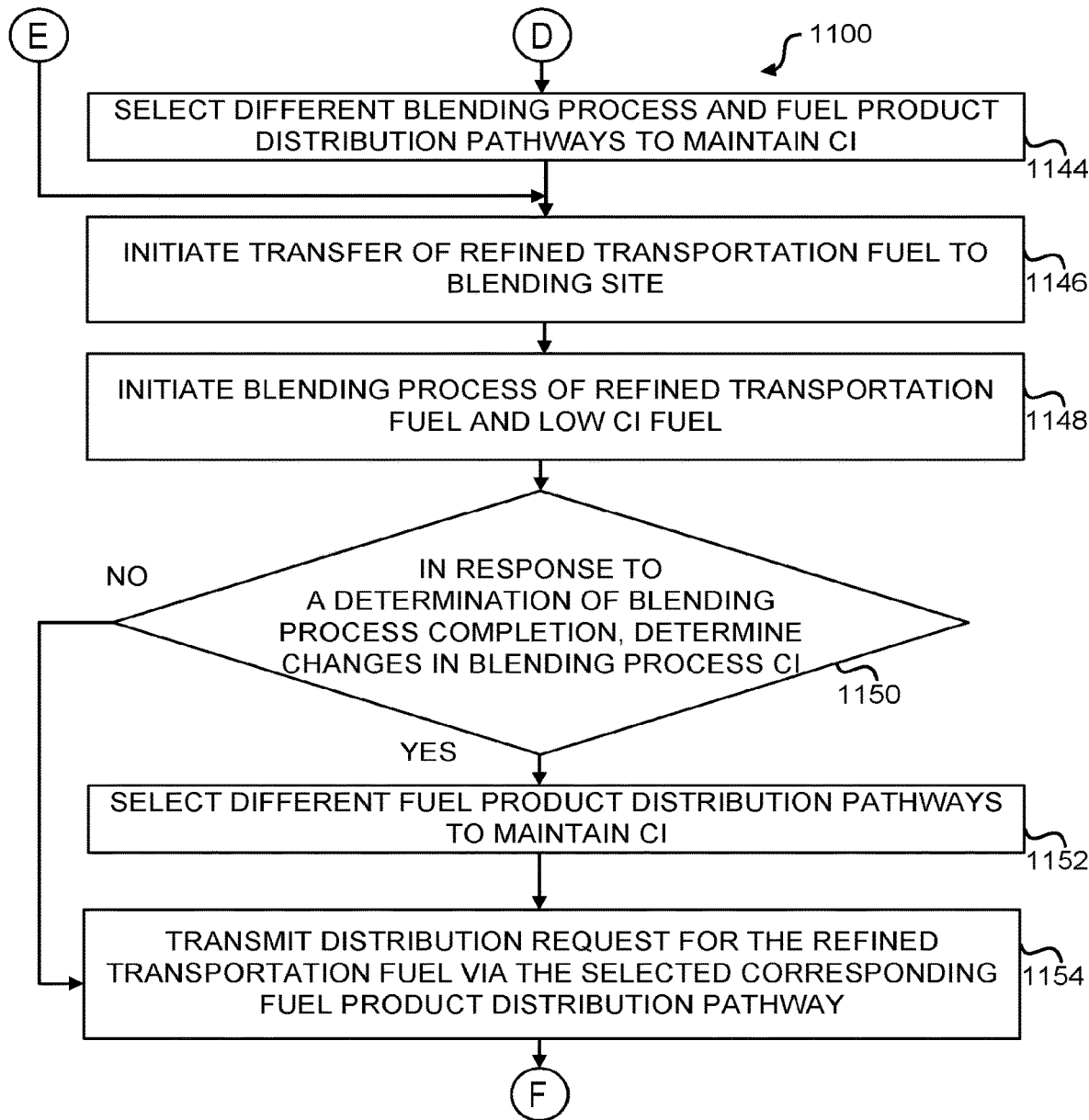
Figure 13E:
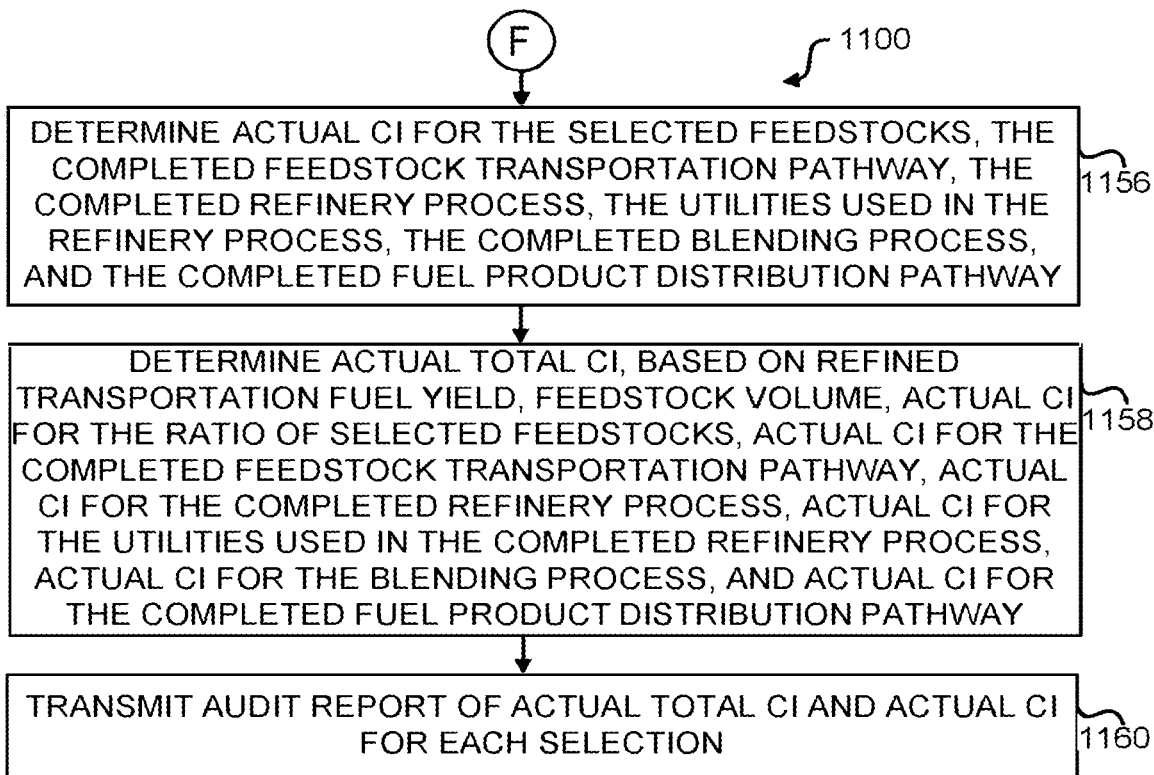

FIG. 12 illustrates an embodiment of a fuel integration controller 1000 for managing low carbon intensity energy production. As noted above and as illustrated in FIG. 8, a fuel integration controller 1000 may manage the operations of low carbon intensity transportation fuel production. The fuel integration controller 1000 may be one or more controllers, a supervisory controller, programmable logic controller (PLC), a computing device (such as a laptop, desktop computing device, and/or a server), and/or other suitable devices. The fuel integration controller 1000 may be located at or near a refinery. The fuel integration controller 1000, as noted, may be more than one controller. In such cases, the fuel integration controller 1000 may be located near or at various feedstock sources, near or at one or more refineries, and/or at other off-site locations. The fuel integration controller 1000 may include a processor 1002, or one or more processors, and memory 1004. The memory 1004 may include instructions. In an example, the memory 1004 may be a machine-readable storage medium. As used herein, a "machine-readable storage medium" may be any electronic, magnetic, optical, or other physical storage apparatus to contain or store information such as executable instructions, data, and the like. For example, any machine-readable storage medium described herein may be any of random access memory (RAM), volatile memory, non-volatile memory, flash memory, a storage drive (e.g., hard drive), a solid state drive, any type of storage disc, and the like, or a combination thereof. As noted, the memory 1004 may store or include instructions executable by the processor 1002. As used herein, a "processor" may include, for example one processor or multiple processors included in a single device or distributed across multiple computing devices. The processor 1002 may be at least one of a central processing unit (CPU), a semiconductor-based microprocessor, a graphics processing unit (GPU), a field-programmable gate array (FPGA) to retrieve and execute instructions, a real time processor (RTP), other electronic circuitry suitable for the retrieval and execution instructions stored on a machine-readable storage medium, or a combination thereof.

As used herein, "signal communication" refers to electric communication such as hard wiring two components together or wireless communication, as understood by those skilled in the art. For example, wireless communication may be Wi-Fi®, Bluetooth®, ZigBee, or forms of near field communications. In addition, signal communication may include one or more intermediate controllers or relays disposed between elements that are in signal communication with one another.

The fuel integration controller 1000 may include various modules in memory 1004. The modules may include or define a set of instructions, executable by the processor 1002 for different aspects involved in managing low carbon intensity transportation fuel production. Each module may be in signal communication with other controllers, sensors, data inputs, computing devices, servers, refinery components, and/or user interfaces. The fuel integration controller 1000 may include a refinery process selection module 1014, a transportation selection module 1006, a feedstock selection module 1010, and/or an audit report module 1012. The refinery process selection module 1014 may be in signal communication with a refinery controller 1016 and/or a utility controller 1020. The refinery process selection module 1014 may be in signal communication with a plurality of refinery controllers (e.g., each refinery controller located at a different and/or separate refinery). In another example, the refinery process selection module 1014 may be in signal communication with a refinery controller 1016 including the functionality of a utility controller 1020. In yet another example, the fuel integration controller 1000 may include the functionality of a refinery controller 1016 and/or a utility controller 1020. The transportation selection module 1006 may connect to a procurement computing device 1008, a distribution computing device 1024, a procurement and distribution computing device, a controller, a user interface, a server, database, and/or another device. The feedstock selection module 1010 may be in signal communication with a procurement computing device 1008, a procurement and distribution computing device, a procurement controller, a user interface, a server, database, and/or another device. The audit report module 1012 may be in signal communication with a user interface 1026. In such an example, a user may request an audit report via the user interface 1026. The user interface 1026 may be in signal communication with the fuel integration controller 1000 and/or the audit report module 1012. In such examples, the user interface 1026 may send and receive data to and from, respectively, the fuel integration controller 1000.

As noted above, the fuel integration controller 1000 may be in signal communication with the user interface 1026. The user interface 1026 may include an input (such as a keyboard, mouse, touchscreen, etc.) and a display. In another example, the user interface 1026 may be a computing device, such as a laptop, desktop computer, server, smartphone, tablet, or a terminal. A user may enter data into the user interface 1026 to send to the fuel integration controller 1000. For example, a user may enter in a threshold CI for a particular transportation fuel production. A user may input a low CI fuel specification for a particular transportation fuel production, the low CI fuel specification noting or including the threshold CI. The low CI fuel specification may be or may include the definition of a low CI fuel. In yet another example, the fuel integration controller 1000 may connect to a database. The database may store the threshold CI and the fuel integration controller 1000 may obtain the threshold CI from the database for a particular transportation fuel production. The fuel integration controller 1000 may include or store the threshold CI in memory 1004. In another example, a user may enter or input other data into the fuel integration controller 1000 via the user interface 1026, such as available feedstock, available feedstock transportation pathways, available refinery processes, available utilities, and/or available fuel product distribution pathways. A user may also enter or input the algorithms and/or calculations to determine a CI for any particular process.

In response to a reception of a threshold CI, whether from the user interface 1026, a database, another device, or from memory 1004, the fuel integration controller 1000 may set, assign, or utilize the threshold CI as a current threshold CI for a particular transportation fuel production. As such, the fuel integration controller 1000 may select various portions of the transportation fuel production process to ensure that the current threshold CI is not exceeded. Further, the fuel integration controller 1000 may simulate, model, or determine many different variations to determine the best possible path, combination, or selection based on various data points or factors. The fuel integration controller 1000 may determine the best possible path, combination, or selection via a brute-force method, a min-max method, an admissible decision method, and/or via some other decision making method as will be understood by those skilled in the art.

For example, upon reception of the threshold CI, the fuel integration controller 1000 may determine a CI for a number of or all selections of one or more available feedstock (in other words, feedstock variations). The fuel integration controller 1000 may further determine a CI for a number of or all selections of blends of the one or more available feedstock. In other words, the feedstock variations may include varying blends of one or more selected feedstock (e.g., 30% of feedstock 1 and 70% of feedstock 2, 25% of feedstock 1 and 75% of feedstock 2, etc.). The feedstock selection module 1010, fuel integration controller 1000, or another module may perform the CI determination for the feedstock variations. The feedstock selection module 1010, fuel integration controller 1000, or another module may determine the CI of each feedstock variation based on data received from the procurement computing device 1008, a procurement and distribution computing device, a database, a user input from the user interface 1026, a feedstock controller in signal communication with the fuel integration controller 1000, memory 1004, or another device storing such data. The data received may include a volume or number of barrels of a feedstock, a type of feedstock (for example, heavy or light crude, biofuel, etc.), and/or a location of the feedstock (for example, city, state, country, etc.). The data may also include the innate or inherent CI of the feedstock (or the transportation fuel) or, in other words, the carbon emissions of the energy content of the feedstock (or transportation fuel), as disclosed above. The data may also include a CI (or raw data to determine the CI) associated with producing, obtaining, and/or any other processing of the feedstock (e.g., a CI associated with fracking, offshore, tar sand steaming, processing soybean oil or corn oil, etc.). Once a number of or all of the feedstock variations CI are determined, the fuel integration controller 1000 may store each CI in memory 1004, at a database, and/or at the procurement computing device 1008 for future use.

The fuel integration controller 1000 may further determine a feedstock transportation CI for a number of or all available feedstock transportation pathways for each or a number of each feedstock variations. The transportation selection module 1006 or another module in the fuel integration controller 1000 may determine the CI. The fuel integration controller 1000 or transportation selection module 1006 may determine the feedstock transportation CIs based on the selected one or more available feedstock or feedstock variations, for any particular iteration or determination. For example, in the case that a feedstock from overseas is chosen, marine delivery modes or pathways may be considered, while for a local feedstock (or a feedstock within the same country), rail, vehicular (e.g., a truck), and/or pipeline delivery, if available, may be considered. The fuel integration controller 1000 or transportation selection module 1006 may obtain available feedstock transportation pathways from the procurement computing device 1008, the user interface 1026, a database, from memory 1004, and/or from another device. Further, the fuel integration controller 1000 or the transportation selection module 1006 may base the CI on the volume of each feedstock transportation pathway, the fuel type utilized by each feedstock transportation pathway (e.g., gas, electricity, steam, other liquid fuels, etc.), and/or a distance from the source of the feedstock to the refinery. Once a number of or all of the feedstock transportation pathway variations CI, based on the feedstock variations, are determined, the fuel integration controller 1000 may store each CI in memory 1004, at a database, and/or at the procurement computing device 1008 for future use.

The fuel integration controller 1000 may further via a refinery process selection module 1014, determine a refinery process and utilities CI for a number of or all available refinery processes and utility options for each or a number of each feedstock variations. The fuel integration controller 1000 may, rather than determining a refinery process and utility CI, determine a refinery process CI and/or a utilities CI. The refinery process selection module 1014 or other modules within the fuel integration controller 1000 may determine the refinery process and utilities CI. As noted above, a refinery process may utilize various utilities for any given refinery process. To offset carbon emissions for standard refining processes, renewable utilities (e.g., solar, wind, geothermal, renewable gas, etc.) may be utilized in the refining process, thus reducing overall CI (as well as carbon emissions). In another example, heat integration through a heat exchanger network and/or carbon sequestration may be utilized or selected to reduce or offset the CI for a particular refining process, thus reducing the overall CI for a transportation fuel production. In an example, the fuel integration controller 1000 or refinery process selection module 1014 may determine available refinery processes and utilities based on a list from a refinery controller 1016, utility controller 1020, or from memory 1004. The heat exchanger network may include one or more heat exchangers that are arranged to provide heat to process streams (e.g., process streams to be heated) by exchanging heat with other process streams to be cooled. Such a heat exchanger network arrangement thus reduces overall heating and cooling utilities (e.g., energy and/or fuel utilized to heat and/or cool). In another example, the fuel integration controller 1000 or refinery process selection module 1014 may determine available refinery processes and utilities based on the selected one or more available feedstock or feedstock variations (in other words, different feedstock may utilize different refinery processes, thus choices may be limited based on the particular feedstock variations). In such examples, the fuel integration controller 1000 and/or the refinery process selection module 1014 may determine CI for each available refinery process and utility option for each feedstock variation. The fuel integration controller 1000 and/or refinery process selection module 1014 may determine the CI for each available refinery process and utility option based on the type or types of the selected feedstock variations, the utilities to be used during the refinery processes, the yield of each refinery process, and/or other factors, as will be understood by those skilled in the art. The fuel integration controller 1000 may consider other refineries as well. The fuel integration controller 1000 may determine a CI for other refineries, as described above. The fuel integration controller 1000 may further base refinery process CI on availability, at one of the refineries, of a refined transportation fuel and/or component (e.g., other fuel used in a blend or refining process) of a refined transportation fuel. Once a number of or all of the refinery processes and utilities CI (for one or more refineries), based on the feedstock variations, are determined, the fuel integration controller 1000 may store each CI in memory 1004 or at a database for future use.

As noted, the fuel integration controller 1000 may, rather than determining a refinery process and utility CI, determine a refinery process CI and/or a utilities CI. The utility CI may be based on the utilities used in a corresponding refinery process, the utilities used to store a feedstock, the utilities used to store a refined product, other utilities used for various other processes at the refinery, and/or at other points in the transportation fuel production (e.g., utilities used in pumps to transfer feedstock or refined transportation fuels).

The fuel integration controller 1000 may further determine a refined product distribution CI for a number of or all available fuel product distribution pathways for each or a number of each feedstock variations. The transportation selection module 1006 or another module in the fuel integration controller 1000 may determine the refined product distribution CI. The fuel integration controller 1000 or transportation selection module 1006 may determine the refined product distribution CI based on the selected one or more available feedstock and refinery process yield, for any particular iteration or determination. For example, one refinery process for a feedstock variation may produce a certain amount of a refined product, while another refinery process for another feedstock variation may produce a different amount of refined product. The fuel integration controller 1000 or transportation selection module 1006 may obtain available fuel product distribution pathways from the distribution computing device 1024, the user interface 1026, a database, from memory 1004, and/or from another device. Further, the fuel integration controller 1000 or the transportation selection module 1006 may determine the refined product distribution CI based on the volume of each fuel product distribution pathway, the fuel type utilized by each fuel product distribution pathway, and/or a distance from the refinery to convenience store, distribution point, and/or an end destination/point. Once a number of or all of the fuel product distribution pathway variations CI, based on the feedstock variations, are determined, the fuel integration controller 1000 may store each CI in memory 1004, at a database, distribution computing device 1024, and/or procurement and distribution computing device for future use.

Once a number of or all CIs for each selection (as in, the selection of the one or more available feedstock, the feedstock transportation pathway, the refinery process and utilities, and the refined product distribution) are determined, the fuel integration controller 1000 may determine a set of variations, combinations, or selections of each of the selections noted above. For example, one set of the variations, combinations, or selections may include a selected one or more available feedstock, a selected one or more available feedstock transportation pathways (corresponding to the feedstock variation), a selected one or more refinery processes (corresponding to the feedstock variation), a selected one or more utilities (corresponding to the refinery processes and/or other processes to use utilities), and a selected one or more fuel product distribution pathways (corresponding to the refined product from the refinery). Further, the fuel integration controller 1000 may determine a total CI for each variation, combination, or set of selections. The fuel integration controller 1000 may determine the total CI based on the volume of the selected one or more available feedstock, the yield from the corresponding or selected refinery process for a refined transportation fuel, the determined feedstock CI, the determined feedstock transportation CI, the determined refinery process and utilities CI, and/or the determined refined product distribution CI. Other factors may be considered when determining a total CI. For example, the fuel integration controller 1000 may further base the total CI on a feedstock storage tank CI (if utilized), a refined product tank CI (if utilized), emissions (e.g., VOC emissions through working losses, breathing losses, and flashing losses), carbon sequestration (if utilized), and/or other carbon offsetting practices as will be understood by those skilled in the art. In such examples, once the fuel integration controller 1000 determines the total CI for each variation, the fuel integration controller 1000 may store each total CI in memory 1004 and/or at a database.

Once each total CI variation is determined, the fuel integration controller 1000 may determine a selection from the set of combinations. The combinations may include the various selections, described above, with a CI less than the threshold CI. In an example, if there are no variations with a CI less than the CI threshold, the fuel integration controller 1000 may notify a user that all selections exceed the threshold CI, prompt a user to enter a new threshold CI, and/or prompt a user to accept the selection with the lowest total CI (the lowest total CI, in this case, exceeding the threshold CI). In another example, the fuel integration controller 1000 may automatically select a new threshold CI. In another example, the fuel integration controller 1000 may determine the selection based on the lowest total CI (the lowest total CI not exceeding the threshold CI). In yet another example, multiple combinations may include a similar or the same total CI. However, each combination may exhibit different properties, such as a cost issue or a timing issue (e.g., from feedstock to customer). In such examples, the fuel integration controller 1000 may select one of the combinations, with the similar or same CI or a CI lower than threshold, further based on the time of availability of each of the selected one or more available feedstock, a time for delivery to the refinery by the feedstock transportation pathway, a time to process a feedstock utilizing the selected one or more refinery processes, a time to delivery from the refinery to the customer (e.g., convenience store, distribution point, etc.), and/or any refinery processes queued or in production. Upon determination of a selection, the fuel integration controller 1000 may initiate transportation fuel production or transmit a request to confirm initiation of the transportation fuel production.

Figure 15:
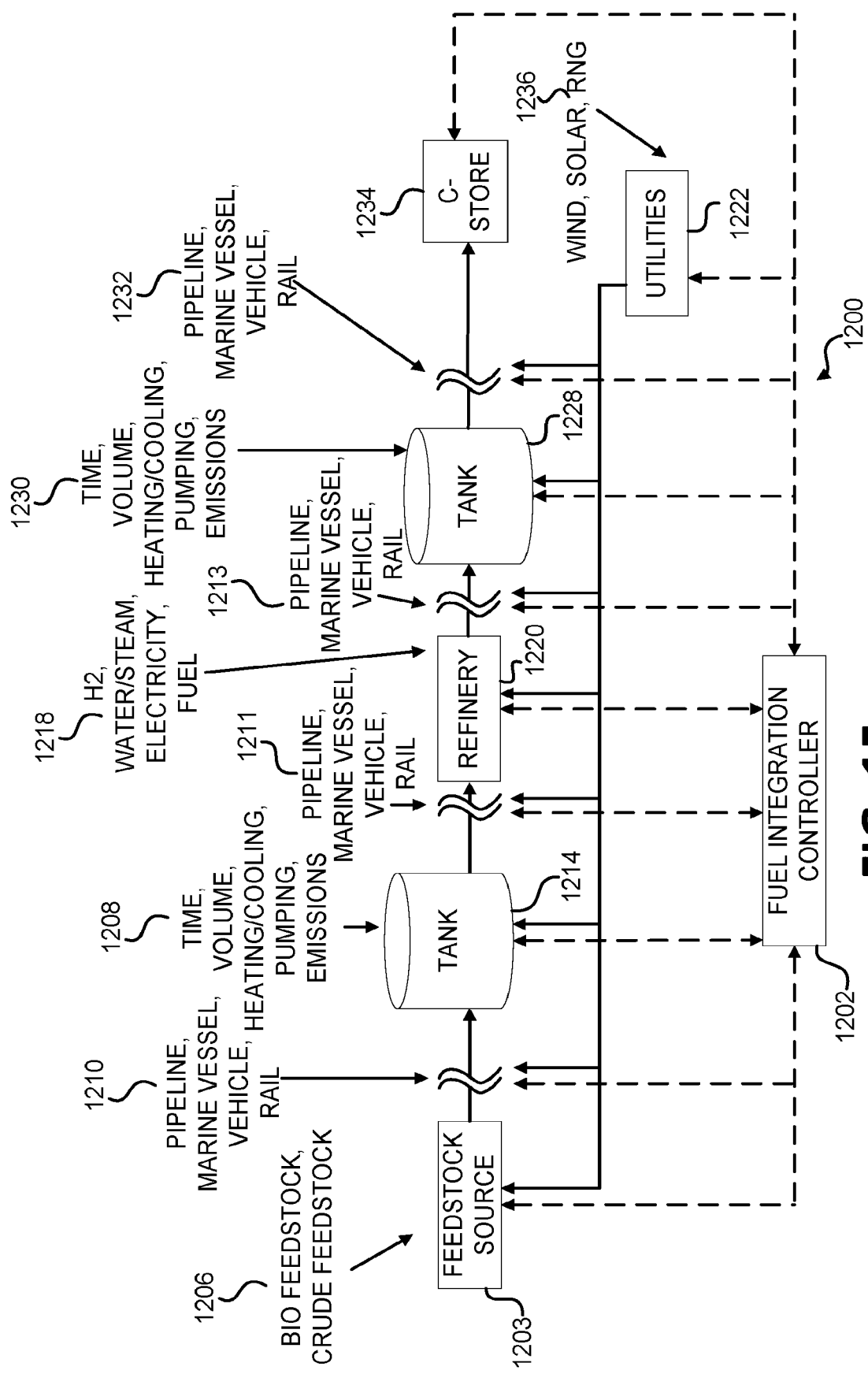
FIG. 15 is a block diagram illustrating a system for managing the low carbon intensity energy production according to an embodiment.

FIG. 15 is a block diagram illustrating a system 1200 for managing the low carbon intensity energy production according to an embodiment. The system 1200 may include a fuel integration controller 1202. The fuel integration controller 1202 may connect to various other controllers, sensors, and/or computing devices utilized throughout a refined transportation fuel production to plan and/or control a refined transportation fuel production. For example, the fuel integration controller 1202 may connect to a controller at a feedstock source 1203 or to a database storing information regarding the feedstock source 1203, as well as other feedstock sources. As such, the fuel integration controller 1202 may obtain various data points or information in relation to different available feedstock at feedstock sources and the fuel integration controller 1202 may select one or more of the available feedstock for a refined transportation fuel production, based on the data points or information obtained. The fuel integration controller 1202 may connect to controllers, sensors, a database and/or computing devices related to a feedstock transportation pathway. As such, the fuel integration controller 1202 may obtain various data points or information in relation to different available feedstock transportation pathways and the fuel integration controller 1202 may select one or more of the available feedstock transportation pathways for the refined transportation fuel production, based on the various data points or information.

Further, the fuel integration controller 1202 may connect to controllers, sensors, and/or computing devices associated with a tank 1214 (e.g., a feedstock storage tank) and/or tank 1228 e.g., a fuel product storage tank). The tank 1214, tank 1228, or tanks may be positioned at various points between a feedstock source 1203, the refinery 1220, and a distribution point or terminal (e.g., convenience store 1234). For example, the tank 1214 may be located on-site at the refinery 1220. The fuel integration controller 1202 may obtain various data points or information in relation to feedstock or refined transportation fuel stored in tank 1214 or tank 1228 (e.g., time and power utilized) and the fuel integration controller 1202 may select feedstock or refined transportation fuel stored in the tank 1214, tank 1228, or other tanks for use in the refined transportation fuel production.

The fuel integration controller 1202 may control a refinery 1220 and/or connect to controllers, sensors, and/or computing devices at the refinery 1220. The fuel integration controller 1202 may obtain various data points or information in relation to different available refinery processes of the refinery 1220 and the fuel integration controller 1202 may select one or more of the available refinery processes for the refined transportation fuel production, based on the various data points or information. The fuel integration controller 1202 may initiate and/or control the selected refinery processes at the refinery 1220. For example, when a particular refinery process is selected, the fuel integration controller 1202 may initiate the refinery process or transmit an initiation to a controller of the refinery 1220.

The fuel integration controller 1202 may connect to a utility provider 1222 or controllers, sensors, and/or computing devices of a utility provider 1222. The utility provider 1222 may provide utilities for use in the refinery 1220, as well as at various other points throughout the refined transportation fuel production. The utility provider 1222 may be proximate to, nearby, or at the refinery 1220 and may utilize renewable resources. For example, the utility provider 1222 may provide and/or track utilities for use at the feedstock source, at each transportation/distribution pathway, at each tank (e.g., tank 1214 and tank 1228), at a blending site, and/or at other points or processes in the refined transportation fuel production. As such, the fuel integration controller 1202 may obtain data regarding the available utilities, as well as available utilities for the refined transportation fuel production. Based on such data, the fuel integration controller 1202 may select one or more utilities for the refined transportation fuel production (e.g., utilities for use in the one or more selected refinery processes).

The fuel integration controller 1202 may connect to controllers, sensors, a database, and/or computing devices related to a refined product distribution pathway. As such, the fuel integration controller 1202 may obtain various data points or information in relation to different available refined product distribution pathways and the fuel integration controller 1202 may select one or more of the available refined product distribution transportation pathways based on the various data points or information.

The fuel integration controller 1202 may connect to controllers, sensors, and/or computing devices at a distribution point or terminal (e.g., a convenience store 1234). For example, the fuel integration controller 1202 may monitor or track fuel consumption (in other words, demand) at the convenience store 1234. Based on the consumption or demand, the fuel integration controller 1202 may initiate a refined transportation fuel production for a particular refined transportation fuel. Further, based on consumption or demand, the fuel integration controller 1202 may select different aspects of the refined transportation fuel production (e.g., a low CI feedstock, carbon sequestration, renewable utilities, etc.).

FIGS. 13A through 13E illustrate flow diagrams, implemented in a controller, for managing the low carbon intensity energy production according to an embodiment. The method is detailed with reference to the fuel integration controller 1202 and system 1200 of FIG. 15. Unless otherwise specified, the actions of method 1100 may be completed within the fuel integration controller 1202. Specifically, method 1100 may be included in one or more programs, protocols, or instructions loaded into the memory of the fuel integration controller 1202 and executed on the processor or one or more processors of the fuel integration controller 1202. The order in which the operations are described is not intended to be construed as a limitation, and any number of the described blocks may be combined in any order and/or in parallel to implement the methods.

At block 1102, the fuel integration controller 1202 may receive a threshold CI. The fuel integration controller 1202 may receive the threshold CI from a user, user interface, a low CI fuel specification (e.g., input by a user or stored in a database), a controller, memory of the fuel integration controller 1202, and/or another device. In response to a reception of the threshold CI, the fuel integration controller 1202 may utilize or assign the input threshold CI as a current threshold CI. The current threshold CI may correspond to a particular transportation fuel production process or operation.

Once a current threshold CI is set, assigned, received, and/or determined, at block 1104, the fuel integration controller 1202 may select one or more available feedstock from a fuel or feedstock source 1203. As noted above, the available feedstock may include plant/animal-based and/or crude feedstock 1206 from a variety of sources (e.g., wellhead, biomass facilities, storage tanks, etc.). In an example, the fuel integration controller 1202 may determine a list or set of available feedstock from a user input (via a user interface), a database, a procurement controller, procurement computing device, procurement and distribution computing device, the memory of the fuel integration controller 1202, and/or another device.

In response to a selection of the one or more available feedstock, at block 1106, the fuel integration controller 1202 may determine a feedstock CI. The fuel integration controller 1202 may determine feedstock CI based on the ratio, percentage, or blend of the feedstock's inherent CI, the type of feedstock, the location of the feedstock (e.g., distance from the refinery 1220, tanks 1214, 1228, or blending site), the power used or emissions generated by obtaining or producing the feedstock, and/or the volume of the feedstock. In another example, the feedstock CI may be known or given (e.g., via the user interface, database, controller, etc.). Further, as one or more available feedstock are determined or selected, the feedstock CI may be determined based on the ratio or blend of the determined or selected one or more available feedstock.

In response to a determination of the feedstock CI, at block 1108, the fuel integration controller 1202 may determine a feedstock transportation CI for each available feedstock transportation pathway for the selected one or more available feedstock. The available feedstock transportation pathways may include pipeline transportation, marine vessel transportation, vehicular transportation (e.g., a truck), and/or rail transportation 1210. As noted above, different feedstock may be deliverable via particular feedstock transportation pathways. As such, based on the selected one or more available feedstock, the fuel integration controller 1202 may determine the feedstock transportation CI. The fuel integration controller 1202 may further determine the feedstock transportation CI for each available feedstock transportation pathway based on the volume of the feedstock transportation pathway, the fuel utilized by the feedstock transportation pathway, and the distance the feedstock transportation pathway may travel to deliver the feedstock from the feedstock source 1203 to a tank 1214 or refinery 1220.

As noted above, feedstock storage in a tank 1214 (e.g., a feedstock storage tank) may be associated with a CI. In other words, storing a feedstock in a tank 1214 may lead to carbon emissions, based on various factors, such as time of storage, volume of tank 1214, volume of feedstock to be stored, power required to transfer feedstock to and from the tank 1214 (e.g., via a pump), power and time required to heat/cool the feedstock, and/or the emissions associated with the storage of the feedstock 1208 (e.g., VOC emissions through working losses, breathing losses, and flashing losses). In such cases where feedstock storage may be an option, the fuel integration controller 1202 may determine feedstock storage CI based on those factors. Further, a CI may be associated with transporting the stored feedstock to the refinery 1220. The stored feedstock may be transported via pipeline, marine vessel, vehicle (e.g., a truck), and/or rail 1211. The stored feedstock transportation CI may be based on the volume of the stored feedstock transportation pathway, the fuel utilized by the stored feedstock transportation pathway, and the distance the stored feedstock transportation pathway may travel to deliver the stored feedstock from the tank 1214 to the refinery 1220.

In response to a determination of the feedstock transportation CI, at block 1110, the fuel integration controller 1202 may determine the refinery process CI. In such examples, the fuel integration controller 1202 may obtain a list of available refinery processes from a refinery controller at the refinery 1220, a database, or the memory of the fuel integration controller 1202. In another example, the fuel integration controller 1202 may determine the refinery process CI for each refinery processes based on the type of feedstock selected and the yield of the refinery process. As noted above, high CI refinery operations may be offset by the use of offsetting practices. For example, a refinery 1220 may be capable of heat integration via a heat exchanger network. Further, the refinery may be capable of generating electricity through the letdown of high pressure steam across a power turbine, the steam to be used in typical refinery processes. Further still, the refinery may utilize carbon sequestration to offset high CI refinery, as will be understood by those skilled in the art.

In response to a determination of the refinery process CI, at block 1112, the fuel integration controller 1202 may determine the utilities CI. In such examples, the fuel integration controller 1202 may obtain a list of available utilities from a refinery controller at the refinery 1220, a utility controller, a database, or the memory of the fuel integration controller 1202. In another example, the fuel integration controller 1202 may determine the utilities CI for each available utility based on the type utilities to be used during refinery processes. As noted above, high CI refinery operations may be offset by the use of low CI utilities. For example, renewable fuels from a utility provider 1222 may be provided to a refinery 1220 to refine a high CI feedstock. The utilities may include different sources or forms of hydrogen, of water/steam, of electricity (e.g., solar, wind, renewable gas, etc. 1236), and/or of other fuels 1218. The utilities CI may further include a CI associated with utilities used throughout the transportation fuel production. The utilities CI may be further based on utilities used at the feedstock source 1203 (e.g., utilities used to obtain or produce a feedstock), during feedstock transportation (e.g., power utilized at a pump to pump feedstock to another location), used at the tank 1214 (e.g., a feedstock storage tank), during refined transportation fuel distribution (e.g., power utilized at a pump to pump refined transportation fuel to another location), used at a blending site (e.g., utilities to power a mixing element or component of a blend tank or to power pumps to an in-line mixer), and/or used at any other point in the transportation fuel production.

As noted above, fuel product storage in a tank 1228 (e.g., a fuel product storage tank) may be associated with a CI. In other words, storing a refined transportation fuel in a tank 1228 may lead to carbon emissions, based on various factors, such as time of storage, volume of tank 1228, volume of feedstock to be stored, power required to transfer refined transportation fuel to and from the tank 1228 (e.g., via a pump), power and time required to heat/cool the refined transportation fuel, and/or the emissions associated with the storage of the refined transportation fuel 1230 (e.g., VOC emissions through working losses, breathing losses, and flashing losses). In such cases where refined transportation fuel storage may be an option, the fuel integration controller 1202 may determine refined transportation fuel storage CI based on those factors. Further, a CI may be associated with transporting the refined transportation fuel from the refinery 1220 or a blending site to the tank 1228. The stored refined transportation fuel may be transported via pipeline, marine vessel, vehicle (e.g., a truck), and/or rail 1213. The stored fuel transportation CI may be based on the volume of the stored fuel transportation pathway, the fuel utilized by the stored fuel transportation pathway, and the distance the stored fuel transportation pathway may travel to deliver the stored refined transportation fuel from the refinery 1220 to the tank 1228.

In response to a determination of the utilities CI, at block 1114, the fuel integration controller 1202 may determine a blending process CI for each available blending process at one or more blending sites and for a refined transportation fuel and low CI blending fuels (e.g., ethanol or biodiesel).

The fuel integration controller 1202 may base the blending process CI on a CI of the low CI blending fuel, the transportation pathway (including distance) that the low CI blending fuel may travel to a blending site, the power utilized for the blending process, and/or other factors that generate a CI, as will be understood by those skilled in the art. In an example, to lower a high CI feedstock, the fuel integration controller 1202 may select a blending process, the blending process including a low CI blending fuel (e.g., ethanol or biodiesel).

In response to a determination of the blending process CI, at block 1116, the fuel integration controller 1202 may determine a fuel product distribution process CI for each available fuel product distribution pathway for one or more refined transportation fuels from the refinery 1220, a blending site, or tanks (e.g., tank 1228). The available fuel product distribution pathways may include pipeline transportation, marine vessel transportation, truck or vehicular transportation, and/or rail transportation 1232. The fuel integration controller 1202 may further determine the refined product distribution CI for each available fuel product distribution pathway based on the volume of the fuel product distribution pathway, the fuel utilized by the fuel product distribution pathway, the distance the fuel product distribution pathway may travel to deliver the refined transportation fuel from the refinery 1220 to a tank 1228 or convenience store 1234, and/or the one or more refined transportation fuels (e.g., volume and type).

In response to a determination of the refined product distribution CI, at block 1118, the fuel integration controller 1202 may determine the total CI for each variation of selections noted above. For example, for the selected one or more available feedstock, the fuel integration controller 1202 may determine total CI based on a first feedstock transportation pathway, a first refinery process, a first utility, a first blending process, and a first refined product distribution method. The fuel integration controller 1202 may then determine the total CI for the next variation and so on. The fuel integration controller 1202 may further base the total CI on the volume of the selected one or more available feedstock and/or the yield percentage of the refinery process (in other words, the volume of the refined transportation fuel per the original feedstock volume). Other factors may be taken into account for total CI.

In response to a determination of total CI, at block 1120, the fuel integration controller 1202 may determine whether all blends or selections or, at least, a number of blends or selections of the one or more available feedstock (and the variations of the other selections described above) have been considered (e.g., if a total CI has been determined for all variations of feedstock combinations or paths). If all blends or selections or a number of blends or selections of the one or more available feedstock have not been considered, at block 1128, the fuel integration controller 1202 may select another of the one or more available feedstock and determine total CI, as described above. If all of the one or more available feedstock or, at least, a particular amount or set of ratios or blends of the one or more available feedstock have been considered, then the fuel integration controller 1202, at block 1122, may determine whether any path, combination, variation, or final selection does not exceed the threshold CI. If no path, combination, variation, or final selection does not exceed the threshold CI (in other words, if all paths, combinations, variations, or final selections exceed the threshold CI), at block 1124, the fuel integration controller 1202 may transmit a notification to a user, prompting the user to select a new threshold CI. In another example, the fuel integration controller 1202 may automatically increase the threshold CI based on a specified amount. The fuel integration controller 1202, at block 1126, may wait until a new threshold CI is received. When a new threshold CI is submitted or received by the fuel integration controller 1202, the current threshold CI is set to the new threshold CI and, at block 1128, another of the one or more available feedstock may be selected and each iteration or a number of iterations may be determined again, as described above.

If at least one path, combination, variation, or final selection does not exceed the threshold CI, at block 1130, the fuel integration controller 1202 may determine a set of paths, combinations, variations, or selections with the lowest total CI. In some cases, one path, combination, variation, or selection may not exceed the threshold CI, while in other cases many paths or selections may not exceed the threshold CI. Each path, combination, variation, or selection may include a selected one or more available feedstock, one or more selected feedstock transportation pathways, one or more selected refinery operations, one or more selected utilities, one or more selected blending processes, and/or one or more selected fuel product distribution pathways, as well as a corresponding CI for each selection.

Based on the set of paths, combinations, variations, or selections, at block 1132, the fuel integration controller 1202 may determine a selection of a path, combination, variation, or selection from the set of paths or selections. The fuel integration controller 1202 may select the path, combination, variation, or selections based on, in addition to lowest total CI, time of availability of each of the selected one or more available feedstock, a time for delivery to the refinery by the feedstock transportation pathway, a time to process a feedstock utilizing the selected one or more refinery processes, a time to delivery from the refinery to a convenience store by each of the selected one or more fuel product distribution pathways, the cost of each selection, transportation fuel productions currently in progress or in queue, and/or customer demand for a particular refined transportation fuel. So, as an example, the fuel integration controller 1202 may select the path, combination, variation, or selection having a lower than threshold CI (although not necessarily the lowest CI) and more efficient pathway (e.g., from feedstock to customer), as described above. An efficient pathway may include a shorter distance to travel overall (e.g., from feedstock source to customer), the time of availability for the feedstock, the length of time to refine a particular feedstock (which may be based on a type of feedstock), the length of time a feedstock or refined transportation fuel may be stored at any point in the transportation fuel production, cost issues associated with each of the selection, and/or a high demand for a particular low CI refined transportation fuel (e.g., based on sales at a convenience store 1234).

In response to determination of a selection of the path, combination, variation, or selections, at block 1134, the fuel integration controller 1202 may generate and transmit an estimated or initial audit report to a user, user interface, database, and/or other device. The audit report may include the CI of each selection and the total CI. The estimated audit report may include other information regarding each part of the planned or selected transportation fuel production, such as where the selected feedstock is from, the type and volume of the selected feedstock, the type of feedstock transportation pathways (as well as other details on the feedstock transportation pathway), the selected refinery process, the estimated yield of the refinery process, the selected utilities, the source of the selected utilities, the selected blending process, the type and volume of the low CI blending fuel, the type of fuel product distribution pathways (as well as other details on the fuel product distribution pathway), length of time for tank storage at any point in the process, and/or an overall timeline of the transportation fuel production. In another example, the fuel integration controller 1202 may generate the estimated or initial audit report based on a request from a user and/or user interface.

In another example, the fuel integration controller 1202, at block 1136, may transmit a feedstock request. The feedstock request may include the selected one or more available feedstock and the selected feedstock transportation pathway. In another example, the fuel integration controller 1202 may transmit a confirmation of the feedstock request prior to transmitting the feedstock request. For example, the fuel integration controller 1202 may transmit a request for confirmation of a feedstock request of the selected one or more available feedstock to a user interface or a procurement computing device. In response to reception of the confirmation (e.g., from the user interface or procurement computing device), the fuel integration controller 1202 may transmit the feedstock request to a procurement computing device, procurement controller, the user interface (which may include a procurement sub-routine or instructions), a procurement and distribution computing device, or other device.

Once the feedstock request has been delivered to the refinery 1220, at block 1138, the fuel integration controller 1202 may determine the actual CI for the selected one or more available feedstock and corresponding feedstock transportation pathway. The fuel integration controller 1202 may determine whether, in relation to the determined feedstock CI and feedstock transportation CI, the actual CI for either the selected one or more available feedstock and corresponding feedstock transportation pathway has increased. If an increase is determined, the fuel integration controller 1202, at block 1140, may select one or more different refinery processes, utilities, blending processes and/or fuel product distribution pathways to maintain the total CI, cost, and/or timeline of transportation fuel production, if such a selection is available. In another example, the fuel integration controller 1202 may send a prompt or notification to a user or user interface. Further, the prompt may include the available options or paths, such as one or more different refinery processes, utilities, blending processes, storage tanks, and/or fuel product transportation pathways. In such examples, the user may select the new options or paths to maintain the total CI (e.g., from the estimate audit report) or lower the total CI further. In another example, the user may choose to continue with the prior selections.

In response to the determination that the determined feedstock CI and feedstock transportation CI have not increased or in response to a selection of one or more different refinery processes, the fuel integration controller 1202 may, at block 1141, initiate any selected refinery process. In another example, the fuel integration controller 1202 may connect to a refinery controller and transmit the initiation to the refinery controller. The fuel integration controller 1202 may notify a user of the initiation of the refinery processes. In another example, the fuel integration controller 1202 may send a prompt to a user to initiate or confirm initiation of the refinery process.

In response to a reception of or determination of completion of the selected refinery process, at block 1142, the fuel integration controller 1202 may determine the actual CI for the selected refinery process and utilities. The fuel integration controller 1202 may determine whether, in relation to the determined refinery process CI and utility CI, the actual CI for the refinery process and utilities has increased. If an increase is determined, the fuel integration controller 1202, at block 1144, may select one or more different blending processes and/or fuel product distribution pathways to maintain CI, cost, and/or timeline of fuel production, if such a selection is available.

At block 1146, the fuel integration controller 1202 may initiate the transfer of the refined transportation fuel to a blending site. Once the refined transportation fuel and a low CI blending fuel are received at a blending site, the fuel integration controller 1202 may initiate the blending process at block 1148. In response to a reception of or determination of completion of the selected blending process, at block 1150, the fuel integration controller 1202 may determine the actual CI for the selected blending process. The fuel integration controller 1202 may determine whether, in relation to the determined blending process CI, the actual CI for the blending process has increased. If an increase is determined, the fuel integration controller 1202, at block 1152, may select one or more different fuel product distribution pathways to maintain CI, cost, and/or timeline of fuel production, if such a selection is available.

Once the blending process is complete or once a new fuel product distribution pathway is selected, the fuel integration controller 1202, at block 1154 may transmit a distribution request for the refined transportation fuel via the selected fuel product distribution pathway. The distribution request may include the refined transportation fuel and the selected fuel product distribution pathway. In another example, the fuel integration controller 1202 may transmit a request for confirmation of a distribution request of the refined transportation fuel to a user interface or a distribution computing device. In response to reception of the confirmation (e.g., from the user interface or distribution computing device), the fuel integration controller 1202 may transmit the feedstock request to a distribution computing device, distribution controller, the user interface (which may include a distribution sub-routine or instructions), a procurement and distribution computing device, or other device.

At block 1156, the fuel integration controller 1202 may determine the actual CI for the selected one or more available feedstock, the completed feedstock transportation pathway, the completed refinery operations including utilities, the completed blending process, and the completed fuel product distribution pathway. At block 1158, the fuel integration controller 1202 may determine the actual total CI. The actual total CI may be based on the actual refined product yield, the actual feedstock volume, and the actual CI for the selected one or more available feedstock, the completed feedstock transportation pathway, the completed refinery operations including utilities, the completed blending process, and the completed fuel product distribution pathway.

At block 1160, the fuel integration controller 1202 may generate and transmit an actual or final audit report to a user, user interface, database, and/or other device. The actual or final audit report may include the actual total CI and the actual CI for each process (e.g., the actual CI for the selected one or more available feedstock, the completed feedstock transportation pathway, the completed refinery operations including utilities, the completed blending process, and the completed fuel product distribution pathway). The fuel integration controller 1202 may generate the actual or final audit report based on a request from a user and/or user interface.

Figure 14A:
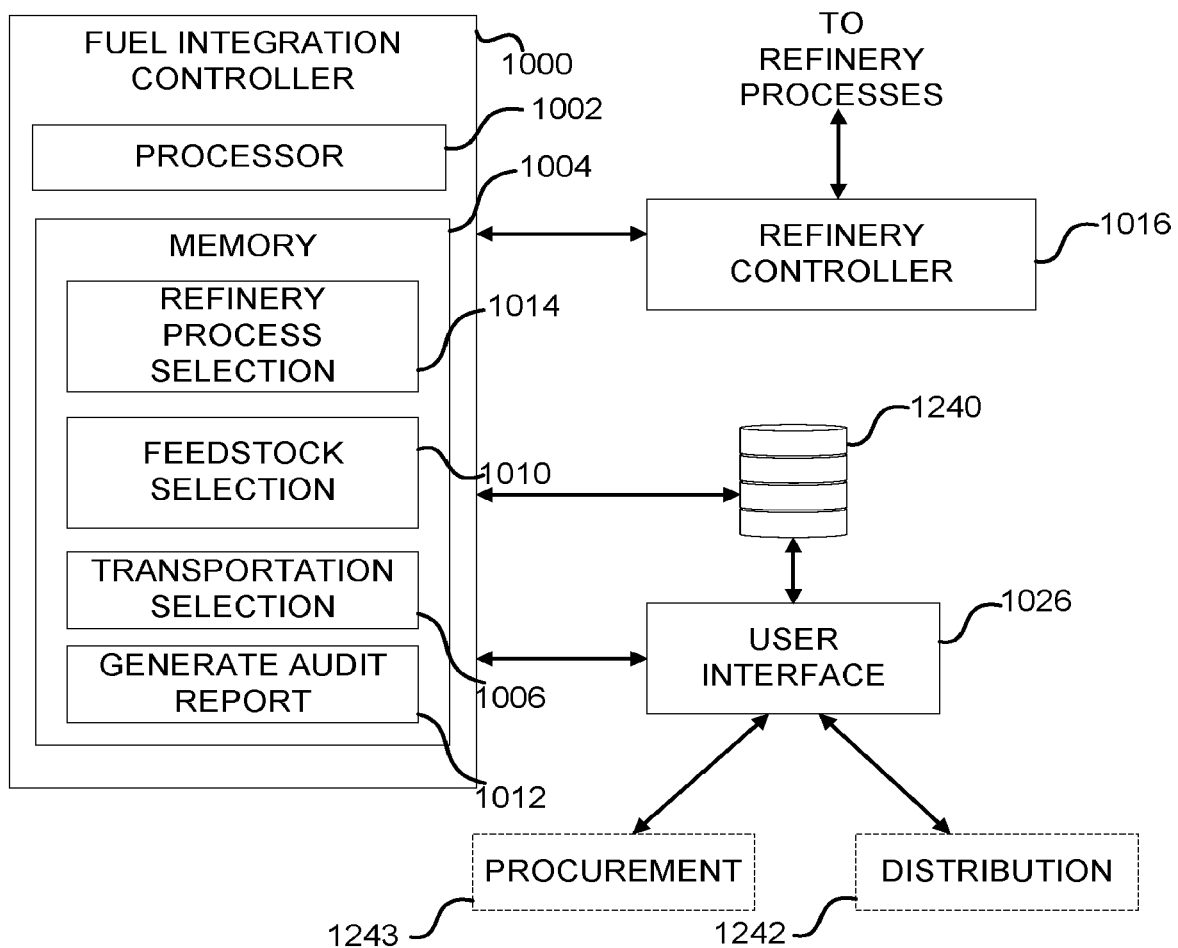
FIGS. 14A-B are simplified diagrams illustrating a control system for managing the low carbon intensity energy production according to an embodiment

FIG. 14A illustrates another simplified diagram illustrating a control system for managing the low carbon intensity energy production according to an embodiment. In such examples, rather than connecting to a procurement and distribution computing device, the fuel integration controller may connect to a user interface 1026. The user interface 1026 may connect to or include a procurement module 1243. For example, the procurement module 1243 may be a set of instructions included in the user interface to order feedstock from various feedstock sources. The procurement module 1243 may be a controller, computing device, server, and/or other device. The user interface 1026 may also connect to or include a distribution module 1242. For example, the distribution module 1242 may be a set of instructions included in the user interface 1026 to initiate delivery of refined product from a refinery to a convenience store (or other distribution point or terminal). The distribution module 1242 may be a controller, computing device, server, and/or other device. In such examples, the procurement module 1243 and distribution module 1242 may allow for order of feedstock, via specified transportation modes, and delivery of refined product, via specified transportation modes.

As noted above, the fuel integration controller 1000 may determine a combination of a selection of one or more feedstock, one or more feedstock transportation pathways, a selection of one or more refinery processes, a selection of one or more utilities, a selection of one or more blending processes, and a selection of one or more refined feedstock transportation pathways. The fuel integration controller 1000 may determine such a combination based on a determination of the feedstock CI (based on, for example, a ratio or blend of available feedstock volume and type), the feedstock transportation CI (based on available feedstock transportation delivery distance and fuel type), the refinery process CI (based on the type of refinery process, the volume and type of feedstock, the length of time of the refinery process, and/or the yield of the refinery process), the utility CI of one or more utilities (based on the type of utility utilized in the refinery process and the distance the utility travels to reach the refinery), the blending process CI of one or more blending processes (based on the type of blending process and a low CI blending fuels CI and volume), and/or refined product distribution CI (based on available refined product distribution delivery distance and fuel type). Other factors may be utilized in determining a combination, such as cost of each process, margin or profit based on a sale of the final product, availability, yield, and/or one-time costs (such as increasing refinery capacity or increasing efficiency of an aspect of the refinery).

In another example, the fuel integration controller 1000 may connect to a database 1240. The database 1240 may include various data points, such as available feedstock (and corresponding raw data), available transportation modes (and corresponding raw data), available storage tanks (and corresponding raw data), available refinery process (and corresponding raw data), and/or available utility options (and corresponding raw data). In another example, a user may update, via the user interface 1026, the data stored at the database 1240. In another example, the fuel integration controller 1000 may update the data at the database 1240, for example, based on reception of data from various controllers and/or computing devices. In another example, the fuel integration controller 1000 may store determined CIs, total CIs, and/or audit reports at the database, which other devices or user interfaces may access.

Figure 14B:
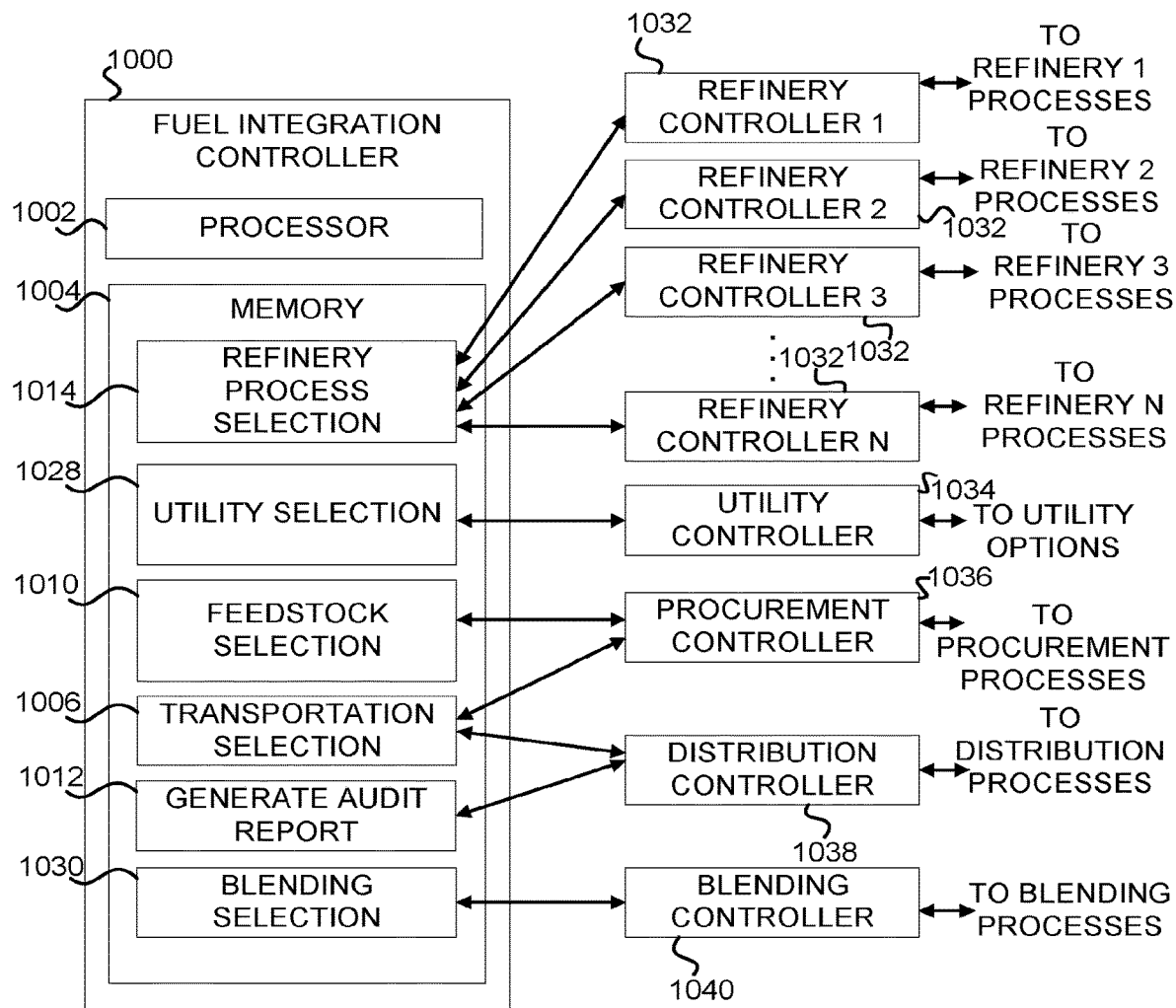

FIG. 14B illustrates another simplified diagram illustrating a control system for managing the low carbon intensity energy production according to an embodiment. In such examples, the fuel integration controller may connect to many different controllers, each controller to control a different process. In such examples, the fuel integration controller 1000 may be considered a supervisory or master controller. The fuel integration controller 1000 may connect to one or more refinery controllers 1032. Each refinery controller 1032 may be located at different and separate refineries. The fuel integration controller 1000 may further connect to other controllers located at a refinery, each of the controllers controlling different processes within the refinery (e.g., a controller for a cracker to control a cracking process).

Further, the fuel integration controller 1000 may connect to a utility controller 1034. The utility controller 1034 may control which utilities (e.g., wind, solar, RNG, geothermal, or conventional fuels) are used for a refinery process. Further, the utility controller 1034 may control or track utilities used in other processes of the transportation fuel production (e.g., the process of during obtaining or producing feedstock, transporting the feedstock, storing the feedstock, blending the refined transportation fuel, storing the refined transportation fuel, and/or transporting the refined transportation fuel).

Further still, the fuel integration controller 1000 may connect to a procurement controller 1036 and/or a distribution controller 1038. The fuel integration controller 1000 may transmit requests for delivery of feedstock to a refinery (e.g., including a selected feedstock and transportation pathway). The fuel integration controller 1000 may transmit requests for delivery of refined transportation fuel to a convenience store, distribution point, or terminal (e.g., including a refined transportation fuel and distribution pathway). The fuel integration controller 1000 may also transmit an audit report to the distribution controller 1038, corresponding to a refined transportation fuel. The fuel integration controller 1000 may also connect to a blending controller 1040. The fuel integration controller 1000 may conduct a blending selection 1030 based on the available refined products, fuels (e.g., biodiesel, ethanol), additives and/or blending agents and transmit such blending selection 1030 to one or more of the refined products storage, distribution mode, terminal/distribution point, and retail outlet to prepare the blend accordingly.

TABLE I

Fuel Production Case Study

|  | Base Case | Study Case 1 | Base Delta | Study Case 2 | Base Delta |
|---|---|---|---|---|---|
| Threshold CI, gCO$_2$/Mj | 100 | 90 | −10 | 90 | −10 |
| Margin, SIB | 11.00 | 6.75 | −4.25 | 7.25 | −3.75 |
| Crude 1, BPD (Low CI) | 17,000 | 30,000 | +13,000 | 50,000 | +33,000 |
| Crude 2, MBPD (Mid CI) | 0 | 60,000 | +60,000 | 29,000 | +29,000 |
| Crude 3, BPD (High CI) | 83,000 | 10,000 | −73,000 | 21,000 | −62,000 |
| Gas Yield, BPD | 57,000 | 63,000 | +6,000 | 64,000 | +7,000 |
| Diesel Yield, MBPD | 41,000 | 35,000 | −6,000 | 34,000 | −7,000 |
| Jet Yield, MBPD | 2,000 | 2,000 | 0 | 1,000 | +2,000 |
| CO2 Emissions, Mg/Day | 53,000 | 47,000 | −6,000 | 47,000 | −6,000 |
| CO2 Abatement Cost, $/Mg | — | — | 70 | — | 63 |

Table I will now be described with respect to three prophetic examples. In the base case, a LCFS may specify that a refined transportation fuel have a CI of no more than 100 gCO2/MJ. Thus, a user may enter, at the user interface 1026, a threshold CI of 100 (Table I). Three different types of feedstock (in this case, crude oil) may be available, crude 1 (with a low CI, e.g., crude that may be obtained from fracked shale), crude 2 (with a mid-level CI, e.g., an imported crude), and crude 3 (with a high CI, e.g., crude that may be obtained from tar sands). Each crude oil may have a corresponding available volume that is a constraint to the use thereof. For example, crude 1 may correspond to a volume capable of providing, at least, 30,000 barrels per day (BPD), crude 2 may correspond to a volume capable of providing, at least, 60,000 thousand BPD (MBPD), and crude 3 may correspond to a volume capable of providing, at least, 83,000 BPD. In such examples, after the user enters a threshold CI of 100 at the user interface 1026 or after the fuel integration controller 1000 determines or obtains the threshold CI, the fuel integration controller 1000 may determine a path, combination, variation, or selections of one or more of the feedstock, a feedstock transportation pathway, a refinery process, utilities for the refinery process, and/or a fuel product distribution pathway. The determination may be based on one or more blends of the three crudes CI (for example, and as shown on Table I, 17% crude 1, 0% crude 2, and 83% crude 3). However, the carbon intensities of each component of the blend may be considered for each of: the corresponding available feedstock transportation pathways, the corresponding available refinery processes, the corresponding available utilities, and/or the corresponding refined product distribution. Other considerations or constraints may include the cost of each combination, the margin associated with each combination, and/or time of availability (either of the specific crude at the refinery, of the refined product to the end user location, etc.). In such examples, the CI for the components noted above may correspond to different values based on the various factors described in the present disclosure. The fuel integration controller 1000 may determine a total CI for a particular refined transportation fuel, such as diesel, gasoline, and/or jet, based on the total CI of each crude (represented as CI1, CI2, CI3, etc.), or in other words, the sum of each CI for each refined component of a particular crude. In this example, a determination of the total CI for diesel is described, however, those skilled in the art will understand that the determination may be readily made for any other refined transportation fuel. The fuel integration controller 1000 may determine the total CI for each selected crude and the associated CIs for producing and providing the diesel from each crude (e.g., crude 1 total CI for diesel (CR1D), crude 2 total CI for diesel (CR2D), and crude 3 total CI for diesel (CR3D)). The fuel integration controller 1000 may then determine the product of the CI and the volume of an associated refined product. In an example, prior to determining the product of the CI and the volume of the associated refined product, the fuel integration controller may convert the CI to grams of $CO_2$ utilizing the standard energy of a barrel of oil (BOE), as will be understood by those skilled in the art. The fuel integration controller 1000 may then determine the total CI for producing and providing the diesel, based on crude total CI for diesel for each selected crude, the yield for diesel via the refinery process per the selected crude volume (in other words, the percentage of refined transportation fuel, such as diesel, based on the yield of the refined transportation fuel per the amount of crude feedstock (YD %)) and the volume of each selected crude (V), the equation represented below. While the equation below does not include the unit conversions based on standard energy of a barrel of oil (BOE), it is understood by those skilled in the art that such unit conversions may be used in the calculation of total CI:

$$\frac{(CR1D \times V1 \times YD1\%) + (CR2D \times V2 \times YD2\%) + (CR3D \times V3 \times YD3\%)}{(YD1\% \times V1) + (YD2\% \times V2) + (YD3\% \times V3)}$$

For the present example, and with respect to diesel yield, the fuel integration controller 1000 may determine total diesel CI based on the CI of crude 1 and crude 3, CI of the crude 1 transport and the crude 3 transport, CI of the crude 1 refinery process and crude 3 refinery process (including utilities), CI of a diesel distribution pathway, the volume of crude 1 and crude 3, and the diesel yield of crude 1 and crude 3. The fuel integration controller 1000 may determine total CI for gasoline and jet in the same manner, except substituting gasoline distribution pathways and yield and jet distribution pathways and yield, respectively. For the base case that satisfies the LCFS CI limitation, the selected path, combination, variation, or selection, may include 17,000 BPD of crude 1, zero barrels of crude 2, and 83,000 BPD of crude 3, which provides a margin of approximately 11 dollars per barrel. The refined transportation fuel of this base case has a determined carbon emission of 53,000 Mg per day. Further, the selected crude blends of the base case may have a gas yield of 57,000 BPD, a diesel yield of 41,000 BPD, and a jet yield of 2,000 BPD.

In the second example (Study Case 1 of Table I), a user may input a lower threshold CI than what is specified by the LCFS or by some other low CI fuel specification. For example, a user may enter a threshold CI of 90% of the maximum allowed CI. While a lower threshold CI may be entered, various combination blends of crude oils, based on availability and/or capacity of downstream processing options (e.g., feedstock, transportation, etc.), may exceed the threshold CI. For example, refining capacity may severely limit the number of blends of crudes that will meet the threshold CI. For this Study Case 1, the user may enter the threshold CI of 90 at the user interface 1026. The fuel integration controller 1000 may perform the same processes as described above. After these determinations, the fuel integration controller 1000 may select a blend of 30,000 BPD of crude 1, 60,000 BPD of crude 2, and 10,000 BPD of crude 3. Here, the refining capacity of crude 1 is limited to 30,000 BPD. Working within this constraint, the fuel integration controller 1000 nonetheless maximizes the selection of crude 1 at 30,000 BPD, while compensating for this constraint by including crude 2 into blend. Previously, in the base case, no amount of crude 2 was used. Here in Study Case 1, the margin, approximately 6.75 dollars per barrel, may be lower than in the base case, but the CI may be lower as well. In fact, the crude blend of Study Case I may reduce carbon emission by as much as 6,000 Mg per day relative to the base case. This crude blend alters the refined product yield such that gasoline has a yield of 63,000 BPD, diesel has a yield of 35,000 BPD, and jet yield has a yield of 2,000 BPD. Specific refined product yields may also have constraints that are to be considered by fuel integration controller 1000.

In the third example (Study Case 2 of Table I), the fuel integration controller 1000 may consider other factors when determining a crude selection or combination. For example, a user may permit the fuel integration controller 1000 to increase the capacity of one or more refinery processing units at a one-time capital cost. Such a factor—alleviating refining processing unit bottlenecks—may be considered when determining possible paths to achieve the target CI threshold. Further, such refinery capacity constraints may be specific to a particular type of crude, e.g., low CI crude. As provided in Table I, Study Case 2 has a threshold CI of 90, which is the same as Study Case 1 and represents a 10% reduction in CI as compared to the base case. Here, however, the fuel integration controller 1000 may consider selecting a crude blend with the possible amount of crude 1 limited to 50,000 BPD (rather than 30,000 BPD with respect to Study Case 1). Obviously, increases in the amount of crude 1 above 30,000 BPD will require a capital expenditure to debottleneck this design constraint. After the determinations described above, the fuel integration controller 1000 selected 50,000 BPD of crude 1, 29,000 BPD of crude 2, and 21,000 BPD of crude 3. Again, the fuel integration controller 1000 maximized the use of crude 1, even at the higher constraint of 50,000 BPD. This crude selection, in conjunction adding refinery capacity for crude 1, may yield gasoline at 64,000 BPD, diesel at 34,000 BPD, and jet fuel at 1,000 BPD. Further, the calculated margin of approximately 7.25 dollars per barrel, is much increased over the margin of Study Case 1 even while reducing the carbon emission the same as in Study Case 1. Moreover, this increase in margin, provides an estimated payback period of 2.5 years for the capital expenditure to increase refining capacity.

FIGS. 16A-F are block diagrams of a system for managing the low carbon intensity energy production according to an embodiment. As described above, a fuel integration controller 1301 may be utilized to manage low carbon intensity (CI) production. For example, a fuel integration controller 1301 may include an input/output in signal communication with procurement data storage 1302, procurement computing device, procurement and distribution computing device, and/or a database. The procurement data storage 1302 may store and send lists of available feedstock, from various and multiple fuel sources 1316, such as from a plant or animal derived feedstock 1318 source or from a wellhead 1320, to the fuel integration controller 1301. The procurement data storage 1302 may include other data corresponding to each of the available feedstock (e.g., volume, availability, type, location, etc.). Further, the procurement data storage 1302 may store a list of associated feedstock transportation pathways 1305 and data corresponding to each feedstock transportation pathway 1305 (e.g., volume of the feedstock transportation pathway 1305, type of fuel consumed by the feedstock transportation pathway 1305, etc.). In an example, the procurement data storage 1302 may gather the data directly or indirectly from each fuel source 1316. For example, a controller 1310, sensor, or some other device, may transmit the data to the procurement data storage 1302 and thus to the fuel integration controller 1301. In another example, a user may, via the user interface 1306, gather the data and store the data at the procurement data storage 1302 or another database. In another example, the fuel integration controller 1301 may include the functionality of the procurement data storage 1302. In other words, rather than including both a separate procurement data storage 1302 and fuel integration controller 1301, the system may only include the fuel integration controller 1301.

Figure 16A:
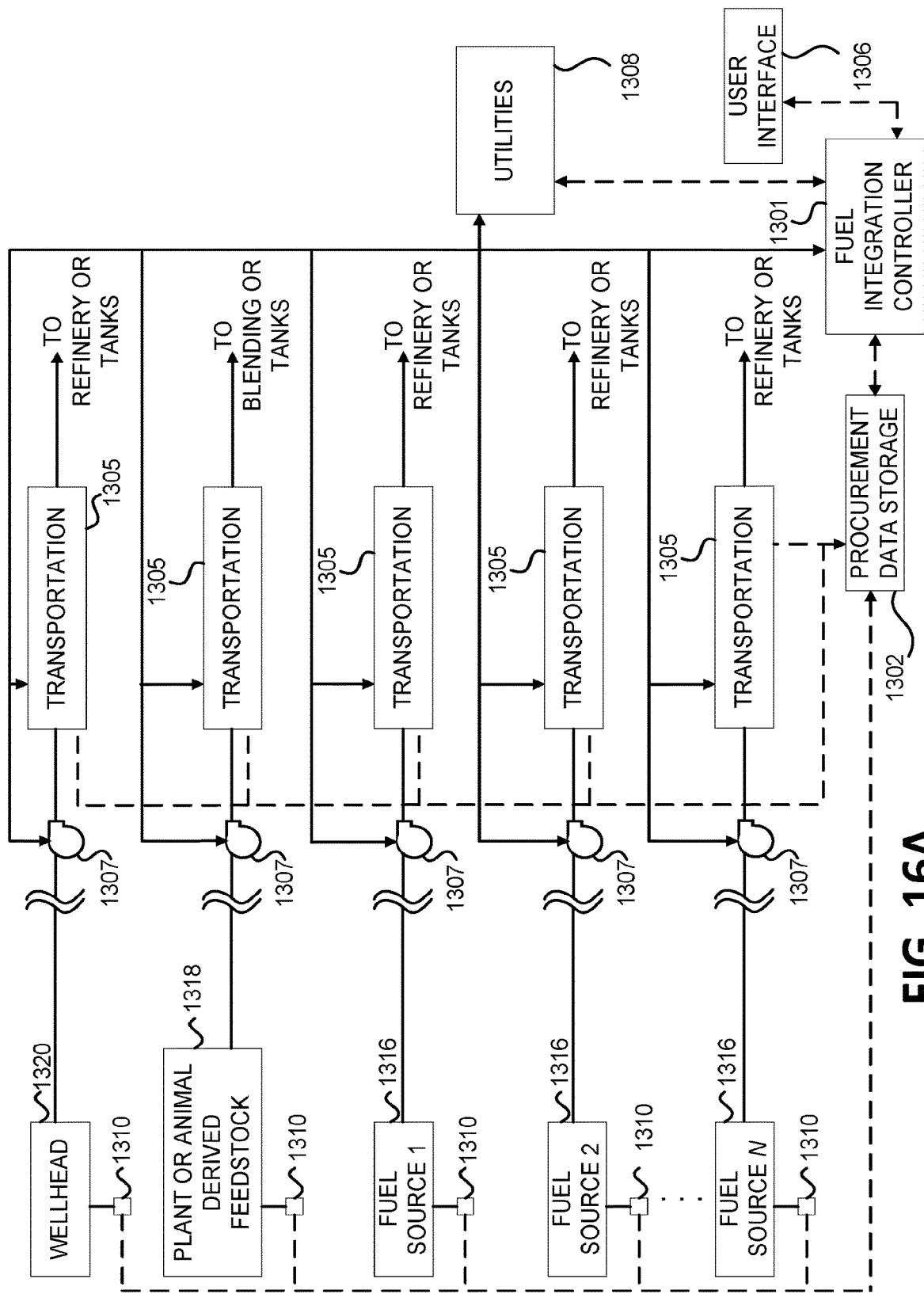
FIGS. 16A-F are block diagrams illustrating a system for managing the low carbon intensity energy production according to an embodiment.
Figure 16B:
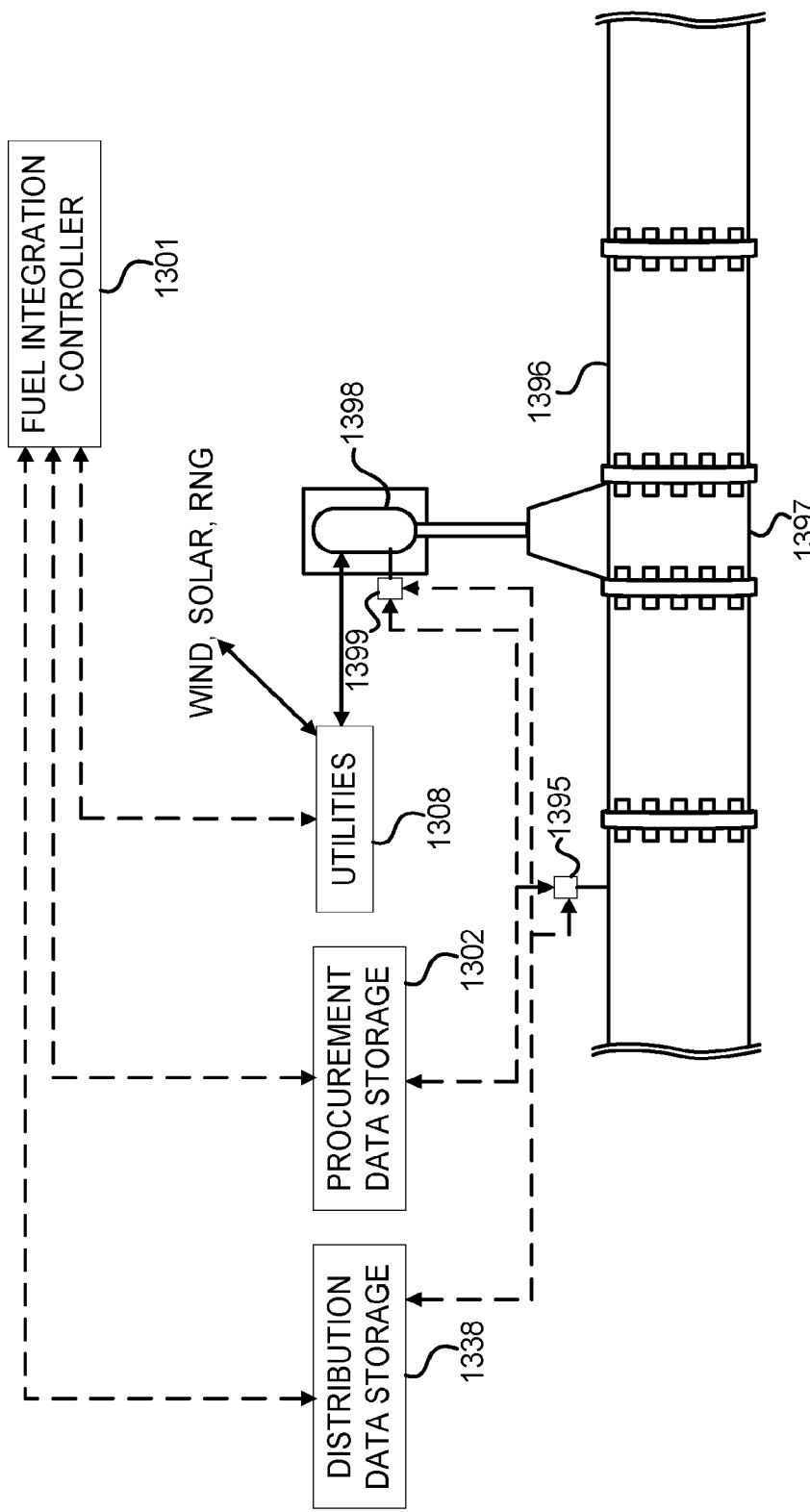

In an embodiment, one pathway or method of transportation/distribution may include a pipeline 1396 (as illustrated in a top-down view in FIG. 16B). The pipeline 1396 may transport fuel from one point to another via motor 1398 driven pumps 1397 located at varying lengths along the pipeline 1396. Other pumps and/or motors or engines may be utilized by the pipeline 1396, as will be understood by those skilled in the art. The pipeline 1396 may include a controller or sensor 1395 and the motor 1398 may include a controller 1399 or sensor. In such examples, utilities 1308 may be provided to the motor 1398 to drive the pump 1397 (and thus move fluid through the pipeline 1396). The utilities 1308 may include low CI and renewable options, such as solar electricity, wind generated electricity, RNG, and/or other renewable fuels. Other information from the pipeline's 1396 controller or sensor 1395 and the motor's 1398 controller 1399 or sensor may be sent to the procurement data storage 1302 and distribution data storage 1338. Such information may include a total length of the pipeline 1396, the diameter of the pipeline 1396, the number of pumps 1397, the start and end point of the pipeline 1396, and other information as will be understood by those skilled in the art. The information may be sent, through either the distribution data storage 1338, the procurement data storage 1302, or directly, to the fuel integration controller 1301.

The data received from each fuel source may allow for the fuel integration controller 1301 to choose a fuel source (in other words, a feedstock from a fuel source) that may lower overall carbon emissions based on CI and other factors. For example, a plant or animal derived feedstock 1318 may be environmentally friendly, as it is renewable, but may require a longer shipment to be delivered to customers who need such a fuel. In such examples, the longer shipment may balance out the benefit of a renewable resource in relation to the detriment of the shipment method. Such a balance may be reflected in the CI for the plant or animal derived feedstock 1318.

The fuel integration controller 1301 may further include an input/output in signal communication with a user interface 1306. The fuel integration controller 1000 may be configured to receive inputs from user interface 1306. A user may enter a threshold CI into the user interface 1306. The threshold CI may correspond to a particular transportation fuel production process. The user may enter information, other than the threshold CI, regarding the particular fuel production process. For example, a user may enter or input a low CI fuel specification. The low CI fuel specification may include the threshold CI, a maximum cost associated with the fuel production process, a type of refined product desired, and/or at least one type of feedstock to be utilized.

Figure 16C:
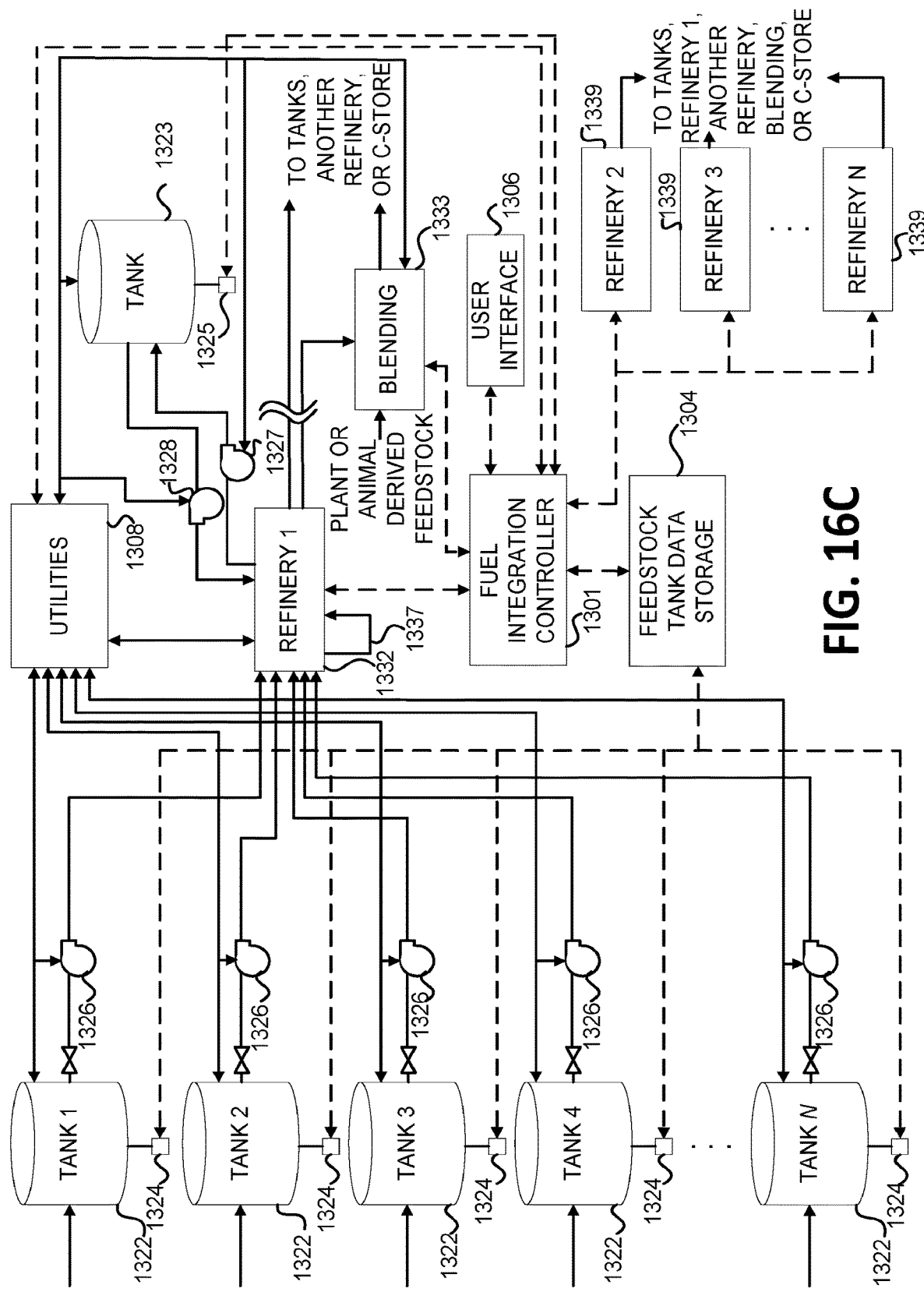

Turning to FIG. 16C, and as noted above, feedstock storage tanks 1322 may be utilized. Such feedstock storage tanks 1322 may contain feedstocks obtained from several sources, including but not limited to intermediate products, e.g., naphtha, from other refineries. Further, each feedstock storage tank 1322 may include a controller 1324. The controller 1324 may transmit data related to a feedstock storage tanks 1322 to feedstock tank data storage 1304, a database, and/or the fuel integration controller 1301. The data sent from controller 1324 may include the power utilized to pump, via pumps 1326, a feedstock to the refinery 1332, the power utilized to heat or cool the feedstock in the feedstock storage tank 1322, a volume of the feedstock at the initial point of storage, a volume of the feedstock as the feedstock is pumped from the feedstock storage tank 1322, and/or an emissions associated with the feedstock. The fuel integration controller 1301 may request the data from the feedstock tank data storage 1304. Other tanks, such as tank 1323 (or more tanks) may be included at or near refinery 1332. Fuels and/or various other components from refinery processes may be pumped to tank 1323. During certain refinery processes the fuels and/or various other components may be pumped back to the refinery for use. The fuels and/or various other components may be low CI fuels and, when used in future refinery processes, may further reduce total CI of a transportation fuel production. In another example, such fuels and/or other components may be recirculated, at 1337, through refinery 1332 to be utilized immediately or soon in a refinery process or sub-process.

Figure 16D:
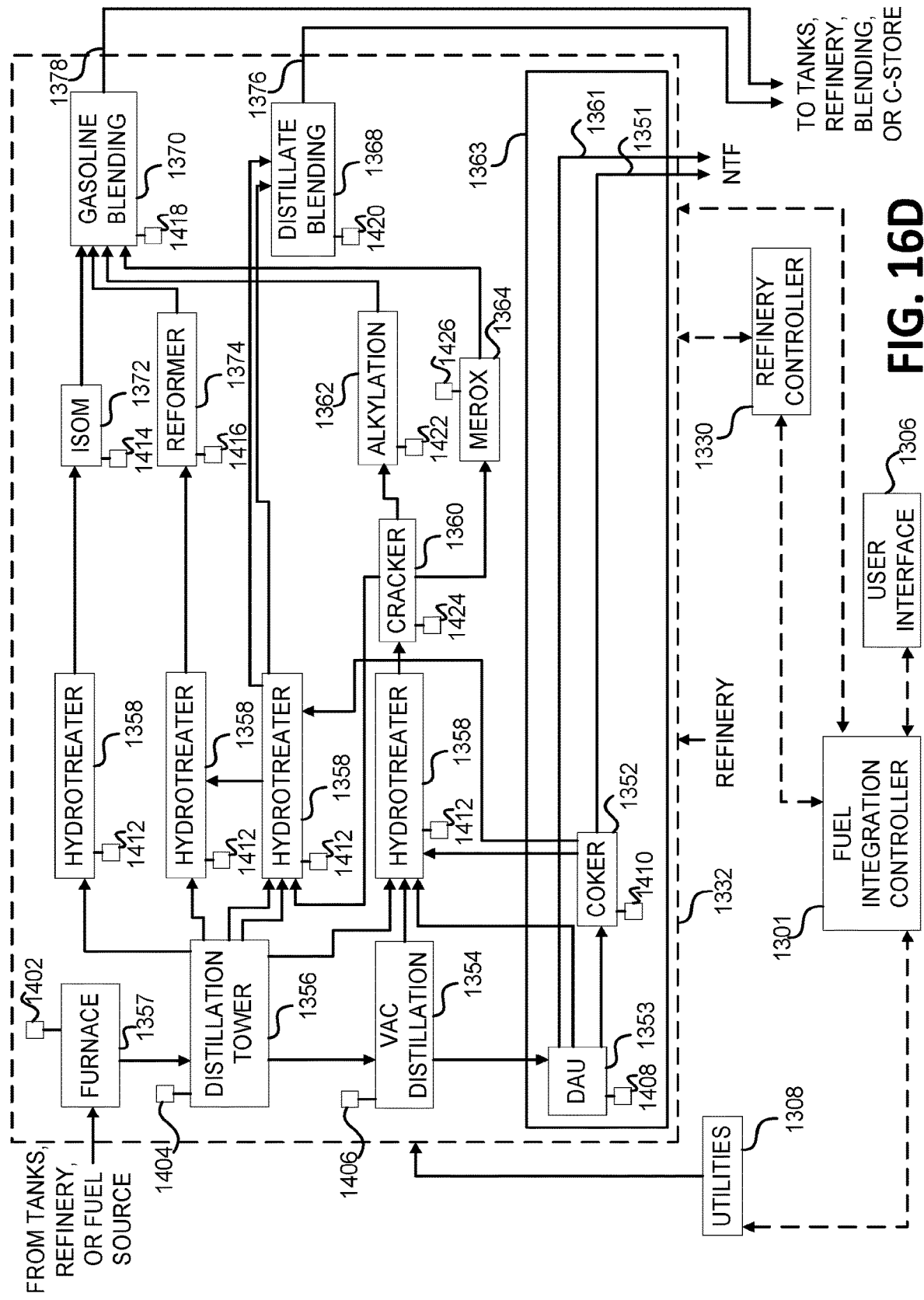
Figure 16E:
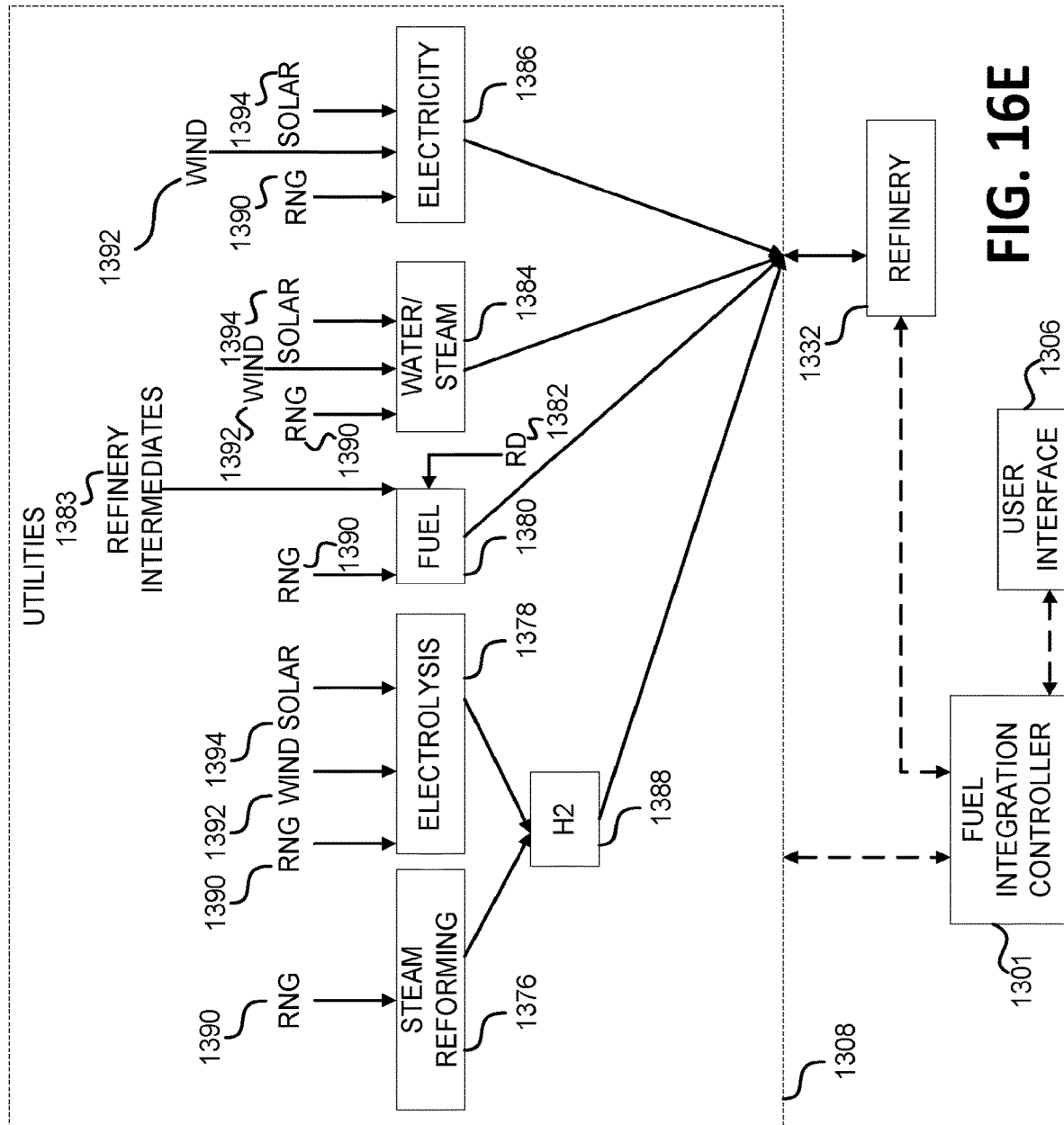
Figure 16F:
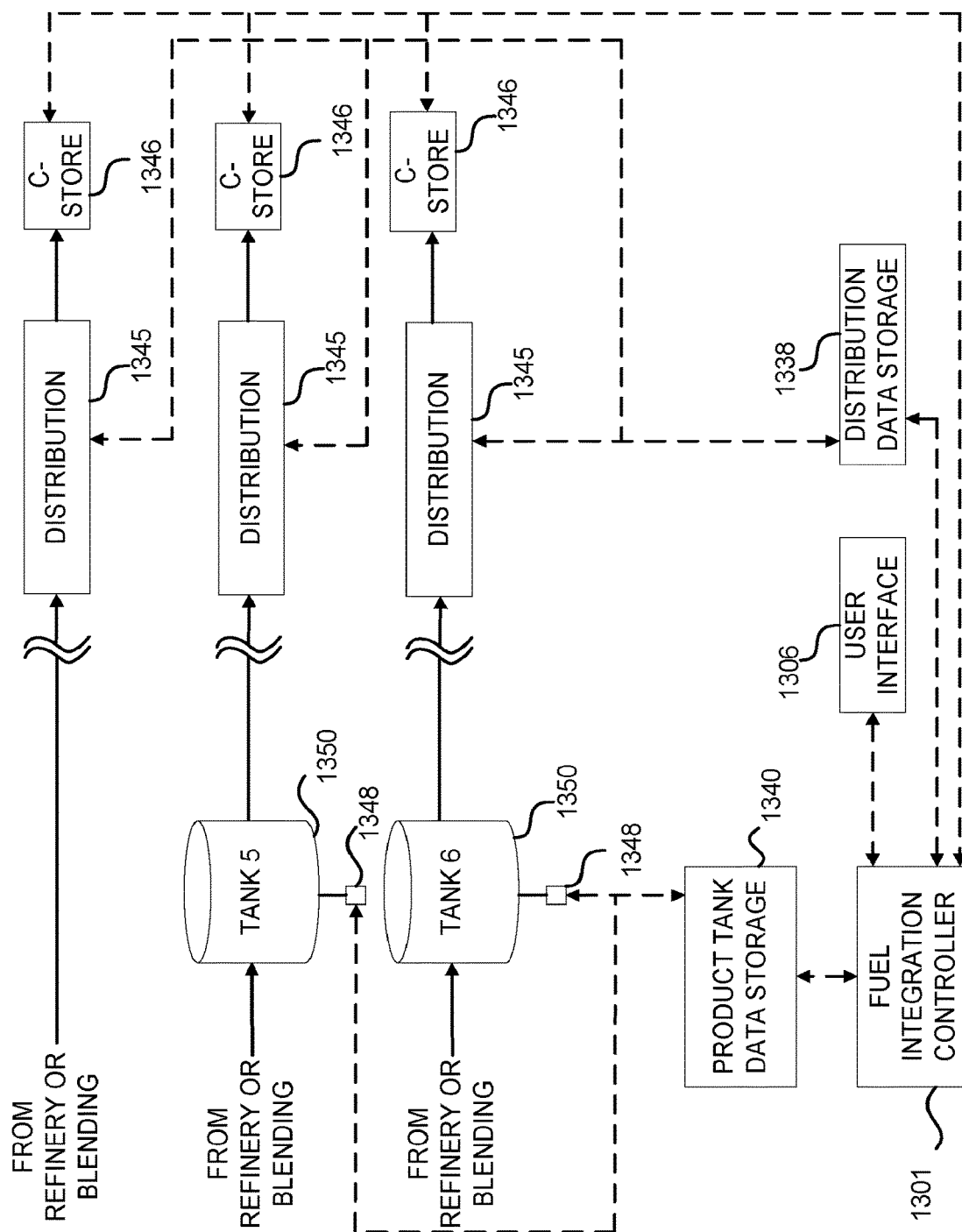
Figure 17:
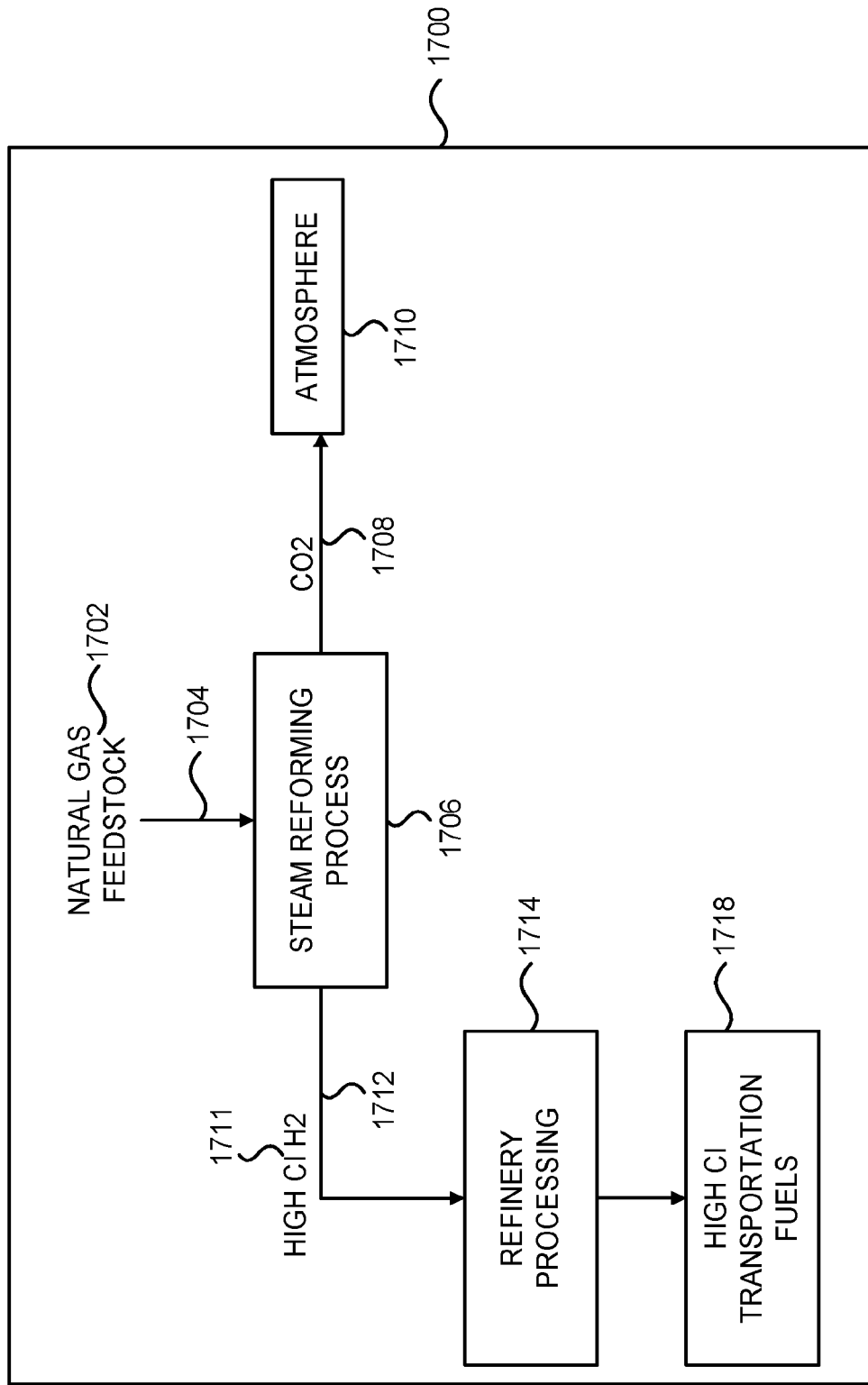
FIG. 17 is a simplified diagram that illustrates a typical implementation of a hydrogen production strategy in which higher carbon intensity hydrogen is provided to a refinery to produce a high carbon intensity transportation fuel provided to the end user via a distribution chain.

Turning to FIG. 16D, the fuel integration controller 1301 may include an input/output in signal communication with a refinery controller at the refinery 1332. The fuel integration controller 1301 may request data from the refinery 1332 or refinery controller 1330. For example, the fuel integration controller 1301 may receive a list of available refinery processes from the refinery 1332 or refinery controller 1330 as well as data corresponding to each refinery process (e.g., time to process a feedstock, yield for process, etc.). The fuel integration controller 1301 may, rather than connecting to the refinery controller 1330 include the functionality of the refinery controller 1330. The fuel integration controller 1301 or refinery controller 1330 may control various components and/or processes within the refinery 1332. The fuel integration controller 1301 or refinery controller 1330 may connect to a furnace/crude heater controller 1402 to control and/or determine a fuel (e.g., RNG or another suitable fuel as will be understood by those skilled in the art) and temperature for a furnace/crude heater 1357 to heat an incoming feedstock. The heated incoming feedstock may flow to a distillation tower 1356, where different components of the feedstock may be separated. The fuel integration controller 1301 may connect to a distillation tower controller or sensor 1404 to control or monitor the distillation process. A portion may flow to vacuum distillation tower 1354. The vacuum distillation tower 1354 may separate the portion it receives further. The fuel integration controller 1301 may connect to the vacuum distillation tower controller or sensor 1406 to control or monitor the vacuum distillation process (e.g., such as controlling pressure and/or fuel used). A section 1363 of the refinery 1332 may be utilized to produce or refine non-transportation fuels, such as asphalt 1361 and/or petroleum coke 1351. The section 1363 may include a de-asphalter unit (DAU) 1353 and a coker 1352. In such examples, another portion from the vacuum distillation tower 1354 may be sent to the DAU 1353 to separate asphalt from the portion flowing to the DAU 1353. The DAU 1353 may include a DAU controller 1408 or sensor to connect to the fuel integration controller 1301 to control or monitor the DAU 1353. From the DAU 1353, a portion may be output as asphalt 1361 and another portion, for example, pitch, may be sent to the coker 1352. The coker 1352 may output petroleum coke 1351 and other gases/oils to other components of the refinery 1332. The fuel integration controller 1301 may connect to a coker controller 1410 or sensor to control or monitor the coker 1352. In another example, various hydrotreaters 1358 may desulfurize various portions of distillate or other portions (e.g., light naphtha, heavy naphtha, kerosene, distillate, and/or other fluids as will be understood by those skilled in the art) from the distillation tower 1356, the vacuum distillation tower 1354, the DAU 1353, and the coker 1352. For example, light naphtha from the distillation tower 1356 may flow to a hydrotreater 1358 for desulfurization. The fuel integration controller 1301 may connect to a hydrotreater controller 1412 to control the desulfurization process (e.g., type of fuel used in the process, temperature, and pressure). The refinery 1332 may include other components, such as an isomerization unit 1372 (e.g., to convert linear molecules to higher octane branched molecules) and isomerization controller 1414, a reformer 1374 (e.g., to convert desulfurized naphtha molecules into higher-octane molecules and to produce reformate) and reformer controller 1416, a cracker 1360 (e.g., to upgrade heavy residual oil, by thermally cracking, to a lighter and reduced viscosity fluid) and cracker controller 1424, a merox unit 1364 (e.g., to desulfurize liquefied gas, kerosene, or jet fuel) and merox controller 1426, an alkylation unit 1362 (e.g., to produce high-octane components for gasoline blending) and alkylation controller 1422, gasoline blending unit 1370 (e.g., to produce regular gasoline, premium gasoline, blend grade gasoline, and/or other types of gasoline 1373, as will be understood by those skilled in the art) and gasoline blending controller 1418, and a distillate blending unit 1368 (e.g., to produce kerosene, jet, diesel, or other distillate fuels 1371, as will be understood by those skilled in the art) and distillate blending controller 1420. Each of the components or devices described above and herein may be referred to as refinery equipment. Different groups or selections of each of the components or devices may be referred to as a refinery processing unit to perform refinery processes (e.g., refine a refinery feedstock). For example, a refinery processing unit may include a distillation tower 1356, a hydrotreater 1358, a reformer 1374, a blending unit, and/or other additional or different components. As noted, the fuel integration controller 1000 or refinery controller 1330 may control each of the various components or units of the refinery 1332 listed above, such as by selecting a particular process for a component or unit, determining utilities to power each component or unit, reducing units used in a transportation fuel production, increasing capacity of various units, determining efficient temperatures and/or pressure at which to operate different components or units (e.g., operating a cracker 1360 at a specified temperature and/or pressure), and/or other improvements or controls, as will be understood by those skilled in the art.

As noted above, several outputs from a refinery 1332 may include non-transportation fuels or products. As noted, asphalt 1361 and/or petroleum coke 1351 may be products of the refinery 1332. The asphalt 1361 and petroleum coke 1351, or other products of the refinery 1332, may also include a total CI based on the feedstock CI, the feedstock transportation CI, the refinery process CI, the utility CI, and/or any distribution process CI associated with the asphalt 1361 and petroleum coke 1351. Further, the total CI of the asphalt 1361 and petroleum coke 1351 may be based on the yield of the asphalt 1361 or petroleum coke 1351, respectively. In other words, the total CI for any transportation or non-transportation fuel may be based on the portion or ratio of the CI associated with that particular transportation or non-transportation fuel, including products like asphalt 1361, petroleum coke 1351, and/or other construction products output by the refinery 1332 as will understood by those skilled in the art.

The fuel integration controller 1301 may further be connected to other refineries 1339. The fuel integration controller 1301 may, to further lower CI for a particular transportation fuel production, request refined transportation fuels or other refined fuels from the other refineries 1339 to be sent to tanks for storage, refinery 1332, to other refineries, to blending 1333, and/or directly to a convenience store.

The fuel integration controller 1301 may include an input/output in signal communication with a blending controller as well. The fuel integration controller 1301 may request data from the blending controller controlling blending operations. The fuel integration controller 1301 may consider any CI associated with the blending operation, when determining a set of paths, combinations, or selections for a fuel production process.

In another example, the fuel integration controller 1301 may include an input/output in signal communication with a utility controller. The fuel integration controller 1301 may request data from utilities 1308 or a utility controller at utilities 1308. In another example, the refinery 1332 may include utility data or control utility options (e.g., the source of utilities used at the refinery). The utilities 1308 data may include a list of available utilities, the source of each utility, and/or a CI associated with obtaining the utilities 1308. The utilities may provide hydrogen 1388 to a refinery via either steam reforming 1376 (provided a RNG 1390) and/or electrolysis 1378 (provided either a RNG 1390, wind power 1392, and/or solar power 1394) and/or by separation for hydrogen from refinery gas streams, e.g., via membrane or pressure swing adsorption. The utilities 1308 may provide fuel 1380 (from a RNG 1390, refinery intermediates, or RD) to the refinery 1332. The utilities may provide water/steam 1384 (created by a RNG 1390, wind power 1392, and/or solar power 1394) or electricity 1386 (from a RNG 1390, wind power 1392, and/or solar power 1394) to the refinery 1332. The utilities 1308 may further provide power to pumps 1307, 1326 throughout the transportation fuel production or, at least, the fuel integration controller 1301 may track power associated with pumps 1307, 1326 utilized throughout the transportation fuel production (in relation to the utilities CI). The utilities 1308 may further provide power to feedstock transportation pathways 1305 or, at least, the fuel integration controller 1301 may track power associated with feedstock transportation pathways 1305 (e.g., power for additional pumps utilized in a pipeline).

As noted above, a refined product storage tank 1350 may be utilized. Further, each refined product storage tank 1350 may include a controller 1348. The controller 1348 may transmit data related to a refined product storage tank 1350 to product tank data storage 1340, a database, and/or the fuel integration controller 1301. The data sent from controller 1348 may include the power utilized to pump a refined product from the refined product storage tank 1350, the power utilized to heat or cool the refined product in the refined product storage tank 1350, a volume of the refined product at the initial point of storage, a volume of the refined product as the refined product is pumped from the refined product storage tank 1350, and/or an emissions associated with the refined product. The fuel integration controller 1301 may request the data from the product tank data storage 1340.

The fuel integration controller 1301 may include an input/output in signal communication with distribution data storage 1338, a distribution computing device, a procurement and distribution computing device and/or a database. The fuel integration controller 1301 may request data from a distribution data storage 1338. The distribution data storage 1338 may include a list of available fuel product distribution pathways 1345 and corresponding data. The corresponding data may include a volume of the fuel product distribution pathways 1345, a type of fuel consumed by the fuel product distribution pathway 1345, and/or a location of convenience stores 1346.

The fuel integration controller 1301 may include an input/output in signal communication with a convenience store 1346 or data storage including convenience store data. The data may include demand for a particular low CI fuel or low CI fuels in general. The fuel integration controller 1301 may base selections further on demand for the particular low CI fuel. The fuel integration controller 1301 may set a threshold CI based on demand for a particular low CI fuel (e.g., the fuel integration controller 1301 may use a threshold CI of 90 if demand for a fuel with a CI of 90 is high).

As illustrated, the fuel integration controller 1301 may choose options for a fuel throughout the fuel production process (e.g., from the fuel source to the refinery 1332 to the customer). In another example, the selections noted above may be made prior to any process actually starting, such as, creating a plan for a future fuel production process. For example, a fuel integration controller 1301 may create a plurality of fuel production process plans based on a set of specifications and/or requirements. The fuel integration controller 1301 may then send a request for the user to accept one of the plans or adjust a plan as needed. In another example, the selections may be made sequentially or as the fuel production process is occurring. For example, a user or the fuel integration controller 1301 may select the feedstock and feedstock transportation pathway. The user or the fuel integration controller 1301 may not select the refinery process until the feedstock has arrived at the refinery 1332, and so on. In yet another example, the fuel integration controller 1301 may create and select a plan, as well as initiate the fuel product process (with or without confirmations from a user). Further, the fuel integration controller 1301 may adjust a plan as the actual transportation fuel production process is occurring.

Figure 18:
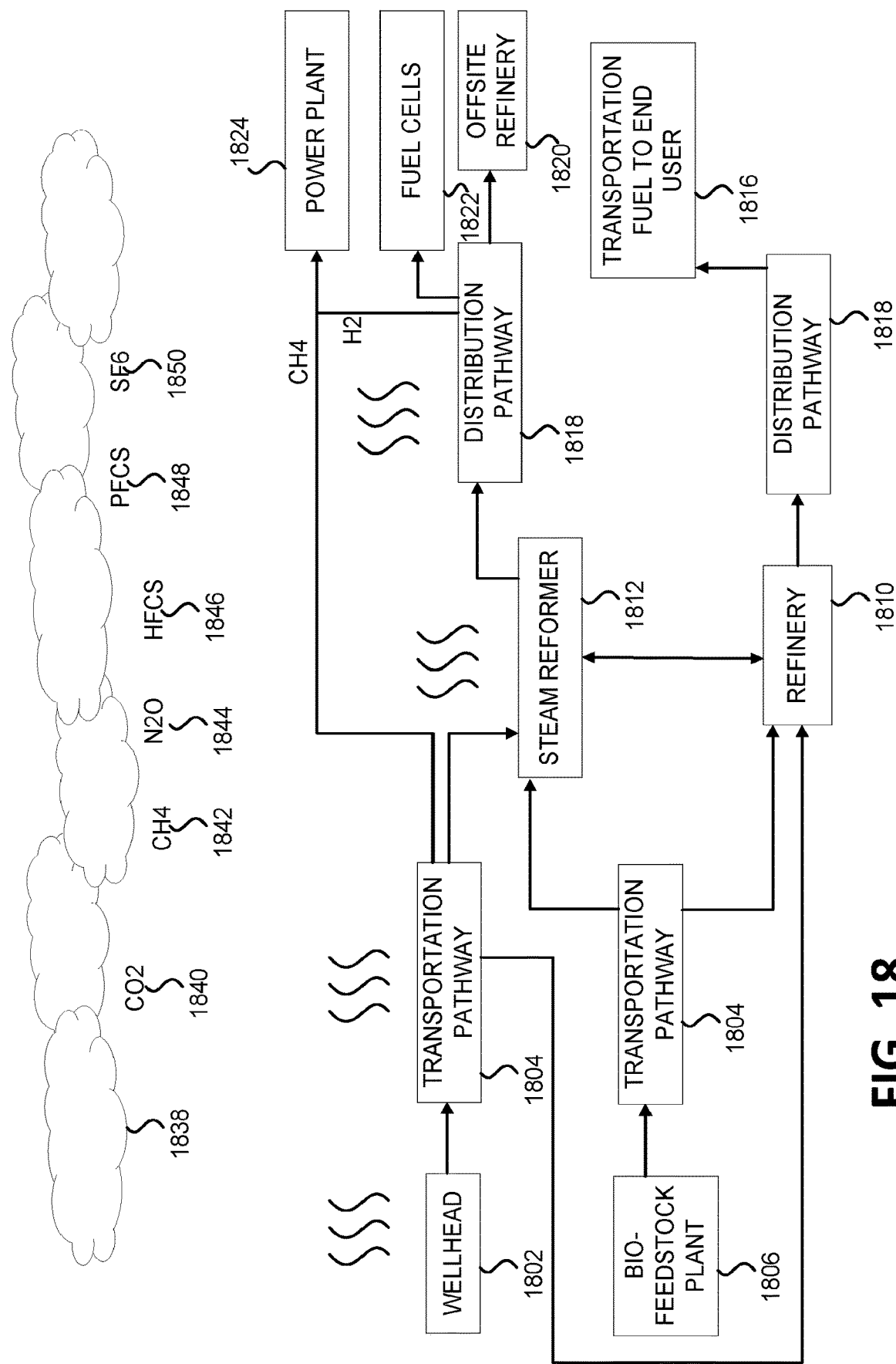
FIG. 18 is a diagram illustrating one or more embodiments that reduce carbon intensity from feedstock procurement to hydrogen delivery to various end user locations according to an embodiment.

FIG. 18 is a diagram illustrating one or more embodiments that reduce carbon intensity from feedstock procurement to hydrogen delivery to various end user locations according to an embodiment. Further, FIG. 18 illustrates, as noted above and as disclosed in one or more embodiments of the present disclosure, a more holistic approach to reducing carbon intensity, as well as limiting emission of certain chemicals into the atmosphere 1838. Chemicals introduced into the atmosphere 1838 as a result of a hydrogen production may include carbon dioxide ($CO_2$) 1840, methane ($CH_4$) 1842, nitrous oxide ($N_2O$) 1844, sulfur hexafluoride ($SF_6$) 1850, hydrofluorocarbons (HFCs) 1846, perfluorinated compounds (PFCs) 1848, and/or other chemicals, as will be understood by those skilled in the art. As a more holistic approach to carbon intensity is sought, the carbon intensity of each process or stage in hydrogen production (e.g., indirect and direct processes or stages) may be considered to target carbon intensity reduction. As such, the carbon intensity associated with a wellhead 1802 and/or bio-feedstock plant 1806 may be considered for targeted carbon intensity reductions (in other words, an indirect process or stage in relation to the steam reformer 1812). In other words, carbon intensity reductions may be sought via selections of different wellheads 1802, bio-feedstock plants 1806, and/or other feedstock sources (e.g., byproducts from a refinery 1810 or a water/electricity source for electrolysis). The carbon intensity of feedstock transportation pathways 1804 (such as vehicular, rail, marine, or pipeline transportation) may be considered for targeted carbon intensity reductions (in other words, an indirect process or stage in relation to the steam reformer 1812). Further, the carbon intensity at the steam reformer 1812 may be considered for targeted carbon intensity reductions, such as by powering at least a portion of hydrogen production source equipment with electricity generated by a renewable source (from the grid or from off-grid), burning renewable natural gas in hydrogen production source fired heaters, generating steam through renewable natural gas-fed boilers, and sequestering carbon dioxide produced at the steam reformer 1812. Such processes may be considered direct processes or stages in relation to the steam reformer 1812. The carbon intensity for other processes or stages may be considered for carbon intensity reduction, such as refinery processes (e.g., direct and indirect), utilities (e.g., indirect) to operate steam reforming processes at the steam reformer 1812, and/or hydrogen product distribution pathways 1818 for transportation of hydrogen to a power plant 1824, hydrogen fuel cells 1822, and/or an offsite refinery 1820 or distribution via pipeline/piping to a refinery 1810 co-located with the steam reformer 1812 (e.g., indirect). Further, a low CI hydrogen produced at the steam reformer 1812 (or at another hydrogen production facility or source) may be utilized at the refinery 1810 (e.g., a co-located refinery) to produce a low CI refined transportation fuel 1816 (e.g., the CI potentially lower than typical, due to the CI of the hydrogen utilized in refinery processes).

Figure 19:
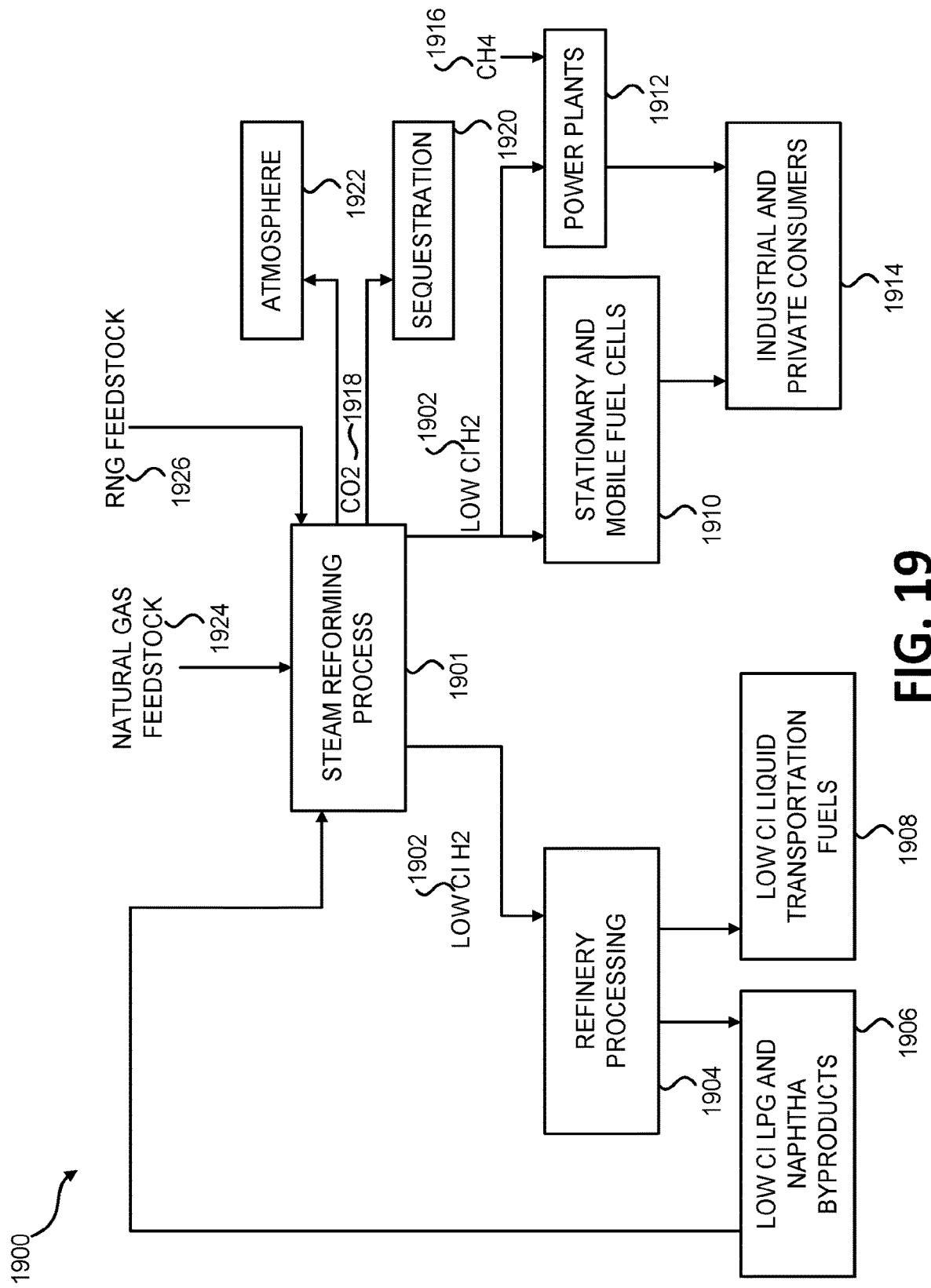
FIG. 19 is a simplified diagram that illustrates a novel implementation of a low carbon intensity hydrogen strategy in which lower carbon energy is introduced and used during the acquisition and refining of feedstock as well as the distribution of the resulting low carbon intensity hydrogen to the end user, according to one or more embodiment of the disclosure.

FIG. 19 illustrates a novel implementation 1900 of a low carbon intensity hydrogen strategy in which lower carbon intensity energy feedstock 1926, 1906 replaces or is integrated into the procurement and converting or transforming of natural gas feedstock 1924, as well as the distribution of resulting hydrogen to locations accessible to end users. Such integration of lower carbon intensity energy feedstock 1926, 1906 in the selection, acquisition, and conversion or transformation of natural gas feedstock and the distribution of resulting hydrogen lowers the overall carbon intensity of conventional transportation and other refined products made available to the end user. Thus, Applicants recognized that a similar low carbon benefit to the direct use of alternative, renewable energy sources by the consumer (see FIG. 1) could be achieved by integrating the use of such lower carbon intensity energy feedstock in replacing or in processing of higher carbon intensity energy feedstocks to create hydrogen that may ultimately be used (e.g., directly or indirectly) by the consumer through traditional liquid fuel pathways, e.g., fuels, refined via refinery processing 1904, purchased at retail outlets.

As illustrated in FIG. 19, various combinations of low carbon intensity feedstock may be utilized in a steam reforming process 1901 to produce hydrogen. The low carbon intensity feedstock may include a low carbon intensity LPG and/or naphtha 1906 procured from refinery processing 1904 of various refinery feedstock, a renewable natural gas feedstock 1926, as described above, a natural gas feedstock 1924 which may or may not be a low carbon intensity natural gas feedstock, and/or some combination thereof. While a feedstock may be of a high carbon intensity, various other steam reforming options may be selected to reduce the overall carbon intensity of the output hydrogen (e.g., low carbon intensity hydrogen 1902). For example, a RNG feedstock 1926 may be utilized, rather than a natural gas feedstock, as a fuel to operate the steam reforming process 1901. In another example, refinery by-products (e.g., the low CI LPG and naphtha 1906 from refinery processing 1904) may be utilized in the steam reforming process 1901, rather than either burning off the by-products or selling the by-products at a low cost. In another example, the carbon dioxide 1918 produced during the steam reforming process 1901 may be sequestered (e.g., via carbon sequestration 1920) to reduce the total overall carbon intensity, rather than releasing the carbon dioxide 1918 into the atmosphere 1922.

Such low CI hydrogen 1902 may be utilized in a variety of ways. The low CI hydrogen 1902 may be utilized to further reduce the carbon intensity of a transportation fuel produced via the refinery processing 1904. Such a use may enable refinery processing 1904 to output a low CI liquid transportation fuel 1908. In another example, the low CI hydrogen 1902 may be utilized in hydrogen fuel cells 1910 (e.g., vehicular fuel cells, stationary fuel cells, or other types of fuel cells that utilize hydrogen, as will be understood by those skilled in the art). In particular, a stationary fuel cell power system may be utilized in refinery processing 1904 and/or at steam reforming processes 1901 to power such processes. In yet other examples, the low carbon intensity hydrogen 1902 may be utilized to generate power for the grid via a power plant 1912. Stated another way, the low carbon intensity hydrogen 1902 may be distributed to a power plant 1912. At or prior to reaching the power plant 1912, the low CI hydrogen 1902 may be blended with another gas normally utilized in generating power at the power plant (e.g., $CH_4$ 1916 or methane). The blended gas may be utilized at the power plant 1912 to produce energy with a lower than normal carbon intensity (particularly lower than if mostly methane is utilized). Such a blended gas could include an amount of low CI hydrogen 1902 from 1% to 20%. Further, the amount of low CI hydrogen 1902 may be provided at a fixed or steady amount to the power plant 1912. In another example, the amount of low CI hydrogen 1902 supplied to a power plant 1912 may be dependent on the configuration of the power plant 1912 (in other words, is the power plant 1912 configured to burn a specified fuel including some percentage of hydrogen). Such power plants 1912 and fuel cells 1910 may provide power to industrial and/or private consumers 1914 (e.g., fuel cells 1910 for vehicles, power generation for homes, power generation for industrial processes, etc.). In other examples, the low CI hydrogen 1902 may be combined with nitrogen to form ammonia. The low carbon intensity ammonia may be used as a fertilizer, a fuel, or as an alternative for transporting pure or substantially pure hydrogen.

In another example, the utilities utilized at the steam reforming processes 1901 may include low carbon intensity renewable power, such as power generated at wind farms, solar farms, hydroelectric facilities, geothermal power plants/facilities, and/or hydrogen fuel cell power systems. Rather than transmitting this electrical power over long distances directly to an end user, the renewable power may be integrated near its generation into the steam reforming processes 1901, that may include the acquisition of feedstock and the processing of those feedstock into hydrogen at conventional refineries (e.g., the refinery including co-located steam reforming processes 1901) and other points of integration. Acquisition activities in which renewable electric power may be employed are far ranging and may include the production of natural gas from wells by pumps and other production equipment powered by the renewable electric power. Other acquisition activities may also include use of renewable electric power in electric power vehicles and/or pipeline pumps to transport the natural gas to the steam reforming processes 1901. Further, renewable electric power may be used in electric power vehicles and/or pipeline pumps to transport the hydrogen to distribution points accessible by the end user.

Rather than being transported directly to consumers by truck and/or pipeline, renewable natural gas feedstock 1924 produced from biomass waste at various facilities may also be integrated closer to hydrogen production. Similar to renewable electric power, renewable natural gas feedstock 1926 may be used to acquire and process natural gas feedstock 1924 into low CI hydrogen 1902 at conventional refineries (e.g., the conventional refinery including steam reforming processes 1901) and other points of integration. In an example, such renewable natural gas may be burned in steam reforming fired heaters or used to generate steam through renewable natural gas-fed boilers. Further, the renewable natural gas may be burned to power pumps and/or used in natural gas powered transportation modes, e.g., truck, rail, barge, etc., to transport feedstock and/or finished hydrogen.

Other alternative, low carbon intensity intermediates may be employed and integrated into the processing of hydrogen to lower the overall carbon intensity of the hydrogen (as well as any other products utilizing the hydrogen). For example, biodiesel may be generated from one or more renewable energy sources, e.g., soybeans, for reforming (e.g., naphtha or steam reforming). Such biodiesel generation may occur in close proximity to or co-located with a refinery. In one or more embodiments, such biodiesel may be transported to a refinery location by vehicle (e.g., truck), rail, pipeline, or barge that employs a low carbon intensity fuel, such as renewable natural gas, renewable diesel, or renewable electric power. Another alternative, low carbon intensity intermediate may include ethanol that is derived from corn and/or other plant-based materials. The reforming location for these alternative, low carbon intensity intermediates may include a steam reformer or naphtha reformer at a refinery. Once at the steam reformer location, the biodiesel, ethanol, or other low CI intermediate may be converted or transformed into hydrogen or used as a fuel at the reformer.

Figure 20:
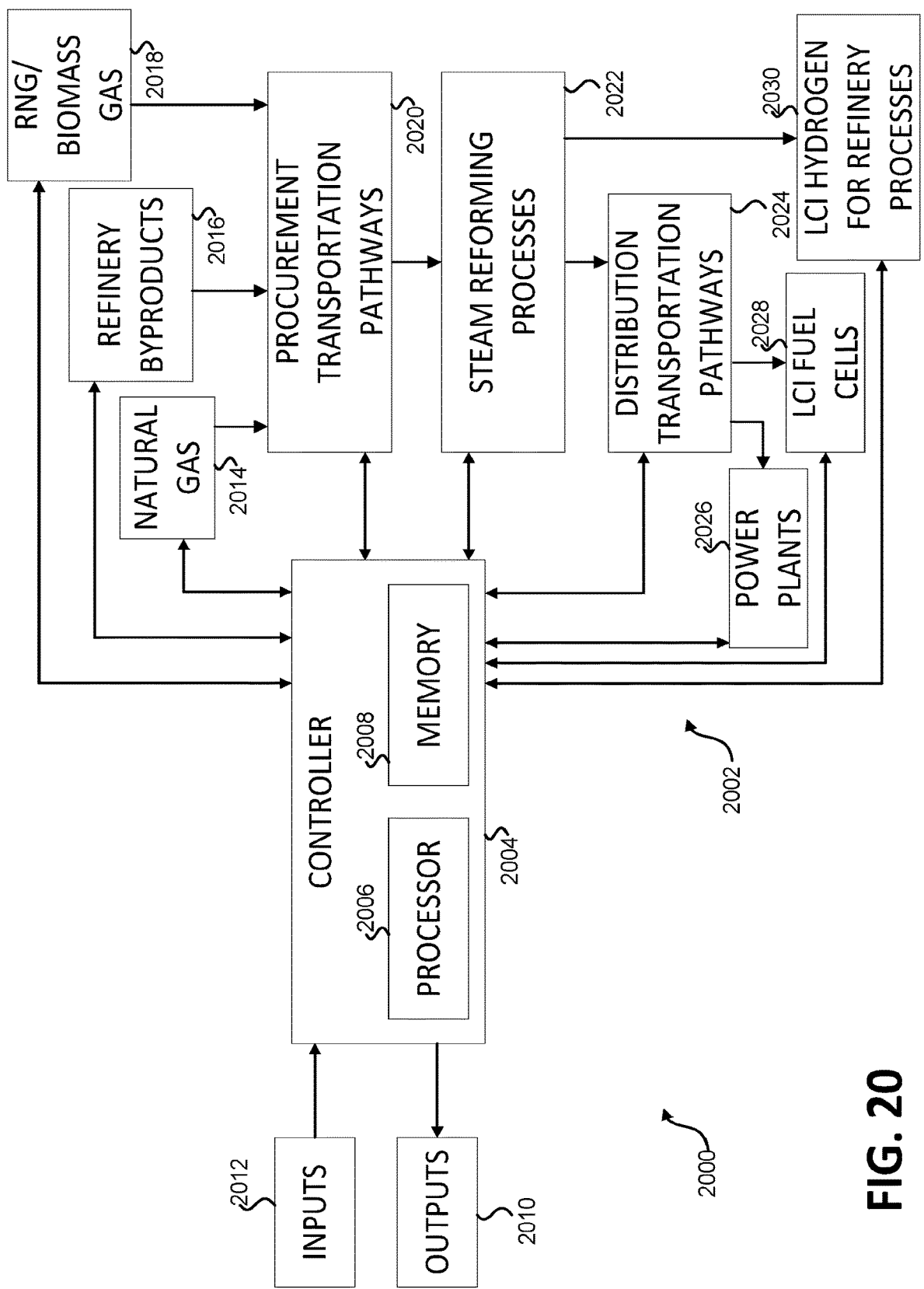
FIG. 20 is a simplified diagram illustrating a control system for managing the low carbon intensity hydrogen production according to the shown flow chart according to an embodiment.

FIG. 20 illustrates an embodiment of a control system 2000 for managing the low carbon intensity hydrogen production, as represented by the flow diagram 2002. The controller 2004 of system 2000 may include a processor 2006 (or one or more processors) and memory 2008, uses certain inputs 2012 and provides certain outputs 2010 relative to the low carbon intensity hydrogen production. These inputs 2012 may include, but are not limited to, raw energy data regarding each production step, the carbon intensity of standard steam reforming processing steps, the definition of a low carbon intensity fuel in total grams of carbon dioxide equivalent per mega joule, algorithms for calculating carbon emissions for various process steps, yields of converted or transformed products based on the feedstock(s), and/or carbon emissions for process steps not determined by the controller 2004.

Responsive to these inputs 2012, controller 2004 may perform several functions. In one or more embodiments, the controller 2004 may receive raw process data from which the carbon emissions for each production step may be determined, and then determines the carbon emissions associated with that production step on a grams of carbon dioxide equivalent per mega joule basis. The controller 2004 may also select one or more transportation and/or hydrogen production processes to achieve a desired reduction in carbon emissions. For example, the controller 2004 may select one or more procurement transportation pathways 2020 to the exclusion of other viable transportation pathways in order to reduce the grams of carbon dioxide equivalent per mega joule for the material transported. The controller 2004 may similarly select one or more hydrogen production processes (e.g., steam reforming processes 2022) to achieve reductions in carbon emissions. These hydrogen production processing reductions in carbon emissions may be as much as about 5%, about 10%, about 15%, about 20%, about 25%, or more as compared to standard hydrogen production processing steps. In at least one embodiment, the controller 2004 may verify the carbon emissions for each selected production step and generate an audit record with the total carbon intensity, e.g., grams of carbon dioxide equivalent per mega joule, for all production steps from feedstock being acquired from its source to the finished hydrogen delivered to their distribution locations, i.e., from natural gas at the wellhead or other feedstock from other sources to hydrogen delivered to the end user (e.g., power plants 2026, low CI fuel cells 2028, and/or refinery processes 2030).

Outputs 2010 from the controller 2004 may be displayed through a graphical user interface positioned at the steam reformer (or co-located refinery) and/or at remote locations, such as at feedstock sources, transportation hubs, etc. These outputs 2010 may include, but are not limited to, the selection and control of transportation and/or hydrogen production processes, the determined carbon emissions for each possible production step, the verified carbon emissions for each selected production step, and/or an audit record detailing the total carbon intensity, e.g., grams of carbon dioxide equivalent per mega joule, for the complete production of distributed hydrogen from selected feedstock. In one or more embodiments, the audit record may list the carbon emissions for each production step such that the total carbon intensity for the complete production of the hydrogen may be verified. In one or more embodiments, controller 2004 sends signals to process equipment, e.g. pumps, boiler, furnaces, etc. at the hydrogen production facility or source (e.g., at a refinery, an electrolysis facility or source, etc.) to implement the controller-determined strategy to achieve a low carbon hydrogen production. In one or more embodiments, the controller 2004 may send signals to acquire certain feedstock, to transport one or more feedstock, to store the one or more feedstock, to store converted/processed/transformed hydrogen, and to transport the hydrogen to distribution locations.

FIG. 20 provides flow diagram 2002. As described herein, several production step variables account for low carbon intensity hydrogen production. As shown, the feedstock may be selected from one or more natural gas feedstock at 2014 (e.g., methane), one or more refinery byproducts 2016 (e.g., low carbon intensity LPG or naphtha, other offgas, or refinery byproducts), and/or RNG/biomass gas feedstock at 2018, each at various locations relative to the hydrogen production processing facility or source. The feedstock may be selected, at least in part, on the basis of their innate carbon intensity when combusted, as measured by grams of carbon dioxide equivalent per mega joule. Alternatively, and in addition, the feedstock may be selected on the basis of the carbon intensity associated with their procurement or acquisition at the source. The selection of one or more procurement transportation modes 2020 to transport such feedstock to the hydrogen production processing facility or source increases the carbon emissions associated with the selected feedstock. These carbon emissions may be reduced by selecting lower carbon emission options from one or more of vehicles (e.g., trucks), rail, pipeline or ship/barge, depending on the availability of such transportation modes and the distance to be transported. Other transportation mode variables include the type of transportation fuel used, e.g., a high carbon intensity fuel versus a renewable, low carbon intensity fuel. For example, renewable diesel may be used in trucks, trains, and ships/barges. However, renewable diesel and/or renewable electrical power may be used to operate pipeline pumps.

At the hydrogen production processing facility or source, converting, transforming, and/or processing steps (e.g., steam reforming processes 2022) are conducted to transform the feedstock into hydrogen of varying purities, such as 99% pure hydrogen. With respect to the converting or transforming of feedstock, the choice of converting, transforming, and/or processing steps is largely dependent, however, on the properties and quantities of both the selected feedstock and the type of hydrogen production facility or source (e.g., electrolysis may utilize water as a feedstock, while reforming may utilize various hydrocarbon materials as feedstock). Thus, while the converting, transforming, and/or processing steps are themselves variables, they also depend at least in part on other variables. Each of the converting, transforming, and/or processing steps for a particular feedstock or intermediate has associated carbon emissions that may increase or decrease the carbon intensity of its product, as measured in grams of carbon dioxide equivalent per mega joule. Responsive to input data, controller 2004 determines the carbon intensity added or subtracted for each converting, transforming, and/or processing step, which is dependent on other variables, e.g., feedstock selection, properties, or other steps that decrease or increase carbon intensity (e.g., carbon sequestration as described further below).

The converting, transforming, and/or processing steps (e.g., steam reforming process 2022) may have at least some of their carbon emissions offset such that their products have a lower carbon intensity than without the offset. For example, hydrogen production and other processes that are driven by low carbon energy sources, such as renewables, may offset the higher carbon emissions of standard hydrogen production (e.g., steam reforming) and/or processing steps. These offsetting processes may include one or more of: producing electrical power for the benefit of the hydrogen production facility or source through renewable sources such as wind, solar, geothermal power plants/facilities, hydroelectric (e.g., via grid tied renewable sources or nearby off-grid renewable sources), and/or hydrogen fuel cell power systems, employing renewable fuels such as renewable diesel and renewable natural gas in hydrogen production facility or source boilers and/or fired heaters, reducing by at least one or more the number of hydrogen production processing units that convert or transform the feedstock, using low carbon intensity fuels for heat generation, etc.

One or more distribution transportation modes 2024 may also be selected to transport the final hydrogen to a distribution location accessible to the end user. As with the transport of feedstock, the transport of refined products may increase the carbon emissions associated with the transportation fuel provided to the end user. These carbon emissions may be reduced by selecting lower carbon emission options from one or more of vehicles (e.g., trucks), rail, pipeline or ship/barge, depending on the availability of such transportation modes and the distance to be transported. The type of transportation fuel used, e.g., a high carbon intensity fuel versus a renewable, low carbon intensity fuel, is another variable for each transportation mode that may be selected to reduce the carbon emissions associated with this production step. Finally, the gas or liquid hydrogen may be made available to different end users for different purposes. For example, hydrogen may be stored as a gas or as a liquid. Further, as a gas, hydrogen may be stored under pressure (e.g., in a pressurized storage vessel). Such storage may indirectly cause some increase in carbon intensity. As noted, different users may utilize the hydrogen in different ways. For example, if the end user is a refinery, the hydrogen may be utilized in various refinery processes 2030, such as hydrotreating or hydrocracking or as fuel or to be mixed with fuel to power the refinery. Further, the refinery may be co-located with or include the steam reformer. As such, the carbon intensity for the distribution may be minimal (e.g., the power to pump the hydrogen to either storage or relevant refinery processes). The end user may be low CI hydrogen fuel cells 2028. In other words, the hydrogen may be provided to fuel cells as fuel for the generation of electricity. In such examples, the fuel cells may be smaller fuel cells for vehicles or larger fuel cells for stationary fuel cell power systems (e.g., to provide power to a refinery). In another example, the hydrogen may be provided to a hydrogen fueling station. The hydrogen fueling station may provide pumps for consumers to re-fuel hydrogen fuel cell based vehicles. The end user may also be a power plant 2026. The power plant 2026 may primarily utilize methane or other similar gases to produce electricity. In such examples, blending the methane or other gases with hydrogen may lower the total overall carbon intensity of the energy produced at the power plant.

Figure 21:
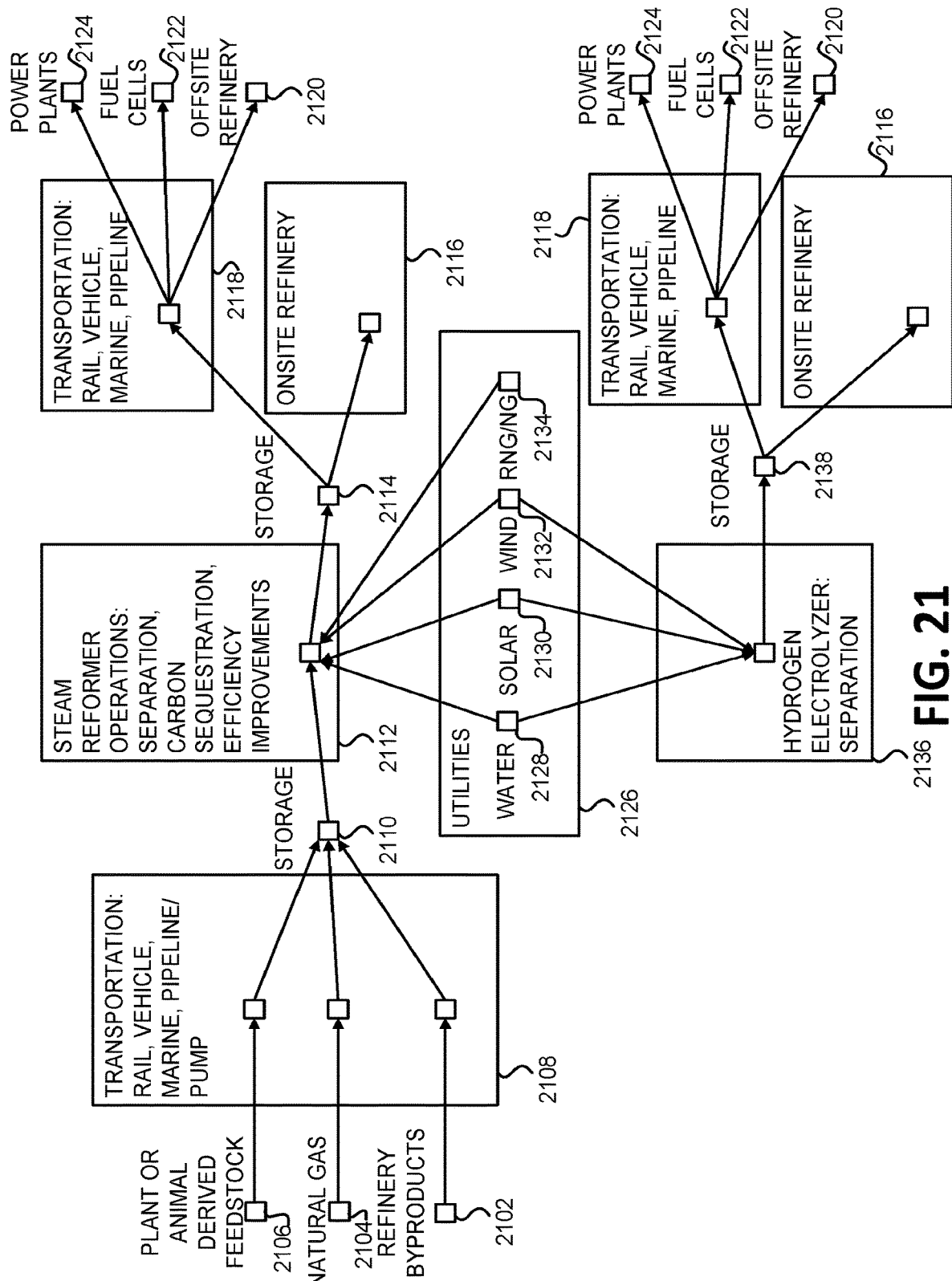
FIG. 21 is a nodal diagram illustrating the interconnectivity of lower carbon energy sources at various nodes during the acquisition and transformation of higher carbon intensity feedstock into lower carbon intensity hydrogen as well as the distribution of the resulting lower carbon intensity hydrogen to the end user, according to one or more embodiment of the disclosure.

FIG. 21 is a nodal diagram illustrating the interconnectivity of lower carbon energy sources at various nodes during the acquisition and conversion or transformation of higher carbon intensity feedstock into lower carbon intensity hydrogen as well as the distribution of the resulting lower carbon intensity hydrogen to the end user. Selected refinery byproducts 2102, natural gas 2104, and/or plant/animal derived feedstock 2106 may be transported via various transportation modes 2108, which may include one or more of vehicle, rail, marine or pipeline transport. The transport mode may be selected to further limit carbon emissions by employing low carbon intensity fuels, such as renewable diesel, renewable natural gas, petroleum natural gas, etc. In one or more embodiments, the transported feed stocks are stored in tanks or facilities 2110 The manner and length of time of such storage may be selected so as to decrease the carbon emissions resulting from storage.

The stored feedstock are then converted, transformed, and/or processed (e.g., at a steam reformer 2112 or at other hydrogen production processes) through conventional processing steps, each of which increases (or in some situations decreases) the carbon emissions attributable to the converted/transformed/processed materials. However, as described previously, certain hydrogen production processes may be employed to decrease the carbon emissions with respect to conventional processing steps. The most numerous of these carbon intensity reducing processing steps are associated with the utility infrastructure 2126. In addition to the feedstock, refineries, hydrogen production facilities or sources, and/or biomass processing facilities largely depend on various utilities, including electrical power (e.g., solar 2130, wind 2132, hydroelectric, geothermal power plants/facilities, fuel cell power systems, etc.), fuel 2134 (e.g., natural gas, diesel, refined intermediates), and water/steam 2128, to operate. As shown in FIG. 21, there are several options for providing these required utilities with lower carbon intensity than they may otherwise normally be supplied. For example, electrical power may be supplied by wind turbines 2132, solar arrays 2130, renewable natural gas/natural gas 2134, hydroelectric power, and/or hydrogen fuel cell power systems. Similarly, the pumping and treatment of water and the generation of steam may employ energy obtained from wind turbines 2132, solar arrays 2130, renewable natural gas/natural gas 2134, hydroelectric power, and/or hydrogen fuel cell power systems. Renewable natural gas may also be used along with one or more of renewable diesel and/or refinery intermediates as fuels for boilers and fired heaters. Hydrogen generation may be accomplished at lower carbon intensity through an electrolyzer 2136 in addition to a steam reformer 2112. The electrolyzer 2136 may be powered by electricity generated from wind turbines 2132, solar arrays 2130, renewable natural gas/natural gas 2134, hydroelectric power, hydrogen fuel cell power systems, RNG-fired turbines, and/or RNG-produced steam letdown. The feedstock for the electrolyzer 2136 may include varying types of water 2128, such as gray water, treated gray water, salt water, fresh water, and/or other types of water 2128, as will be understood by those skilled in the art. Carbon capture/sequestration may also be used anywhere in the hydrogen production and/or processing facility that hydrocarbon fuels are combusted to carbon dioxide or that the process creates carbon dioxide and the carbon dioxide is released to the atmosphere as a by-product. Sequestering carbon dioxide that otherwise would go to the atmosphere may have a carbon emissions neutral effect or even subtract from the carbon intensity of the fuel product associated with the carbon sequestration. Heat integration and efficiency improvements may be included as additional techniques to reduce the carbon emissions attributable to converting or transforming feedstock into hydrogen.

In one or more embodiments, the hydrogen may be stored in tanks or facilities 2114, 2138 prior to transport or distribution. The manner and length of time of such storage may be selected so as to decrease the carbon emissions resulting from storage. The type of storage may vary depending on the use of the hydrogen. For example, the hydrogen may be stored in a pressurized storage vessel as a gas. In another example, the hydrogen may be converted to ammonia and may be stored as a liquid. In yet another example, the hydrogen may be cooled to a liquid and stored in thermally insulated and pressurized storage vessels. Other types of storage may be utilized for the hydrogen, as will be understood by those skilled in the art. The hydrogen may also be transported directly after production for immediate use (e.g., transported via pipeline/piping to a co-located or onsite refinery 2116 for immediate use in refinery processes utilizing hydrogen). After storage, the hydrogen may be transported via various transportation modes 2118 to various distribution locations, such as to an offsite refinery 2120, to facilities as a fuel for fuel cells 2122, and/or to a power plant 2124 for blending with fuel for the power plant (e.g., blending with methane to reduce the overall carbon intensity of the methane and, thus, reducing the carbon intensity of the power generated by the power plant 2124). As with the feedstock transportation 2108, the transportation modes 2118 for the hydrogen may include one or more of vehicles (e.g., trucks), rail, marine or pipeline transport. The transport mode may be selected to further limit carbon emissions by employing low carbon intensity fuels, such as renewable diesel, renewable natural gas, regular natural gas, etc.

Figure 22:
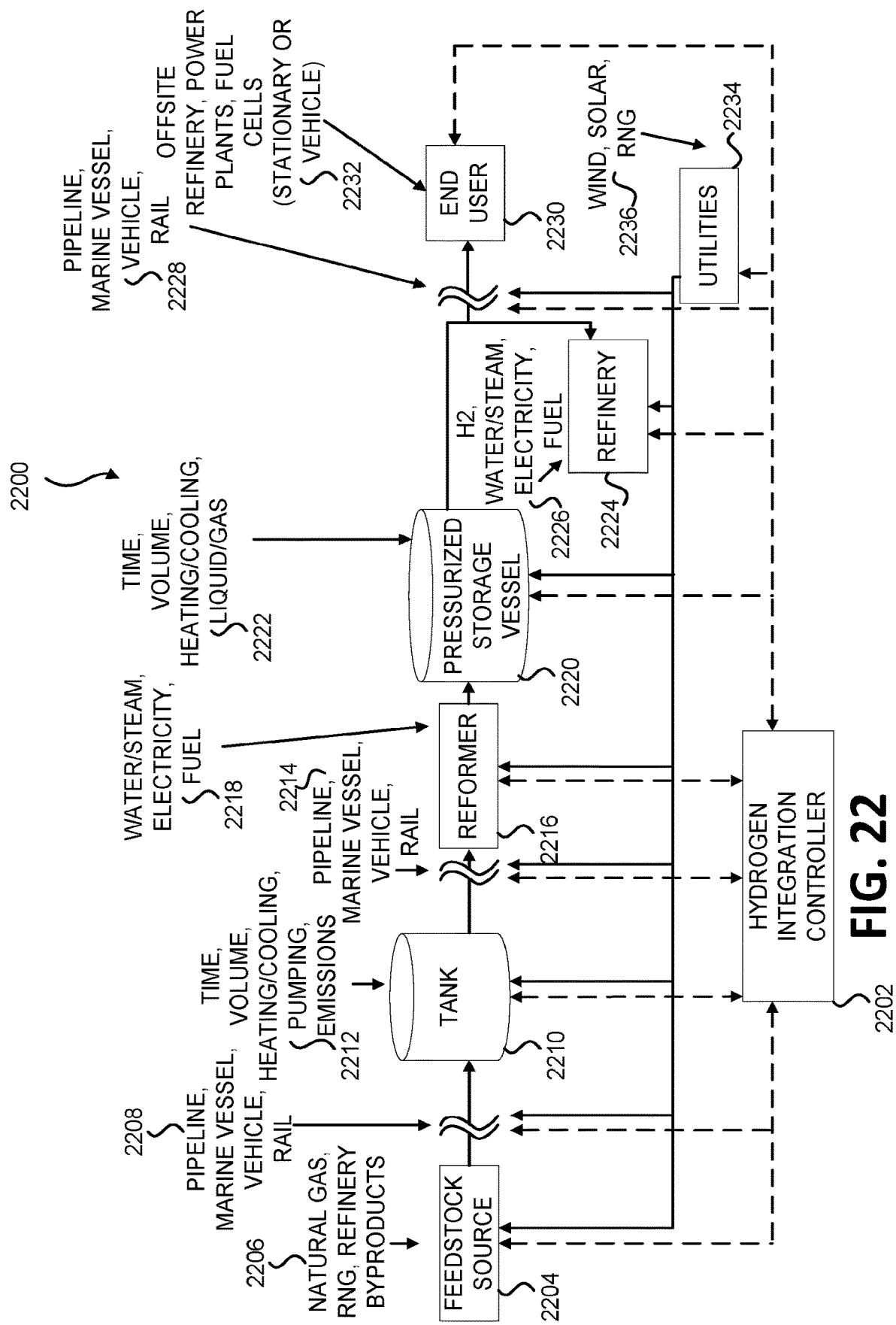
FIG. 22 is a block diagram illustrating a system for managing the low carbon intensity hydrogen production according to an embodiment.
Figure 23A:
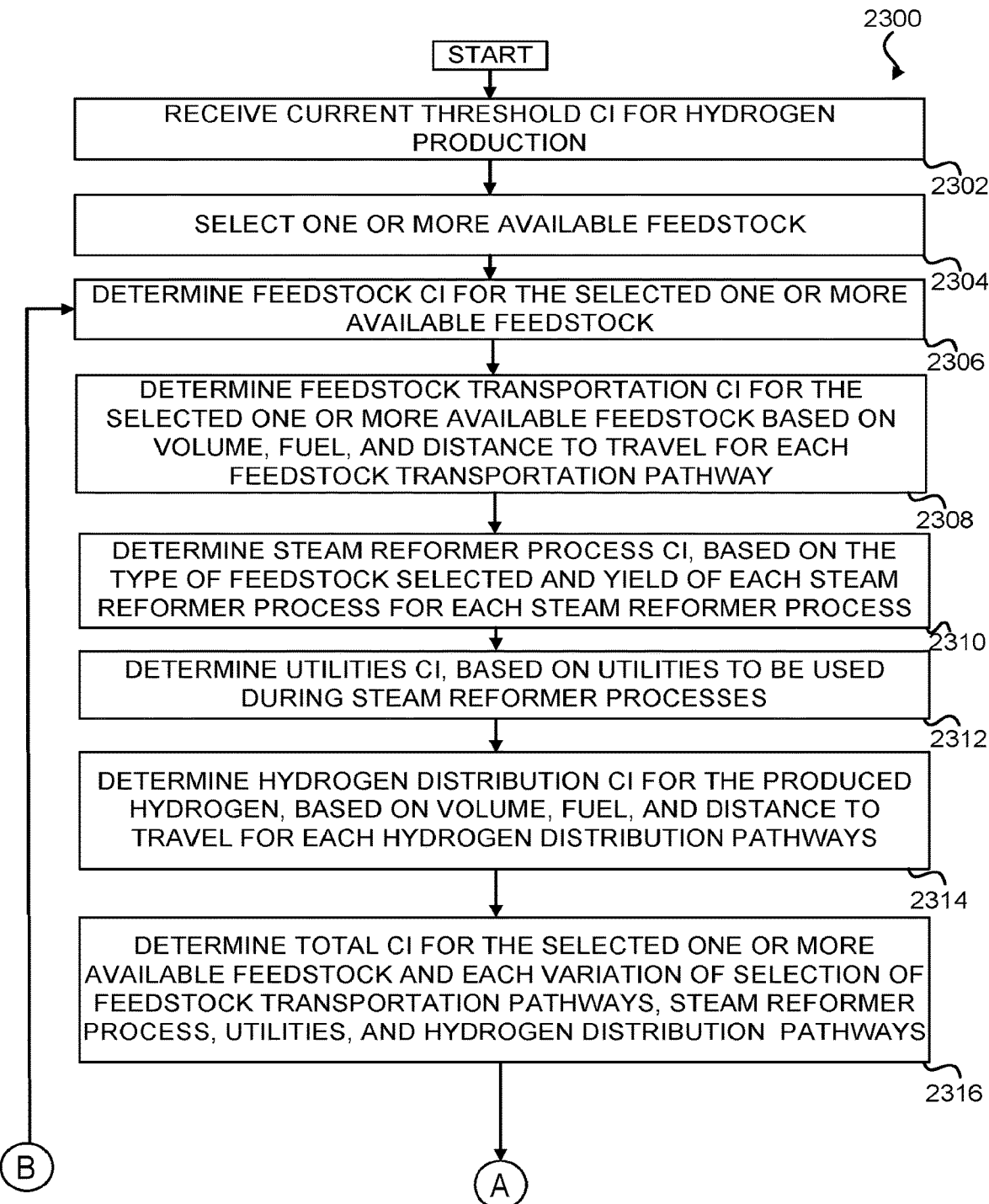
FIGS. 23A-D are flow diagrams, implemented in a controller, for managing the low carbon intensity hydrogen production according to an embodiment.
Figure 23B:
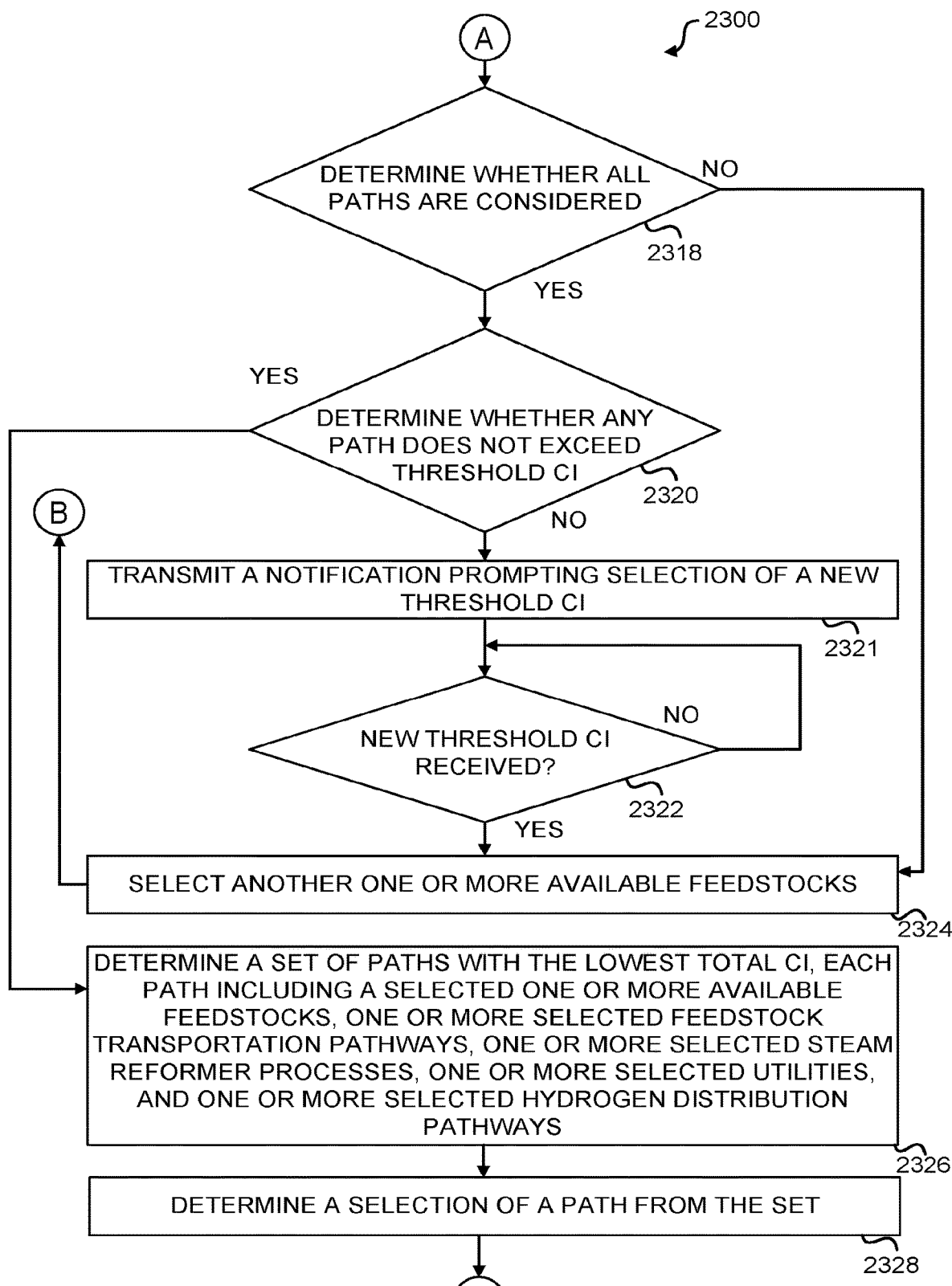
Figure 23C:
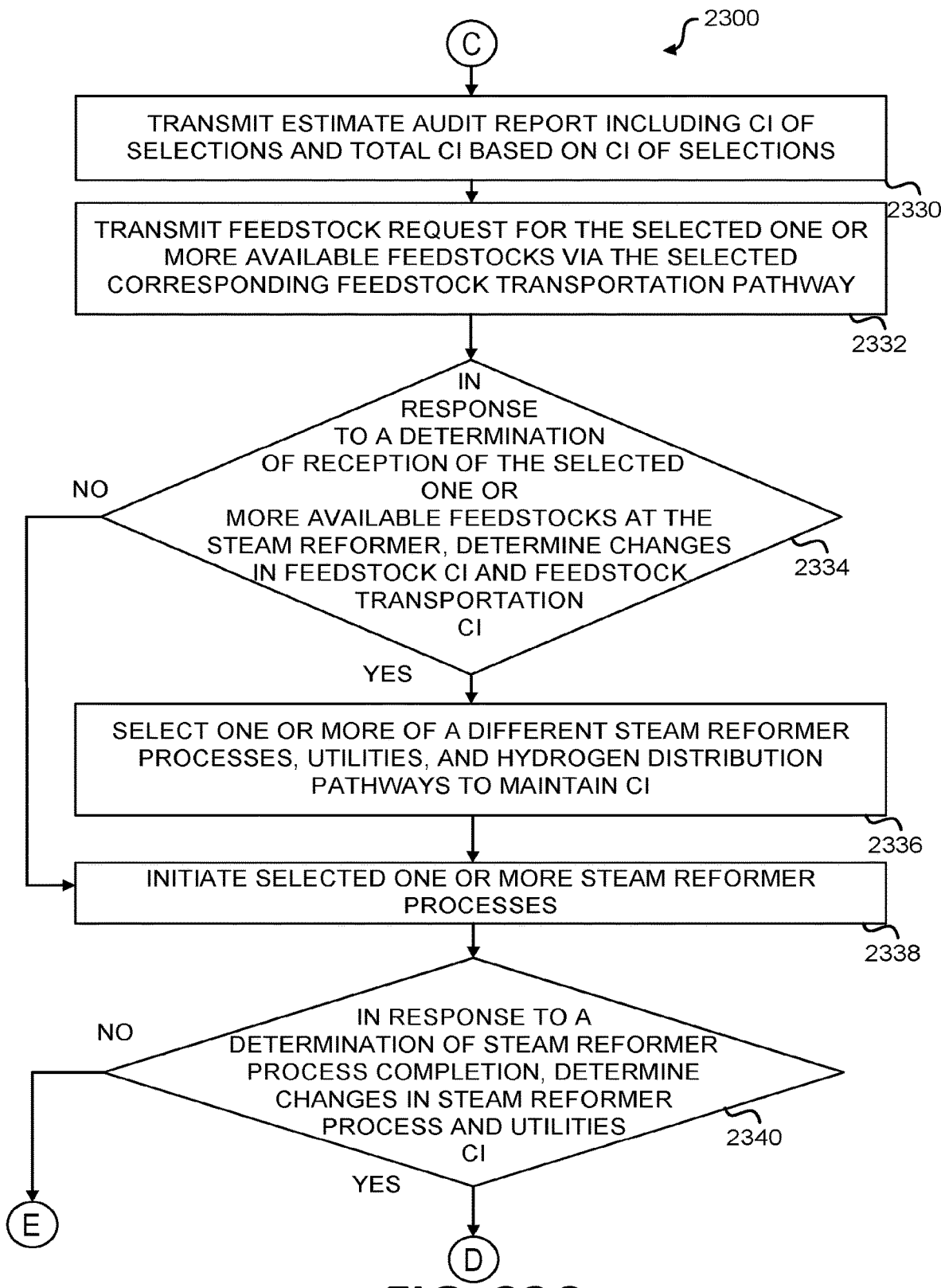
Figure 23D:
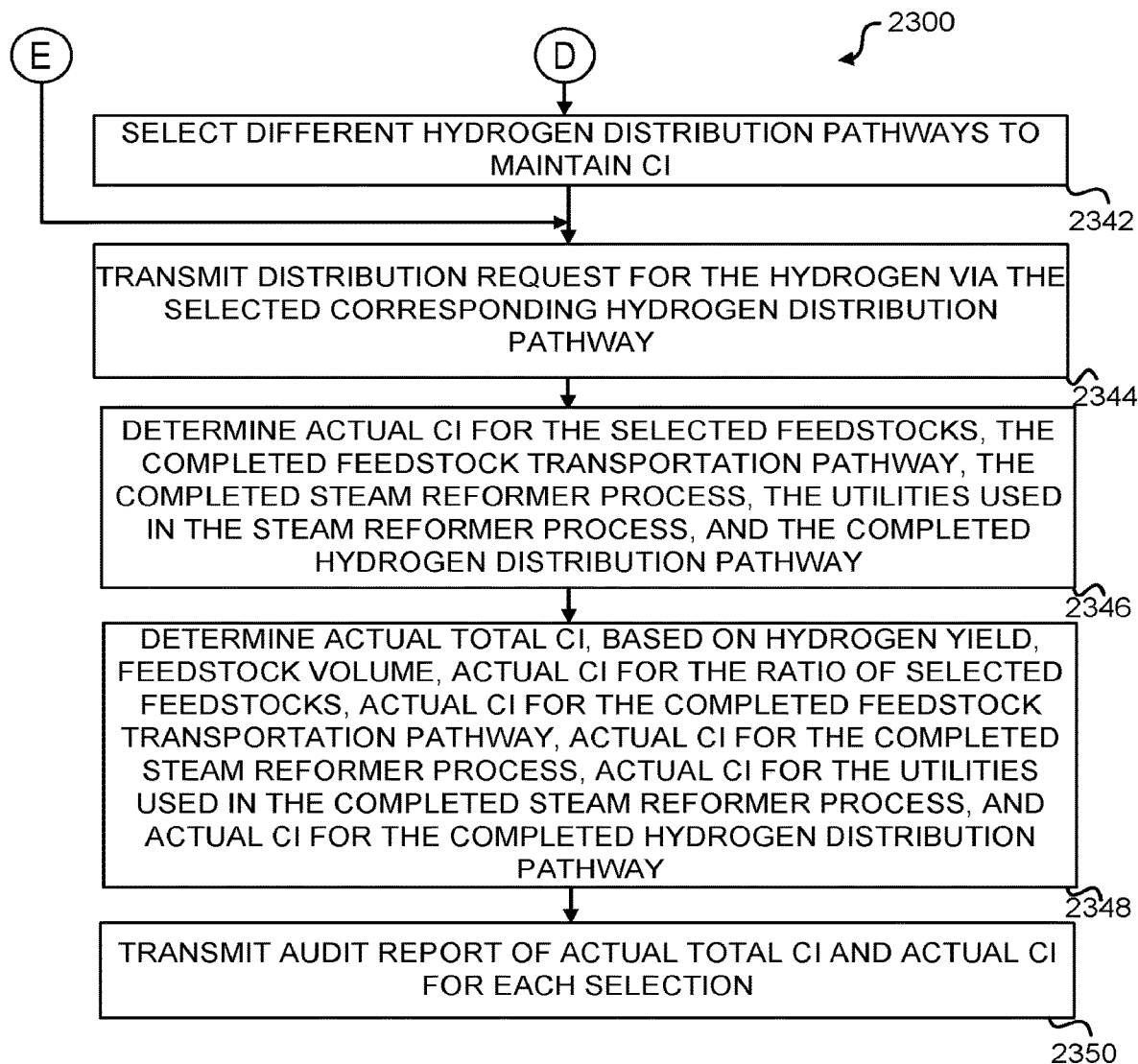

FIG. 22 is a block diagram illustrating a system 2200 for managing the low carbon intensity hydrogen production according to an embodiment. The system 2200 may include a hydrogen integration controller 2202. The hydrogen integration controller 2202 may connect to various other controllers, sensors, and/or computing devices utilized throughout hydrogen production to plan and/or control the hydrogen production. For example, the hydrogen integration controller 2202 may connect to a controller at a feedstock source 2204, other controllers at other feedstock sources, or to a database storing information regarding the feedstock source 2204 and/or other feedstock sources. As such, the hydrogen integration controller 2202 may obtain various data points or information in relation to different available feedstock at feedstock sources and the hydrogen integration controller 2202 may select one or more of the available feedstock for hydrogen production, based on the data points or information obtained. Such data points or information may include type of available feedstock, amount of available feedstock, location of available feedstock, and general availability of feedstock (e.g., when the feedstock may be available for shipment). Examples of feedstock may include natural gas, renewable natural gas, and/or refinery byproducts 2206. The natural gas may be located at a wellhead or other location where natural gas may be located. The natural gas may be methane or another natural gas suitable for conversion to hydrogen. The refinery byproducts may include offgas produced at a refinery. In particular, the offgas may include methane, ethane, propane, butane, and/or other gases produced as byproducts from various refinery processes (e.g., naphtha reforming or catalytic reforming). Other feedstock, such as water, may be included in the available feedstock sources 2204 (e.g., to be utilized for electrolysis).

The hydrogen integration controller 2202 may connect to controllers, sensors, a database and/or computing devices related to a feedstock transportation pathway. As such, the hydrogen integration controller 2202 may obtain various data points or information in relation to different available feedstock transportation pathways and the hydrogen integration controller 2202 may select one or more of the available feedstock transportation pathways for the hydrogen production, based on the various data points or information. In an example, the available types of transportation (e.g., pipeline, marine vessel, vehicle, and/or rail 2208) may depend on various factors, such as the type and amount of feedstock selected, as well as the type of one or more hydrogen production processes to be utilized in the hydrogen production (e.g., electrolysis or steam reforming).

Further, the hydrogen integration controller 2202 may connect to controllers, sensors, and/or computing devices associated with a tank 2210 (e.g., a feedstock storage tank) and/or pressurized storage vessel 2220 (e.g., for hydrogen storage). The tank 2210, pressurized storage vessel 2220, or various other tanks may be positioned at various points between a feedstock source 2204, the reformer 2216 (or other hydrogen producing source), and an end user 2230 (e.g., offsite refinery, power plants, and/or fuel cells 2232). For example, the tank 2210 may be located on-site at the reformer 2216 (e.g., at a co-located refinery 2224). The hydrogen integration controller 2202 may obtain various data points or information in relation to feedstock stored in tank 2210 (e.g., time, volume, heating/cooling, pumping, and emissions 2212) and/or hydrogen stored in a pressurized storage vessel (e.g., time, volume, heating/cooling, and/or liquid/gas 2222). The hydrogen integration controller 2202 may select feedstock stored in the tank 2210 or other tanks for use in the hydrogen production and/or where to distribute the produced hydrogen stored in the pressurized storage vessel 2220 or other pressurized storage vessels (e.g., to a co-located refinery 2224 or an offsite refinery, power plants, or fuel cells 2232).

The hydrogen integration controller 2202 may control a reformer 2216 and/or connect to controllers, sensors, and/or computing devices at the reformer 2216. The controllers, sensors, and/or computing devices may further be separate from or located at a co-located refinery 2224. The hydrogen integration controller 2202 may obtain various data points or information in relation to different available reformer processes of the reformer 2216 and the hydrogen integration controller 2202 may select one or more of the available reformer processes for the hydrogen production, based on the various data points or information. The hydrogen integration controller 2202 may initiate and/or control the selected reformer processes at the reformer 2216. For example, when a particular reformer process is selected, the hydrogen integration controller 2202 may initiate the reformer process or transmit an initiation to a controller of the reformer 2216. The hydrogen integration controller 2202 may connect to other controllers, sensors, and/or computing devices at other hydrogen producing facilities or sources. The hydrogen producing facilities or sources may include a hydrogen electrolyzer plant or facility, a naphtha reformer or catalytic reformer, and/or other refinery processes that produce hydrogen.

The hydrogen integration controller 2202 may connect to a utility provider 2234 or controllers, sensors, and/or computing devices of a utility provider 2234. The utility provider 2234 may provide utilities for use in the reformer 2216, as well as at various other points throughout the hydrogen production. The utility provider 2234 may be proximate to, nearby, or at the reformer 2216 and may utilize renewable resources. For example, the utility provider 2234 may provide and/or track utilities for use at the feedstock source 2204, at each transportation/distribution pathway, at each tank (e.g., tank 2210 and pressurized storage vessel 2220), and/or at other points or processes in the hydrogen production. As such, the hydrogen integration controller 2202 may obtain data regarding the available utilities, as well as available utilities for the hydrogen production. Based on such data, the hydrogen integration controller 2202 may select one or more utilities for the hydrogen production (e.g., utilities, such as power generated by wind, solar, and/or RNG 2236, for use in the one or more selected hydrogen production processes).

The hydrogen integration controller 2202 may connect to a refinery (or co-located refinery 2224), a fuel integration controller (as described above), and/or other controllers, sensors, and/or computing devices of a refinery (or co-located refinery 2224). The hydrogen integration controller 2202 may, rather than selecting a distribution pathway, determine that direct transfer or transportation of hydrogen is appropriate. For example, an amount of hydrogen may be required for a particular transportation fuel production process. A fuel integration controller or other controller of the refinery may signal the amount of hydrogen to be utilized. The hydrogen integration controller 2202, after production of the hydrogen at the reformer 2216, may select or set a certain amount of the produced hydrogen for transfer or transportation to the refinery (e.g., the co-located refinery 2224). In such examples, a low CI hydrogen may further lower the CI of a transportation fuel. Further, the excess hydrogen produced at the reformer 2216 may be distributed for other uses.

The hydrogen integration controller 2202 may connect to controllers, sensors, a database, and/or computing devices related to a hydrogen distribution pathway. As such, the hydrogen integration controller 2202 may obtain various data points or information in relation to different available hydrogen distribution pathways and the hydrogen integration controller 2202 may select one or more of the available hydrogen distribution transportation pathways based on the various data points or information.

The hydrogen integration controller 2202 may connect to controllers, sensors, and/or computing devices at a distribution point or terminal (e.g., offsite refinery, power plants, and/or fuel cells 2232). For example, the hydrogen integration controller 2202 may monitor or track hydrogen consumption (in other words, demand) at the offsite refinery, power plants, and/or fuel cells 2232. Based on the consumption or demand, the hydrogen integration controller 2202 may initiate hydrogen production for a hydrogen with a particular CI. Further, based on consumption or demand, the hydrogen integration controller 2202 may select different aspects of the hydrogen production (e.g., a low CI feedstock, carbon sequestration, renewable utilities, etc.). Such selections may further be based on carbon credits currently held by a hydrogen producer. In other words, a reformer 2216 may produce large quantities of low CI hydrogen, which may not or may minimally affect currently held carbon credits. Based on the currently held carbon credits, as well as other factors (cost of feedstock, demand, etc.), the hydrogen integration controller 2202 may initiate selection of aspects of a low CI or a high CI hydrogen production process. Further still, the selections may be based on currently available utilities. For example, solar power may not be available for electrolysis for a specific day or period of time. Based on such availability, the hydrogen integration controller 2202 may select the reformer 2216 for producing hydrogen for that particular time frame (e.g., the time frame where solar power is not available for electrolysis).

FIGS. 23A-D are flow diagrams, implemented in a controller, for managing the low carbon intensity hydrogen production according to an embodiment. The method 2300 is detailed with reference to the hydrogen integration controller 2202 and system 2200 of FIG. 22. Unless otherwise specified, the actions of method 2300 may be completed within the hydrogen integration controller 2202. Specifically, method 2300 may be included in one or more programs, protocols, or instructions loaded into the memory of the hydrogen integration controller 2202 and executed on the processor or one or more processors of the hydrogen integration controller 2202. The order in which the operations are described is not intended to be construed as a limitation, and any number of the described blocks may be combined in any order and/or in parallel to implement the methods.

At block 2302, the hydrogen integration controller 2202 may receive a threshold CI for an amount of hydrogen to be produced during a hydrogen production process. The hydrogen integration controller 2202 may receive the threshold CI from a user, user interface, a low CI hydrogen specification (e.g., input by a user or stored in a database), a controller, memory of the hydrogen integration controller 2202, a fuel integration controller, a supervisory controller, and/or another device. In response to a reception of the threshold CI, the hydrogen integration controller 2202 may utilize or assign the input threshold CI as a current threshold CI. The current threshold CI may correspond to a particular hydrogen production process or operation. In other words, the threshold CI may vary for different hydrogen production processes.

Once a current threshold CI is set, assigned, received, and/or determined, at block 2304, the hydrogen integration controller 2202 may select one or more available feedstock from a fuel or feedstock source 2204. As noted above, the available feedstock may include natural gas (e.g., from a wellhead and/or hydrocarbon gases or liquids derived from crude oil or naphtha), renewable natural gas (e.g., hydrocarbon gases or liquids derived from pyrolysis oil, naphtha, soybeans, and tallow), and/or refinery byproducts (e.g., offgas or other gases produced as byproducts at a refinery or co-located refinery 2224) 2206 from a variety of sources. In an example, the hydrogen integration controller 2202 may determine a list or set of available feedstock from a user input (via a user interface), a database, a procurement controller, procurement computing device, procurement and distribution computing device, the memory of the hydrogen integration controller 2202, and/or another device. Further, data or information on available feedstock may be a subset of data or information on all available feedstock based on available hydrogen production sources or facilities (e.g., if electrolysis is not an option for producing hydrogen, then water may not be available as a feedstock). As such, the hydrogen integration controller 2202 may select one or more available feedstock from the subset of available feedstock.

In response to a selection of the one or more available feedstock, at block 2306, the hydrogen integration controller 2202 may determine a feedstock CI. The hydrogen integration controller 2202 may determine feedstock CI based on the ratio, percentage, or blend of the feedstock's inherent CI, the type of feedstock, the location of the feedstock (e.g., distance from the reformer 2216, tank 2210, or other tanks), the power used or emissions generated by obtaining or producing the feedstock, and/or the volume of the feedstock. In another example, the feedstock CI may be known or given (e.g., via the user interface, database, controller, etc.). Further, as one or more available feedstock are determined or selected, the feedstock CI may be determined based on the ratio or blend of the determined or selected one or more available feedstock (e.g., the ratio of the CI of two or more different feedstock).

In response to a determination of the feedstock CI, at block 2308, the hydrogen integration controller 2202 may determine a feedstock transportation CI for each available feedstock transportation pathway for the selected one or more available feedstock. The available feedstock transportation pathways may include pipeline transportation, marine vessel transportation, vehicular transportation (e.g., a truck), and/or rail transportation 2208. As noted above, different feedstock may be deliverable via particular feedstock transportation pathways. As such, based on the selected one or more available feedstock, the hydrogen integration controller 2202 may determine the feedstock transportation CI. The hydrogen integration controller 2202 may further determine the feedstock transportation CI for each available feedstock transportation pathway based on the volume of the feedstock transportation pathway, the fuel utilized by the feedstock transportation pathway, and the distance the feedstock transportation pathway may travel to deliver the feedstock from the feedstock source 2204 to a tank 2210, reformer 2216, or other hydrogen production facilities or sources.

As noted above, feedstock storage in a tank 2210 (e.g., a feedstock storage tank) may be associated with a CI. In other words, storing a feedstock in a tank 2210 may lead to carbon emissions, based on various factors, such as time of storage, volume of the tank 2210, volume of the feedstock to be stored, power required to transfer feedstock to and from the tank 2210 (e.g., via a pump), power and time required to heat/cool the feedstock, and/or the emissions associated with the storage of the feedstock 2212 (e.g., VOC emissions through working losses, breathing losses, and flashing losses). In such cases where feedstock storage may be an option, the hydrogen integration controller 2202 may determine feedstock storage CI based on those factors. Further, a CI may be associated with transporting the stored feedstock to the reformer 2216 or other hydrogen production facilities or sources. The stored feedstock may be transported via pipeline, marine vessel, vehicle (e.g., a truck), and/or rail 2214. The stored feedstock transportation CI may be based on the volume of the stored feedstock transportation pathway, the fuel utilized by the stored feedstock transportation pathway, and the distance the stored feedstock transportation pathway may travel to deliver the stored feedstock from the tank 2210 to the reformer 2216 or other hydrogen production facilities or sources.

In response to a determination of the feedstock transportation CI (or feedstock storage CI), at block 2310, the hydrogen integration controller 2202 may determine the reformer process CI and/or the CI for other hydrogen production facility or source processes. In such examples, the hydrogen integration controller 2202 may obtain a list of available hydrogen production facility or source processes from a hydrogen production facility or source controller at, for example, the reformer 2216 or other hydrogen production facilities or sources, a database, or the memory of the hydrogen integration controller 2202. In another example, the hydrogen integration controller 2202 may determine the hydrogen production facility or source process CI for each hydrogen production facility or source processes based on the type of feedstock selected and the yield of the hydrogen production facility or source process. As noted above, high CI hydrogen production facility or source operations or processes may be offset by the use of offsetting practices. For example, a steam reformer (e.g., reformer 2216) may be capable of utilizing heat from a heat exchanger network. Further, the hydrogen production facility or source may utilize carbon sequestration to offset high CI hydrogen production facility or source processes, as will be understood by those skilled in the art. For example, a steam reformer (e.g., reformer 2216) may produce an amount of hydrogen ($H_2$) and carbon dioxide ($CO_2$), as well as other gases or liquids. The carbon dioxide may, if released into the atmosphere, contribute to the overall CI of the produced hydrogen. Rather than releasing the carbon dioxide into the atmosphere, the carbon dioxide may be captured or sequestered, thus lowering the overall CI of the hydrogen.

In response to a determination of the reformer or hydrogen production facility or source process CI, at block 2312, the hydrogen integration controller 2202 may determine the utilities CI. In such examples, the hydrogen integration controller 2202 may obtain a list of available utilities from a reformer controller at the reformer 2216, a controller at another hydrogen production facility or source, a utility controller at a utility provider 2234, a database, the memory of the hydrogen integration controller 2202. In another example, the hydrogen integration controller 2202 may determine the utilities CI for each available utility based on the type utilities to be used during refinery processes. As noted above, high CI hydrogen production facility or source (e.g., reformer 2216) operations may be offset by the use of low CI utilities. For example, renewable fuels from a utility provider 2234 may be provided to a hydrogen production facility or source (e.g., reformer 2216) to convert or transform a high CI feedstock. The utilities may include different sources or forms of water/steam, of electricity (e.g., solar, wind, renewable gas, etc. 2236), and/or of other fuels 2218 (e.g., renewable natural gas or natural gas). Other utilities may include hydroelectric utilities and/or hydrogen fuel cell power systems. In an example, a utility provider 2234 may be an energy producing facility connected to the grid, an energy producing facility nearby or proximate to the refinery 2234 and/or the reformer 2216, or an energy producing facility nearby or at and dedicated to the refinery 2234 and/or reformer 2216. As noted, the utility provider 2234 (e.g., the energy producing facility) may produce energy via renewable resources (e.g., a wind farm located nearby or at the refinery 2234 and/or reformer 2216). In another example, the utility provider 2234 (e.g., the energy producing facility) may produce energy via fossil fuels and/or renewable resources. The utilities CI may further include a CI associated with utilities used throughout the hydrogen production. The utilities CI may be further based on utilities used at the feedstock source 2204 (e.g., utilities used to obtain, procure, or produce a feedstock), during feedstock transportation (e.g., power utilized at a pump to pump feedstock to another location), used at the tank 2210 (e.g., a feedstock storage tank), during hydrogen distribution (e.g., power utilized at a pump to pump hydrogen to another location), and/or used at any other point in the hydrogen production.

As noted above, hydrogen storage in a pressurized storage vessel 2220 (in other words, a hydrogen storage tank) may be associated with a CI. In other words, storing hydrogen in a pressurized storage vessel 2220 may lead to carbon emissions, based on various factors, such as time of storage, volume of the pressurized storage vessel 2220, volume of hydrogen to be stored, power required to transfer feedstock to and from the pressurized storage vessel 2220 (e.g., via a pump), power and time required to heat/cool the hydrogen, and/or the emissions associated with the storage of the hydrogen, and the type of hydrogen to be stored 2222 (e.g., liquid or gas). In such cases where hydrogen storage may be an option, the hydrogen integration controller 2202 may determine hydrogen storage CI based on those factors. Further, a CI may be associated with transporting the hydrogen from the hydrogen production facility or source (e.g., reformer 2216) to a co-located refinery 2224 or the pressurized storage vessel 2220. The hydrogen may be transported via pipeline, marine vessel, vehicle (e.g., a truck), and/or rail 2228. The stored hydrogen transportation CI may be based on the volume of the stored hydrogen pathway, the fuel utilized by the stored hydrogen pathway, and the distance the stored hydrogen pathway may travel to deliver the hydrogen from the hydrogen production facility or source (e.g., reformer 2216) to the pressurized storage vessel 2220.

In response to a determination of the utilities CI, at block 2314, the hydrogen integration controller 2202 may determine a hydrogen distribution CI for each available hydrogen distribution pathway for hydrogen from a hydrogen production facility or source, a reformer 2216, or pressurized storage vessels (e.g., pressurized storage vessel 2220). The available hydrogen distribution pathways may include pipeline transportation, marine vessel transportation, truck or vehicular transportation, and/or rail transportation 2228. The hydrogen integration controller 2202 may further determine the hydrogen distribution CI for each available hydrogen distribution pathway based on the volume of the hydrogen distribution pathway, the fuel utilized by the hydrogen distribution pathway, and the distance the hydrogen distribution pathway may travel to deliver the hydrogen from the hydrogen production facility or source or a reformer 2216 to a pressurized storage vessel 2220, an offsite refinery, power plants, and/or fuel cells 2232.

In response to a determination of the hydrogen distribution CI, at block 2316, the hydrogen integration controller 2202 may determine the total CI for each variation of selections noted above. For example, for the selected one or more available feedstock, the hydrogen integration controller 2202 may determine total CI based on a first feedstock transportation pathway, a first hydrogen production facility or source process, a first utility, and/or a first hydrogen distribution method. The hydrogen integration controller 2202 may then determine the total CI for the next variation and so on. The hydrogen integration controller 2202 may further base the total CI on the volume of the selected one or more available feedstock and/or the yield percentage of the hydrogen production facility or source process (in other words, the volume of the hydrogen per the original feedstock volume). Other factors may be taken into account for total CI.

In response to a determination of total CI, at block 2318, the hydrogen integration controller 2202 may determine whether all blends or selections or, at least, a number of blends or selections of the one or more available feedstock (and the variations of the other selections described above) have been considered (e.g., if a total CI has been determined for all variations of feedstock combinations or paths). If all blends or selections or a number of blends or selections of the one or more available feedstock have not been considered, at block 2324, the hydrogen integration controller 2202 may select another of the one or more available feedstock and determine total CI, as described above. If all of the one or more available feedstock or, at least, a particular amount or set of ratios or blends of the one or more available feedstock have been considered, then the hydrogen integration controller 2202, at block 2320, may determine whether any path, combination, variation, or final selection does not exceed the threshold CI. If no path, combination, variation, or final selection does not exceed the threshold CI (in other words, if all paths, combinations, variations, or final selections exceed the threshold CI), at block 2321, the hydrogen integration controller 2202 may transmit a notification to a user, prompting the user to select a new threshold CI. In another example, the hydrogen integration controller 2202 may automatically increase the threshold CI based on a specified amount. The hydrogen integration controller 2202, at block 2322, may wait until a new threshold CI is received. When a new threshold CI is submitted or received by the hydrogen integration controller 2202, the current threshold CI is set to the new threshold CI and, at block 2324, another of the one or more available feedstock may be selected and each iteration or a number of iterations may be determined again, as described above.

If at least one path, combination, variation, or final selection does not exceed the threshold CI, at block 2326, the hydrogen integration controller 2202 may determine a set of paths, combinations, variations, or selections with the lowest total CI. In some cases, one path, combination, variation, or selection may not exceed the threshold CI, while in other cases many paths or selections may not exceed the threshold CI. Each path, combination, variation, or selection may include a selected one or more available feedstock, one or more selected feedstock transportation pathways, one or more selected hydrogen production operations or processes, one or more selected utilities, and/or one or more selected hydrogen distribution pathways, as well as a corresponding CI for each selection.

Based on the set of paths, combinations, variations, or selections, at block 2328, the hydrogen integration controller 2202 may determine a selection of a path, combination, variation, or selection from the set of paths or selections. The hydrogen integration controller 2202 may select the path, combination, variation, or selections based on, in addition to lowest total CI, time of availability of each of the selected one or more available feedstock, a time for delivery to the one or more hydrogen production facilities or sources by the feedstock transportation pathway, a time to process a feedstock utilizing the selected one or more hydrogen production operations or processes, a time to delivery from the one or more hydrogen production facilities or sources to an end user 2230 by each of the selected one or more hydrogen distribution pathways, the cost of each selection, any hydrogen production currently in progress or in queue, and/or customer demand for hydrogen of a particular CI. So, as an example, the hydrogen integration controller 2202 may select the path, combination, variation, or selection having a lower than threshold CI (although not necessarily the lowest CI) and more efficient pathway (e.g., from feedstock to customer), as described above. An efficient pathway may include a shorter distance to travel overall (e.g., from feedstock source to customer), the time of availability for the feedstock, the length of time to convert or transform a particular feedstock (which may be based on a type of feedstock), the length of time a feedstock or hydrogen may be stored at any point in the hydrogen production, cost issues associated with each of the selection, and/or a high demand for a hydrogen of a particular CI.

In response to determination of a selection of the path, combination, variation, or selections, at block 2330, the hydrogen integration controller 2202 may generate and transmit an estimated or initial audit report to a user, user interface, database, and/or other device. The audit report may include the CI of each selection and the total CI. The estimated audit report may include other information regarding each part of the planned or selected hydrogen production, such as where the selected feedstock is from, the type and volume of the selected feedstock, the type of feedstock transportation pathways (as well as other details on the feedstock transportation pathway), the selected hydrogen production process, the estimated yield of the hydrogen production process, the selected utilities, the source of the selected utilities, the type of hydrogen distribution pathways (as well as other details regarding the hydrogen distribution pathway), length of time for storage at any point in the process, and/or an overall timeline of the hydrogen production. In another example, the hydrogen integration controller 2202 may generate the estimated or initial audit report based on a request from a user and/or user interface.

In another example, the hydrogen integration controller 2202, at block 2332, may transmit a feedstock request. The feedstock request may include the selected one or more available feedstock and the selected feedstock transportation pathway. In another example, the hydrogen integration controller 2202 may transmit a confirmation of the feedstock request prior to transmitting the feedstock request. For example, the hydrogen integration controller 2202 may transmit a request for confirmation of a feedstock request of the selected one or more available feedstock to a user interface or a procurement computing device. In response to reception of the confirmation (e.g., from the user interface or procurement computing device), the hydrogen integration controller 2202 may transmit the feedstock request to a procurement computing device, procurement controller, the user interface (which may include a procurement sub-routine or instructions), a procurement and distribution computing device, or other device.

Once the feedstock request has been delivered to the hydrogen production facility or source (e.g., reformer 2216), at block 2334, the hydrogen integration controller 2202 may determine the actual CI for the selected one or more available feedstock and corresponding feedstock transportation pathway. The hydrogen integration controller 2202 may determine whether, in relation to the determined feedstock CI and feedstock transportation CI, the actual CI for either the selected one or more available feedstock and corresponding feedstock transportation pathway has increased. If an increase is determined, the hydrogen integration controller 2202, at block 2336, may select one or more different hydrogen production processes at one or more hydrogen production facilities or sources, utilities, and/or hydrogen distribution pathways to maintain the total CI, cost, and/or timeline of hydrogen production, if such a selection is available. In another example, the hydrogen integration controller 2202 may send a prompt or notification to a user or user interface. Further, the prompt may include the available options or paths, such as one or more different hydrogen production processes at one or more hydrogen production facilities or sources, utilities, storage tanks, pressurized storage vessels, and/or hydrogen distribution pathways. In such examples, the user may select the new options or paths to maintain the total CI (e.g., from the estimate audit report) or lower the total CI further. In another example, the user may choose to continue with the prior selections.

In response to the determination that the determined feedstock CI and feedstock transportation CI have not increased or in response to a selection of one or more different hydrogen production processes at one or more hydrogen production facilities or sources, the hydrogen integration controller 2202 may, at block 2338, initiate any selected hydrogen production processes or operations. In another example, the hydrogen integration controller 2202 may connect to a hydrogen production facility or source controller and transmit the initiation to the hydrogen production facility or source controller. The hydrogen integration controller 2202 may notify a user of the initiation of the hydrogen production processes or operations. In another example, the hydrogen integration controller 2202 may send a prompt to a user to initiate or confirm initiation of the hydrogen production processes or operations.

In response to a reception of or determination of completion of the selected hydrogen production processes or operations, at block 2340, the hydrogen integration controller 2202 may determine the actual CI for the selected hydrogen production processes or operations and utilities. The hydrogen integration controller 2202 may determine whether, in relation to the determined hydrogen production processes or operations CI and utility CI, the actual CI for the hydrogen production processes or operations and utilities has increased. If an increase is determined, the hydrogen integration controller 2202, at block 2342, may select one or more different hydrogen distribution pathways to maintain CI, cost, and/or timeline of fuel production, if such a selection is available.

Once a new hydrogen distribution pathway is selected or if no new hydrogen distribution pathway is selected, the hydrogen integration controller 2202, at block 2344 may transmit a distribution request for the hydrogen via the selected hydrogen pathway. The distribution request may include the hydrogen (e.g., the amount or volume of hydrogen and type of hydrogen) and the selected hydrogen distribution pathway. In another example, the hydrogen integration controller 2202 may transmit a request for confirmation of a distribution request of the hydrogen to a user interface or a distribution computing device. In response to reception of the confirmation (e.g., from the user interface or distribution computing device), the hydrogen integration controller 2202 may transmit the feedstock request to a distribution computing device, distribution controller, the user interface (which may include a distribution sub-routine or distribution instructions), a procurement and distribution computing device, or other device.

At block 2346, the hydrogen integration controller 2202 may determine the actual CI for the selected one or more available feedstock, the completed feedstock transportation pathway, the completed hydrogen production processes or operations including utilities, and the completed hydrogen distribution pathway. At block 2348, the hydrogen integration controller 2202 may determine the actual total CI. The actual total CI may be based on the actual hydrogen yield, the actual feedstock volume, and the actual CI for the selected one or more available feedstock, the completed feedstock transportation pathway, the completed hydrogen production processes or operations including utilities, and the completed hydrogen distribution pathway.

At block 2350, the hydrogen integration controller 2202 may generate and transmit an actual or final audit report to a user, user interface, database, and/or other device. The actual or final audit report may include the actual total CI and the actual CI for each process (e.g., the actual CI for the selected one or more available feedstock, the completed feedstock transportation pathway, the completed hydrogen production processes or operations including utilities, the completed blending process, and the completed fuel product distribution pathway). The hydrogen integration controller 2202 may generate the actual or final audit report based on a request from a user and/or user interface.

Figure 24A:
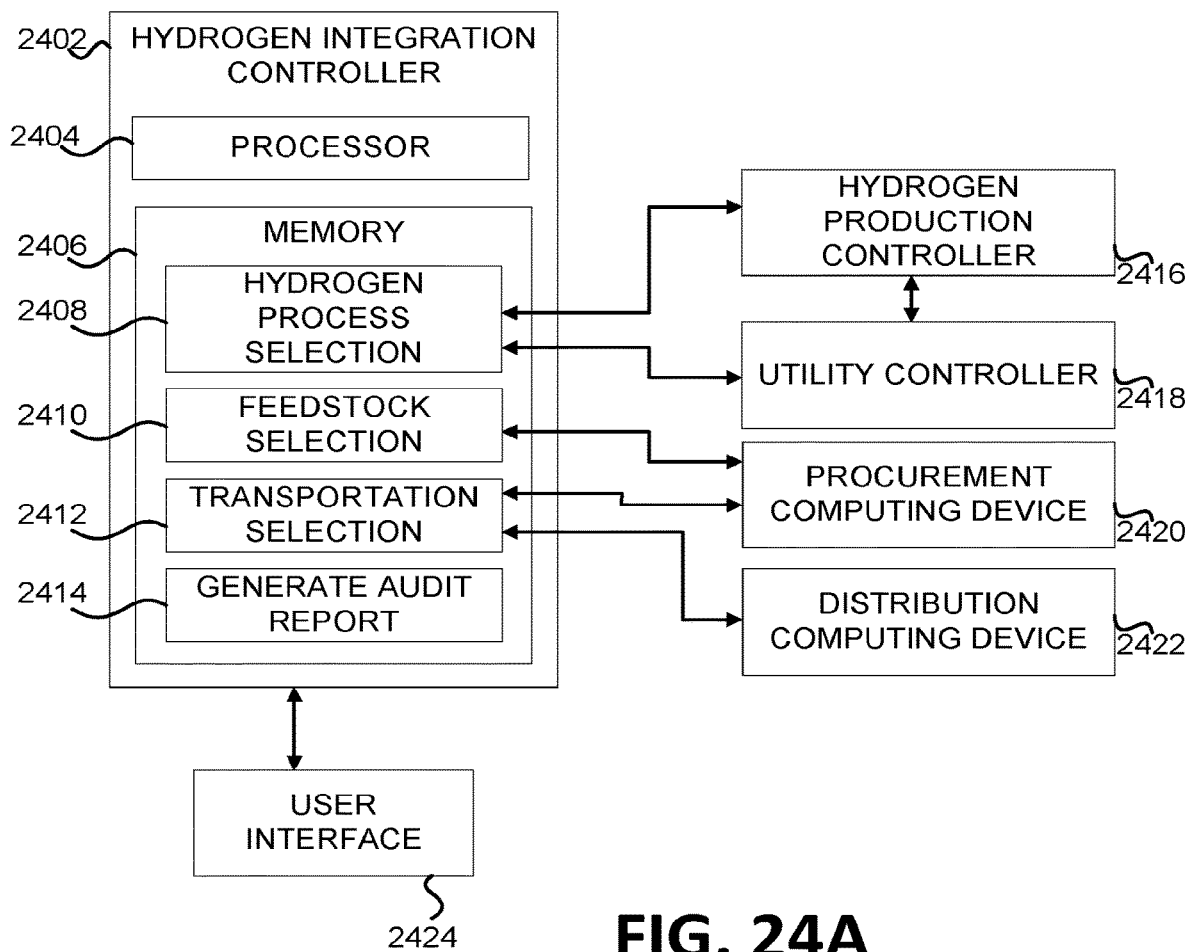
FIGS. 24A-E are simplified diagrams illustrating a control system for managing the low carbon intensity hydrogen production according to an embodiment.

FIGS. 24A-E are simplified diagrams illustrating a control system for managing the low carbon intensity hydrogen production according to an embodiment. FIG. 24A illustrates an embodiment of a hydrogen integration controller 2402 for managing low carbon intensity energy production. As noted above and as illustrated in FIG. 20, a hydrogen integration controller 2402 may manage the operations of hydrogen production (e.g., low and/or high CI hydrogen production processes or operation). The hydrogen integration controller 2402 may be one or more controllers, a supervisory controller, programmable logic controller (PLC), a computing device (such as a laptop, desktop computing device, and/or a server), and/or other suitable devices. The hydrogen integration controller 2402 may be located at or near a hydrogen production facility or source. The hydrogen integration controller 2402, as noted, may be more than one controller. In such cases, the hydrogen integration controller 2402 may be located near or at various feedstock sources, near or at one or more hydrogen production facilities or sources, and/or at other off-site locations. The hydrogen integration controller 2402 may include a processor 2404, or one or more processors, and memory 2406. The memory 2406 may include instructions. In an example, the memory 2406 may be a machine-readable storage medium.

The hydrogen integration controller 2402 may include various modules in memory 2406. The modules may include or define a set of instructions, executable by the processor 2404 for different aspects involved in managing low and/or high carbon intensity hydrogen production. Each module may be in signal communication with other controllers, sensors, data inputs, computing devices, servers, refinery components, and/or user interfaces. The hydrogen integration controller 2402 may include a hydrogen process selection module 2408, a transportation selection module 2412, a feedstock selection module 2410, and/or an audit report module 2414. The hydrogen process selection module 2408 may be in signal communication with a hydrogen production controller 2416 and/or a utility controller 2418. The hydrogen process selection module 2408 may be in signal communication with a plurality of hydrogen production controllers (e.g., each hydrogen production controller located at a different and/or separate hydrogen production facilities or sources, such as steam reformers, naphtha reformers, electrolyzers, and/or refineries). In another example, the hydrogen process selection module 2408 may be in signal communication with a hydrogen production controller 2416 including the functionality of a utility controller 2418. In yet another example, the hydrogen integration controller 2402 may include the functionality of a hydrogen production controller 2416 and/or a utility controller 2418. The transportation selection module 2412 may connect to a procurement computing device 2420, a distribution computing device 2422, a procurement and distribution computing device, a controller, a user interface, a server, database, and/or another device. The feedstock selection module 2410 may be in signal communication with a procurement computing device 2420, a procurement and distribution computing device, a procurement controller, a user interface, a server, database, and/or another device. The audit report module 2414 may be in signal communication with a user interface 2424. In such an example, a user may request an audit report via the user interface 2424. The user interface 2424 may be in signal communication with the hydrogen integration controller 2402 and/or the audit report module 2414. In such examples, the user interface 2424 may send and receive data to and from, respectively, the hydrogen integration controller 2402.

As noted above, the hydrogen integration controller 2402 may be in signal communication with the user interface 2424. The user interface 2424 may include an input (such as a keyboard, mouse, touchscreen, etc.) and a display. In another example, the user interface 2424 may be a computing device, such as a laptop, desktop computer, server, smartphone, tablet, or a terminal. A user may enter data into the user interface 2424 to send to the hydrogen integration controller 2402. For example, a user may enter in a threshold CI for a particular hydrogen production process. A user may input a low CI hydrogen specification for a particular hydrogen production process, the low CI hydrogen specification noting or including the threshold CI. The low CI hydrogen specification may be or may include the definition of a low CI hydrogen. In yet another example, the hydrogen integration controller 2402 may connect to a database. The database may store the threshold CI and the hydrogen integration controller 2402 may obtain the threshold CI from the database for a particular hydrogen production process. The hydrogen integration controller 2402 may include or store the threshold CI in memory 2406. In another example, a user may enter or input other data into the hydrogen integration controller 2402 via the user interface 2424, such as available feedstock, available feedstock transportation pathways, available hydrogen production processes at hydrogen production facilities or sources, available utilities, and/or available hydrogen distribution pathways. A user may also enter or input the algorithms and/or calculations to determine a CI for any particular process.

In response to a reception of a threshold CI, whether from the user interface 2424, a database, another device, or from memory 2406, the hydrogen integration controller 2402 may set, assign, or utilize the threshold CI as a current threshold CI for a particular hydrogen production process. As such, the hydrogen integration controller 2402 may select various portions of the hydrogen production process to ensure that the current threshold CI is not exceeded. Further, the hydrogen integration controller 2402 may simulate, model, or determine many different variations to determine the best possible path, combination, or selection based on various data points or factors. The hydrogen integration controller 2402 may determine the best possible path, combination, or selection via a brute-force method, a min-max method, an admissible decision method, and/or via other decision making methods as will be understood by those skilled in the art.

For example, upon reception of the threshold CI, the hydrogen integration controller 2402 may determine a CI for a number of or all selections of one or more available feedstock (in other words, feedstock variations). The hydrogen integration controller 2402 may further determine a CI for a number of or all selections of blends of the one or more available feedstock. In other words, the feedstock variations may include varying blends of one or more selected feedstock (e.g., 30% of feedstock 1 and 70% of feedstock 2, 25% of feedstock 1 and 75% of feedstock 2, etc.). The feedstock selection module 2410, hydrogen integration controller 2402, or another module may perform the CI determination for the feedstock variations. The feedstock selection module 2410, hydrogen integration controller 2402, or another module may determine the CI of each feedstock variation based on data received from the procurement computing device 2420, a procurement and distribution computing device, a database, a user input from the user interface 2424, a feedstock controller in signal communication with the hydrogen integration controller 2402, memory 2406, or another device storing such data. The data received may include a volume of a feedstock, a type of feedstock (for example, natural gas, renewable natural gas, refinery byproducts, etc.), and/or a location of the feedstock (for example, city, state, country, etc.). The data may also include the innate or inherent CI of the feedstock (or the hydrogen) or, in other words, the carbon emissions of the energy content of the feedstock (or hydrogen), as disclosed above. The data may also include a CI (or raw data to determine the CI) associated with producing, obtaining, and/or any other processing of the feedstock (e.g., a CI associated with obtaining, procuring, and/or processing a feedstock from a feedstock source, etc.). Once a number of or all of the feedstock variations CI are determined, the hydrogen integration controller 2402 may store each CI in memory 2406, at a database, and/or at the procurement computing device 2420 for future use.

The hydrogen integration controller 2402 may further determine a feedstock transportation CI for a number of or all available feedstock transportation pathways for each or a number of each feedstock variations. The transportation selection module 2412 or another module in the hydrogen integration controller 2402 may determine the CI. The hydrogen integration controller 2402 or transportation selection module 2412 may determine the feedstock transportation CIs based on the selected one or more available feedstock or feedstock variations, for any particular iteration or determination. For example, in the case that a feedstock from overseas is chosen, marine delivery modes or pathways may be considered, while for a local feedstock (or a feedstock within the same country), rail, vehicular (e.g., a truck), and/or pipeline delivery, if available, may be considered. The hydrogen integration controller 2402 or transportation selection module 2412 may obtain available feedstock transportation pathways from the procurement computing device 2420, the user interface 2424, a database, from memory 2406, and/or from another device. Further, the hydrogen integration controller 2402 or the transportation selection module 2412 may base the CI on the volume of each feedstock transportation pathway, the fuel type utilized by each feedstock transportation pathway (e.g., gas, electricity, steam, other liquid fuels, etc.), and/or a distance from the source of the feedstock to the hydrogen production facility or source. Once a number of or all of the feedstock transportation pathway variations CI, based on the feedstock variations, are determined, the hydrogen integration controller 2402 may store each CI in memory 2406, at a database, and/or at the procurement computing device 2420 for future use.

The hydrogen integration controller 2402 may further, via a hydrogen process selection module 2408, determine a hydrogen production process of a hydrogen production facility or source and utilities CI for a number of or all available hydrogen production processes of one or more hydrogen production facilities or sources and utility options for each or a number of each feedstock variations. The hydrogen integration controller 2402 may, rather than determining a hydrogen production process and utility CI, determine a hydrogen production process CI and/or a utilities CI. The hydrogen process selection module 2408 or other modules within the hydrogen integration controller 2402 may determine the hydrogen production process and utilities CI. As noted above, a hydrogen production process may utilize various utilities for any given hydrogen production process. To offset carbon emissions for standard hydrogen production processes, renewable utilities (e.g., solar, wind, geothermal, renewable gas, etc.) may be utilized in the hydrogen production process, thus reducing overall CI (as well as carbon emissions). In another example, heat integration through a heat exchanger network and/or carbon sequestration may be utilized or selected to reduce or offset the CI for a particular hydrogen production process, thus reducing the overall CI for a hydrogen production. In an example, the hydrogen integration controller 2402 or hydrogen process selection module 2408 may determine available hydrogen production processes and utilities based on a list from a hydrogen production controller 2416, utility controller 2418, or from memory 2406. In another example, the hydrogen integration controller 2402 or hydrogen process selection module 2408 may determine available hydrogen production processes and utilities based on the selected one or more available feedstock or feedstock variations (in other words, different feedstock may utilize different hydrogen production processes, thus choices may be limited based on the particular feedstock variations). In such examples, the hydrogen integration controller 2402 and/or the hydrogen process selection module 2408 may determine CI for each available hydrogen production process and utility option for each feedstock variation. The hydrogen integration controller 2402 and/or hydrogen process selection module 2408 may determine the CI for each available hydrogen production process and utility option based on the type or types of the selected feedstock variations, the utilities to be used during the hydrogen production processes, the yield of each hydrogen production process, and/or other factors, as will be understood by those skilled in the art. The hydrogen integration controller 2402 may consider other hydrogen production facilities or sources. The hydrogen integration controller 2402 may determine a CI for other refineries, as described above. Once a number of or all of the hydrogen production processes and utilities CI (for one or more hydrogen production facilities or sources), based on the feedstock variations, are determined, the hydrogen integration controller 2402 may store each CI in memory 2406 or at a database for future use.

As noted, the hydrogen integration controller 2402 may, rather than determining a hydrogen production process and utility CI, determine a hydrogen production process CI and/or a utilities CI. The utility CI may be based on the utilities used in a corresponding hydrogen production process, the utilities used to store a feedstock, the utilities used to store a hydrogen, other utilities used for various other processes at hydrogen production facilities or sources, and/or at other points in the hydrogen production process (e.g., utilities used in pumps to transfer feedstock or hydrogen).

The hydrogen integration controller 2402 may further determine a hydrogen distribution CI for a number of or all available hydrogen distribution pathways for each or a number of each feedstock variations. The transportation selection module 2412 or another module in the hydrogen integration controller 2402 may determine the hydrogen distribution CI. The hydrogen integration controller 2402 or transportation selection module 2412 may determine the hydrogen distribution CI based on the selected one or more available feedstock and hydrogen production process yield, for any particular iteration or determination. For example, one hydrogen production process for a feedstock variation may produce a certain amount of hydrogen and, potentially, other gases, while another hydrogen production process for another feedstock variation may produce a different amount of hydrogen and other gases. The hydrogen integration controller 2402 or transportation selection module 2412 may obtain available hydrogen distribution pathways from the distribution computing device 2422, the user interface 2424, a database, from memory 2406, and/or from another device. Further, the hydrogen integration controller 2402 or the transportation selection module 2412 may determine the hydrogen distribution CI based on the volume of each hydrogen distribution pathway, the fuel type utilized by each hydrogen distribution pathway, and/or a distance from the hydrogen production source to distribution point and/or an end destination/point. Once a number of or all of the hydrogen distribution pathway variations CI, based on the feedstock variations, are determined, the hydrogen integration controller 2402 may store each CI in memory 2406, at a database, distribution computing device 1024, and/or procurement and distribution computing device for future use.

Once a number of or all CIs for each selection (as in, the selection of the one or more available feedstock, the feedstock transportation pathway, the hydrogen production process and utilities, and the hydrogen distribution) are determined, the hydrogen integration controller 2402 may determine a set of variations, combinations, or selections of each of the selections noted above. For example, one set of the variations, combinations, or selections may include a selected one or more available feedstock, a selected one or more available feedstock transportation pathways (corresponding to the feedstock variation), a selected one or more hydrogen production processes (corresponding to the feedstock variation), a selected one or more utilities (corresponding to the hydrogen production processes and/or other processes to use utilities), and a selected one or more hydrogen distribution pathways (corresponding to the hydrogen from the hydrogen production facility or source). Further, the hydrogen integration controller 2402 may determine a total CI for each variation, combination, or set of selections. The hydrogen integration controller 2402 may determine the total CI based on the volume of the selected one or more available feedstock, the yield from the corresponding or selected hydrogen production processes to produce hydrogen, the determined feedstock CI, the determined feedstock transportation CI, the determined hydrogen production process and utilities CI, and/or the determined hydrogen distribution CI. Other factors may be considered when determining a total CI. For example, the hydrogen integration controller 2402 may further base the total CI on a feedstock storage tank CI (if utilized), a pressurized storage vessel CI (if utilized), emissions (e.g., VOC emissions through working losses, breathing losses, and flashing losses), carbon sequestration (if utilized), and/or other carbon offsetting practices as will be understood by those skilled in the art. In such examples, once the hydrogen integration controller 2402 determines the total CI for each variation, the hydrogen integration controller 2402 may store each total CI in memory 2406 and/or at a database.

Once each total CI variation is determined, the hydrogen integration controller 2402 may determine a selection from the set of combinations. The combinations may include the various selections, described above, with a CI less than the threshold CI. In an example, if there are no variations with a CI less than the CI threshold, the hydrogen integration controller 2402 may notify a user that all selections exceed the threshold CI, prompt a user to enter a new threshold CI, and/or prompt a user to accept the selection with the lowest total CI (the lowest total CI, in this case, exceeding the threshold CI). In another example, the hydrogen integration controller 2402 may automatically select a new threshold CI. In another example, the hydrogen integration controller 2402 may determine the selection based on the lowest total CI (the lowest total CI not exceeding the threshold CI). In yet another example, multiple combinations may include a similar or the same total CI. However, each combination may exhibit different properties, such as a cost issue or a timing issue (e.g., from feedstock to customer). In such examples, the hydrogen integration controller 2402 may select one of the combinations, with the similar or same CI or a CI lower than threshold, further based on the time of availability of each of the selected one or more available feedstock, a time for delivery to the hydrogen production facility or source by the feedstock transportation pathway, a time to process a feedstock utilizing the selected one or more hydrogen production processes, a time to delivery from the hydrogen production facility or source to the end user (e.g., a refinery, distribution point, power plant, or fuel cells, etc.), and/or any hydrogen production processes queued or in production. Upon determination of a selection, the hydrogen integration controller 2402 may initiate hydrogen production or transmit a request to confirm initiation of the hydrogen production.

Figure 24B:
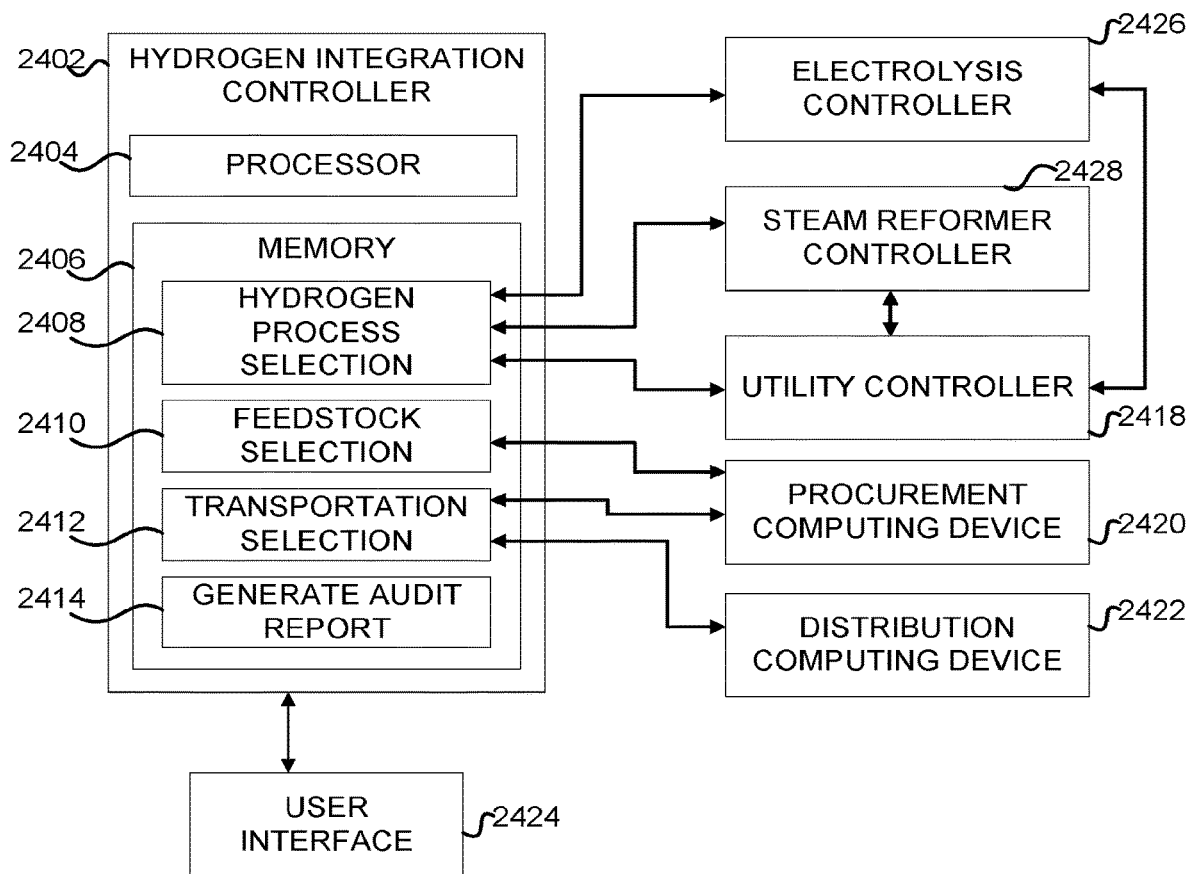

FIG. 24B illustrates another simplified diagram illustrating a control system for managing the low carbon intensity energy production according to an embodiment. As noted, the hydrogen integration controller 2402 may connect to controllers for various other hydrogen production facilities or sources. For example, the hydrogen integration controller 2402 and/or the hydrogen process selection module 2408 may be in signal communication with an electrolysis controller 2426 to control an electrolysis process (e.g., the process to convert water to hydrogen and oxygen via electricity). The hydrogen integration controller 2402 and/or the hydrogen process selection module 2408 may be in signal communication with a steam reformer controller 2428. The hydrogen integration controller 2402 and/or the hydrogen process selection module 2408 may connect to other controllers at similar or different hydrogen production facilities or sources (e.g., a refinery, a naphtha reformer, a gasification facility, etc.).

Figure 24C:
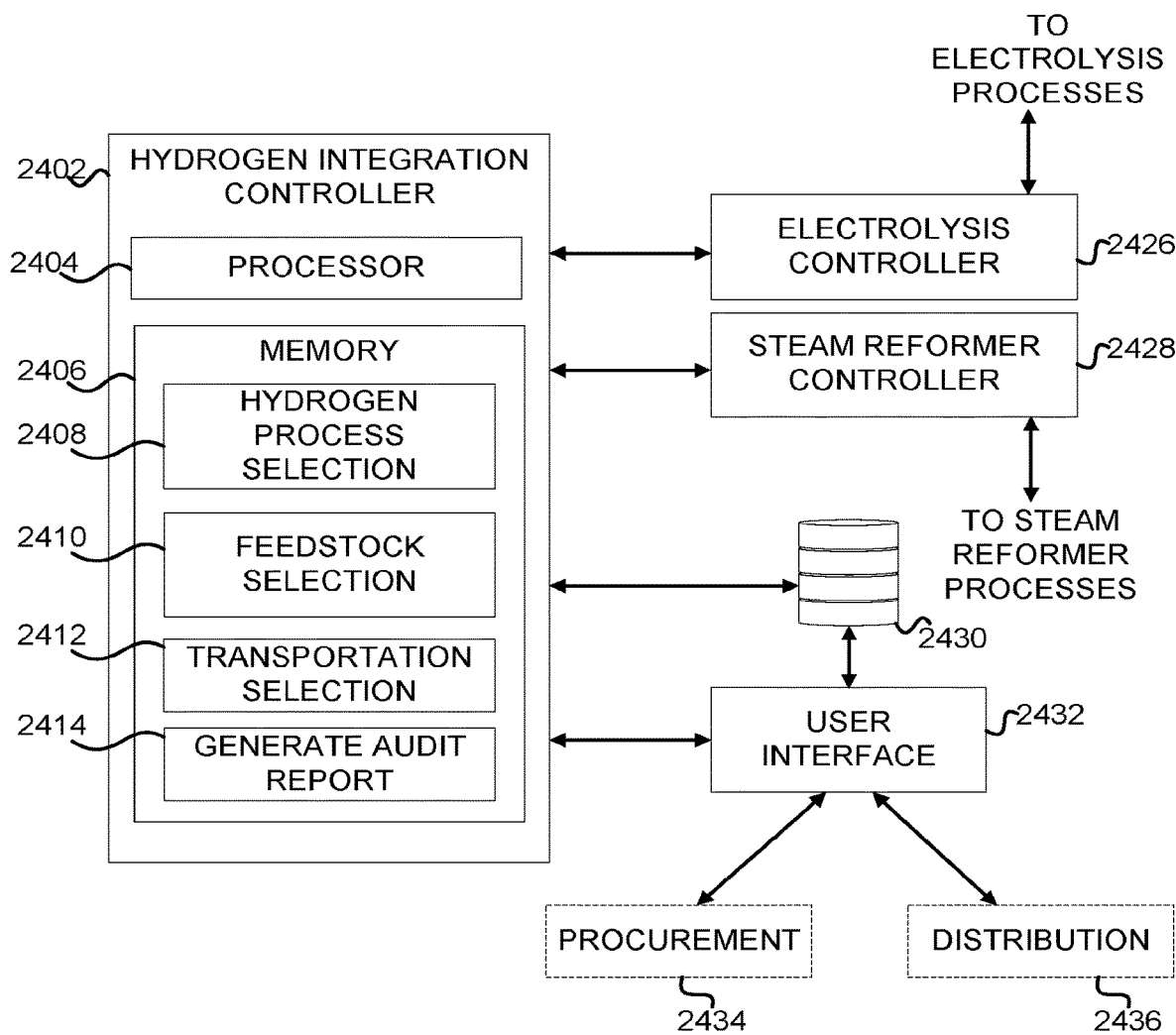

FIG. 24C illustrates another simplified diagram illustrating a control system for managing the low carbon intensity energy production according to an embodiment. In such examples, rather than connecting to a procurement and distribution computing device, the hydrogen integration controller 2402 may connect to a user interface 2432. The user interface 2432 may connect to or include a procurement module 2434. For example, the procurement module 2434 may be a set of instructions included in the user interface 2432 to order feedstock from various feedstock sources. The procurement module 2434 may be a controller, computing device, server, and/or other device. The user interface 2432 may also connect to or include a distribution module 2436. For example, the distribution module 2436 may be a set of instructions included in the user interface 2432 to initiate delivery of hydrogen from a hydrogen production facility or source to an end user (or other distribution point or terminal). The distribution module 2436 may be a controller, computing device, server, and/or other device. In such examples, the procurement module 2434 and distribution module 2436 may allow for order of feedstock, via specified transportation modes, and delivery of refined product, via specified transportation modes.

As noted above, the hydrogen integration controller 2402 may determine a combination of a selection of one or more feedstock, one or more feedstock transportation pathways, a selection of one or more hydrogen production processes, a selection of one or more utilities, and a selection of one or more hydrogen distribution pathways. The hydrogen integration controller 2402 may determine such a combination based on a determination of the feedstock CI (based on, for example, a ratio or blend of available feedstock volume and type), the feedstock transportation CI (based on available feedstock transportation delivery distance and fuel type), the hydrogen production process CI (based on the type of hydrogen production process, the volume and type of feedstock, the length of time of the hydrogen production process, and/or the yield of the hydrogen production process process), the utility CI of one or more utilities (based on the type of utility utilized in the hydrogen production process and the distance the utility travels to reach the hydrogen production facility or source), and/or hydrogen distribution CI (based on available hydrogen distribution delivery distance and fuel type). Other factors may be utilized in determining a combination, such as cost of each process, margin or profit based on a sale of the final product, availability, yield, and/or one-time costs (such as increasing hydrogen production capacity or increasing efficiency of an aspect of the hydrogen production facility or source).

In another example, the hydrogen integration controller 2402 may connect to a database 2430. The database 2430 may include various data points, such as available feedstock (and corresponding raw data), available transportation modes (and corresponding raw data), available storage tanks (and corresponding raw data), available hydrogen production processes (and corresponding raw data), and/or available utility options (and corresponding raw data). In another example, a user may update, via the user interface 2432, the data stored at the database 2430. In another example, the hydrogen integration controller 2402 may update the data at the database 2430, for example, based on reception of data from various controllers and/or computing devices. In another example, the hydrogen integration controller 2402 may store determined CIs, total CIs, and/or audit reports at the database, which other devices or user interfaces may access.

Figure 24D:
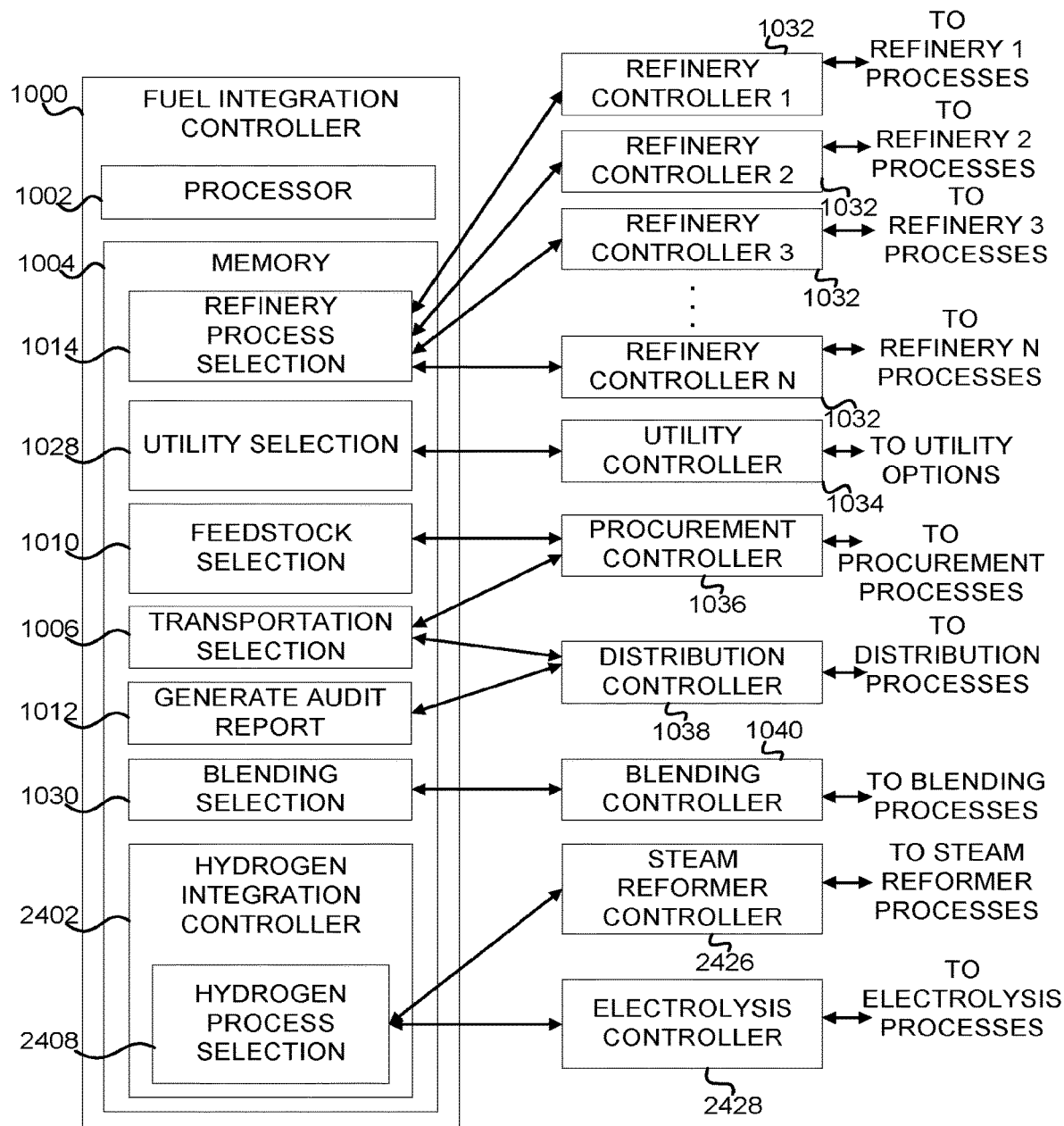
Figure 24E:
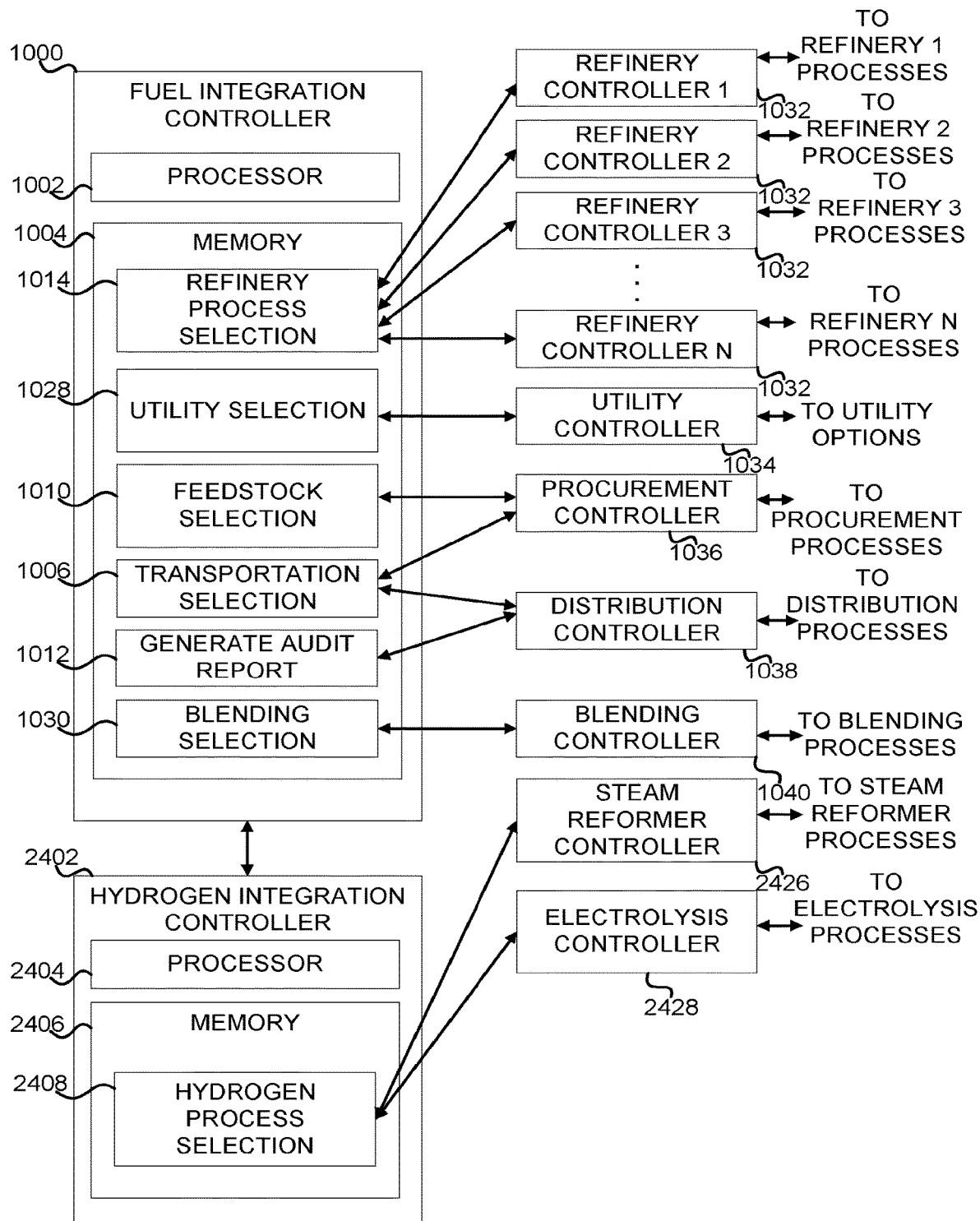

FIGS. 24D and 24E illustrate other simplified diagrams illustrating control systems for managing the low carbon intensity energy production according to an embodiment. In such examples, the fuel integration controller 1000 include the functionality of or connect to the hydrogen integration controller 2402. As such, the fuel integration controller 1000 may control the hydrogen integration controller 2402 to produce a low carbon intensity hydrogen to further reduce the carbon intensity of a refined transportation fuel. In another example, a supervisory controller may connect to the fuel integration controller 1000 and/or the hydrogen integration controller 2402 to orchestrate or control refined transportation fuel production processes and/or hydrogen production processes. In such examples, the supervisory controller may connect to other controllers related to refinery, hydrogen, water, utilities, feedstock sources, and/or other processes.

Figure 25A:
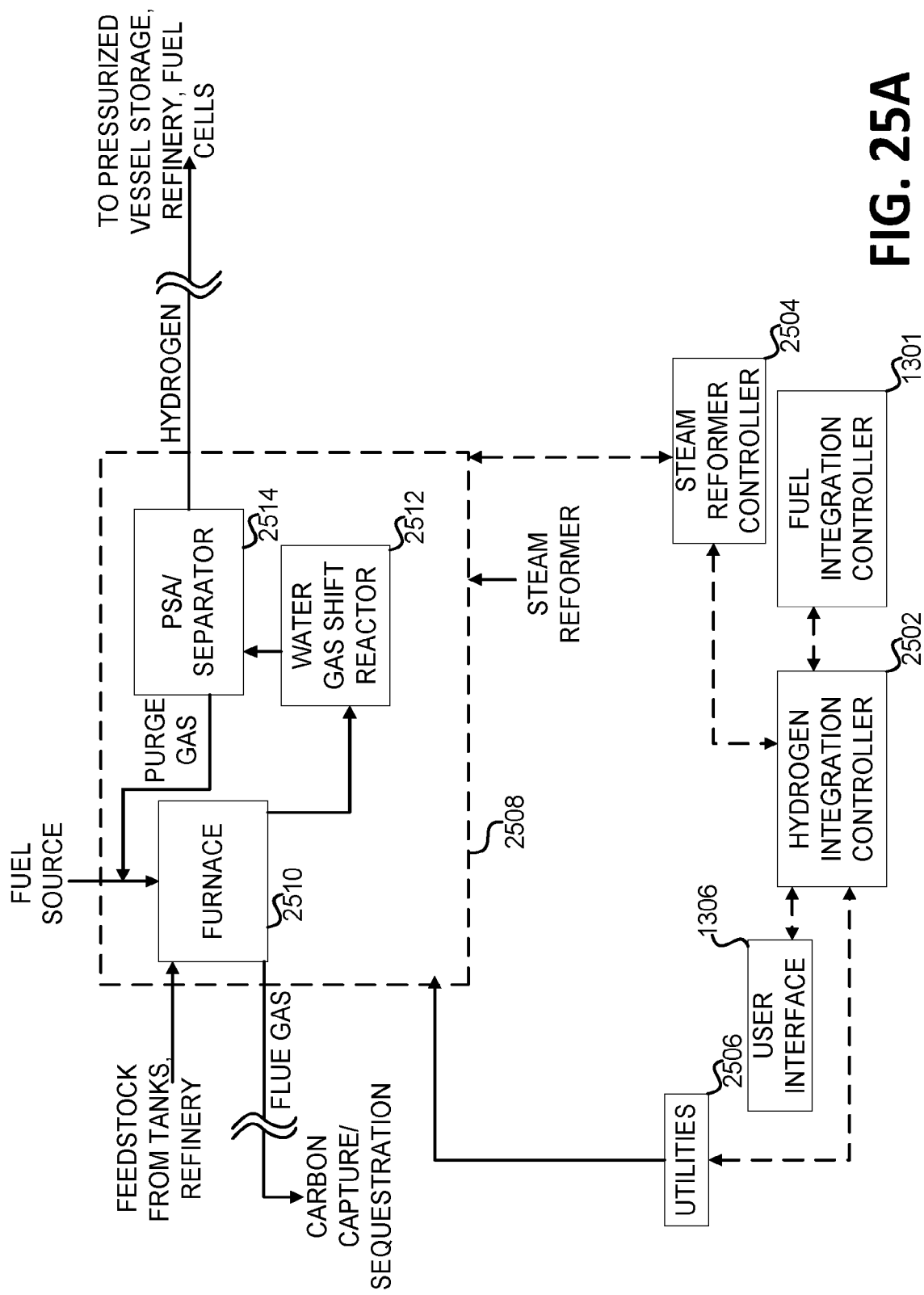
FIGS. 25A-C are block diagrams illustrating a system for managing the low carbon intensity hydrogen production according to an embodiment.
Figure 25B:
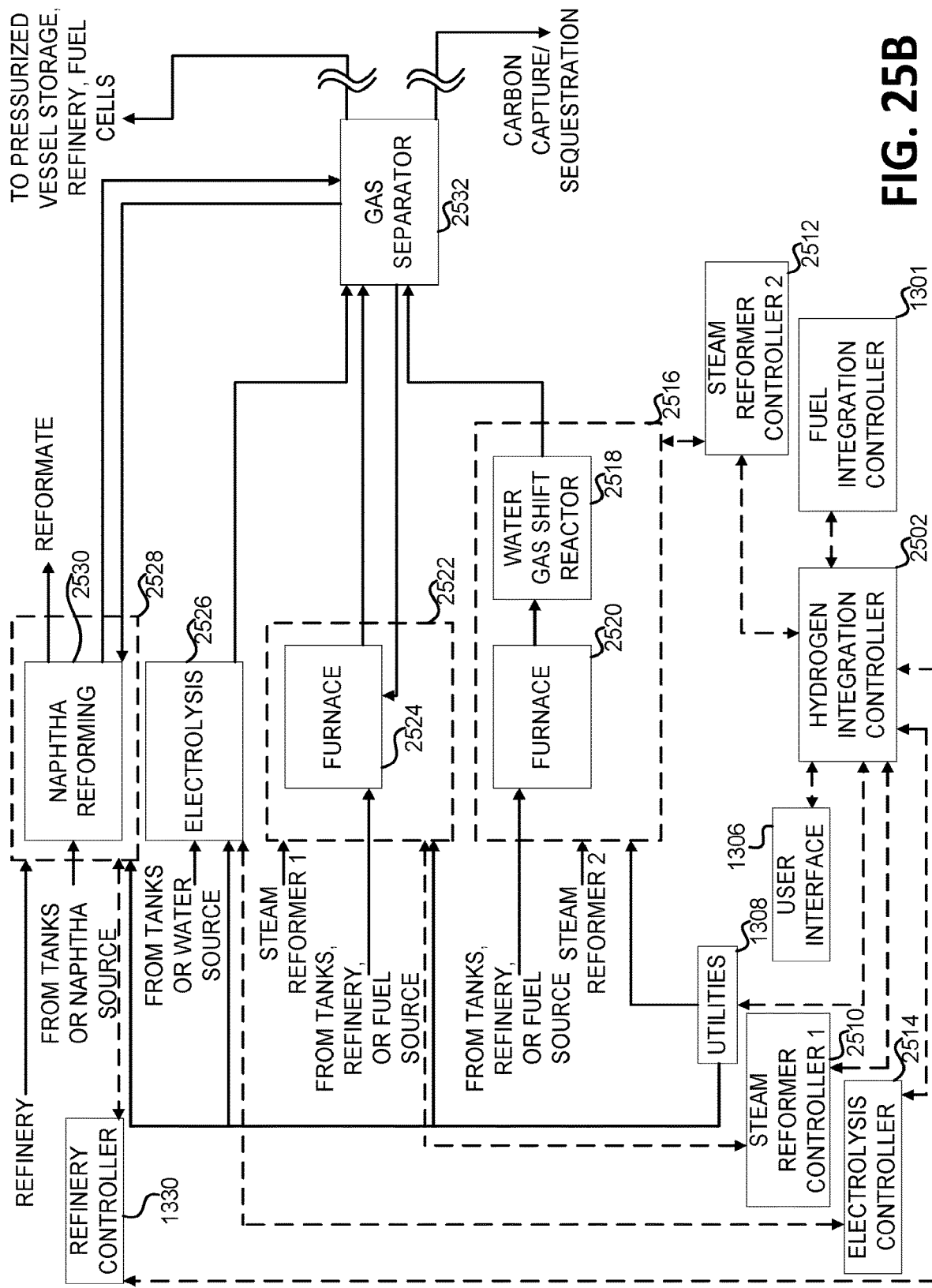
Figure 25C:
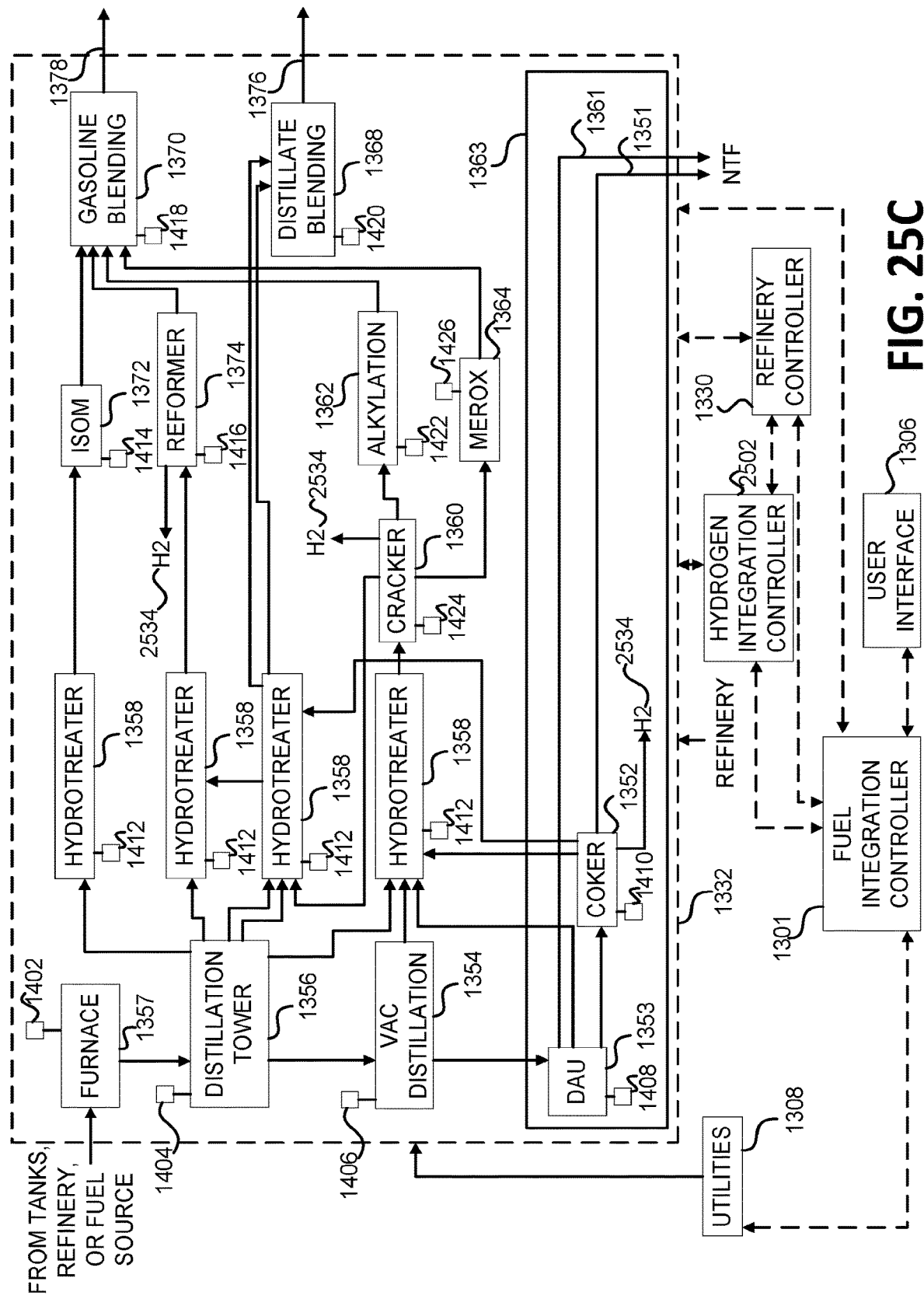

FIGS. 25A-C are block diagrams illustrating a system for managing the low carbon intensity hydrogen production according to an embodiment. As described above, a hydrogen integration controller 2502 may be utilized to manage low carbon intensity (CI) hydrogen production. The hydrogen integration controller 2502 may connect to a user interface 1306, a utilities provider 2506, and/or various controllers (e.g., steam reformer controller 2504, steam reformer controller 1 2510, steam reformer controller 2 2512, electrolysis controller 2514, and/or refinery controller 1330). The hydrogen integration controller 2502 may control operations or processes, via the controllers, to produce hydrogen.

For example, the hydrogen integration controller 2502 may connect to steam reformer controller 2504. The hydrogen integration controller 2502 may select the feedstock for steam reformer 2508. The hydrogen integration controller 2502 may also select the transportation method to deliver the feedstock to the steam reformer 2508. The hydrogen integration controller 2502 may select the utilities or fuel from the utilities provider 2506 or other fuel source to power the steam reformer 2508. For example, utilities or fuels, such as gas (e.g., renewable or fossil fuel based gas) may power a furnace 2511. The feedstock may combine with steam and pass through the heated furnace 2511 absorbing the produced heat (e.g., an endothermic reaction). The reaction may produce various gases, for example, hydrogen, carbon monoxide, carbon dioxide, methane, and/or water. Such products may pass through a water gas shift reactor 2513, to transform the carbon monoxide to carbon dioxide and hydrogen, as will be understood by those skilled in the art. The gases may further be pumped to a pressure swing adsorber (PSA)/separator 2515, to purify the hydrogen and remove any other gases, as will be understood by those skilled in the art. In another example, the purification of the hydrogen may occur at a membrane separator. The other gases, e.g., purge gases, produced by the PSA/separator may be transported to the heated furnace 2511 of the steam reformer 2508 and utilized as fuel. In another example, the purge gas may be mixed or blended with fuel from a fuel source (e.g., renewable or fossil fuel based gas) and then transported to the heated furnace 2511 to be utilized as fuel. The heated furnace 2511, after burning the fuel and purge gas may produce heat and flue gas. The flue gas may include or be comprised of carbon dioxide, which, as noted, may be sequestered to further reduce the overall carbon intensity of the hydrogen produced at the steam reformer 2508. The produced hydrogen may be distributed to the end user and, as noted, the carbon dioxide may be sequestered or released to the atmosphere.

In other examples, the hydrogen integration controller 2502 may select various aspects of steam reformer 1 2522 (e.g., including a furnace 2524, but no water gas shift reactor), steam reformer 2 2516 (e.g., including a furnace 2520 and water gas shift reactor 2518), electrolysis 2526 (e.g., utilizing water as a feedstock and electricity to produce hydrogen and oxygen, as will be understood by those skilled in the art), or naphtha reforming 2530. In such examples, the PSA or gas separator 2532 may be external to each of the hydrogen producing processes. In an example, the naphtha reforming process may produce a feedstock for a steam reformer (e.g., the naphtha reformer may produce offgas and reformate). In another example, the naphtha reformer may include steps or processes to further produce hydrogen and reformate. In another example, the hydrogen integration controller 2502 may connect to a refinery controller 1330. Various refinery processes may produce hydrogen 2534, such as a coker 1352, a cracker 1360, a reformer (as noted above), and/or other processes within the refinery 1332. The hydrogen produced by these processes may be utilized at the refinery 1332 for certain processes (e.g., at hydrotreaters 1358 and other processes). In other examples, the hydrogen 2534 produced may be more than is utilized in such processes. As such, an excess of hydrogen 2534 may be produced at the refinery 1332. The hydrogen integration controller 2502 may control the allocation and use of such hydrogen 2534, as well as how the excess hydrogen 2534 may be utilized (e.g., distributed to an end user, such as other refineries, power plants, and/or for fuel cells). In another example, steam reformer 1 2522 and steam reformer 2 2516 may illustrate various options or configurations within a refinery. For example, one option may include operating a steam reformer process without utilizing or bypassing a water gas shift reactor 2518 (e.g., steam reformer 1 2522), while another option may include the use of the water gas shift reactor 2518 (e.g., steam reformer 2516).

Figure 26:
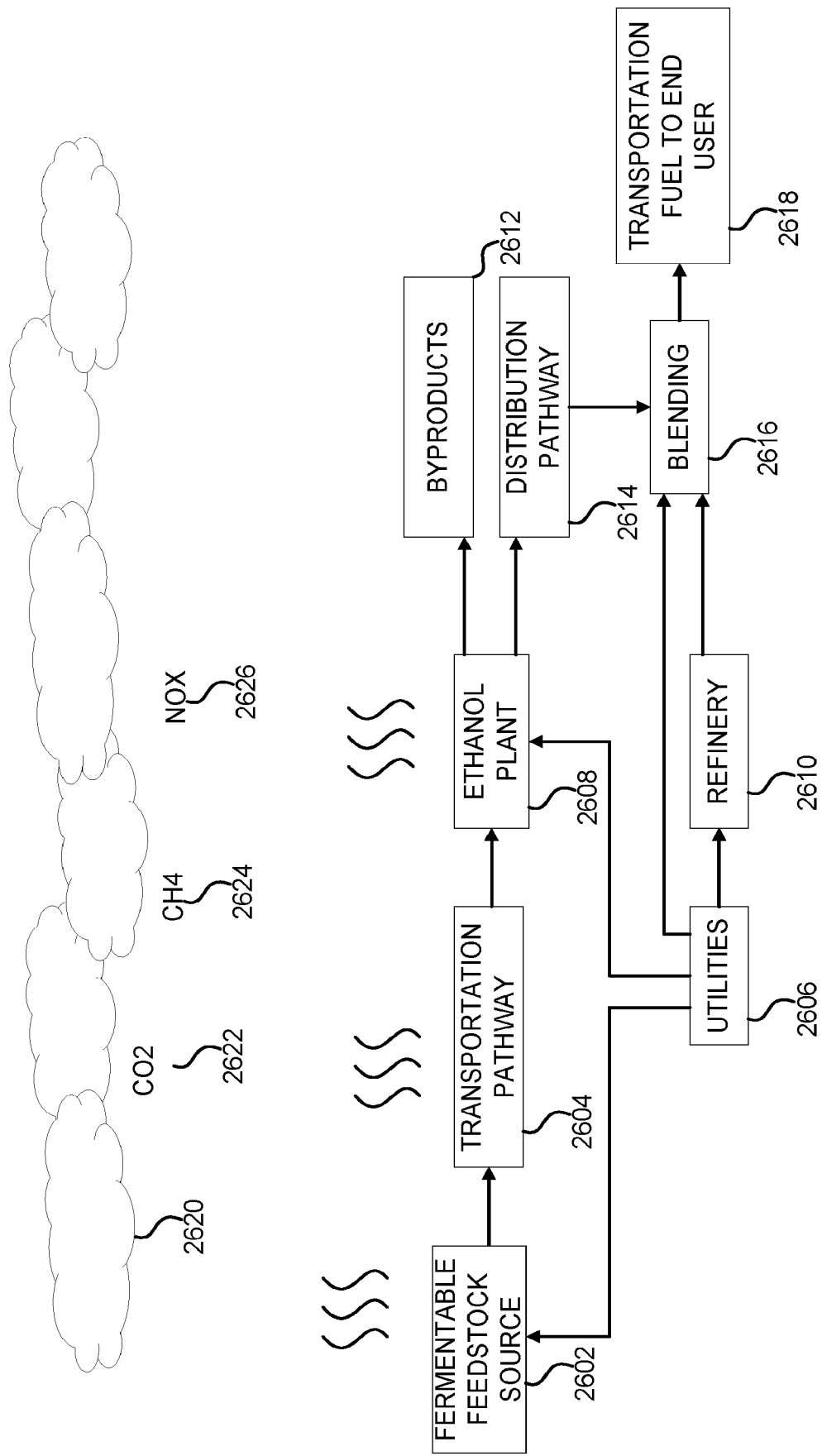
FIG. 26 is a diagram illustrating one or more embodiments that reduce carbon intensity from fermentation feedstock procurement to transportation fuel delivery to an end user location according to an embodiment.

FIG. 26 illustrates, as noted above and as disclosed in one or more embodiments of the present disclosure, a more holistic approach to reducing carbon intensity, as well as limiting emission of certain chemicals into the atmosphere 2620. Chemicals introduced into the atmosphere 2620 as a result of ethanol production, as well as an ethanol blending operation with refined transportation fuel, may include carbon dioxide ($CO_2$) 2622, methane ($CH_4$) 2624, nitrogen oxides ($NO_x$) 2626, and/or other chemicals, as will be understood by those skilled in the art. As a more holistic approach to carbon intensity is sought, the carbon intensity of each process or stage in an ethanol production (e.g., indirect and direct processes or stages) may be considered as an approach to target its carbon intensity reduction of the produced ethanol, as well as to target carbon intensity reduction of the overall carbon intensity of an ethanol-blended transportation fuel to an end user location 2618 (e.g., an ultra-low carbon intensity ethanol may significantly or further reduce the carbon intensity of a refined transportation fuel). As such, the carbon intensity associated with a fermentable feedstock source 2602 (e.g., an agricultural site, farm, waste facility, or other source of fermentable feedstock) may be considered for targeted carbon intensity reductions (e.g., an indirect process or stage in relation to the ethanol plant 2608). In other words, carbon intensity reductions may be achieved through the selection of different carbon intensity reducing methods (e.g., the use of low carbon intensity utilities 2606 or the use of low carbon intensity fertilizer, such as that derived from low CI hydrogen) of obtaining or producing fermentable feedstock at the fermentable feedstock source 2602. As used herein, "fermentable feedstock" may refer to a variety of different feedstock, each including an amount of starch, which may be converted to sugar, or sugar. A typical fermentable feedstock may be corn. Other fermentable feedstock may include wheat, barley, rice, other grains, fruits, vegetables, other vegetation, other organic matter, other organic waste, sugar solutions, or any other material including an amount of starch and/or sugar. The carbon intensity of feedstock transportation pathways 2604 (such as vehicular, rail, or marine transportation) may also be considered for targeted carbon intensity reductions (e.g., an indirect process or stage in relation to the ethanol plant 2608). Further, the carbon intensity at the ethanol plant 2608 may be considered for targeted carbon intensity reductions, such as by the use of renewable or low carbon intensity utilities 2606, through the use of carbon capture/sequestration, and/or by ethanol production process improvements. Such low carbon intensity utilities 2606 may be co-located at, proximate with, and/or dedicated to the ethanol plant 2608. In another example, the low carbon intensity utilities 2606 may be considered off-grid, i.e., the low carbon intensity utilities 2606 may not be tied to a grid supplied power source and may provide power to the ethanol plant 2608 and no other end user or consumer. The carbon intensity for other processes or stages may be considered for carbon intensity reduction, such as ethanol distribution pathways 2614 for transportation of ethanol to a blending site 2616 (e.g., indirect carbon intensity reduction) and/or through further use of byproducts 2612 (e.g., distiller's grain, oil, and/or other byproducts) produced at the ethanol plant 2608. The carbon intensity for other processes or stages of a blended transportation fuel operation, as described above, may be considered for carbon intensity reduction, such as blending processes at a blending site 2616 (e.g., indirect carbon intensity reduction) and/or a blended transportation fuel distribution pathway for transportation of a blended transportation fuel (e.g., a blend of ethanol and refined transportation fuel) to an end user location 2618 (e.g., indirect carbon intensity reduction).

Figure 27:
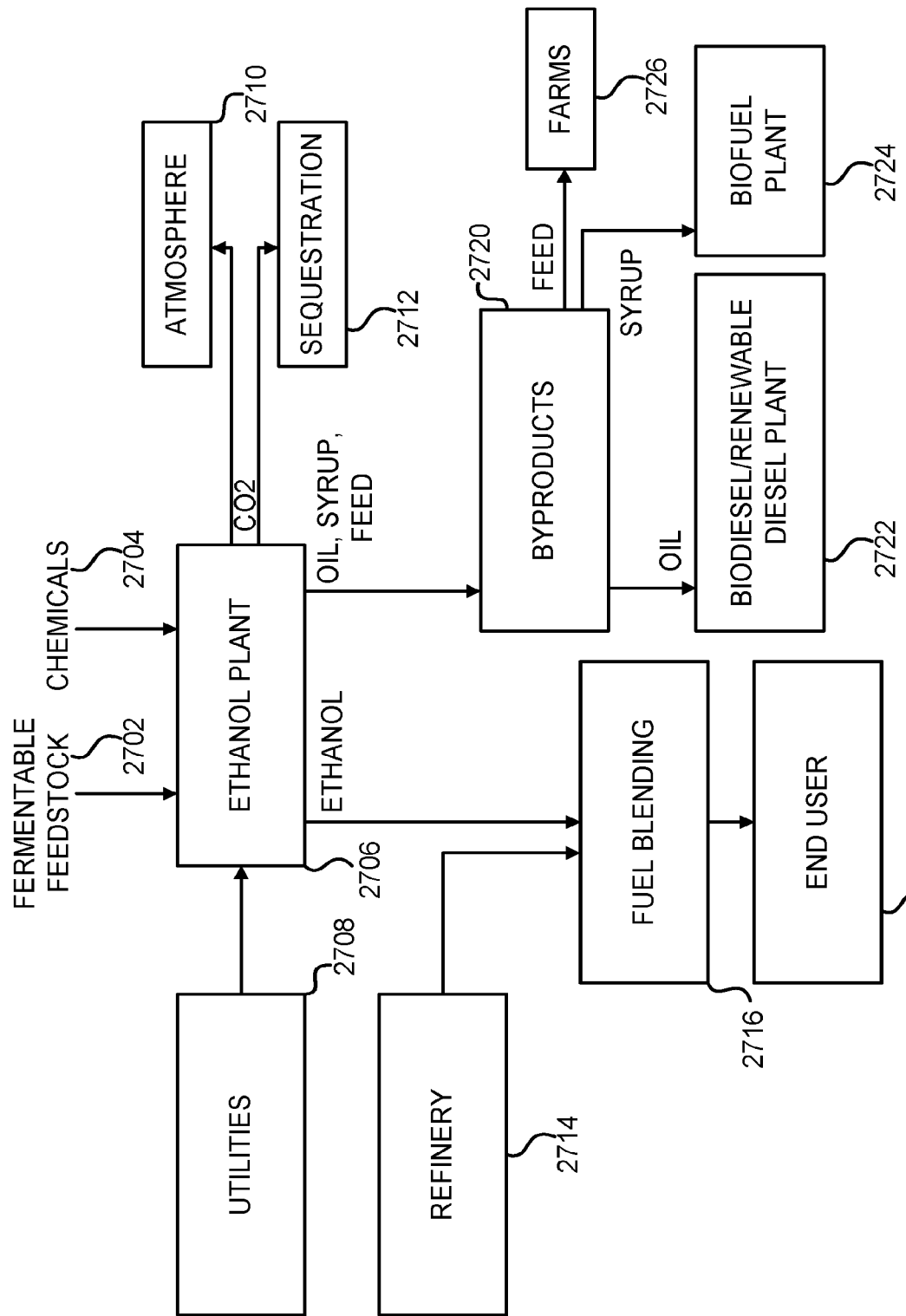
FIG. 27 is a simplified diagram that illustrates a novel implementation of a low carbon intensity ethanol strategy in which lower carbon energy is introduced and used during the acquisition and distillation of fermentation feedstock as well as the distribution of the resulting low carbon intensity ethanol to a fuel blending site, according to one or more embodiments of the disclosure.
Figure 28:
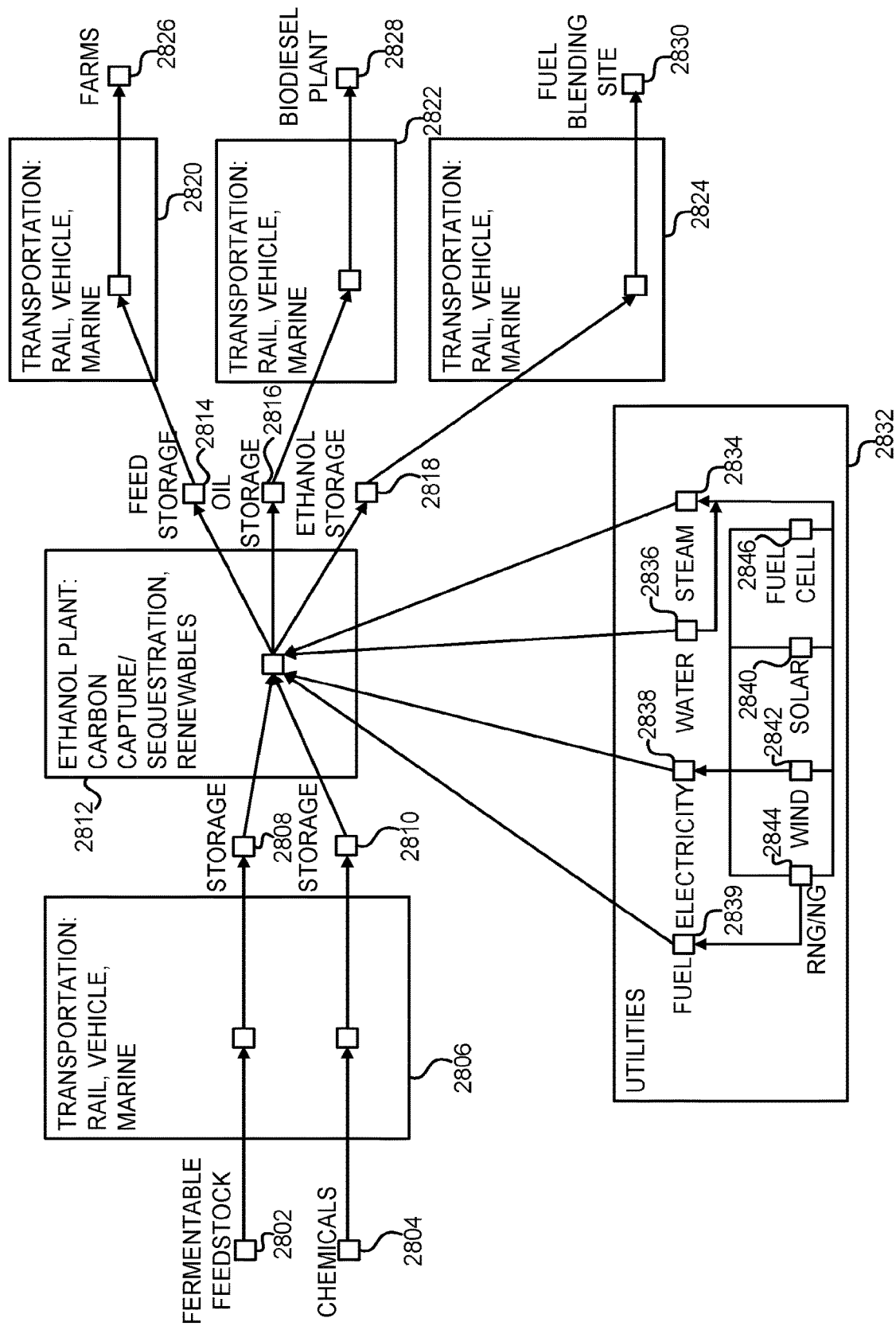
FIG. 28 is a nodal diagram illustrating the interconnectivity of lower carbon energy sources at various nodes during the acquisition and transformation of fermentation feedstock into lower carbon intensity ethanol, according to one or more embodiments of the disclosure.

FIG. 27 is a simplified diagram that illustrates a novel implementation of a low carbon intensity ethanol strategy in which lower carbon energy is introduced and used during the acquisition, fermentation, and distillation of feedstock (e.g., fermentable or fermentation feedstock) as well as the distribution of the resulting low carbon intensity ethanol to a fuel blending site 2716 and ultimately to an end user 2718 as a low carbon intensity blended transportation fuel (e.g., the blend including a ratio of ethanol and refined transportation fuel). As illustrated in FIG. 28, by employing low carbon energy sources or utilities 2708 to generate ethanol for blending with conventional or low carbon intensity liquid transportation fuel, the higher or lower carbon intensity of the refined transportation fuel, e.g., gasoline, is lowered in carbon intensity. These conventional, lower carbon intensity liquid transportation fuels, which are verifiably lower in carbon emissions, are then transported and delivered to distribution points, such as an end user 2718 (e.g., retail outlet or convenience store), for conventional purchase by a consumer. Thus, the consumer is not required to purchase or use any special equipment, e.g., an electric or natural gas-powered vehicle, to realize the advantage of low carbon energy sources that may be far removed in distance from the consumer, because such low carbon energy sources have been integrated into purchased liquid transportation fuels through the, e.g., blended ethanol.

Further, FIG. 27 illustrates a novel implementation of a low carbon intensity energy strategy in which lower carbon intensity energy (e.g., from utilities 2708) is integrated into the procurement, fermenting, and distillation of fermentable feedstocks 2702 and chemicals 2704 (such as enzymes and/or yeast to aid in the production of sugar and for fermentation), e.g., at a conventional ethanol plant 2706 and other points of integration. As noted, low carbon intensity utilities 2708 (e.g. wind farms, solar arrays, hydroelectric power sources, geothermal power plants/facilities, stationary fuel cell power systems) may be integrated into the processing (e.g., fermentation and distillation) of fermentable feedstocks 2702 to lower the overall carbon intensity of ethanol to be blended with refined transportation fuels associated with a refinery 2714 at a fuel blending site 2716. However, these low carbon intensity blended transportation fuels support the existing renewable energy infrastructure and are transported to locations accessible to end users 2718. As an example, low carbon intensity blended transportation fuels and other refined products provided through this strategy (and the strategy described above) may be used to at least partially construct and provide renewable energy infrastructure, e.g., electric-powered vehicles, natural gas-powered vehicles, dedicated charging/refueling stations, to permit the customer to take advantage of the renewable energy. Further, low carbon intensity fuels using ethanol from ethanol plant 2706 and conventional fuels from refinery 2714 may be necessary to partially, if not fully, produce renewable energy, such as renewable diesel and low carbon intensity blending fuels (e.g., biodiesel and ethanol), and to transport renewable energy to distribution points accessible by the end user 2718. Thus, low carbon intensity blended transportation fuels produced through the integration of renewable energy and/or other ethanol plant 2706 improvement processes (e.g., carbon capture/sequestration 2712, rather than atmospheric release 2710) may benefit the current range of transportation fuel options from pure renewables supplied directly to the consumer to more conventional—but low carbon intensity—liquid transportation fuels, such as gasoline blended with ethanol.

Further, carbon intensity of the overall blended transportation fuel may be lowered through the re-use of byproducts 2720 produced at the ethanol plant 2706. For example, if a grain, such as corn is utilized as the fermentable feedstock 2702, a byproduct 2720 may include distillers grain or dried distillers grain and solubles (DDGS), which includes high amounts of protein and other nutrients and may be used as feed for animals at farms 2726, among other uses as known to those skilled in the art. In another example, a byproduct 2720 may include an oil, depending on the type of fermentable feedstock 2702 (such as grains). To further reduce carbon intensity of the ethanol and, potentially, of a biodiesel or renewable diesel, the oil may be transported to a biodiesel or renewable diesel plant 2722 and processed into a low carbon intensity biodiesel or renewable diesel. In another example, a byproduct 2720 may include syrup, depending on the type of fermentable feedstock 2702. The syrup may include an amount of sugar and/or starch leftover from the fermentation process. To further reduce carbon intensity of the ethanol and, potentially, of another biofuel, the syrup may be transported to a biofuel plant 2724 and processed into a low carbon intensity biofuel (e.g., bio-gasoline). In another example, the syrup may be mixed with wet grain, from a centrifuge, create the wet distillers grain (WDG), as will be understood by those skilled in the art. In another example, the WDG may not include additional syrup. The WDG, while produced without the use of a dryer and, thus, of a potentially lower CI than DDGS, may have a shorter shelf life than DDGS. For example, the shelf life for WDG (which may include about 65% to 75% moisture) may be days (for example, three days), while DDGS may have an almost indefinite shelf life. In yet another example, an amount of syrup may be mixed with the wet grain from the centrifuge, as will be understood by those skilled in the art. The mixture may be dried to produce DDGS or modified WDG. The modified WDG (which may include about 50% to 55% moisture) may include more moisture than the DDGS (which may include about 10% to 12% moisture), have a longer shelf life than WDG (for example, three weeks), and/or require less energy to dry. The production of such byproducts 2720 may further offset or reduce the carbon intensity of the ethanol.

FIG. 28 is a nodal diagram illustrating the interconnectivity of lower carbon energy sources at various nodes during the acquisition and transformation of fermentable feedstock into lower carbon intensity ethanol for blending with a refined transportation fuel. Selected fermentable feedstock 2802 (e.g., materials including sufficient amounts of starch and/or sugar to produce ethanol during fermentation) and chemicals 2804 (e.g., enzymes to aid in saccharification and/or yeast to produce ethanol from sugar) are transported via various transportation modes 2806, which may include one or more of truck, rail, or marine transport (the distance contributing to the carbon intensity of produced ethanol and, ultimately, the blended transportation fuel). The transportation mode may be selected to further limit carbon emissions by employing low carbon intensity fuels, such as renewable diesel, renewable natural gas, petroleum natural gas, etc. In one or more embodiments, the transported fermentable feedstock 2802 may be stored in vessels, silos, or other storage structures 2808 or facilities. In a further example, different types of fermentable feedstock 2802, particularly grains, may be stored in storage structures 2808 for a period time for malting (e.g., to develop enzymes to convert starches in the fermentable feedstock 2802 to sugar), thus allowing for fewer chemicals 2804 to be utilized in the ethanol production process or operation, as will be understood by those skilled in the art. Further, the transported chemicals 2804 may be stored in a similar manner or in a different type of storage structure 2810, as will be understood by those skilled in the art. The manner and length of time of such storage may be selected so as to decrease the carbon emissions resulting from storage (e.g., due to decomposition, leakage, etc.).

The stored fermentable feedstock 2802 and/or chemicals 2804 may be transported to an ethanol plant 2812 and then fermented and distilled through conventional processing steps, each of which increases (or in some situations decreases) the carbon emissions attributable to the produced ethanol. However, as described previously, certain ethanol production processes may be employed to decrease the carbon emissions with respect to conventional processing steps. The most numerous of these carbon intensity reducing processing steps are associated with the utility infrastructure 2832 and/or carbon capture/sequestration. In addition to the fermentable feedstock 2802, ethanol plants 2812 or facilities may largely depend on various utilities, including electricity 2838, fuel 2839 (e.g., natural gas, diesel, refined intermediates 2844), water 2836, and/or steam 2834, to operate. As illustrated, there are several options for providing these utilities with lower carbon intensity than they may otherwise normally be supplied. For example, electricity may be supplied by wind turbines 2842, solar arrays 2840, renewable natural gas 2844, and/or stationary fuel cell power systems 2846. Similarly, the pumping and treatment of water 2836 and the generation of steam 2834 may employ energy obtained from wind turbines 2842, solar arrays 2840, renewable natural gas 2844, and/or stationary fuel cell power systems 2846. Renewable natural gas 2844 may also be used along with one or more of renewable diesel and/or refinery intermediates as fuel 2839 for generating heat in the liquefaction, saccharification, and/or distillation processes of ethanol production. During fermentation of the ethanol production process, large amounts of carbon dioxide may be produced. Further, fuel 2839 may be burned to generate heat for distillation. With respect to ethanol plant 2812, carbon capture/sequestration may be used in the fermentation process, distillation process, or anywhere hydrocarbon fuels are combusted to carbon dioxide along with atmospheric release. Sequestering carbon dioxide that otherwise would go to the atmosphere may have a neutral effect or even subtract from the carbon intensity of the ethanol produced. Further efficiency improvements or other techniques may be used to reduce the carbon emissions attributable to ethanol production from feedstock.

In one or more embodiments, the ethanol plant 2812 may produce more than ethanol. For example, the ethanol production process may produce a high protein feed (e.g., from distiller's grain), syrup (which may be mixed with the distillers grain or may be used as a feedstock for a biofuel plant), and/or oil (which, based on the type of feedstock, may be used as a biodiesel feedstock or for human and/or animal consumption). In such examples, the ethanol may be stored in tanks (e.g., ethanol storage 2818) prior to transport (via transportation 2820) to a fuel blending site 2830. The byproducts (e.g., oil, feed/distillers grain, and/or syrup) may be stored in storage 2814, 2816 prior to transport (via transportation 2820) to a farm 2826 and/or in oil storage 2816 prior to transport (via transportation 2822) to a biodiesel plant 2828 or other location for further processing. The manner and length of time of such storage may be selected so as to decrease the carbon emissions resulting from storage (e.g. decomposition, leakage, etc.). After storage of the ethanol, the ethanol may be transported via various transportation modes 2824 to a fuel blending site 2830, to blend the ethanol with a refined transportation fuel from a refinery. The manner and length of time of such storage may be selected so as to decrease the carbon emissions resulting from storage (e.g., evaporation, leakage, etc.). In one or more embodiments, the ethanol may be transported directly to the fuel blending site 2830 without intermediate storage. As with transportation 2806, the transportation 2824 modes for ethanol may include one or more of vehicle (e.g., truck), rail, or marine transport. The transport mode may be selected to further limit carbon emissions by employing low carbon intensity fuels, such as renewable diesel, renewable natural gas, regular natural gas, etc. After blending the ethanol with a refined transportation fuel at the fuel blending site 2830, the blended transportation fuel may then be transported to retail outlets, convenience stores, and other final distribution locations accessible to the end user and/or consumer. As noted above and as illustrated in FIG. 10, blending at a fuel blending site may occur (i.e., a fuel blending site may be) at a storage tank 883, during or prior to transport 884, at a terminal/rack 885, and/or at a retail 886 location.

Figure 29:
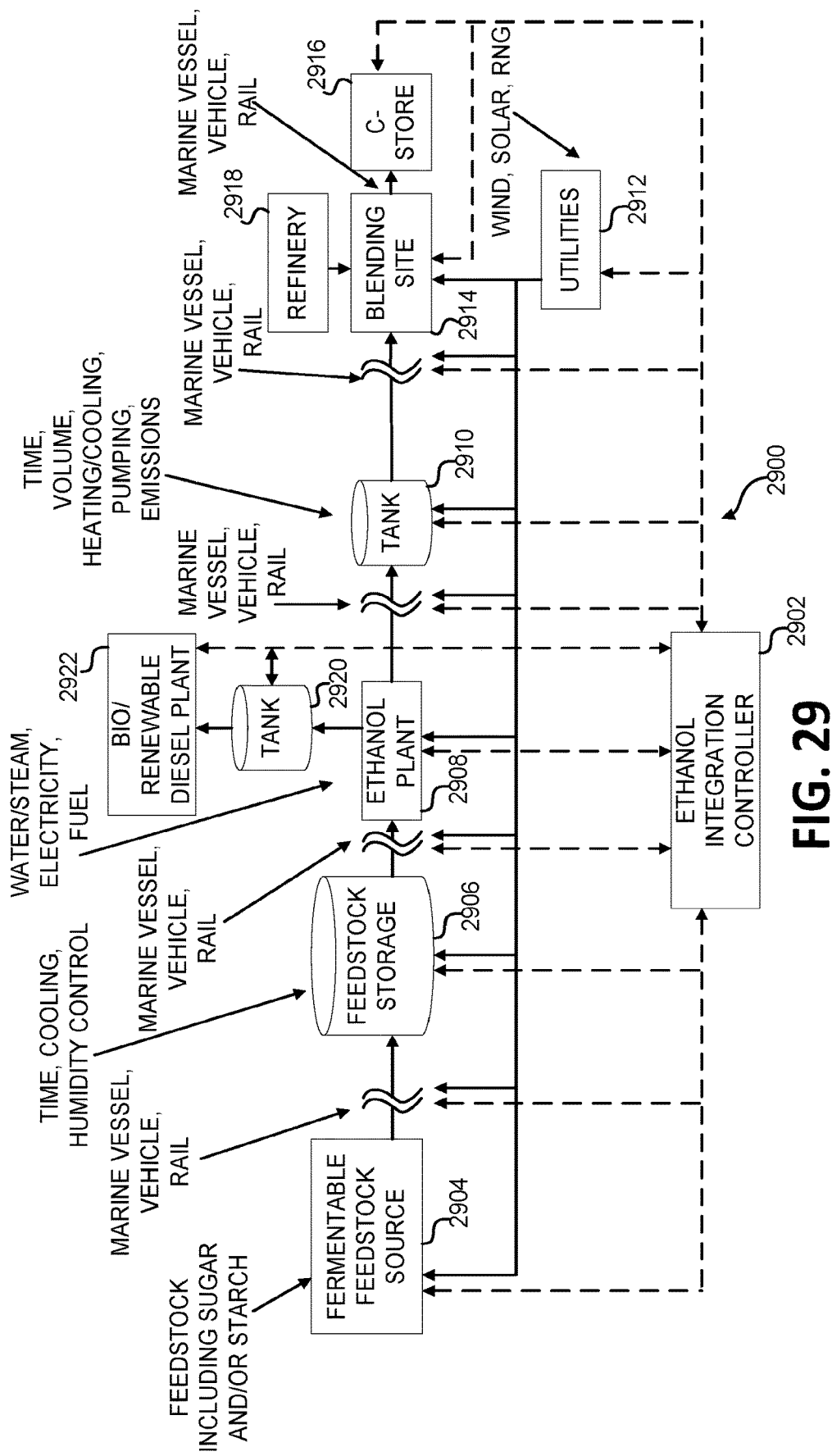
FIG. 29 is a block diagram illustrating a system for managing the low carbon intensity ethanol production according to an embodiment.

FIG. 29 is a block diagram illustrating a system 2900 for managing the low carbon intensity ethanol production according to an embodiment. The system 2900 may include an ethanol integration controller 2902 and/or fuel integration controller. The ethanol integration controller 2902 and/or fuel integration controller may connect to various other controllers, sensors, and/or computing devices utilized throughout an ethanol production process or operation to plan and/or control ethanol production and/or refined and blended transportation fuel production. For example, the ethanol integration controller 2902 and/or fuel integration controller may connect to a controller at a fermentable feedstock source 2904 or to a database storing information regarding the fermentable feedstock source 2904, as well as other fermentable feedstock sources. As such, the ethanol integration controller 2902 and/or fuel integration controller may obtain various data points or information in relation to different available fermentable feedstock at the fermentable feedstock source 2904. The ethanol integration controller 2902 and/or fuel integration controller may select one or more of the available fermentable feedstock for use in ethanol production (as well as for a refined and blended transportation fuel production), based on the data points or information obtained. Various data points may include the type of fertilizer used (e.g., conventional versus low carbon intensity fertilizer produced from low carbon intensity hydrogen), the type of fermentable feedstock, the distance of the fermentable feedstock source 2904 from the ethanol plant 2908 (which may or may not be co-located with the fermentable feedstock source 2904, or located proximate to or nearby the fermentable feedstock source 2904), and the type of fuel and utilities used by the equipment utilized at the fermentable feedstock source 2904 (renewable fuel, fossil fuel, etc.).

The ethanol integration controller 2902 and/or fuel integration controller may connect to controllers, sensors, a database and/or computing devices related to a fermentable feedstock transportation pathway. As such, the ethanol integration controller 2902 and/or fuel integration controller may obtain various data points or information in relation to different available fermentable feedstock transportation pathways (such as distance between the fermentable feedstock source 2904 and fermentable feedstock storage 2906 or the ethanol plant 2908, the type of fermentable feedstock transportation pathway, the type of fuel utilized by the fermentable feedstock transportation pathway, and/or the volume of the fermentable feedstock transportation pathway). The ethanol integration controller 2902 and/or fuel integration controller may select one or more of the available fermentable feedstock transportation pathways for the ethanol, based on the various data points or information.

Further, the ethanol integration controller 2902 and/or fuel integration controller may connect to controllers, sensors, and/or computing devices associated with fermentable feedstock storage 2906 (e.g., a grain silo) and/or tank 2910 (e.g., a liquid product storage tank). The fermentable feedstock storage 2906, tank 2910, or other types of storage may be positioned at various points between a fermentable feedstock source 2904, the ethanol plant 2908, the refinery 2918, the blending site 2914, and a distribution point or terminal (e.g., convenience store 2916). For example, the fermentable feedstock storage 2906 may be located on-site at the ethanol plant 2908. The ethanol integration controller 2902 and/or fuel integration controller may obtain various data points or information in relation to fermentable feedstock, ethanol, refined transportation fuel, and/or refined and blended transportation fuel stored in any storage location (e.g., time and power utilized). The ethanol integration controller 2902 and/or fuel integration controller may select fermentable feedstock, ethanol, refined transportation fuel, and/or refined and blended transportation fuel stored in the storage locations for use in the ethanol production and/or the refined and blended transportation fuel production.

The ethanol integration controller 2902 and/or fuel integration controller may control an ethanol plant 2908 and/or connect to controllers, sensors, and/or computing devices at the ethanol plant 2908. The ethanol integration controller 2902 and/or fuel integration controller may obtain various data points or information in relation to different available ethanol production processes of the ethanol plant 2908 and the ethanol integration controller 2902 and/or fuel integration controller may select one or more of the available ethanol production processes for the ethanol and/or refined and blended transportation fuel production, based on the various data points or information. The ethanol integration controller 2902 and/or ethanol integration controller may initiate and/or control the selected ethanol production processes at the ethanol plant 2908. For example, when a particular ethanol production process is selected, the ethanol integration controller 2902 and/or fuel integration controller may initiate the ethanol production process or transmit an initiation to a controller of the ethanol plant 2908. The ethanol integration controller 2902 and/or fuel integration controller may determine where to send or transport byproducts of the ethanol plant 2908. For example, a byproduct may include oil. The oil may include a CI proportional to the CI of the produced ethanol and the volume of fermentable feedstock utilized at the ethanol plant 2908. As such, the ethanol integration controller 2902 and/or fuel integration controller may initiate transportation of the oil to a tank 2920 (or other type of storage, as will be understood by those skilled in the art). From tank 2920, the oil, along with the associated CI of the oil, may be transported to a bio/renewable diesel plant to be converted or processed to a bio diesel or renewable diesel with a particular CI partially based on the oil's CI. Other byproducts may be produced and transported for other uses from the ethanol plant 2908 (e.g., feed and/or syrup). As described above, the fuel integration controller, which may include the functionality of the ethanol integration controller 2902, may control a refinery 2918 and/or connect to controllers, sensors, and/or computing devices at the refinery 2918.

The ethanol integration controller 2902 and/or fuel integration controller may connect to a utility provider 2912 or controllers, sensors, and/or computing devices of a utility provider 2912. The utility provider 2912 may provide utilities for use in the ethanol plant 2908, as well as at various other points throughout ethanol production and/or throughout the refined and blended transportation fuel production. The utility provider 2912 may be proximate to, nearby, or at the ethanol plant 2908 and may utilize renewable resources. Further, the utility provider 2912 may be off-grid and/or dedicated to the ethanol plant 2908. For example, a wind farm may be constructed next to or nearby the ethanol plant 2908. In another example, the utility provider 2912 may provide and/or track utilities for use at the fermentable feedstock source 2904, at each transportation/distribution pathway, at each storage location or tank (e.g., feedstock storage 2906 and tank 2910), at a blending site 2914, and/or at other points or processes in the ethanol production and/or at the refined and blended transportation fuel production. As such, the ethanol integration controller 2902 and/or fuel integration controller may obtain data regarding the available utilities, as well as available utilities for ethanol production and/or the refined and blended transportation fuel production. Based on such data, the ethanol integration controller 2902 and/or fuel integration controller may select one or more utilities for ethanol production and/or the refined and blended transportation fuel production (e.g., utilities for use in the one or more selected ethanol production processes).

The ethanol integration controller 2902 and/or fuel integration controller may connect to controllers, sensors, a database, and/or computing devices related to an ethanol distribution pathway and/or a blended product distribution pathway. As such, the ethanol integration controller 2902 and/or fuel integration controller may obtain various data points or information in relation to different available ethanol distribution pathways and/or blended product distribution pathways and the ethanol integration controller 2902 and/or fuel integration controller may select one or more of the available ethanol distribution pathways and/or blended product distribution pathways based on the various data points or information.

The ethanol integration controller 2902 and/or fuel integration controller may connect to a blending site 2914 or to controllers, sensors, and/or computing devices at a blending site 2914. The ethanol integration controller 2902 and/or fuel integration controller may provide data regarding a produced ethanol to such components at the blending site 2914. For example, an ethanol integration controller 2902 may connect to a blending site 2914 controller. The ethanol integration controller 2902 may initiate shipment of the produced ethanol to the blending site 2914. The ethanol integration controller 2902 may also provide the CI of the ethanol, as well as various other aspects of the ethanol production process (e.g., CI and type fermentable feedstock utilized, CI and type fermentable feedstock transportation utilized, CI and types of ethanol processes utilized, CI and type of utilities utilized, CI and type of byproducts produced and where the byproducts may be shipped, and/or CI and type of ethanol distribution utilized) The ethanol integration controller 2902 and/or fuel integration controller may obtain various data points or information in relation to the blending site (e.g., amount of each component to be blended, power required to blend, type of blending operation, etc.). The ethanol integration controller 2902 and/or fuel integration controller may select one or more of the available blending processes for the ethanol and the refined transportation fuel, based on the various data points or information. The ethanol integration controller 2902 and/or fuel integration controller may initiate and/or control the selected blending processes. For example, when a particular blending processes is selected, the ethanol integration controller 2902 and/or fuel integration controller may initiate the blending processes or transmit an initiation to a controller of the blending site 2914. In another example, the ethanol integration controller 2902 and/or fuel integration controller may obtain the CI of the refined transportation fuel from the refinery 2918 to be blended with the ethanol at the blending site 2914.

The ethanol integration controller 2902 and/or fuel integration controller may connect to controllers, sensors, and/or computing devices at a distribution point or terminal (e.g., a convenience store 2916). For example, the ethanol integration controller 2902 may monitor or track fuel consumption (i.e., demand) at the convenience store 2916. Based on the consumption or demand, the ethanol integration controller 2902 may initiate ethanol production (e.g., the produced ethanol to be blended with a particular refined transportation fuel). Further, based on consumption or demand for a particular type of blended transportation fuel (e.g., low or high CI), the ethanol integration controller 2902 may select different aspects of the ethanol production (e.g., use of low CI methods at feedstock sources, carbon sequestration, renewable utilities, etc.). In another example, the ethanol integration controller 2902 and/or fuel integration controller may monitor the cost or price of ethanol or fuel blends including ethanol. Based on the cost or price, as well as the cost or price of the feedstock, the ethanol integration controller 2902 and/or fuel integration controller may initiate an ethanol production process.

Figure 30A:
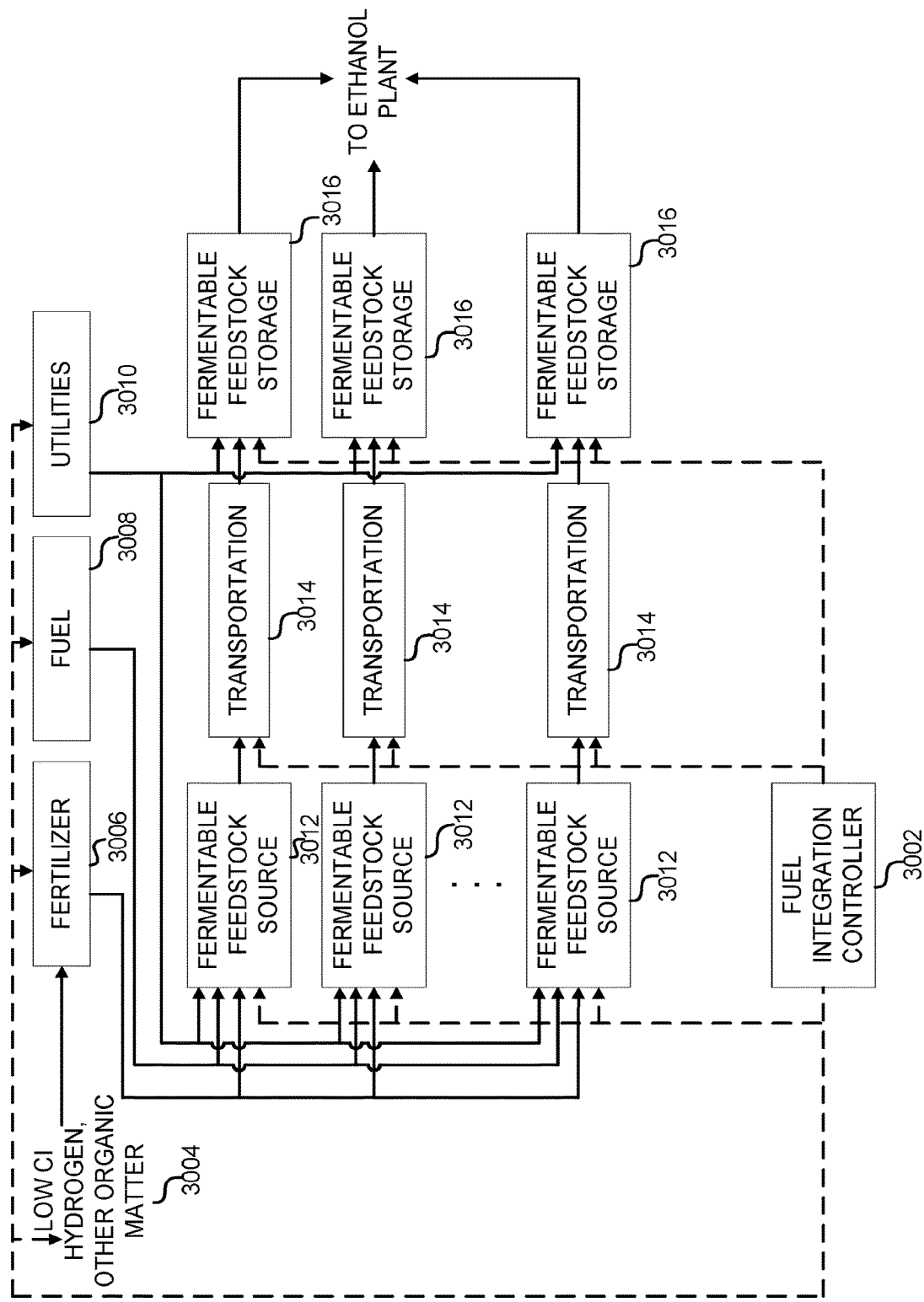
FIGS. 30A-D are block diagrams illustrating a system for managing the low carbon intensity ethanol production according to an embodiment.
Figure 30B:
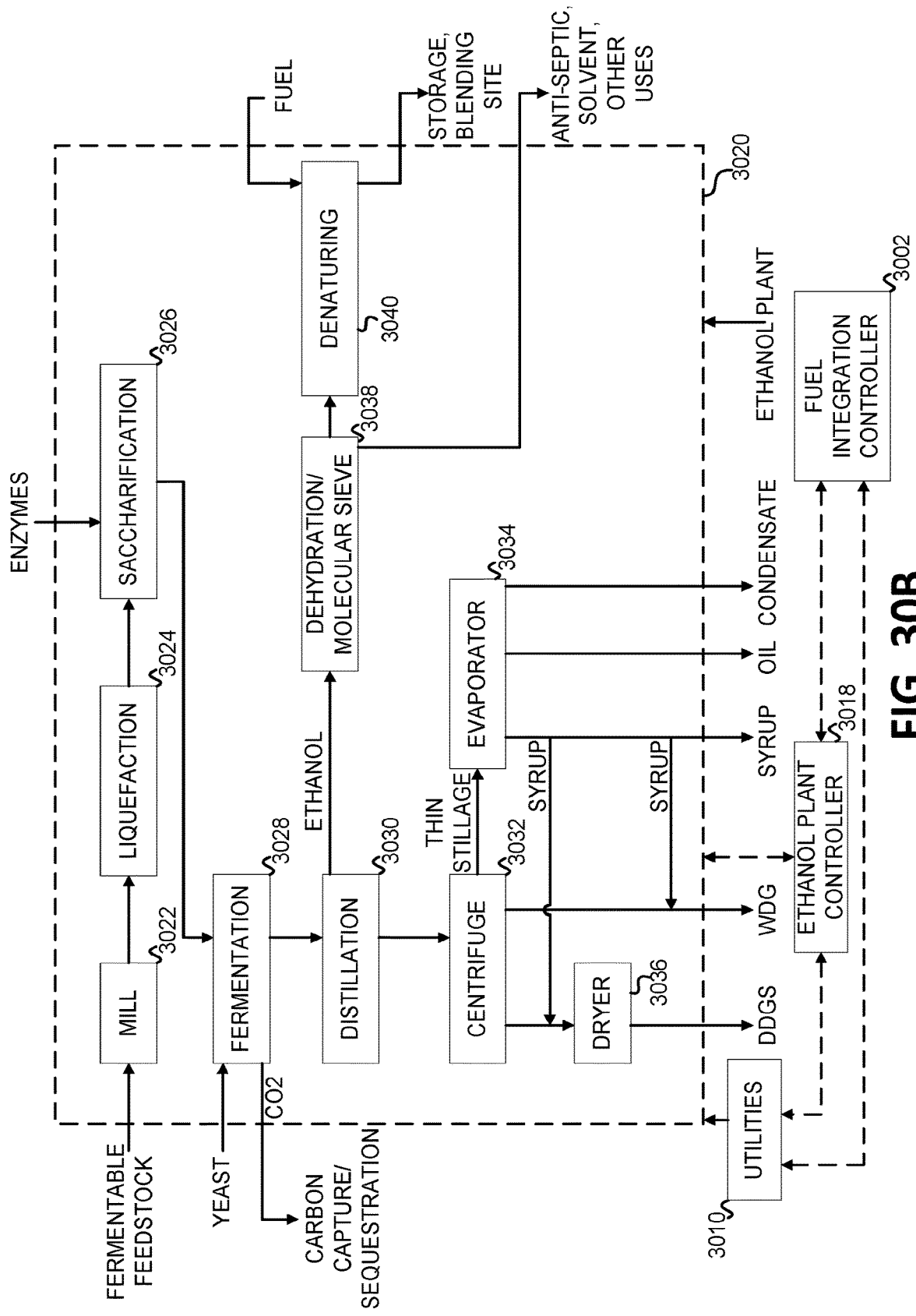
Figure 30C:
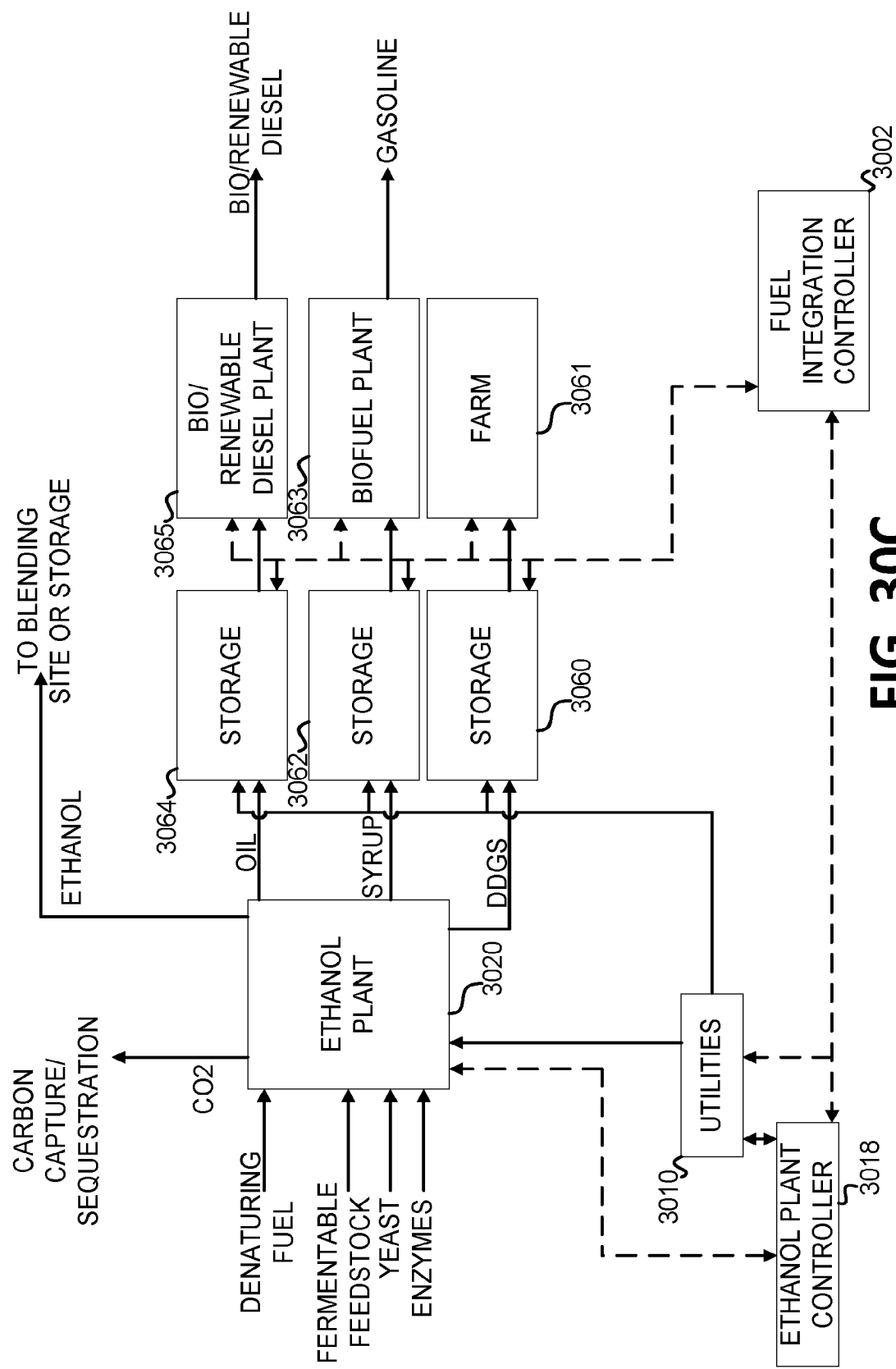

FIGS. 30A-C are block diagrams illustrating a system for managing the low carbon intensity ethanol production according to an embodiment. In such embodiments, the system may utilize a fuel integration controller 3002, an ethanol plant controller 3018, an ethanol integration controller, and/or various other controllers or computer devices utilized throughout the ethanol production process. Such controllers may select and initiate various aspects of the ethanol production processes. Further, the production of ethanol may be a sub-process in an overall process of a refined and blended transportation fuel production or process. In other words, a particular CI may be set for a refined and blended transportation fuel. Based on that set CI, the fuel integration controller 3002 may select and control ethanol production (as well as, hydrogen production and/or various other aspects of a refined product transportation fuel production) to lower the CI of the overall transportation fuel. In another example, rather than utilizing a set CI or threshold CI, the fuel integration controller 3002 may initiate ethanol production for an ethanol based on the lowest possible CI (based on available options), the lowest possible cost, the shortest amount of time to produce the ethanol, demand for a particular ethanol (e.g., low CI), or some combination thereof. For example, the fuel integration controller 3002 may consider a lower cost ethanol at a higher CI for a lower CI fuel or an ultra-low cost CI ethanol based on available utilities, such as a wind farm, and other options available at a specific time (e.g., the wind farm may be operating and carbon capture may be available). In another example, the fuel integration controller 3002 may produce large quantities of ethanol of a particular CI for a period of time. Such an ethanol may be stored until requested for a particular blended fuel operation. In yet another example, the fuel integration controller 3002 may factor in tax credits when considering the cost of ethanol production.

As illustrated in FIG. 30A, the fuel integration controller 3002 may connect to various and different stages of the ethanol process or to databases, computing devices, or other controllers including information regarding each stage. For example, the fuel integration controller 3002 may connect to various fermentable feedstock sources 3012 (e.g., with computing devices and/or controllers at the fermentable feedstock sources 3012 or a database including data relating to the fermentable feedstock sources 3012). The fuel integration controller 3002 may select a fermentable feedstock based on various factors at each of the fermentable feedstock sources 3012. For example, one or more of the fermentable feedstock sources 3012 may utilize fertilizer 3006, fuel 3008, utilities 3010, or some combination thereof. In such examples, different fermentable feedstock sources 3012 may utilize different types of fertilizer 3006, fuel 3008, and/or utilities 3010. For example, the fertilizer 3006 may be composed of ammonia, and the ammonia may include a low CI hydrogen, as described above. In another example, one or more of the fermentable feedstock sources 3012 may be waste facility to provide organic waste including starches and/or sugars and, thus, may not utilize fertilizer 3006. Further, various fermentable feedstock sources implements or equipment (e.g., farming equipment) may utilize fuel 3008. The fuel integration controller 3002 may consider the fuel 3008 utilized (e.g., low CI fuel, renewable fuel, traditional fossil fuels, etc.) and the CI associated with the fuel 3008. Finally, the fuel integration controller 3002 may consider the utilities 3010 used at the fermentable feedstock sources 3012 (e.g., renewable or conventional). Further, the fuel integration controller 3002 may consider the CI of the indirect land use change (ILUC) of the fermentable feedstock sources 3012, in particular, in examples where one or more of the fermentable feedstock sources 3012 are farms (as in, the change of use from food production to fuel production and the potential cause of such a change to further cause a forest, such as a rainforest, to be cleared for farm use). Based on those factors, as well as the type of fermentable feedstock at the fermentable feedstock sources 3012, the type of fermentable feedstock the ethanol plant 3020 is able to process, the time of availability of the fermentable feedstock, and/or the distance between the fermentable feedstock sources 3012 and the ethanol plant 3020, the fuel integration controller 3002 may select a fermentable feedstock from the respective fermentable feedstock source for fermentation in the ethanol process.

In another embodiment, the fuel integration controller 3002 may select or control the type of transportation 3014 to be utilized for transporting the fermentable feedstock between the fermentable feedstock 3012 and to either a fermentable feedstock storage location 3016 or directly to an ethanol plant 3020. The fuel integration controller 3002 may consider and select the type of transportation based on the distance that the transportation 3014 may travel to deliver the fermentable feedstock (whether to fermentable feedstock storage 3016 or directly to an ethanol plant 3020), the amount of fermentable feedstock, the capacity of the transportation 3014, the type of fuel utilized by the transportation 3014, and/or the length of time for delivery. In another example, such data (as in, fermentable feedstock source related data and/or transportation related data) may be stored in a database, controller, procurement controller, procurement computing device, procurement and distribution controller, and/or procurement and distribution computing device. In such examples, the fuel integration controller 3002 may gather the data and choose the options, pathway, paths or processes from such devices.

As noted above, the fuel integration controller 3002 may control an ethanol plant 3020 or connect to an ethanol plant controller 3018 to control the ethanol plant 3020. The ethanol plant controller 3018 and/or fuel integration controller 3002 may control or select the utilities 3010 to be utilized at the ethanol plant 3020 in the various ethanol plant 3020 processes. The utilities 3010 may be renewable utilities. In another example, the utilities 3010 may be from a co-located, nearby, or proximate utility provider. For example, a solar array, wind farm, or geothermal power plants/facilities may be located or constructed nearby the ethanol plant 3020. In another example, the ethanol plant 3020 may have various options in regards to power sources (e.g., via off-grid sources and other grid-based sources). Thus, one method to significantly reduce the CI of ethanol may be to utilize a low CI utility, if available. Further, low CI utilities may only be available intermittently (e.g., wind farms may only provide power during certain weather conditions). Based on such situations, the fuel integration controller 3002 may produce ultra-low CI ethanol for a period of time for a certain type of transportation fuel (e.g., a high CI refined transportation fuel), while, during the period of non-availability of renewable power, produce a low CI ethanol for a different type of transportation fuel.

As illustrated in FIGS. 30B and 30C, the fuel integration controller 3002 and/or ethanol plant controller 3018 may control and select different ethanol production processes at an ethanol plant 3020. The ethanol plant 3020 may be a dry mill, as illustrated in FIG. 30B, or a wet mill, as will be understood by those skilled in the art. A wet mill may include tanks to soak fermentable feedstock (e.g., corn) in a dilute aqueous sulfur dioxide solution. The softened fermentable feedstock (e.g., corn) may be processed to remove the germ. The germ may be processed to produce oil (e.g., corn oil) for various uses (e.g., diesel production or animal feed). The remaining portion of the fermentable feedstock (e.g., after germ removal) is processed to produce feed and starch, as will be understood by those skilled in the art. The starch may further be processed into ethanol, as will be understood by those skilled in the art.

For a dry mill, the fuel integration controller 3002 and/or ethanol plant controller 3018 may control how long to run a mill 3022 at the ethanol plant 3020, thus controlling the granularity of the grist or meal, which in turn may affect the amount of time and energy/heat used during liquefaction 3024 and/or saccharification 3026. The fuel integration controller 3002 and/or ethanol plant controller 3018 may further control the temperature to which the mash or combination of water and grist are to be heated to and for how long in the liquefaction process 3024. Further still, the fuel integration controller 3002 and/or ethanol plant controller 3018 may control the saccharification 3026 process. In particular, the fuel integration controller 3002 and/or ethanol plant controller 3018 may control the temperature, the length of time at a specified temperature, and the amount and type of enzymes (such as amylase) to use (if any are to be used) to aid in the production of sugars/saccharides from starches in the mash or mixture. The fuel integration controller 3002 and/or ethanol plant controller 3018 may also control various processes involved in fermentation 3028. In addition, prior to addition of the yeast for fermentation 3028, the fuel integration controller 3002 may determine the temperature of the mash and whether the mash is to be cooled or heated prior to fermentation. In such examples, a cooling unit may be disposed between fermentation 3028 and saccharification 3026. For example, the fermentation process 3028 may utilize various strains of yeast. The fuel integration controller 3002 and/or ethanol plant controller 3018 may select the type of yeast based on the type of fermentable feedstock used. In another example, the fuel integration controller 3002 and/or ethanol plant controller 3018 may select the length of time the mash or mixture is to be fermented and the type, the amount of yeast to be utilized for fermentation, and/or the temperature to heat/cool the mash to prior to addition of the yeast. The fuel integration controller 3002 and/or ethanol plant controller 3018 may also control where the carbon dioxide produced is directed. For example, to further reduce CI of the ethanol, fuel integration controller 3002 and/or ethanol plant controller 3018 may select a carbon capture/sequestration process to capture the carbon dioxide produced during fermentation. Once fermented, the fuel integration controller 3002 and/or ethanol plant controller 3018 may control transport of the mash or mixture to a distillation unit or column. The fuel integration controller 3002 and/or ethanol plant controller 3018 may control the temperature and time for distillation, as well as the fuel source to heat the mash or mixture.

A further process or improvement to decrease CI of ethanol may be a heat waste recovery system. The heat waste recovery system may reduce CI by reducing the total amount of fuel used in the fermentation and distillation process. In an examples, a fuel integration controller 3002 may consider or factor in a CI reduction based on a heat waste recovery system. For example, the water mixed with the grist or meal may be pre-heated with heat waste, thus requiring less energy to heat the mixture to the proper temperature. Heat waste recovery may be utilized in other processes within the ethanol plant, as will be understood by those skilled in the art.

The fuel integration controller 3002 and/or ethanol plant controller 3018 may control various other aspects of the ethanol production process. For example, the fuel integration controller 3002 and/or ethanol plant controller 3018 may control the filter process by a dehydration/molecular sieve unit 3038 to filter out the remaining water from the distillate or ethanol. Once filtered, the ethanol may have various uses, other than for fuel, such as for antiseptics or solvents. For use in fuels, the ethanol may undergo denaturing 3040 to prevent human consumption and for tax purposes (e.g., ethanol produced for human consumption is taxed differently than ethanol produced for fuel and ethanol produced for fuel may generate tax credits). In such examples, an amount of fuel, such as gasoline, kerosene, or other fuels, may be added to the ethanol (from about 2% to about 5% of the total mixture). To further reduce CI, a low CI refined transportation fuel may be utilized in denaturing 3040.

In another example, the byproducts of distillation 3030 may be a mixture of solids and liquids. The solids and liquids may be separated in a centrifuge 3032 to create wet grain and a thin stillage. The thin stillage may be transported to an evaporator 3034. The evaporator 3034 may produce an amount of condensate water to be utilized or re-used in other processes within the ethanol plant 3020. The evaporator 3034 may also produce oils. The oil may be transported to storage 3064 for later use, such as for either human consumption or for use in a biodiesel or renewable diesel plant 3065. In such examples, the oil may be associated with a CI proportional to the yield of ethanol, the yield of oil and the other byproducts, and the CI of the ethanol production process up to the point of transfer of the oil to the biodiesel or renewable diesel plant 3065. Further, the evaporator 3034 may produce a syrup including protein, other nutrients, sugar, and/or starch. The syrup may be transported to storage 3062 for later use and may be associated with a CI proportional to the yield of ethanol, the yield of syrup and the other byproducts, and the CI of the ethanol production process up to the point of transfer of the syrup to a biofuel plant 3063. At the biofuel plant 3063, the syrup may be converted to a bio-gasoline or other bio-fuel. In another example, the syrup may be combined with the wet grain and transported to a dryer 3036 or transported directly to an end user. The dryer may dehydrate the mixture of wet grains and syrup or wet grains without additional syrup to form a feed or distillers grain (e.g., dried distillers grain and solubles (DDGS)), which may be high in protein and other nutrients. The feed may be transferred to storage 3060 and may be used as animal feed, for example, at a farm 3061. The length of time the feed may be in storage 3060 may be dependent on the type of feed (DDGS, WDG, or modified WDG). The feed may be associated with a CI proportional to the yield of ethanol, the yield of feed and the other byproducts, and the CI of the ethanol production process up to the point of transfer of the feed to the farm 3061. While the process of creating the feed or DDGS, the oil, and/or syrup may create some amount of CI, that amount and more may be offset by the use of such byproducts, which may inherently reduce the CI of the ethanol.

Based on the utilities 3010 used, the production of the byproducts, the use of carbon capture/sequestration, use of a heat waste recovery system, and/or other CI reducing processes, the total CI of the ethanol may be less than or equal to zero. In some cases, the ILUC and other CI processes may be completely offset for a lower up front cost than if such processes were implemented in a refinery. In other cases, while the CI of the ethanol may not be zero, the total CI may completely offset ILUC. In other cases, where ILUC is not utilized to determine carbon intensity, the total CI may be much less than zero. Thus, an ultra-low CI ethanol may be produced and used to significantly reduce the CI of a refined transportation fuel upon blending.

Figure 30D:
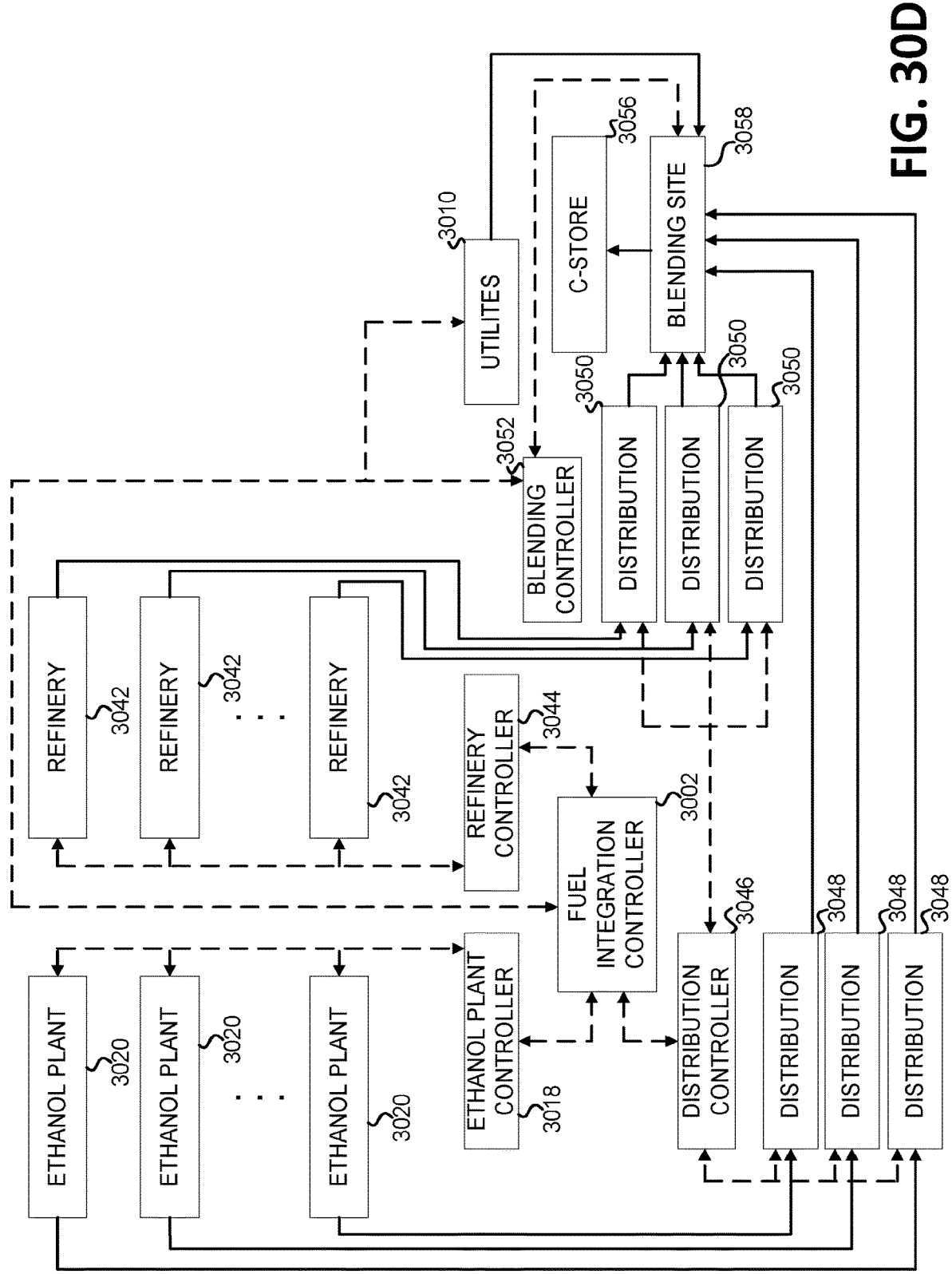

As illustrated in FIG. 30D, the fuel integration controller 3002 may connect to one or more ethanol plants 3002 and refineries 3042 (or to an ethanol plant controller 3018 and refinery controller 3044). In such examples, the fuel integration 3002 may include a CI threshold for a particular refined and ethanol-blended transportation fuel. Based on the CI, the fuel integration controller 3002 may select an amount of ethanol at a particular CI and an amount of refined transportation fuel at a particular CI. The fuel integration controller 3002 may determine the types of ethanol distribution pathways 3048 (similar to transportation 3014) and refined transportation fuel distribution pathways 3050 and the CI associated with each. Based on these CI values, the fuel integration controller 3002 may choose a distribution pathway. Once distributed to the blending site 3058, the fuel integration controller 3002 or blending controller 3052 may initiate blending of the refined transportation fuel and the ethanol. The resulting refined and blended transportation fuel may then be transported to a convenience store 3056 as a low CI blended transportation fuel.

In an example, several of the components of the ethanol production process and/or transportation fuel process may be co-located or proximate. For example, one of the ethanol plants 3020 may be co-located with or proximate to one of the fermentable feedstock sources 3012. In another example, one of the ethanol plants 3020 may be co-located with or proximate to one of the refineries 3042. As noted, each site may be co-located, proximate to, or nearby one of the other sites. Further, each site may include various storage structures or tanks for storing different materials (fermentable feedstock, petroleum based feedstock, renewable feedstock, refined transportation fuels, ethanol, byproducts, hydrogen, etc.).

Figure 31A:
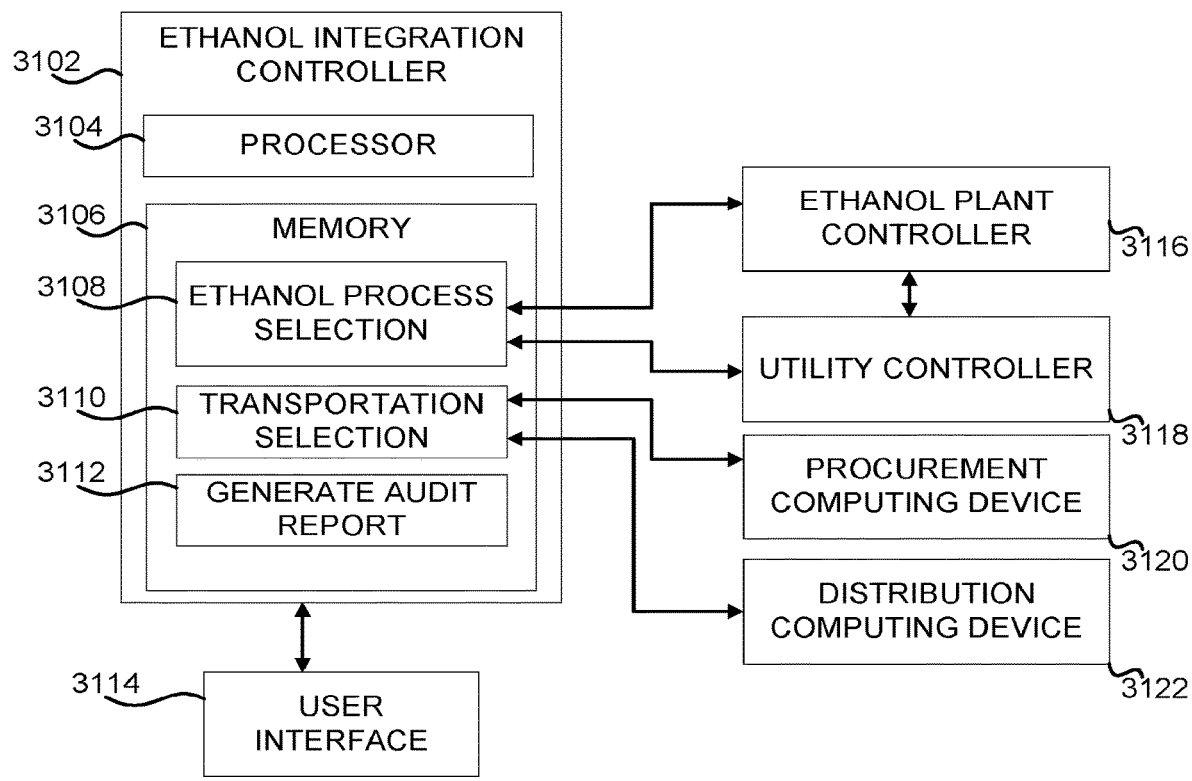
FIGS. 31A-C are simplified diagrams illustrating a control system for managing the low carbon intensity ethanol production according to an embodiment.
Figure 31B:
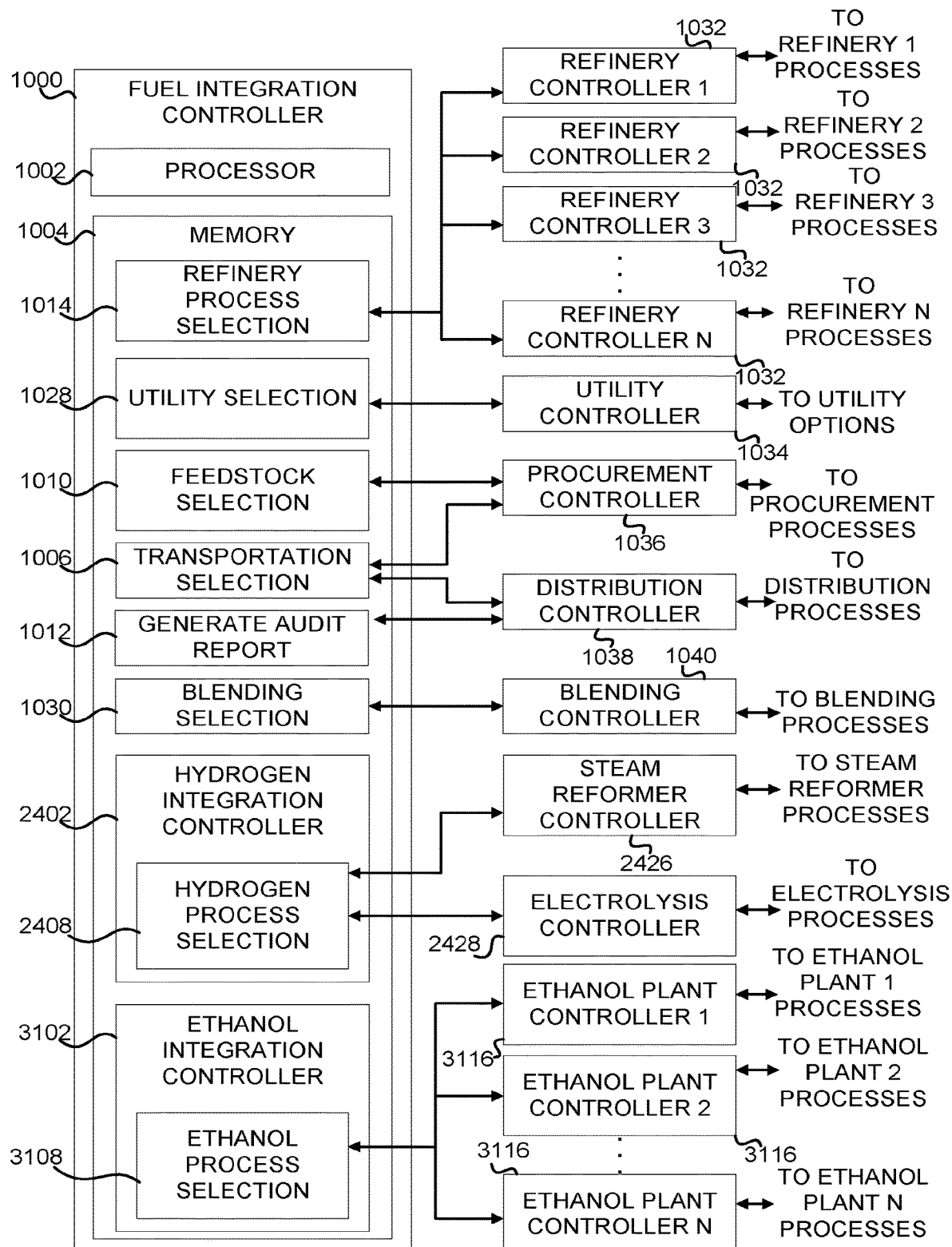
Figure 31C:
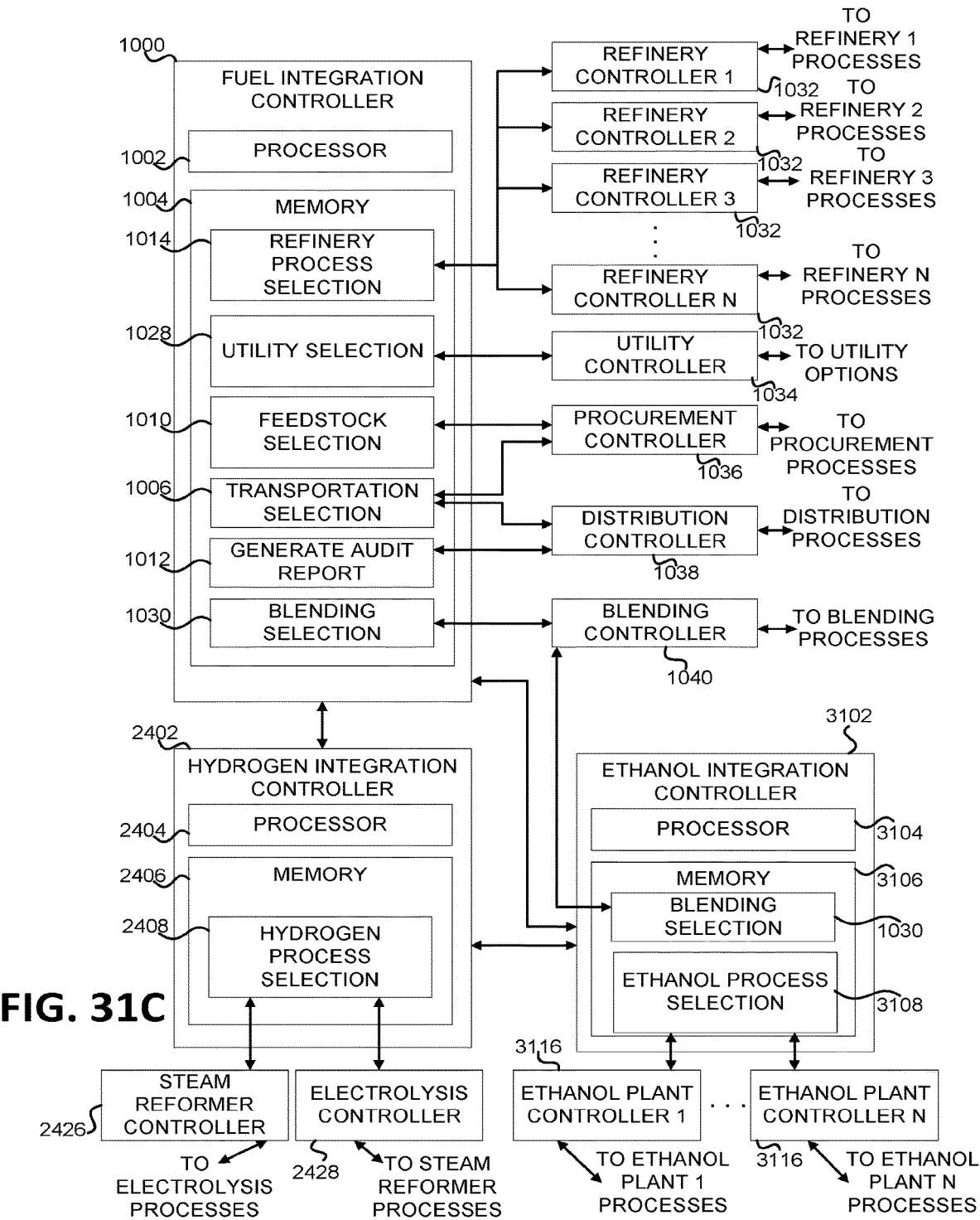

FIGS. 31A-C are simplified diagrams illustrating a control system for managing the low carbon intensity ethanol production according to an embodiment. FIG. 31A illustrates an embodiment of an ethanol integration controller 3102 for managing low carbon intensity ethanol production. As noted above, the ethanol integration controller 3102 may manage the operations of ethanol production (e.g., low and/or high CI ethanol production processes or operation). The ethanol integration controller 3102 may be one or more controllers, a supervisory controller, programmable logic controller (PLC), a computing device (such as a laptop, desktop computing device, and/or a server), and/or other suitable devices. The ethanol integration controller 3102 may be located at or near an ethanol production facility. The ethanol integration controller 3102, as noted, may be more than one controller. In such cases, the ethanol integration controller 3102 may be located near or at various feedstock sources (e.g., farms), near or at one or more ethanol production facilities, and/or at other off-site locations. The ethanol integration controller 3102 may include a processor 3104, or one or more processors, and memory 3106. The memory 3106 may include instructions. In an example, the memory 3106 may be a machine-readable storage medium.

The ethanol integration controller 3102 may include various modules in memory 3106. The modules may include or define a set of instructions, executable by the processor 3104 for different aspects involved in managing low and/or high carbon intensity ethanol production. Each module may be in signal communication with other controllers, sensors, data inputs, computing devices, servers, ethanol production facility components, and/or user interfaces. The ethanol integration controller 3102 may include an ethanol process selection module 3108, a transportation selection module 3110, a fermentable feedstock source selection module, and/or an audit report module 3112. The ethanol process selection module 3108 may be in signal communication with an ethanol plant controller 3116 and/or a utility controller 3118. The ethanol process selection module 3108 may be in signal communication with a plurality of ethanol plant controllers (e.g., each ethanol plant controller located at a different and/or separate ethanol plants). In another example, the ethanol process selection module 3108 may be in signal communication with an ethanol plant controller 3116 including the functionality of a utility controller 3118. In yet another example, the ethanol integration controller 3102 may include the functionality of an ethanol plant controller 3116 and/or a utility controller 3118. The transportation selection module 3110 may connect to a procurement computing device 3120, a distribution computing device 3122, a procurement and distribution computing device, a controller, a user interface, a server, database, and/or another device. The transportation selection module 3110 may include functionality for selecting fermentable feedstock from a fermentable feedstock source. In another example, a separate module, such as fermentable feedstock selection module, may include such functionality. The audit report module 3112 may be in signal communication with a user interface 3114. In such an example, a user may request an audit report via the user interface 3114. The user interface 3114 may be in signal communication with the ethanol integration controller 3102 and/or the audit report module 3112. In such examples, the user interface 3114 may send and receive data to and from, respectively, the ethanol integration controller 3102.

As noted above, the ethanol integration controller 3102 may be in signal communication with the user interface 3114. The user interface 3114 may include an input (such as a keyboard, mouse, touchscreen, etc.) and a display. In another example, the user interface 3114 may be a computing device, such as a laptop, desktop computer, server, smartphone, tablet, or a terminal. A user may enter data into the user interface 3114 to send to the ethanol integration controller 3102. For example, a user may enter in a threshold CI for a particular ethanol production process. A user may input a low CI ethanol specification for a particular ethanol production process, the low CI ethanol specification noting or including the threshold CI. The low CI ethanol specification may be or may include the definition of a low CI ethanol. In another example, the user may prompt or initiate an ethanol production process. In another example, the user may initiate the ethanol production process without a threshold CI. In yet another example, the ethanol integration controller 3102 may connect to a database. The database may store the threshold CI and the ethanol integration controller 3102 may obtain the threshold CI from the database for a particular ethanol production process. The ethanol integration controller 3102 may include or store the threshold CI in memory 3106. In another example, a user may enter or input other data into the ethanol integration controller 3102 via the user interface 3114, such as available feedstock, available feedstock transportation pathways, available ethanol production processes at ethanol plants, available utilities, and/or available ethanol distribution pathways. A user may also enter or input the algorithms and/or calculations to determine a CI for any particular process. As described above, the ethanol production process may be performed without a threshold CI. In such examples, the ethanol production process may be based on various other factors.

In response to a reception of a threshold CI, whether from the user interface 3114, a database, another device, or from memory 3106, the ethanol integration controller 3102 may set, assign, or utilize the threshold CI as a current threshold CI for a particular ethanol production process. As such, the ethanol integration controller 3102 may select various portions of the ethanol production process to ensure that the current threshold CI is not exceeded. Further, the ethanol integration controller 3102 may simulate, model, or determine many different variations to determine the best possible path, combination, or selection based on various data points or factors (e.g., cost, demand, shortest amount of time from feedstock to ethanol, overall or total CI, etc.). In another example, rather than utilizing a set CI or threshold CI, the ethanol integration controller 3102 may initiate ethanol production for an ethanol based on the lowest possible CI (based on available options), the lowest possible cost, the shortest amount of time to produce the ethanol, demand for a particular ethanol (e.g., low CI), or some combination thereof. The ethanol integration controller 3102 may determine the best possible path, combination, or selection via a brute-force method, a min-max method, an admissible decision method, and/or via other decision making methods as will be understood by those skilled in the art.

For example, upon reception of the threshold CI or prompt for initiation, the ethanol integration controller 3102 may determine a CI for a number of or all selections of one or more available feedstock (in other words, feedstock variations). The ethanol integration controller 3102 may further determine a CI for a number of or all selections of blends of the one or more available fermentable feedstock. A fermentable feedstock selection module, ethanol integration controller 3102, transportation selection module 3110, or another module may perform the CI determination for the fermentable feedstock variations (in other words, the CI of obtaining (e.g., farming and harvesting) a particular fermentable feedstock). The fermentable feedstock selection module, ethanol integration controller 3102, transportation selection module 3110, or another module may determine the CI of each fermentable feedstock variation based on data received from the procurement computing device 3120, a procurement and distribution computing device, a database, a user input from the user interface 3114, a fermentable feedstock source controller in signal communication with the ethanol integration controller 3102, memory 3106, or another device storing such data. The data received may include a volume of a fermentable feedstock, a type of fermentable feedstock (for example, grains, fruits, waste products, vegetation, other organic materials, etc.), and/or a location of the fermentable feedstock (for example, city, state, country, etc.). The data may also include the ILUC of the fermentable feedstock, if applicable and as disclosed above. In such examples, ILUC may be applicable when considering ethanol to be shipped to different states (e.g., California may consider ILUC). The data may also include a CI (or raw data to determine the CI) associated with producing, obtaining, and/or any other processing of the fermentable feedstock (e.g., a CI associated with obtaining, procuring, and/or processing a fermentable feedstock from a fermentable feedstock source). Once a number of or all of the fermentable feedstock variations CI are determined, the ethanol integration controller 3102 may store each CI in memory 3106, at a database, and/or at the procurement computing device 3120 for future use.

The ethanol integration controller 3102 may further determine a fermentable feedstock transportation CI for a number of or all available feedstock transportation pathways for each or a number of each feedstock variations. The transportation selection module 3110 or another module in the ethanol integration controller 3102 may determine the CI. The ethanol integration controller 3102 or transportation selection module 3110 may determine the fermentable feedstock transportation CIs based on the selected one or more available fermentable feedstock or fermentable feedstock variations, for any particular iteration or determination. For example, in the case that a fermentable feedstock from overseas is chosen, marine delivery modes or pathways may be considered, while for a local fermentable feedstock (or a fermentable feedstock within the same country), rail and vehicular (e.g., a truck) transportation may be considered. The ethanol integration controller 3102 or transportation selection module 3110 may obtain available fermentable feedstock transportation pathways from the procurement computing device 3120, the user interface 3114, a database, from memory 3106, and/or from another device. Further, the ethanol integration controller 3102 or the transportation selection module 3110 may base the CI on the volume of each fermentable feedstock transportation pathway, the fuel type utilized by each fermentable feedstock transportation pathway (e.g., gas, electricity, steam, other liquid fuels, etc.), and/or a distance from the source of the fermentable feedstock to the ethanol plant. Once a number of or all of the fermentable feedstock transportation pathway variations CI, based on the fermentable feedstock variations, are determined, the ethanol integration controller 3102 may store each CI in memory 3106, at a database, and/or at the procurement computing device 3120 for future use.

The ethanol integration controller 3102 may further, via an ethanol process selection module 3108, determine an ethanol production process of an ethanol production process and utilities CI for a number of or all available ethanol production processes of one or more ethanol production plants and utility options for each or a number of each feedstock variations. The ethanol integration controller 3102 may, rather than determining an ethanol production process and utility CI, determine an ethanol production process CI and/or a utilities CI. The ethanol process selection module 3108 or other modules within the ethanol integration controller 3102 may determine the ethanol production process and utilities CI. As noted above, an ethanol production process may utilize various utilities. To offset carbon emissions for standard ethanol production processes, renewable utilities (e.g., solar, wind, geothermal, renewable gas, etc.) may be utilized in the ethanol production process, thus reducing overall CI (as well as carbon emissions). In another example, carbon sequestration may be utilized or selected to reduce or offset the CI for a particular ethanol production process, thus reducing the overall CI for ethanol production. In an example, the ethanol integration controller 3102 or ethanol process selection module 3108 may determine available ethanol production processes and utilities based on a list from an ethanol plant controller 3116, utility controller 3118, or from memory 3106. In another example, the ethanol integration controller 3102 or ethanol process selection module 3108 may determine available ethanol production processes and utilities based on the selected one or more available fermentable feedstock or fermentable feedstock variations (in other words, different fermentable feedstock may utilize different ethanol production processes, thus choices may be limited based on the particular fermentable feedstock variations). In such examples, the ethanol integration controller 3102 and/or the ethanol process selection module 3108 may determine CI for each available ethanol production process and utility option for each fermentable feedstock variation. The ethanol integration controller 3102 and/or ethanol process selection module 3108 may determine the CI for each available ethanol production process and utility option based on the type or types of the selected fermentable feedstock variations, the utilities to be used during the ethanol production processes, the yield of each ethanol production process, and/or other factors, as will be understood by those skilled in the art. The ethanol integration controller 3102 may consider other ethanol plants. The ethanol integration controller 3102 may determine a CI for other ethanol plants, as described above. Once a number of or all of the ethanol production processes and utilities CI (for one or more ethanol plants), based on the fermentable feedstock variations, are determined, the ethanol integration controller 3102 may store each CI in memory 3106 or at a database for future use.

As noted, the ethanol integration controller 3102 may, rather than determining an ethanol production process and utility CI, determine an ethanol production process CI and/or a utilities CI. The utility CI may be based on the utilities used in a corresponding ethanol production process, the utilities used to store a feedstock, the utilities used to store ethanol, other utilities used for various other processes at ethanol plants, and/or at other points in the ethanol production process.

The ethanol integration controller 3102 may further determine an ethanol distribution CI for a number of or all available ethanol distribution pathways for each or a number of each feedstock variations. The transportation selection module 3110 or another module in the ethanol integration controller 3102 may determine the ethanol distribution CI. The ethanol integration controller 3102 or transportation selection module 3110 may determine the ethanol distribution CI based on the selected one or more available fermentable feedstock and ethanol production process yield, for any particular iteration or determination. For example, one ethanol production process for a fermentable feedstock variation may produce a certain amount of ethanol and, potentially, other byproducts (e.g., DDGS, syrup, and/or oil), while another ethanol production process for another fermentable feedstock variation may produce a different amount of ethanol and other byproducts. The ethanol integration controller 3102 or transportation selection module 3110 may obtain available ethanol distribution pathways from the distribution computing device 3122, the user interface 3114, a database, from memory 3106, and/or from another device. Further, the ethanol integration controller 3102 or the transportation selection module 3110 may determine the ethanol distribution CI based on the volume of each ethanol distribution pathway, the fuel type utilized by each ethanol distribution pathway, and/or a distance from the ethanol plant to distribution point and/or an end destination/point. Once a number of or all of the ethanol distribution pathway variations CI, based on the fermentable feedstock variations, are determined, the ethanol integration controller 3102 may store each CI in memory 3106, at a database, distribution computing device 3122, and/or procurement and distribution computing device for future use.

Once a number of or all CIs for each selection (as in, the selection of the one or more available fermentable feedstock, the fermentable feedstock transportation pathway, the ethanol production process and utilities, the ethanol distribution, and/or blending processes) are determined, the ethanol integration controller 3102 may determine a set of variations, combinations, or selections of each of the selections noted above. For example, one set of the variations, combinations, or selections may include a selected one or more available fermentable feedstock, a selected one or more available fermentable feedstock transportation pathways (corresponding to the fermentable feedstock variation), a selected one or more ethanol production processes (corresponding to the fermentable feedstock variation), a selected one or more utilities (corresponding to the ethanol production processes and/or other processes to use utilities), and a selected one or more ethanol distribution pathways (corresponding to the ethanol from the ethanol plant). Further, the ethanol integration controller 3102 may determine a total CI for each variation, combination, or set of selections. The ethanol integration controller 3102 may determine the total CI based on the volume of the selected one or more available fermentable feedstock, the yield from the corresponding or selected ethanol production processes to produce ethanol, the determined fermentable feedstock CI, the determined fermentable feedstock transportation CI, the determined ethanol production process and utilities CI, and/or the determined ethanol distribution CI. Other factors may be considered when determining a total CI. For example, the ethanol integration controller 3102 may further base the total CI on fermentable feedstock storage CI (if utilized), an ethanol tank CI (if utilized), emissions (e.g., VOC emissions through working losses, breathing losses, and flashing losses), carbon sequestration (if utilized), a CI based on ILUC (if applicable), the CI of the byproducts of the ethanol production process (which may or may not decrease the overall CI), and/or other carbon offsetting practices as will be understood by those skilled in the art. In such examples, once the ethanol integration controller 3102 determines the total CI for each variation, the ethanol integration controller 3102 may store each total CI in memory 3106 and/or at a database.

Once each total CI variation is determined, the ethanol integration controller 3102 may determine a selection from the set of combinations. The combinations may include the various selections, described above, with a CI less than the threshold CI. In an example, if there are no variations with a CI less than the CI threshold, the ethanol integration controller 3102 may notify a user that all selections exceed the threshold CI, prompt a user to enter a new threshold CI, and/or prompt a user to accept the selection with the lowest total CI (the lowest total CI, in this case, exceeding the threshold CI). In another example, the ethanol integration controller 3102 may automatically select a new threshold CI. In another example, the ethanol integration controller 3102 may determine the selection based on the lowest total CI (the lowest total CI not exceeding the threshold CI). In yet another example, multiple combinations may include a similar or the same total CI. However, each combination may exhibit different properties, such as a cost issue or a timing issue (e.g., from fermentable feedstock to customer). In such examples, the ethanol integration controller 3102 may select one of the combinations, with the similar or same CI or a CI lower than threshold, further based on the time of availability of each of the selected one or more available fermentable feedstock, a time for delivery to the ethanol plant by the fermentable feedstock transportation pathway, a time to process a fermentable feedstock utilizing the selected one or more ethanol production processes, a time to delivery from the ethanol plant to the end user (e.g., a blending site, etc.), and/or any ethanol production processes queued or in production. Upon determination of a selection, the ethanol integration controller 3102 may initiate ethanol production or transmit a request to confirm initiation of the ethanol production.

As noted above, the ethanol integration controller 3102 may determine a combination of a selection of one or more fermentable feedstock, one or more fermentable feedstock transportation pathways, a selection of one or more ethanol production processes, a selection of one or more utilities, and a selection of one or more ethanol distribution pathways. The ethanol integration controller 3102 may determine such a combination based on a determination of the fermentable feedstock CI (based on, for example, a ratio or blend of available fermentable feedstock volume and type), the fermentable feedstock transportation CI (based on available fermentable feedstock transportation delivery distance and fuel type), the ethanol production process CI (based on the type of ethanol production process, the volume and type of fermentable feedstock, the length of time of the ethanol production process, and/or the yield of the ethanol production process process), the utility CI of one or more utilities (based on the type of utility utilized in the ethanol production process and the distance the utility travels to reach the ethanol plant), and/or ethanol distribution CI (based on available ethanol distribution delivery distance and fuel type). Other factors may be utilized in determining a combination, such as cost of each process, margin or profit based on a sale of the final product, availability, yield, ILUC, and/or one-time costs (such as increasing ethanol production capacity or increasing efficiency of an aspect of the ethanol production facility or source).

In another example, the ethanol integration controller 3102 may connect to a database. The database may include various data points, such as available fermentable feedstock (and corresponding raw data), available transportation modes (and corresponding raw data), available and types of storage tanks (and corresponding raw data), available ethanol production processes (and corresponding raw data), and/or available utility options (and corresponding raw data). In another example, a user may update, via the user interface 3114, the data stored at the database. In another example, the ethanol integration controller 3102 may update the data at the database, for example, based on reception of data from various controllers and/or computing devices. In another example, the ethanol integration controller 3102 may store determined CIs, total CIs, and/or audit reports at the database, which other devices or user interfaces may access.

FIGS. 31B and 31C illustrate other simplified diagrams illustrating control systems for managing the low carbon intensity energy production according to an embodiment. In such examples, the fuel integration controller 1000 may include the functionality of or connect to the hydrogen integration controller 2402 and the ethanol integration controller 3102. As such, the fuel integration controller 1000 may control the ethanol integration controller 3102 to produce a low carbon intensity ethanol or ultra-low carbon intensity ethanol to further reduce the carbon intensity of a refined and blended transportation fuel. In another example, a supervisory controller may connect to the fuel integration controller 1000, the hydrogen integration controller 2402, and/or ethanol integration controller 3102 to orchestrate or control refined and blended transportation fuel production processes, hydrogen production processes, and/or ethanol production processes. In such examples, the supervisory controller may connect to other controllers related to the refinery, hydrogen, water, utilities, ethanol production, biodiesel production, feedstock sources, and/or other processes.

Figure 32B:
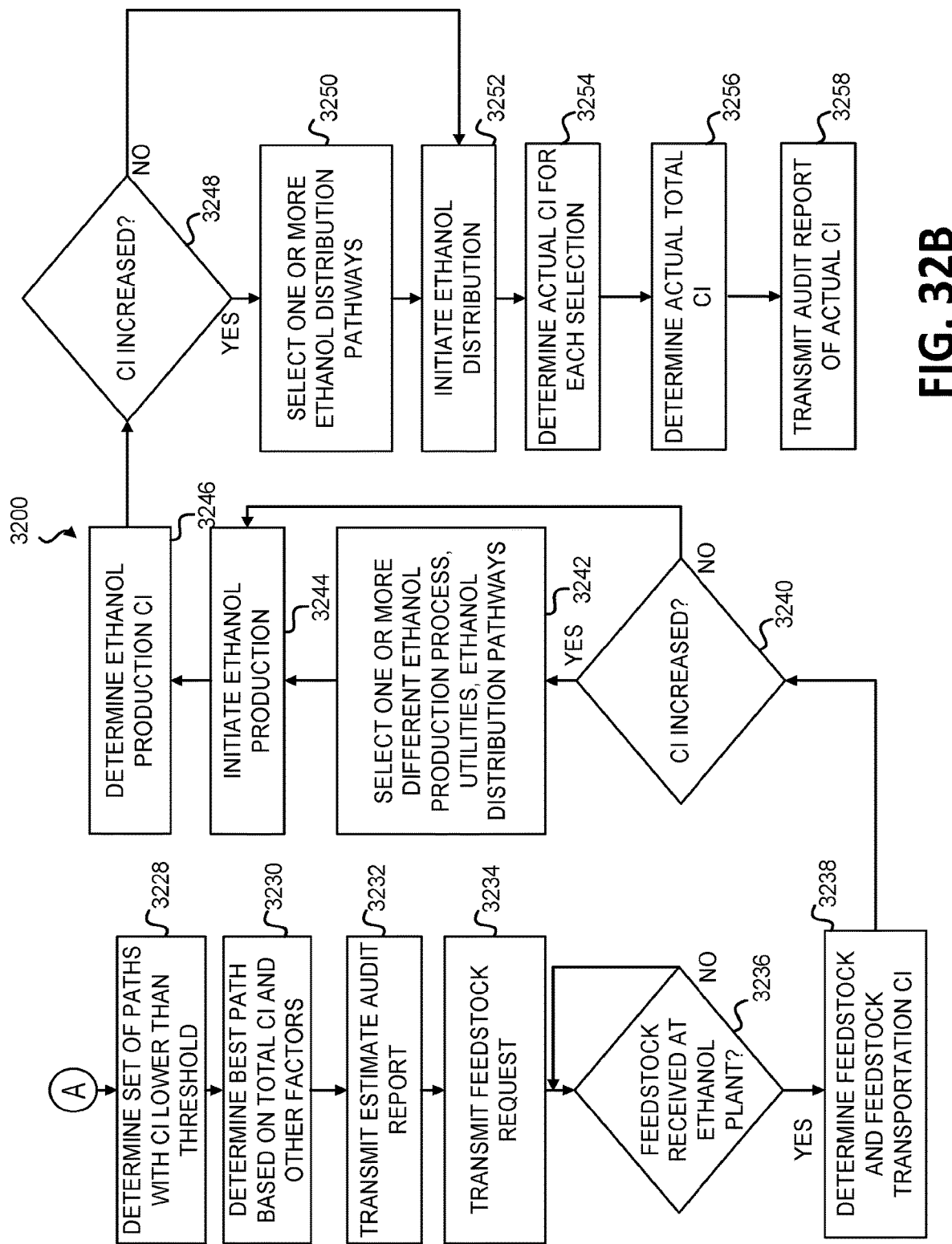
Figure 33:
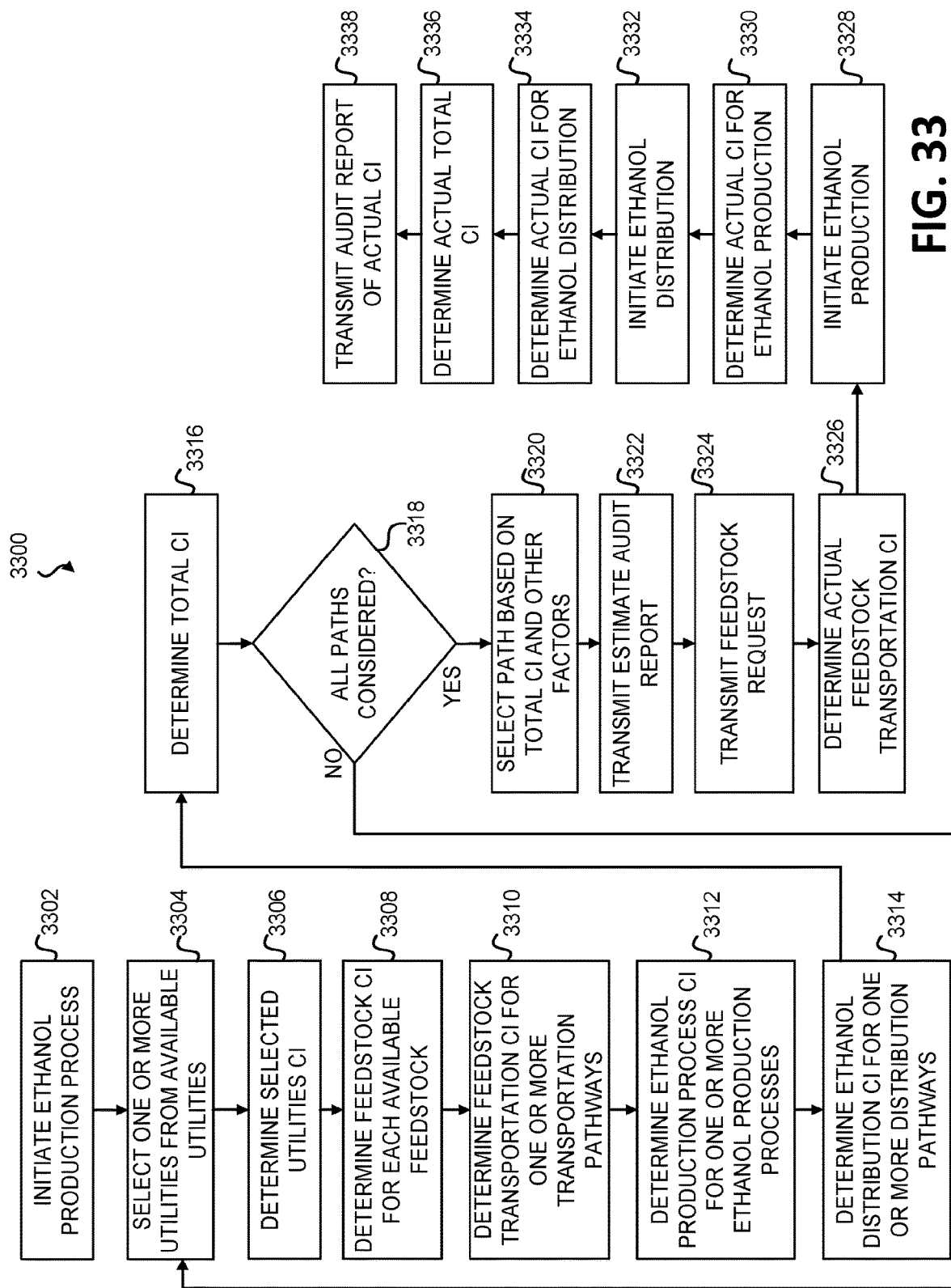
FIG. 33 is a flow diagram, implemented in a controller, for managing the low carbon intensity ethanol production, according to an embodiment.

FIGS. 32A-B and FIG. 33 are flow diagrams, implemented in a controller, for managing the low carbon intensity ethanol production, according to an embodiment. The method is detailed with reference to the ethanol integration controller 2902 and system 2900 of FIG. 29. Unless otherwise specified, the actions of method 3200 and method 3300 may be completed within the ethanol integration controller 2902. Specifically, method 3200 and method 3300 may be included in one or more programs, protocols, or instructions loaded into the memory of the ethanol integration controller 2902 or in a fuel integration controller and executed on the processor or one or more processors of the ethanol integration controller 2902 or fuel integration controller. The order in which the operations are described is not intended to be construed as a limitation, and any number of the described blocks may be combined in any order and/or in parallel to implement the methods.

At block 3202, the ethanol integration controller 2902 may receive a signal or prompt to initiate an ethanol production process. In another example, a user at a user interface may initiate the ethanol production process. At block 3204, the ethanol integration controller 2902 may receive a threshold CI for an amount of ethanol to be produced during an ethanol production process. The ethanol integration controller 2902 may receive the threshold CI from a user, user interface, a low CI ethanol specification (e.g., input by a user or stored in a database), a controller, memory of the ethanol integration controller 2902, a fuel integration controller, a supervisory controller, and/or another device. In response to a reception of the threshold CI, the ethanol integration controller 2902 may utilize or assign the input threshold CI as a current threshold CI. The current threshold CI may correspond to a particular ethanol production process or operation. In other words, the threshold CI may vary for different ethanol production processes.

At block 3206, the ethanol integration controller 2902 may select one or more utilities 2912 to operate the ethanol plant 2908 or ethanol plants from available utilities. In such examples, the ethanol integration controller 2902 may determine the available utilities 2912 based on data from a utility controller at a utility provider, data stored in the ethanol integration controller 2902, a database, or from the memory of an ethanol plant controller. In an example, a dedicated power source may be located at or near the ethanol plant 2908 (e.g., a wind farm). In other examples, the ethanol plant 2908 may include a variety of power sources or access to power sources. In such examples, the utilities 2912 may be one of the largest factors affecting the overall CI of the produced ethanol. As such, the ethanol integration controller 2902 may select a lower or the lowest CI utility. Once the utilities 2912 are selected, at block 3208, the ethanol integration controller 2902 may determine the selected utilities CI. In another example, the ethanol integration controller 2902 may determine the selected utilities CI and various other selections of the ethanol production processes CI. The ethanol integration controller 2902 may then select different one or more utilities 2912 and determine the various CI for selections of the ethanol production processes (e.g., determining CI for each variation, combination, or path). As noted above, ethanol plant 2908 operations may be offset by the use of low CI utilities. For example, renewable fuels from a utility provider may be provided to the ethanol plant 2908 to process a feedstock. The utilities 2912 may include different sources or forms of water/steam, of electricity (e.g., solar, wind, geothermal, renewable gas, etc.), and/or of other fuels (e.g., renewable natural gas or natural gas). Other utilities may include hydroelectric utilities and/or hydrogen fuel cell power systems. In an example, a utility provider may be an energy producing facility connected to the grid, an energy producing facility nearby or proximate to the ethanol plant 2908, or an energy producing facility nearby or at and dedicated to the ethanol plant 2908. As noted, the utility provider (e.g., the energy producing facility) may produce energy via renewable resources (e.g., a wind farm located nearby or at the ethanol plant 2908). In another example, the utility provider (e.g., the energy producing facility) may produce energy via fossil fuels and/or renewable resources. The utilities CI may further include a CI associated with utilities 2912 used throughout the ethanol plant 2908. The utilities CI may be further based on utilities 2912 used at the fermentable feedstock source (e.g., utilities used to obtain, procure, or produce a fermentable feedstock at a farm), used at the fermentable feedstock storage tank 2906, during ethanol distribution (e.g., power utilized at a pump to pump ethanol to another location), and/or used at any other point in the ethanol production process.

At block 3210, the ethanol integration controller 2902 may determine the CI for one or more available fermentable feedstock from a fermentable feedstock source 2904. As noted above, the available fermentable feedstock may include organic matter including starches and/or sugar (e.g., corn, barley, wheat, sugar cane, beets, etc.) from a variety of sources. In an example, the ethanol integration controller 2902 may determine a list or set of available feedstock from a user input (via a user interface), a database, a procurement controller, procurement computing device, procurement and distribution computing device, the memory of the ethanol integration controller 2902, and/or another device. Further, data or information on available fermentable feedstock may be a subset of data or information on all available fermentable feedstock based on available ethanol plants (e.g., different ethanol plants may be equipped to ferment and distill different types of fermentable feedstock, while other ethanol plants may ferment and distill other types of fermentable feedstock). As such, the ethanol integration controller 2902 may determine fermentable feedstock CI for one or more available fermentable feedstock from the subset of available fermentable feedstock. Further, the ethanol integration controller 2902 may determine fermentable feedstock CI based on the ratio, percentage, or blend of the fermentable feedstock's inherent CI, the type of fermentable feedstock, the location of the fermentable feedstock (e.g., distance from the ethanol plant 2908, fermentable feedstock storage 2906, etc.), the power used or emissions generated by obtaining or producing the fermentable feedstock, the CI of fertilizer used for the fermentable feedstock, and/or the volume of the fermentable feedstock. In another example, the fermentable feedstock CI may be known or given (e.g., via the user interface, database, controller, etc.). Further, as one or more available fermentable feedstock are determined or selected, the fermentable feedstock CI may be determined based on the ratio of the determined or selected one or more available fermentable feedstock (e.g., the ratio of the CI of two or more different fermentable feedstock).

At block 3212, the ethanol integration controller 2902 may determine a fermentable feedstock transportation CI for each available fermentable feedstock transportation pathway for the one or more available fermentable feedstock. The available fermentable feedstock transportation pathways may include marine vessel transportation, vehicular transportation (e.g., a truck), and/or rail transportation. Different fermentable feedstock may be deliverable via particular fermentable feedstock transportation pathways. As such, based on one or more available fermentable feedstock, the ethanol integration controller 2902 may determine the fermentable feedstock transportation CI. The ethanol integration controller 2902 may further determine the fermentable feedstock transportation CI for each available fermentable feedstock transportation pathway based on the volume of the fermentable feedstock transportation pathway, the fuel utilized by the fermentable feedstock transportation pathway, and the distance the fermentable feedstock transportation pathway may travel to deliver the fermentable feedstock from the fermentable feedstock source 2904 to fermentable feedstock storage 2906 or the ethanol plant 2908.

As noted above, fermentable feedstock storage in fermentable feedstock storage 2906 may be associated with a CI. In other words, storing a fermentable feedstock in fermentable feedstock storage 2906 may lead to carbon emissions, based on various factors, such as time of storage, volume of the fermentable feedstock storage 2906, volume of the fermentable feedstock to be stored, power or CI required to transfer fermentable feedstock to and from the fermentable feedstock storage 2906, and/or power and time required to heat, cool, or control the humidity of the fermentable feedstock. In such cases where fermentable feedstock storage may be an option, the ethanol integration controller 2902 may determine fermentable feedstock storage CI based on those factors. Further, a CI may be associated with transporting the stored fermentable feedstock to the ethanol plant 2908 or other ethanol plants. The stored fermentable feedstock may be transported via marine vessel, vehicle (e.g., a truck), and/or rail. The stored fermentable feedstock transportation CI may be based on the volume of the stored fermentable feedstock transportation pathway, the fuel utilized by the stored fermentable feedstock transportation pathway, and the distance the stored fermentable feedstock transportation pathway may travel to deliver the stored fermentable feedstock from fermentable feedstock storage 2906 to the ethanol plant 2908 or other ethanol plants.

At block 3214, the ethanol integration controller 2902 may determine the ethanol production process CI and/or the CI for other ethanol plants. In such examples, the ethanol integration controller 2902 may obtain a list of available ethanol plant processes from an ethanol plant controller at, for example, the ethanol plant 2908 or ethanol plants, a database, or the memory of the ethanol integration controller 2902. In another example, the ethanol integration controller 2902 may determine the ethanol production processes CI for each ethanol production process based on the type of fermentable feedstock selected and the yield of the ethanol production process. As noted above, high CI ethanol plant operations or processes may be offset by the use of offsetting practices. For example, the ethanol plant may utilize carbon sequestration to offset fermentation and distillation, as will be understood by those skilled in the art. For example, as a fermentable feedstock is fermented, yeast consumes sugar in the fermentable feedstock producing large quantities of carbon dioxide. Further, during distillation a fuel may be burned to heat the fermented feedstock. The burning of the fuel may produce carbon dioxide. The carbon dioxide may, if released into the atmosphere, contribute to the overall CI of the produced ethanol. Rather than releasing the carbon dioxide into the atmosphere, the carbon dioxide may be captured or sequestered, thus significantly lowering the overall CI of the ethanol.

As noted above, ethanol storage in a tank 2910 may be associated with a CI. In other words, storing the ethanol in a tank 2910 may lead to carbon emissions, based on various factors, such as time of storage, volume of tank 2910, volume of ethanol to be stored, power required to transfer the ethanol to and from the tank 2910 (e.g., via a pump), power and time required to heat/cool the ethanol, and/or the emissions associated with the storage of the ethanol (e.g., VOC emissions through working losses, breathing losses, and flashing losses). In such cases where ethanol storage may be an option, the ethanol integration controller 2902 may determine ethanol storage CI based on those factors. Further, a CI may be associated with transporting the ethanol from the ethanol plant 2908 to the tank 2910. The stored ethanol may be transported via marine vessel, vehicle (e.g., a truck), and/or rail. The stored ethanol CI may be based on the volume of the stored ethanol distribution pathway, the fuel utilized by the stored ethanol distribution pathway, and the distance the stored ethanol distribution pathway may travel to deliver the stored ethanol from the refinery 2918 to the tank 2910.

At block 3216, the ethanol integration controller 2902 may determine an ethanol distribution CI for each available ethanol distribution pathway for ethanol from a tank 2910 or ethanol plant 2908. The available ethanol distribution pathways may include marine vessel transportation, truck or vehicular transportation, and/or rail transportation. The ethanol integration controller 2902 may further determine the ethanol distribution CI for each available ethanol distribution pathway based on the volume of the ethanol distribution pathway, the fuel utilized by the ethanol distribution pathway, and the distance the ethanol distribution pathway may travel to deliver the ethanol from the tank 2910 or ethanol plant 2902 to a blending site 2914 or another end user location.

At block 3218, the ethanol integration controller 2902 may determine the total CI for each variation of selections noted above. For example, for the selected one or more available utilities or fermentable feedstock, the ethanol integration controller 2902 may determine total CI based on a first fermentable feedstock selection, a first fermentable feedstock transportation pathway, a first ethanol production process, a first utility, and/or a first ethanol distribution pathway. The ethanol integration controller 2902 may then determine the total CI for the next variation and so on. The ethanol integration controller 2902 may further base the total CI on the volume of the selected one or more available fermentable feedstock, the yield percentage of the ethanol plant (in other words, the volume of the ethanol per the original feedstock volume), and/or the CI of each selection. Other factors may be taken into account for total CI.

In response to a determination of total CI, at block 3220, the ethanol integration controller 2902 may determine whether all selections or, at least, a number of selections of the one or more available utilities (and the variations of the other selections described above) have been considered (e.g., if a total CI has been determined for all variations of utility combinations or paths). If all selections or a number of selections of the one or more available utilities or fermentable feedstock have not been considered, at block 3220, the ethanol integration controller 2902 may select another of the one or more available utilities or fermentable feedstock and determine total CI, as described above. If all of the one or more available utilities or fermentable feedstock or, at least, a particular amount or set of the one or more available utilities or fermentable feedstock have been considered, then the ethanol integration controller 2902, at block 3222, may determine whether any path, combination, variation, or final selection does not exceed the threshold CI. If no path, combination, variation, or final selection does not exceed the threshold CI (in other words, if all paths, combinations, variations, or final selections exceed the threshold CI), at block 3224, the ethanol integration controller 2902 may transmit a notification to a user, prompting the user to select a new threshold CI. In another example, the ethanol integration controller 2902 may automatically increase the threshold CI based on a specified amount. The ethanol integration controller 2902, at block 3226, may wait until a new threshold CI is received. When a new threshold CI is submitted or received by the ethanol integration controller 2902, the current threshold CI is set to the new threshold CI and, at block 3206, another of the one or more available utilities or fermentable feedstock may be selected and each iteration or a number of iterations may be determined again, as described above.

If at least one path, combination, variation, or final selection does not exceed the threshold CI, at block 3228, the ethanol integration controller 2902 may determine a set of paths, combinations, variations, or selections with the lowest total CI. In some cases, one path, combination, variation, or selection may not exceed the threshold CI, while in other cases many paths or selections may not exceed the threshold CI. Each path, combination, variation, or selection may include a selected one or more available fermentable feedstock, one or more selected fermentable feedstock transportation pathways, one or more selected ethanol production operations or processes, one or more selected utilities, and/or one or more selected ethanol distribution pathways, as well as a corresponding CI for each selection.

Based on the set of paths, combinations, variations, or selections, at block 3230, the ethanol integration controller 2902 may determine a selection of a path, combination, variation, or selection from the set of paths or selections. The ethanol integration controller 2902 may select the path, combination, variation, or selections based on, in addition to lowest total CI, time of availability of each of the selected one or more available fermentable feedstock, a time for delivery to the one or more ethanol plants by the fermentable feedstock transportation pathway, a time to process a fermentable feedstock utilizing the selected one or more ethanol production operations or processes, a time to delivery from the one or more ethanol plants to a blending site, the cost of each selection, any ethanol production process currently in progress or in queue, and/or customer demand for ethanol of a particular CI. So, as an example, the ethanol integration controller 2902 may select the path, combination, variation, or selection having a lower than threshold CI (although not necessarily the lowest CI) and more efficient pathway (e.g., from fermentable feedstock to customer), as described above. An efficient pathway may include a shorter distance to travel overall (e.g., from fermentable feedstock source to an end user), the time of availability for the fermentable feedstock, the length of time to process a particular fermentable feedstock (which may be based on a type of fermentable feedstock), the length of time a fermentable feedstock may be stored at any point in the ethanol production process, cost issues associated with each of the selections, and/or a high demand for a blended fuel of a particular CI.

In response to determination of a selection of the path, combination, variation, or selections, at block 3232, the ethanol integration controller 2902 may generate and transmit an estimated or initial audit report to a user, user interface, database, and/or other device. The audit report may include the CI of each selection and the total CI. The estimated audit report may include other information regarding each part of the planned or selected ethanol production process, such as where the selected fermentable feedstock is from, the type and volume of the selected fermentable feedstock, the type of fermentable feedstock transportation pathways (as well as other details on the fermentable feedstock transportation pathway), the selected ethanol production process, the estimated yield of the ethanol production process, the selected utilities, the source of the selected utilities, the type of ethanol distribution pathways (as well as other details regarding the ethanol distribution pathway), length of time for storage at any point in the process, and/or an overall timeline of the ethanol production process. In another example, the ethanol integration controller 2902 may generate the estimated or initial audit report based on a request from a user and/or user interface.

In another example, the ethanol integration controller 2902, at block 3238, may transmit a fermentable feedstock request. The fermentable feedstock request may include the selected one or more available fermentable feedstock and the selected fermentable feedstock transportation pathway.

In another example, the ethanol integration controller 2902 may transmit a confirmation of the fermentable feedstock request prior to transmitting the fermentable feedstock request. For example, the ethanol integration controller 2902 may transmit a request for confirmation of a fermentable feedstock request of the selected one or more available fermentable feedstock to a user interface or a procurement computing device. In response to reception of the confirmation (e.g., from the user interface or procurement computing device), the ethanol integration controller 2902 may transmit the fermentable feedstock request to a procurement computing device, procurement controller, the user interface (which may include a procurement sub-routine or instructions), a procurement and distribution computing device, or other device.

At block 3236, the ethanol integration controller 2902 may determine whether the fermentation feedstock has been received at the ethanol plant 2908. Once the fermentable feedstock has been delivered to the ethanol plant 2908, at block 3238, the ethanol integration controller 2902 may determine the actual CI for the selected one or more available fermentable feedstock and corresponding fermentable feedstock transportation pathway. The ethanol integration controller 2902 may determine, at block 3240, whether, in relation to the determined fermentable feedstock CI and fermentable feedstock transportation CI, the actual CI for either the selected one or more available fermentable feedstock and corresponding fermentable feedstock transportation pathway has increased. If an increase is determined, the ethanol integration controller 2902, at block 3242, may select one or more different ethanol production processes, utilities, and/or ethanol distribution pathways to maintain the total CI, cost, and/or timeline of ethanol production, if such a selection is available. In another example, the ethanol integration controller 2902 may send a prompt or notification to a user or user interface. Further, the prompt may include the available options or paths, such as one or more different ethanol production processes at one or more ethanol plants, utilities, fermentable feedstock storage, storage tanks, and/or ethanol distribution pathways. In such examples, the user may select the new options or paths to maintain the total CI (e.g., from the estimate audit report) or lower the total CI further. In another example, the user may choose to continue with the prior selections.

In response to the determination that the determined fermentable feedstock CI and fermentable feedstock transportation CI have not increased or in response to a selection of one or more different ethanol production processes at one or more ethanol plants, the ethanol integration controller 2902 may, at block 3244, initiate any selected ethanol production processes or operations. In another example, the ethanol integration controller 2902 may connect to an ethanol plant controller and transmit the initiation to the ethanol plant controller. The ethanol integration controller 2902 may notify a user of the initiation of the ethanol production processes or operations. In another example, the ethanol integration controller 2902 may send a prompt to a user to initiate or confirm initiation of the ethanol production processes or operations.

In response to a reception of or determination of completion of the selected ethanol production processes or operations, at block 3246, the ethanol integration controller 2902 may determine the actual CI for the selected ethanol production processes or operations and utilities. The ethanol integration controller 2902 may, at block 3248, determine whether, in relation to the determined ethanol production processes or operations CI and utility CI, the actual CI for the ethanol production processes or operations and utilities has increased. If an increase is determined, the fuel integration controller 2902, at block 3250, may select one or more different ethanol fuel distribution pathways to maintain CI, cost, and/or timeline of ethanol production, if such a selection is available.

Once a new ethanol distribution pathway is selected or if no new ethanol distribution pathway is selected the ethanol integration controller 2902, at block 3252, may transmit a distribution request or initiate distribution of the ethanol via the selected ethanol distribution pathway. The distribution request may include the ethanol (e.g., the amount or volume of ethanol) and the selected ethanol distribution pathway. In another example, the ethanol integration controller 2902 may transmit a request for confirmation of a distribution request of the ethanol to a user interface or a distribution computing device. In response to reception of the confirmation (e.g., from the user interface or distribution computing device), the ethanol integration controller 2902 may transmit the ethanol request to a distribution computing device, distribution controller, the user interface (which may include a distribution sub-routine or distribution instructions), a procurement and distribution computing device, or other device.

At block 3254, the ethanol integration controller 2902 may determine the actual CI for the selected one or more available fermentable feedstock, the completed fermentable feedstock transportation pathway, the completed ethanol production processes or operations including utilities, and the completed ethanol distribution pathway. At block 3256, the ethanol integration controller 2902 may determine the actual total CI. The actual total CI may be based on the actual ethanol yield (in relation to the proportion of byproducts produced in the ethanol production process), the actual feedstock volume, and the actual CI for the selected one or more available fermentable feedstock, the completed fermentable feedstock transportation pathway, the completed ethanol production processes or operations including utilities, and the completed ethanol distribution pathway.

At block 3258, the ethanol integration controller 2902 may generate and transmit an actual or final audit report to a user, user interface, database, and/or other device. The actual or final audit report may include the actual total CI and the actual CI for each process (e.g., the actual CI for the selected one or more available fermentable feedstock, the completed fermentable feedstock transportation pathway, the completed ethanol production processes or operations including utilities, and the completed ethanol distribution pathway). The ethanol integration controller 2902 may generate the actual or final audit report based on a request from a user and/or user interface.

As illustrated in FIG. 33 and at block 3302, the ethanol integration controller 2902 may receive a signal or prompt to initiate an ethanol production process, as described above. At block 3304, the ethanol integration controller 2902 may select one or more utilities 2912 to operate the ethanol plant 2908, as described above. At block 3306, the ethanol integration controller 2902 may determine the CI for the selected utilities. The ethanol integration controller 2902 may gather other information relating to each of the utilities to determine such a CI, such as, the type of utilities, the amount of utilities to be utilized, and/or the proximity of the utility provider to the ethanol plant 2908.

At block 3308, the ethanol integration controller 2902 may determine the CI for one or more available fermentable feedstock from a fermentable feedstock source 2904, as described above. At block 3310, the ethanol integration controller 2902 may determine a fermentable feedstock transportation CI for each available fermentable feedstock transportation pathway for the one or more available fermentable feedstock, as described above. At block 3312, the ethanol integration controller 2902 may determine the ethanol production process CI and/or the CI for other ethanol plants, as described above. At block 3314, the ethanol integration controller 2902 may determine an ethanol distribution CI for each available ethanol distribution pathway for ethanol from a tank 2910 or ethanol plant 2908, as described above.

At block 3316, the ethanol integration controller 2902 may determine the total CI for each variation of selections, as described above. As an optional step, in response to a determination of total CI, at block 3318, the ethanol integration controller 2902 may determine whether all selections or, at least, a number of selections of the one or more available utilities (and the variations of the other selections described above) have been considered (e.g., if a total CI has been determined for all variations of utility combinations or paths), as described above. In another example, rather than checking if each variation, path, or selection has been considered, the ethanol integration controller 2902 may determine a set amount of variation or paths for an ethanol production process.

In an example, various paths may be considered, while in other examples all paths may be considered (e.g., the ethanol integration controller 2902 may determine the CI and other data points for each variation, path, or set of selections, while in other examples, the ethanol integration controller 2902 may determine the CI and other data points for a subset of each variations, paths, or set of selections). For example, the ethanol integration controller 2902 may consider variations, paths, or sets of selections of a particular cost, of a particular CI, that utilize a particular fermentable feedstock source 2904, that are powered by a particular type of utility or utilities, that will be finished in a particular time frame or time period, based on availability of a particular utility or utilities, and/or based on availability of a particular fermentable feedstock. The ethanol integration controller 2902 may, at block 3320, select the best path based on various factors, regardless of the number of paths considered. For example, the fuel integration controller 2902, when determining the best path, may consider, for each variation, path, or set of selections determined, the total CI of each, the cost of each, the timeline or period of time each may take (e.g., from fermentable feedstock source 2904 to a blending site 2914), the demand of an ethanol of a particular CI or cost, and/or other various factors.

In response to determination of a selection of the path, combination, variation, or selections, at block 3322, the ethanol integration controller 2902 may generate and transmit an estimated or initial audit report to a user, user interface, database, and/or other device, as described above. In another example, the ethanol integration controller 2902, at block 3324, may transmit a fermentable feedstock request, as described above. At block 3326, the ethanol integration controller 2902 may determine the actual CI for the selected one or more available fermentable feedstock and corresponding fermentable feedstock transportation pathway, as described above. After the determination of the actual CI for the selected one or more available fermentable feedstock and corresponding fermentable feedstock transportation pathway, the ethanol integration controller 2902 may, at block 3328, initiate any selected ethanol production processes or operations, as described above.

In response to a reception of or determination of completion of the selected ethanol production processes or operations, at block 3330, the ethanol integration controller 2902 may determine the actual CI for the selected ethanol production processes or operations and utilities, as described above. Once the actual CI for the selected ethanol production processes is determined, the ethanol integration controller 2902, at block 3332, may transmit a distribution request or initiate distribution of the ethanol via the selected ethanol distribution pathway, as described above.

At block 3334, the ethanol integration controller 2902 may determine the actual CI for the selected one or more available fermentable feedstock, the completed fermentable feedstock transportation pathway, the completed ethanol production processes or operations including utilities, and the completed ethanol distribution pathway, as described above. At block 3336, the ethanol integration controller 2902 may determine the actual total CI, as described above. At block 3338, the ethanol integration controller 2902 may generate and transmit an actual or final audit report to a user, user interface, database, and/or other device, as described above.

This application is related to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912 filed Aug. 18, 2020, titled "SYSTEMS AND METHODS FOR HOLISTIC LOW CARBON INTENSITY FUEL PRODUCTION," U.S. Provisional Application No. 63/198,626 filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186 filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety.

In the drawings and specification, several embodiments of systems and methods to provide low carbon intensity transportation fuels and low carbon intensity hydrogen have been disclosed, and although specific terms are employed, the terms are used in a descriptive sense only and not for purposes of limitation. Embodiments of systems and methods have been described in considerable detail with specific reference to the illustrated embodiments. However, it will be apparent that various modifications and changes may be made within the spirit and scope of the embodiments of systems and methods as described in the foregoing specification, and such modifications and changes are to be considered equivalents and part of this disclosure.

What is claimed is:

1. A process to provide a low carbon intensity hydrogen obtained through one or more targeted reductions of carbon emissions associated with a combination of feedstock procurement, feedstock production and hydrogen distribution, the process comprising:

identifying one or more sources of feedstock and one or more transportation pathways to transport feedstock from each of the one or more sources to a hydrogen production source;

determining carbon emissions per unit energy of hydrogen associated with providing each identified feedstock from the one or more feedstock sources;

determining carbon emissions per unit energy of hydrogen associated with each of the one or more transportation pathways;

receiving at the hydrogen production source at least one feedstock selected from at least one of the one or more sources identified and transported by at least one of the one or more transportation pathways identified, the at least one feedstock defining a selected feedstock and the at least one transportation pathway defining a selected transportation pathway;

converting the selected feedstock into hydrogen;

determining a reduction in carbon emissions per unit energy of hydrogen that is attributable to two or more hydrogen production processes selected from a group including, powering at least a portion of hydrogen production source equipment with electricity generated by a renewable source, burning renewable natural gas in hydrogen production source fired heaters, generating steam through renewable natural gas-fed boilers, and sequestering carbon dioxide produced during the one or more hydrogen production processes, the determining the reduction in carbon emissions per unit energy being based in part upon pre-selected operating parameters for each of the two or more hydrogen production processes;

operating the two or more hydrogen production processes to reduce carbon emissions per unit energy of hydrogen while converting the selected feedstock into the hydrogen;

identifying distribution pathways to transport a quantity of the hydrogen to an end user location;

determining carbon emissions per unit energy of hydrogen associated with each distribution pathway that transports the quantity of the hydrogen to the end user location;

determining a total carbon emissions per unit energy of the hydrogen, the determining being a function of at least one or more of the determined carbon emissions per unit energy associated with providing the selected feedstock from its source, the determined carbon emissions per unit energy associated with the selected transportation pathway, the determined reduction in carbon emissions per unit energy associated with converting the selected feedstock together with operating the selected two or more hydrogen production processes, and the determined carbon emissions per unit energy associated with transporting the quantity of the hydrogen to the end user location through at least one distribution pathway;

determining the selected feedstock, the selected transportation pathway, the one or more hydrogen production processes and the at least one distribution pathway to maintain the total carbon emissions per unit energy of the hydrogen below a pre-selected total carbon emissions per unit energy threshold;

maintaining a record of the total carbon emissions per unit energy associated with the quantity of the hydrogen; and outputting the quantity of the hydrogen through the at least one distribution pathway as a low carbon intensity hydrogen.

2. The process according to claim 1, further comprising:
determining a ratio of hydrogen that yields from converting the selected feedstock from the one or more sources.

3. The process according to claim 1, wherein the at least one feedstock from at least one of the one or more sources is selected from the group consisting of a low carbon intensity liquefied petroleum gas (LPG), a low carbon intensity naphtha, natural gas, and renewable natural gas, and wherein the one or more sources of feedstock include one or more of a wellhead, a bio-feedstock plant, an offsite refinery, a co-located refinery, or a water source.

4. The process according to claim 1, wherein the renewable source includes one or more of wind turbines, a solar array, a hydroelectric generator, a geothermal generator, or a stationary fuel cell power system.

5. A system to operate a hydrogen production source for distribution of a low carbon intensity (CI) hydrogen therefrom and obtained through one or more targeted reductions of carbon emissions (CE) associated with combinations of various available feedstock to be supplied to various hydrogen production sources, various selected feedstock transportation and hydrogen distribution pathways, and various hydrogen production processes, the system comprising:

a hydrogen production controller to control one or more various hydrogen production processes to be operated at one or more hydrogen production sources; and a hydrogen integration controller in signal communication with the hydrogen production controller, the hydrogen integration controller including one or more processors and memory storing instructions, the instructions, when executed by the one or more processors, to:

(I) determine a feedstock CI for each of one or more available feedstock from one or more available feedstock sources to be supplied to the one or more hydrogen production sources from one or more available feedstock transportation pathways, (II) for each one or more available feedstock:
  (a) determine a feedstock transportation CI for each of one or more available feedstock transportation pathways based on:
    (1) a volume of a feedstock transportation pathway,
    (2) fuel type utilized by the feedstock transportation pathway, and
    (3) distance to travel to the one or more hydrogen production sources,
  (b) determine a hydrogen production process CI for each of one or more hydrogen production processes based on:
    (1) one or more available hydrogen production processes available at the one or more hydrogen production sources,
    (2) a type of feedstock of the one or more available feedstock, and
    (2) a yield of each one or more available hydrogen production processes,
  (c) determine a utilities CI for each of one or more utilities based on:
    (1) a type of utility to be used during a hydrogen production process and
    (2) a utilities' source,
  (d) determine a hydrogen product distribution CI for each of one or more available hydrogen distribution pathway based on:
    (1) a volume of a hydrogen distribution pathway,
    (2) a type of the hydrogen distribution pathway,
    (3) fuel type utilized by the hydrogen distribution pathway, and
    (4) distance to travel for a delivery of hydrogen,
  (e) determine a set of combinations, each of the set of combinations including:
    (1) one or more available feedstock,
    (2) one or more available feedstock transportation pathways, (3) one or more hydrogen production processes of one or more hydrogen production sources,
(4) one or more utilities, and
(5) one or more available hydrogen distribution pathways, and
(f) determine a total CI for each of the set of combinations,
(III) determine a final selection from the set of combinations including a total CI less than or equal to a threshold CI, the threshold CI being defined as an upper limit of CI in providing hydrogen to an end user location that qualifies the hydrogen as a low CI hydrogen, the CI of the hydrogen being a function of the total carbon emissions per unit energy of the hydrogen, the final selection including:
(a) a selected one or more available feedstock,
(b) a selected one or more feedstock transportation pathways,
(c) a selected one or more hydrogen production processes of one or more hydrogen production sources,
(d) a selected one or more utilities, and
(e) a selected one or more hydrogen distribution pathways,
(IV) in response to the final selection, transmit a feedstock request based on the selected one or more available feedstock and the selected one or more feedstock transportation pathways,
(V) in response to a determined reception of the selected one or more available feedstock at the one or more hydrogen production sources, initiate, at the hydrogen production controller, the selected one or more hydrogen production processes of the one or more hydrogen production processes, and the selected one or more utilities to operate the selected one or more hydrogen production processes thereby to transform the selected one or more available feedstock to hydrogen, and
(VI) in response to determination of completion of the selected one or more hydrogen production processes, transmit a delivery request of the hydrogen via the selected one or more hydrogen distribution pathways.

6. The system according to claim 5, wherein the determination of the feedstock CI further includes:
(a) a volume of each of the one or more available feedstock,
(b) a type of feedstock of each of the one or more available feedstock, and
(c) a location of each of the one or more available feedstock.

7. The system according to claim 5, wherein the determination of the total CI is further based on a feedstock storage tank CI, and wherein the memory further has instructions to:
(a) determine the feedstock storage tank CI based on:
(1) a time each of one or more stored feedstock has been stored in each of one or more feedstock storage tanks,
(2) a time and power associated with regulating the temperature of each of the one or more stored feedstock,
(3) a time and power associated with pumping each of the one or more stored feedstock to the one or more hydrogen production sources, and
(4) a volume associated with emissions associated with each of the one or more stored feedstock.

8. The system according to claim 5, wherein the determination of the total CI is further based on a pressurized storage vessel CI, and wherein the memory further has instructions to:
(a) determine the pressurized storage vessel CI based on:
(1) a time hydrogen will be stored in each of the one or more pressurized storage vessels,
(2) a time and power associated with regulating the temperature of each of the one or more pressurized storage vessels, and
(3) an estimate volume associated with emissions associated with each of the one or more pressurized storage vessel.

9. The system according to claim 5, wherein the one or more hydrogen production processes includes options to:
(a) provide electrical power for the hydrogen production source through renewable sources, the renewable sources comprising wind, solar, and hydroelectric,
(b) employ renewable fuels in boilers and fired heaters of the hydrogen production source, the renewable fuels comprising renewable diesel and renewable natural gas, and
(c) sequester carbon dioxide produced during the one or more hydrogen production processes.

10. The system according to claim 5, wherein the determination of the final selection from the set of combinations is based on:
(a) the total CI,
(b) a time of availability of each of the one or more available feedstock,
(c) a time for delivery to the hydrogen production source by each of the one or more feedstock transportation pathway,
(d) a time to process one or more available feedstock utilizing each of the one or more hydrogen production processes, and
(e) a length of time to deliver, from the hydrogen production source to an end user, hydrogen by each of the one or more hydrogen distribution pathways.

11. The system according to claim 5, wherein the memory further has instructions to:
(a) in response to the determined reception of the selected one or more available feedstock at the hydrogen production source:
(1) determine actual feedstock CI for the selected one or more available feedstock,
(2) determine actual feedstock transportation CI for the selected one or more feedstock transportation pathways, and
(3) in response to a determination of an increase of the combined CI of the actual feedstock CI and actual feedstock transportation CI in relation to the combination of the determined feedstock CI and the determined feedstock transportation CI:
(A) select one or more different hydrogen production processes, one or more different utilities, and one or more different hydrogen distribution pathways to maintain total CI.

12. The system according to claim 11, wherein the memory further has instructions to:
(a) in response to determination of completion of the selected one or more hydrogen production processes:
(1) determine actual hydrogen production process CI for the selected one or more hydrogen production processes,
(2) determine actual utility CI for the selected one or more utilities, and (3) in response to a determination of an increase of the combined CI of the actual hydrogen production process CI and actual utility CI in relation to the combination of the determined hydrogen production process CI and determined utilities CI:
  (A) select one or more different hydrogen distribution pathways to maintain total CI.

13. The system according to claim 12, wherein the memory further has instructions to:
  (a) in response to determination of completion of the selected one or more hydrogen distribution pathways:
    (1) determine actual CI for:
      (A) the selected one or more available feedstock,
      (B) a completed one or more feedstock transportation pathways,
      (C) a completed one or more hydrogen production processes,
      (D) one or more utilities used to operate the completed one or more hydrogen production processes, and
      (E) a completed one or more hydrogen distribution pathway,
    (2) determine actual total CI based on:
      (A) an actual hydrogen yield,
      (B) an actual feedstock volume,
      (C) the actual CI for the completed one or more feedstock transportation pathways,
      (D) the actual CI for the completed one or more hydrogen production processes,
      (E) the actual CI for the one or more utilities used to operate the completed one or more hydrogen processes, and
      (F) the actual CI for the completed one or more hydrogen distribution pathways, and
    (3) transmit an audit report including the actual CI for each selection and the actual total CI.

14. The system according to claim 5, wherein the memory further has instructions to in response to a final selection, generate an audit report including a CI for each selection in the final selection and a total CI of the final selection.

15. A hydrogen integration controller to operate one or more hydrogen production sources for distribution of a low carbon intensity (CI) hydrogen therefrom and obtained through one or more targeted reductions of carbon emissions (CE) associated with various available feedstock to be supplied to the one or more hydrogen production sources, various selected feedstock transportation and hydrogen distribution pathways, and various hydrogen production processes, the hydrogen integration controller comprising:
  a first input/output in signal communication with a procurement computing device, such that the hydrogen integration controller is configured to:
    (a) determine a selection of one or more available feedstock, a selection of one or more feedstock transportation pathways, a selection of one or more hydrogen production processes at one or more hydrogen production sources, a selection of one or more utilities, and a selection of one or more hydrogen transportation pathways, each selection based on:
      (1) a determination of feedstock CI of one or more blends of the one or more available feedstock based on volume and type of feedstock,
      (2) a determination of feedstock transportation CI of one or more feedstock transportation pathways based on delivery distance and fuel type of the feedstock transportation pathway,
      (3) a determination of hydrogen production process CI of one or more hydrogen production processes at one or more hydrogen production sources based on the type of hydrogen production process, the volume and type of feedstock, and the length of time of the hydrogen production process,
      (4) a determination of utility CI of one or more utilities based on the type of utility utilized to operate the one or more hydrogen production processes and a distance the one or more utilities travel to the hydrogen production,
      (5) a determination of hydrogen distribution CI of one or more hydrogen distribution pathways based on delivery distance and fuel type of a hydrogen distribution pathway, and
      (6) a determination of one or more total CIs less than the threshold CI, the total CIs based on varying combinations of the determinations of CI, and
    (b) in response to the selection of the one or more available feedstock, the selection of one or more feedstock transportation pathways, the selection of one or more hydrogen production processes at one or more hydrogen production sources, the selection of one or more utilities, and the selection of one or more hydrogen distribution pathways:
      (1) transmit a feedstock request to the procurement computing device, the feedstock request including the selection of the one or more available feedstock and the selection of the one or more feedstock transportation pathways;
  a second input/output in signal communication with a hydrogen production controller, the hydrogen production controller to control one or more various hydrogen production processes to be operated at the one or more hydrogen production sources, such that the hydrogen integration controller is configured to:
    (a) in response to a determined reception of the selected one or more available feedstock at the one or more hydrogen production sources:
      (1) determine actual feedstock CI and actual feedstock transportation CI,
      (2) in response to a determination that the actual feedstock CI and actual feedstock transportation CI has increased in relation to the determined feedstock CI and determined feedstock transportation CI, determine one or more of a new selection of one or more hydrogen production processes, a new selection of one or more utilities, and a new selection of one or more hydrogen distribution pathways to maintain total CI, and
      (3) initiate, at the hydrogen production controller, the selected one or more hydrogen production processes at the one or more hydrogen production sources and the selected one or more utilities to operate the selected one or more hydrogen production processes at the one or more hydrogen production sources thereby to transform the selected one or more available feedstock to hydrogen; and
  a third input/output in signal communication with a distribution computing device such that the hydrogen integration controller is configured to:
    (a) in response to determination of completion of the selected one or more hydrogen production processes at the selected one or more hydrogen production sources:

(1) determine an actual hydrogen production process CI and an actual utility CI, (2) in response to a determination that the actual hydrogen production process CI and actual utility CI has increased in relation to the determined hydrogen production process CI and determined utility CI, determine one or more new selections of one or more hydrogen distribution pathways, and (3) transmit a delivery request of the hydrogen via the selection of the one or more hydrogen distribution pathways to the distribution computing device.

16. The hydrogen integration controller according to claim 15, wherein the one or more hydrogen production processes includes offsetting practices.

17. The hydrogen integration controller according to claim 16, wherein the offsetting practices include hydrogen production processes to:

(a) provide electrical power for the one or more hydrogen production sources through renewable sources, the renewable sources comprising wind, solar and hydroelectric, (b) employ renewable fuels in boilers and fired heaters of the hydrogen production source, the renewable fuels comprising renewable diesel and renewable natural gas, and (c) sequester carbon dioxide produced during the one or more hydrogen production processes.

18. The hydrogen integration controller according to claim 15, wherein the hydrogen integration controller comprises one or more controllers.

19. The hydrogen integration controller according to claim 15, wherein the hydrogen integration controller comprises a supervisory controller in signal communication with and to control one or more other controllers.

20. The hydrogen integration controller of claim 15, wherein the determination of utility CI is further based on the:

(a) utilities used for one or more feedstock storage tanks,
(b) utilities used for one or more pressurized storage vessels,
(c) utilities used for pumping one or more available feedstock from the one or more feedstock transportation pathways to the hydrogen production source, and
(d) utilities used for transporting hydrogen from the one or more hydrogen production sources to the one or more hydrogen distribution pathways.

* * * * *